(12) United States Patent
Davies-Sekle

(10) Patent No.: US 11,622,877 B2
(45) Date of Patent: Apr. 11, 2023

(54) DYNAMIC RANGE OF MOTION ORTHOSIS

(71) Applicant: Brandon O. Davies-Sekle, Herndon, VA (US)

(72) Inventor: Brandon O. Davies-Sekle, Herndon, VA (US)

(*) Notice: Subject to any disclaimer, the term of this patent is extended or adjusted under 35 U.S.C. 154(b) by 1020 days.

(21) Appl. No.: 16/260,964

(22) Filed: Jan. 29, 2019

(65) Prior Publication Data

US 2019/0365554 A1 Dec. 5, 2019

Related U.S. Application Data

(63) Continuation of application No. 62/680,292, filed on Jun. 4, 2018.

(51) Int. Cl.
*A61F 5/01* (2006.01)
*A61H 1/02* (2006.01)
*B25J 9/00* (2006.01)

(52) U.S. Cl.
CPC ........... *A61F 5/013* (2013.01); *A61H 1/0281* (2013.01); *A61F 2005/0146* (2013.01); *A61F 2005/0165* (2013.01); *B25J 9/0006* (2013.01)

(58) Field of Classification Search
CPC .............. A61F 5/013; A61F 2005/0146; A61F 2005/0151; A61F 2005/0153; A61F 2005/0158; A61F 2005/0165; A61F 2005/0167; A61H 1/02; A61H 1/0206; A61H 1/0274; A61H 1/0277; A61H 1/0281; A61H 1/0203; B25J 9/0006
See application file for complete search history.

(56) References Cited

U.S. PATENT DOCUMENTS

| 2,310,566 | A | * | 2/1943 | Anderson | A61F 5/05808 602/19 |
| 4,180,870 | A | * | 1/1980 | Radulovic | A61F 5/013 601/33 |
| 5,407,420 | A | * | 4/1995 | Bastyr | A61F 5/05858 602/5 |
| 6,113,562 | A | * | 9/2000 | Bonutti | A61F 5/013 602/5 |
| 8,460,222 | B2 | * | 6/2013 | Garrec | B25J 9/0006 602/5 |
| 8,591,441 | B2 | * | 11/2013 | Bonutti | A61F 5/013 602/20 |
| 9,327,398 | B2 | * | 5/2016 | Sankai | B25J 9/0006 |
| 9,737,374 | B2 | * | 8/2017 | Doyle | B25J 9/0006 |

* cited by examiner

*Primary Examiner* — Keri J Nelson
(74) *Attorney, Agent, or Firm* — Karceski IP Law, PLLC

(57) ABSTRACT

An orthosis provides a wearer at least one of forearm supination, forearm pronation, shoulder internal rotation, shoulder external rotation, shoulder adduction, shoulder abduction, shoulder flexion, shoulder extension, elbow flexion, and elbow extension. It includes a shoulder assembly adapted to be secured to a wearer's shoulder and an upper arm assembly connected to the shoulder assembly and adapted to be secured around a wearer's upper arm. The upper arm assembly defines an upper arm assembly axis. A wrist assembly is adapted to be secured around a wearer's wrist. The wrist assembly defines a wrist assembly axis. A splint arm assembly includes an upper splint arm, a lower splint arm, and a pivot pivotally connecting the upper splint arm to the lower splint arm. The upper splint arm adjustably connects to the upper arm assembly and the lower split, arm adjustably connects to the wrist assembly.

12 Claims, 154 Drawing Sheets

DYNAMIC RANGE OF MOTION ORTHOSIS

CROSS-REFERENCE TO RELATED APPLICATION(S)

This application is based on and claims priority to U.S. Provisional Patent Application No. 62/680,292, filed on Jun. 4, 2018, the entire content of which is incorporated herein by reference.

FIELD OF THE INVENTION

The present invention is in the technical field of shoulder and arm orthopedics. More specifically, the present invention is in the technical field of shoulder and arm orthotics, which loosely relates to and overlaps the technical fields of splint and brace making.

The present invention relates to an orthotic device, to be worn by a person, that provides an adjustable amount of forced forearm pronation or supination and an adjustable amount of forced shoulder internal or external rotation. Use of the device provides a means for muscular rehabilitation to users, with some degree of paralysis in the arm or shoulder, through the conjunctional use of resistance training and the stretches provided through any number of possible degrees of motion. In addition to supination, pronation, internal rotation, and external rotation, it may also provide an adjustable amount, of forced shoulder adduction, abduction, flexion, or extension and, with a lockable elbow, ultimately allow the arm to be placed in almost any anatomical position within its range. It allows each rotational degree of freedom to be switched between a state of being locked and a state of being free to move. Overall, this also allows the wearer to adapt to performing certain movements.

With certain angles of rotation selected, the invention provides a means of restricting the use of the stronger muscles in the arm that would otherwise compensate for the weaker ones and prevent them from getting exercised, so that the mental effort used to perform an exercise during resistance training forces the weaker muscles (those effected by paralysis) to be the primary provider of the motion.

DESCRIPTION OF THE RELATED ART

As should be apparent to those skilled in the art, it is common practice to use orthoses to correct or alleviate orthopedic impairments. It is commonplace for an orthotist to mold thermoplastic sheet to the effected or involved body part(s) and to possibly attach the molded part(s) to a mechanical device such that, while the orthosis is being worn and used by the user, the orthopedic impairment is being corrected or alleviated. A molded part may attach to the body using straps, or a tantamount technique, and one or more mechanical adjustments may be used to achieve a proper and more comfortable fit or to achieve a certain stretch or corrective configuration.

As should also be apparent to those skilled in the art, partial paralysis or nerve impairments to the muscles in the arm and shoulder (controlled by the brachial plexus) may be caused by a number of factors, such as injury or stroke, and may be diagnosed as a palsy, such as Erb's. This is typically accompanied by some degree of atrophy and weakness in the effected muscles, a limited range of motion (with or without muscular control), and diminished motor skills, especially when nerve impairments result in tremors. The arm and shoulder has seven degrees of rotational freedom which may become limited, including shoulder internal/external rotation, shoulder abduction/adduction, shoulder flexion/extension, elbow flexion/extension, forearm pronation/supination, and wrist flexion/extension.

Apart from surgical intervention, it is common to try to improve the condition using physical therapy (possibly orchestrated by an occupational or physical therapist) or some form of resistance training. Such resistance training often involves the use of traditional equipment, such as resistance bands, cables, dumbbells, and medicine balls, where an attempt is made to modify the exercises, from those which would be used on an undamaged arm, to make them more effective at rehabilitating the condition.

Unfortunately, current physical therapy and resistance training techniques are generally limited in their capacity to provide the greatest possible recuperation of muscular strength and range of motion. This is due to it being extremely difficult, to impossible to achieve the mechanics of the necessary exercise movements to stop the stronger muscles of the arm and shoulder from compensating for the weaker ones. In this instance, the stronger muscles do the majority of the work that creates the motion, and the weaker ones, not being in an appropriate anatomical configuration, do not receive enough stimulation to realize a significant amount of recovery. Additionally, attempts at putting the arm in such anatomical positions using traditional equipment may put more resistance on the arm than it is presently capable of moving, instead of putting the arm in positions where the resistance created by the weight of the arm itself can be started with before adding any weight beyond that. Furthermore, even when the weaker muscles are put in a position where they're forced to do the majority of the work, strength may be lacked to execute any movement.

The ineffectiveness is also due to the inability to provide a prolonged stretch to the necessary muscles of the arm and shoulder when needed.

The appropriate anatomical configurations and prolonged stretching could be achieved by an orthosis that provides control over one or more of the seven rotational degrees of freedom, and hence the range of motion, of the arm and shoulder. For each degree of freedom, it could do this by providing a mechanical means of restricting the rotational range of the motion, by allowing certain angular positions to be locked, and by allowing the motion to be switched back and forth between a state of being locked and a state of being free to move within the restricted range. The direct stimulation and stretching provided to the effected muscles could instigate hypertrophy, elongation, and nerve recovery that would lead to the greatest possible rehabilitation. The use of the word "dynamic" in regard to such an orthosis refers to its capacity to allow the arm and shoulder to move around within the restricted degrees of freedom and to its capacity to select different lockable positions. Additionally, it means that the bulk of the recovery to impaired muscles is achieved through motion rather than statics. The ideal such orthosis has several characteristics. Firstly, it leaves the hand on the effected arm free so that, exercise equipment may be grasped. Secondly, it can be put on and taken off without assistance if the user has another sufficiently functioning arm. Thirdly, it can be adjusted with one hand. And lastly, it is not excessively cumbersome or heavy so that it's comfortable enough to be worn all the time when needed.

Forearm supination/pronation and shoulder internal/external rotation are two important degrees of freedom of the arm and shoulder that can become impaired by injury. A need, therefore, has developed for an orthotic device, to be worn by a person, that provides an adjustable amount of forced forearm pronation or supination and an adjustable amount of forced shoulder internal or external rotation. Shoulder adduction, abduction, flexion, and extension and elbow flexion or extension are degrees of freedom that may also become impaired by injury. An additional need, therefore, has developed for an orthotic device that provides an adjustable amount of forced shoulder adduction, abduction, flexion, and extension and a means of locking the elbow at different angles.

SUMMARY OF THE INVENTION

The present invention is an orthosis that provides to a wearer at least one of forearm supination, forearm pronation, shoulder internal rotation, shoulder external rotation, shoulder adduction, shoulder abduction, shoulder flexion, shoulder extension, elbow flexion, and elbow extension. In one embodiment, it includes a shoulder assembly adapted to be secured to a wearer's shoulder and an upper arm assembly connected to the shoulder assembly and adapted to be secured around a wearer's upper arm. The upper arm assembly defines an upper arm assembly axis. A wrist assembly is adapted to be secured around a wearer's wrist. The wrist assembly defines a wrist assembly axis. A splint arm assembly includes an upper splint arm, a lower splint arm, and a pivot pivotally connecting the upper splint arm to the lower splint arm. The upper splint arm adjustably connects to the upper arm assembly and the lower split arm adjustably connects to the wrist assembly. The pivot permits alteration of a first angle between the upper arm assembly axis and the wrist assembly axis.

In one contemplated embodiment, the orthosis includes an upper arm adjustment assembly connecting the upper splint arm to the upper arm assembly. The upper arm adjustment assembly permits adjustment of a first distance between the upper arm assembly and the pivot.

Here, the upper arm adjustment assembly also permits adjustment of a first location of the upper splint arm around the upper arm assembly axis.

In a variation of this embodiment, the upper arm adjustment assembly connects the upper splint arm to the upper arm assembly. The upper arm adjustment assembly permits adjustment of a first location of the upper splint arm around the upper arm assembly axis.

Still further, a lower arm adjustment assembly may connect the lower splint arm to the wrist assembly. The lower arm adjustment assembly permits adjustment of a second distance between the pivot and the wrist assembly.

For this embodiment, the lower arm adjustment assembly also is contemplated to permit adjustment of a second location of the lower splint arm around the wrist assembly axis.

In a contemplated variant of this embodiment, the lower arm adjustment assembly may connect, the lower splint arm to the wrist, assembly. The lower arm adjustment assembly permits adjustment of a second location of the lower splint arm around the wrist assembly axis.

The shoulder assembly includes a strap securable around a wearer's chest.

In a second embodiment of the present invention, the orthosis provides to a wearer at least one of forearm supination, forearm pronation, shoulder internal rotation, shoulder external rotation, shoulder adduction, shoulder abduction, shoulder flexion, shoulder extension, elbow flexion, elbow extension, shoulder elevation, and shoulder depression. It includes a torso assembly adapted to be secured to a wearer's torso. The torso assembly defines a torso axis. It also includes an upper arm assembly connected to the torso assembly and adapted to be secured around a wearer's upper arm. The upper arm assembly defines an upper arm assembly axis. A wrist assembly is adapted to be secured around a wearer's wrist. The wrist assembly defines a wrist assembly axis. A splint arm assembly includes an upper splint arm, a lower splint arm, and a pivot pivotally connecting the upper splint arm to the lower splint arm. The upper splint arm adjustably connects to the upper arm assembly, the lower split arm adjustably connects to the wrist assembly, and the pivot permits alteration of a first angle between the upper arm assembly axis and the wrist assembly axis. A scapular assembly includes a front scapular rotation rail, a rear scapular rotation rail, a front pivot pivotally connecting the front scapular rotation rail to the chest side of the torso assembly, and a rear pivot pivotally connecting the rear scapular rotation rail to the back side of the torso assembly. The scapular assembly defines a scapular assembly axis. The front pivot permits adjustment of a first location of the front scapular rotation rail around the scapular assembly axis and the rear pivot permits adjustment of a first location of the rear scapular rotation rail around the scapular assembly axis.

The upper arm adjustment assembly may connect the upper splint arm to the upper arm assembly. If so, the upper arm adjustment assembly is contemplated to permit adjustment of a first distance between the upper arm assembly and the pivot.

In an embodiment, the upper arm adjustment assembly also permits adjustment of a second location of the upper splint arm around the upper arm assembly axis.

Still further, an internal-external rotation assembly may be provided that connects the upper splint arm to the upper arm assembly. The internal-external rotation assembly permits adjustment of a second location of the upper splint arm around the upper arm assembly axis.

In a contemplated alternative, the internal-external rotation assembly may connect the upper arm adjustment assembly to the upper arm assembly. Here, the internal-external rotation assembly defines an internal-external rotation assembly axis. The internal-external rotation assembly is rotatable around the internal-external rotation assembly axis.

Furthermore, a lower arm adjustment assembly may be provided that connects the lower splint arm to the wrist assembly. The lower arm adjustment assembly permits adjustment of a second distance between the pivot and the wrist assembly.

In this embodiment, the lower arm adjustment assembly also may permit adjustment of a third location of the lower splint arm around the wrist assembly axis.

In a variant, the lower arm adjustment assembly may connect the lower splint, arm to the wrist assembly. If so, the lower arm adjustment assembly is contemplated to permit adjustment of a third location of the lower splint arm around the wrist assembly axis.

Still further, it is contemplated that the torso assembly includes a vest securable around a wearer's torso.

And, in yet another contemplated embodiment, a flexion-extension assembly may connect the torso assembly to the upper arm assembly. The flexion-extension assembly defines a flexion-extension assembly axis. The flexion-extension assembly facilitates rotation of the flexion-extension assembly around the flexion-extension assembly axis.

The orthosis also may be constructed to include an adduction-abduction assembly connected to the flexion-extension assembly. The adduction-abduction assembly permits alteration of a second angle between the upper arm assembly axis and the torso axis.

It is also contemplated that the scapular rail assembly may connect to the flexion-extension assembly.

BRIEF DESCRIPTION OF THE DRAWINGS

For a more complete understanding of the invention, reference is made to the following description and accompanying drawings, in which.

Figure 22:
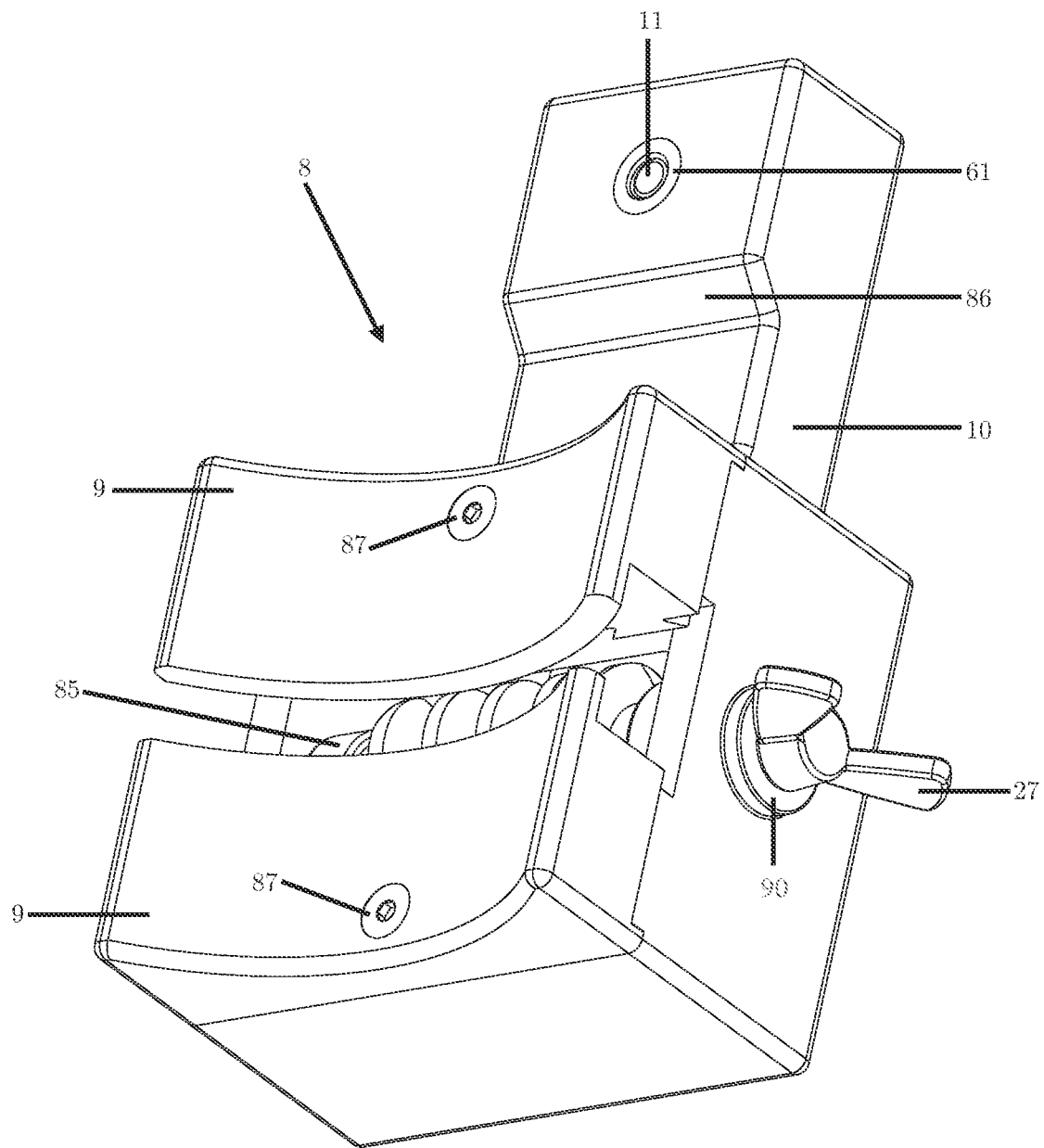
FIG. 22 is a front left perspective view of one contemplated embodiment of the gearbox assembly of the present invention, which is shown assembled to the orthosis in FIGS. 1-5.
Figure 33:
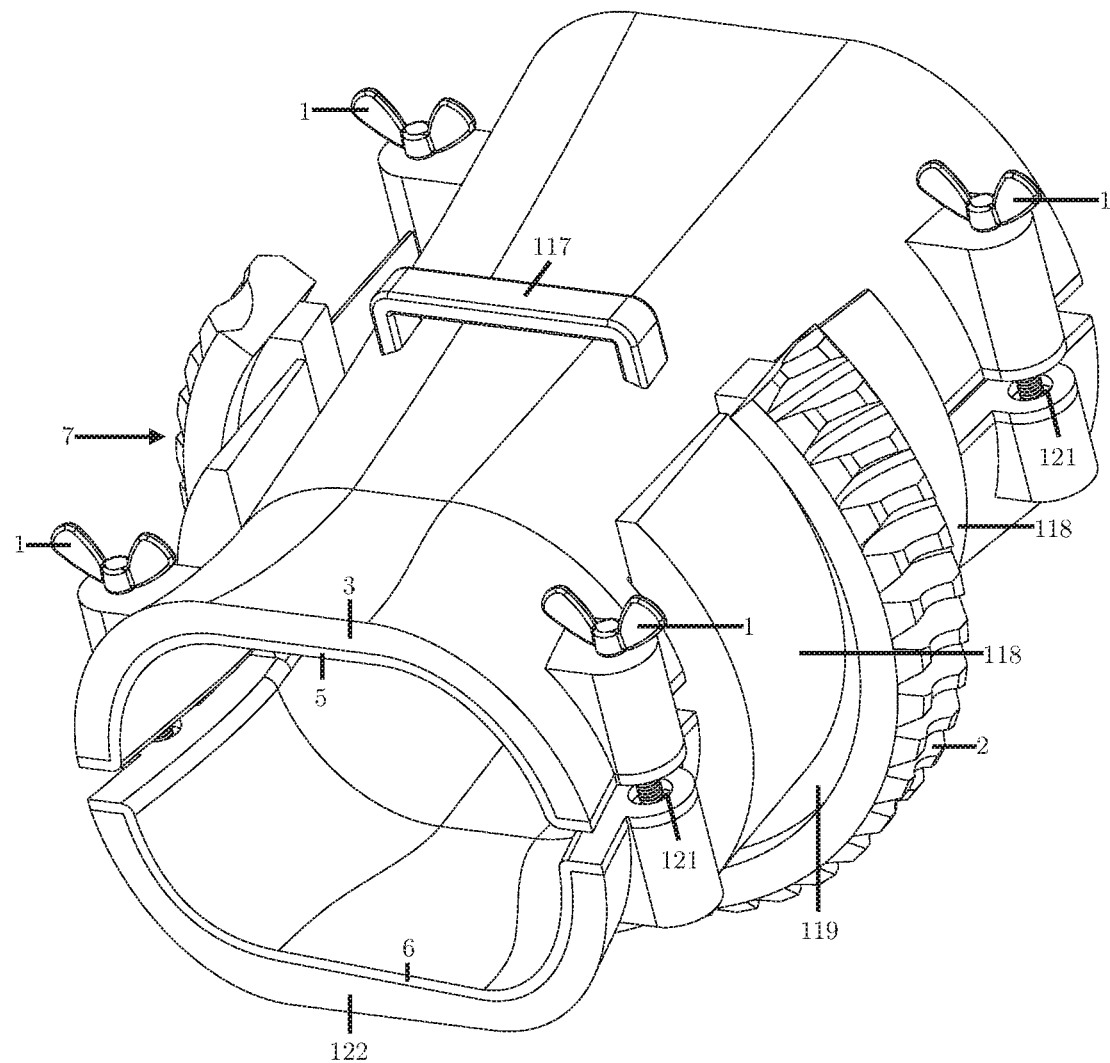
FIG. 33 is a front top perspective view of the embodiment of the wrist cuff assembly of the present invention that uses thumbscrews, which is shown assembled to the orthosis in FIG. 1.
Figure 43:
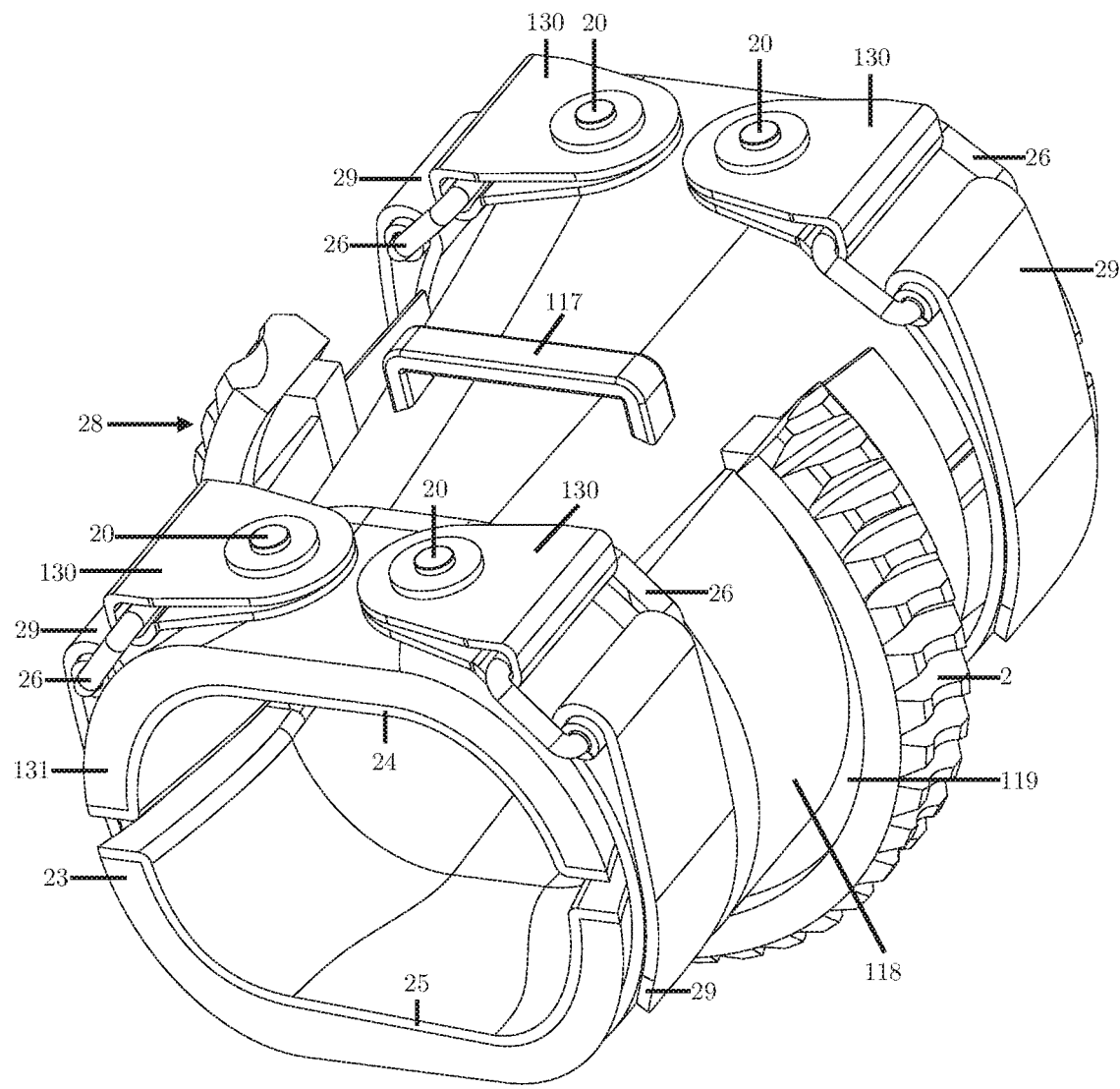
FIG. 43 is a front top perspective view of the embodiment of the wrist cuff assembly of the present invention that uses straps, which is shown assembled to the orthosis in FIG. 2.
Figure 59:
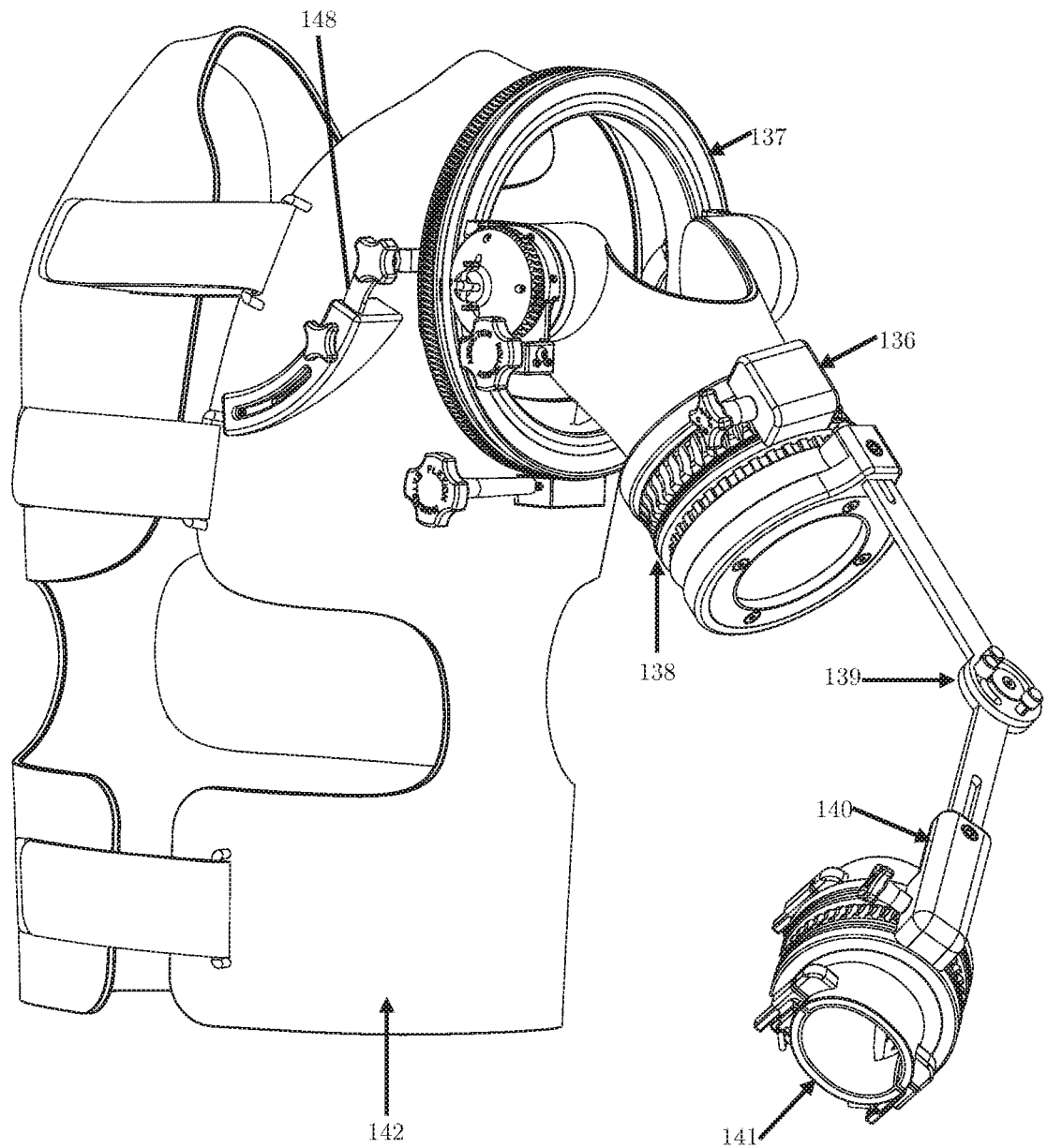
FIG. 59 is a front view perspective view of a third contemplated embodiment of the present invention where the orthosis is secured to the torso using a torso vest in lieu of the shoulder brace of FIG. 6, where a flexion-extension assembly and a shoulder sleeve assembly embodiment replace the upper arm cuff and linear motion carriage assemblies of FIGS. 9 and 13, a second embodiment of the splint arm assembly of FIG. 20 is attached to the shoulder sleeve assembly, a second embodiment of the gearbox assembly of FIG. 22 is attached to the splint arm assembly, and a third embodiment of the wrist cuff assemblies of FIGS. 33 and 43 is attached to the gearbox assembly.
Figure 60:
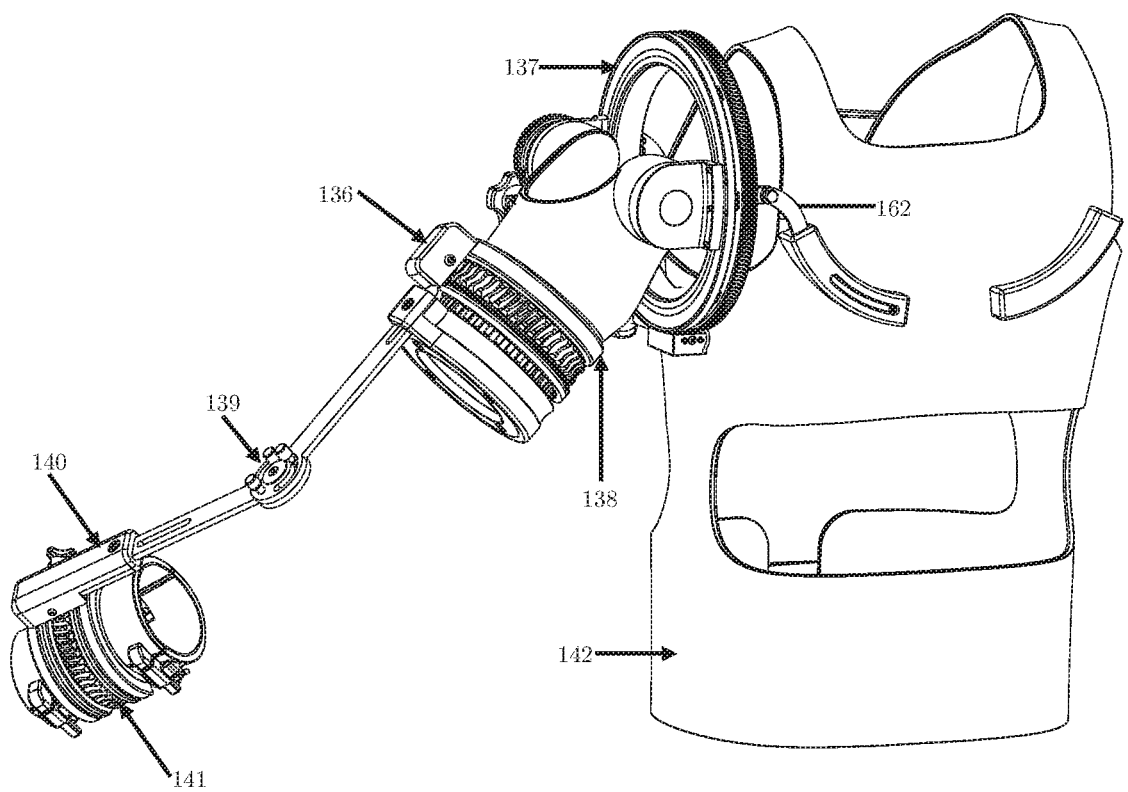
FIG. 60 is a rear right perspective view of the embodiment of the orthosis depicted in FIG. 59.
Figure 69:
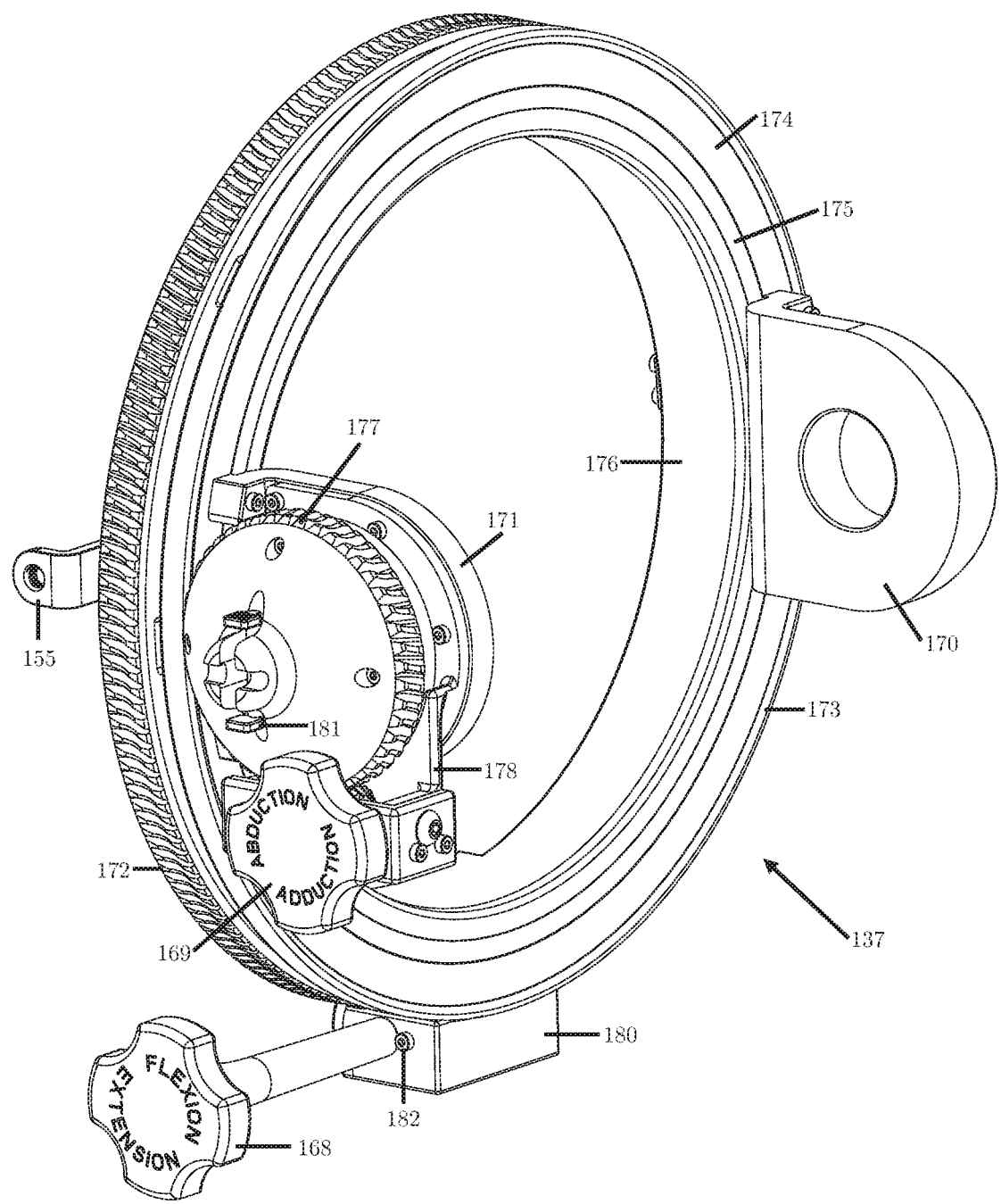
FIG. 69 is a front right perspective view of one contemplated embodiment of the flexion-extension assembly of the present invention and is shown assembled to the orthosis in FIG. 59.
Figure 70:
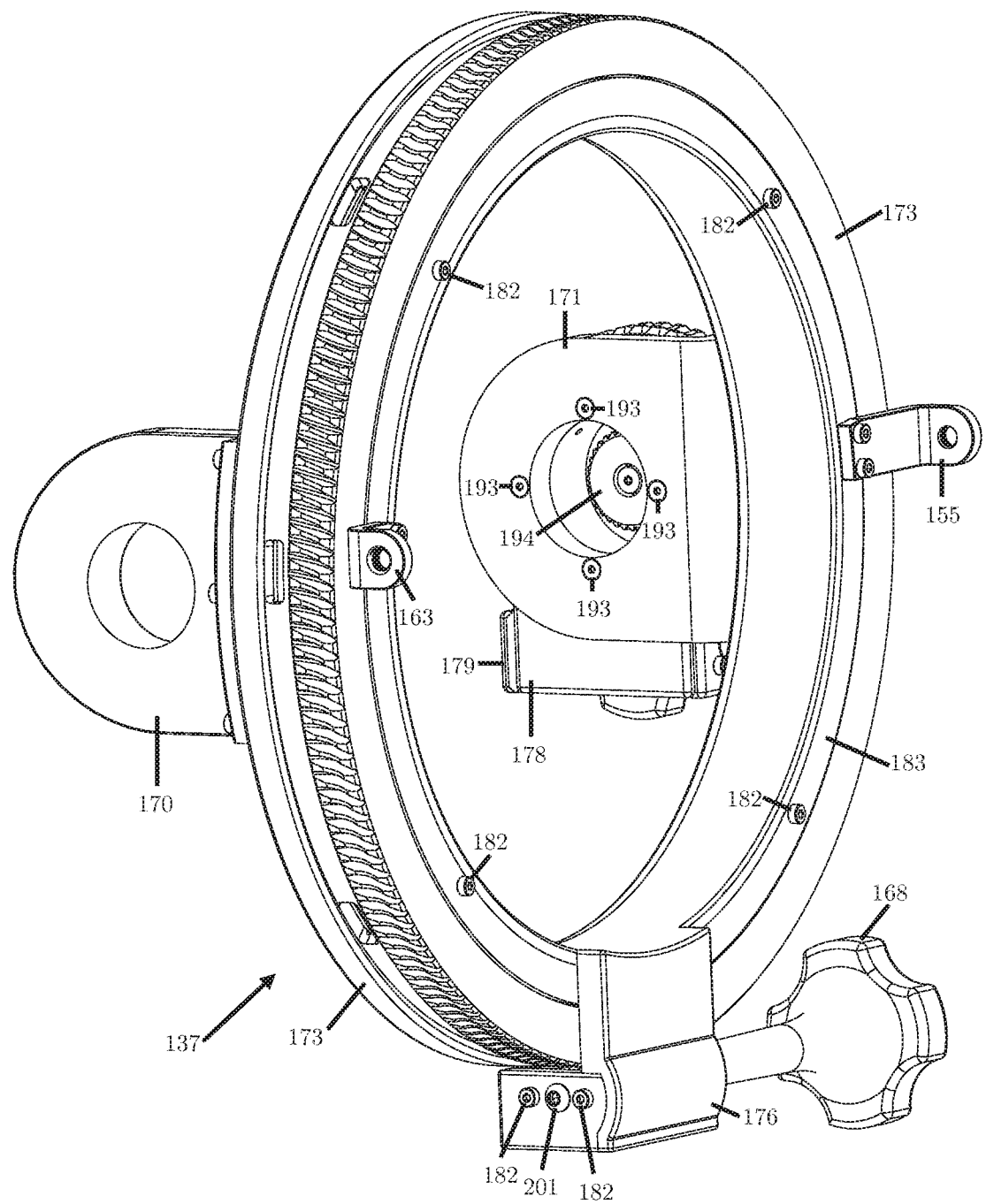
FIG. 70 is a rear left perspective view of the embodiment of the flexion-extension assembly shown in FIG. 69.
Figure 73:
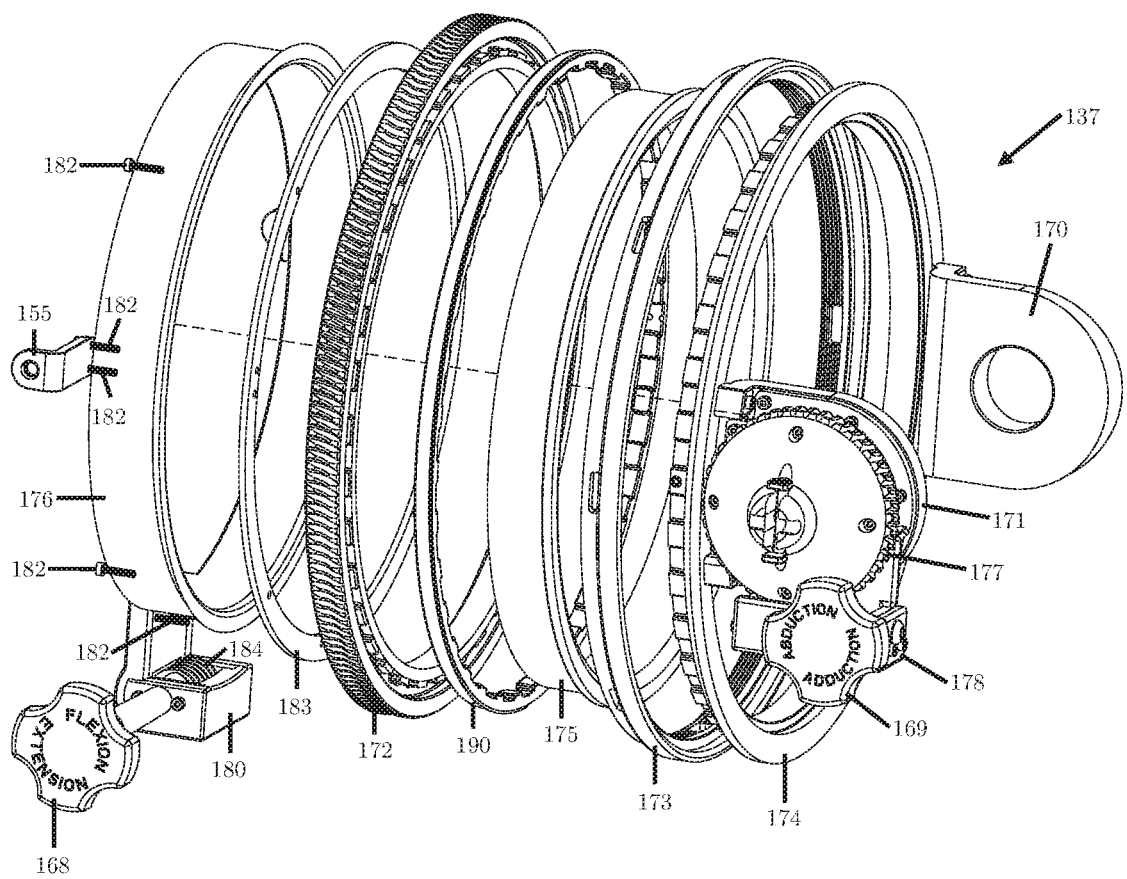
FIG. 73 is an exploded front right perspective view, of the embodiment of the flexion-extension assembly shown in FIG. 69, that emphasizes the components that mount to the flexion-extension axle.
Figure 74:
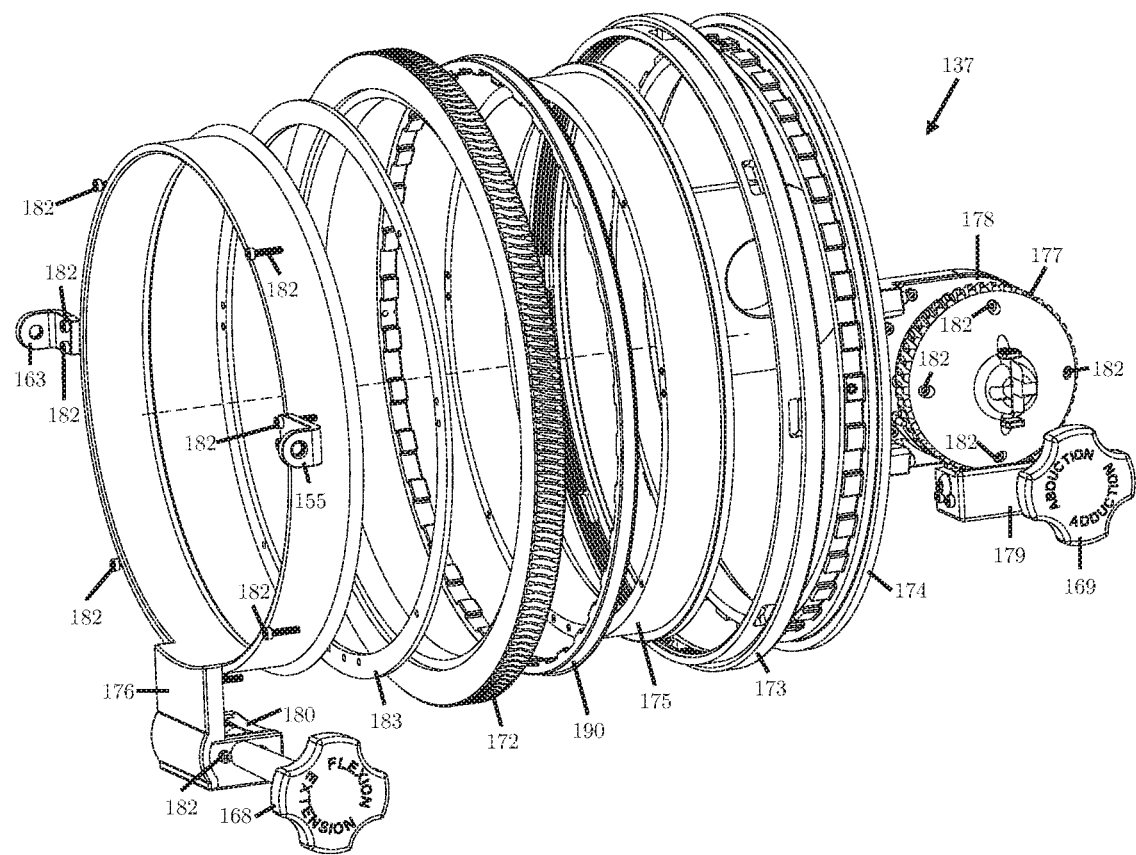
FIG. 74 is an exploded front left perspective view, of the embodiment of the flexion-extension assembly shown in FIG. 69, that emphasizes the components that mount to the flexion-extension axle.
Figure 75:
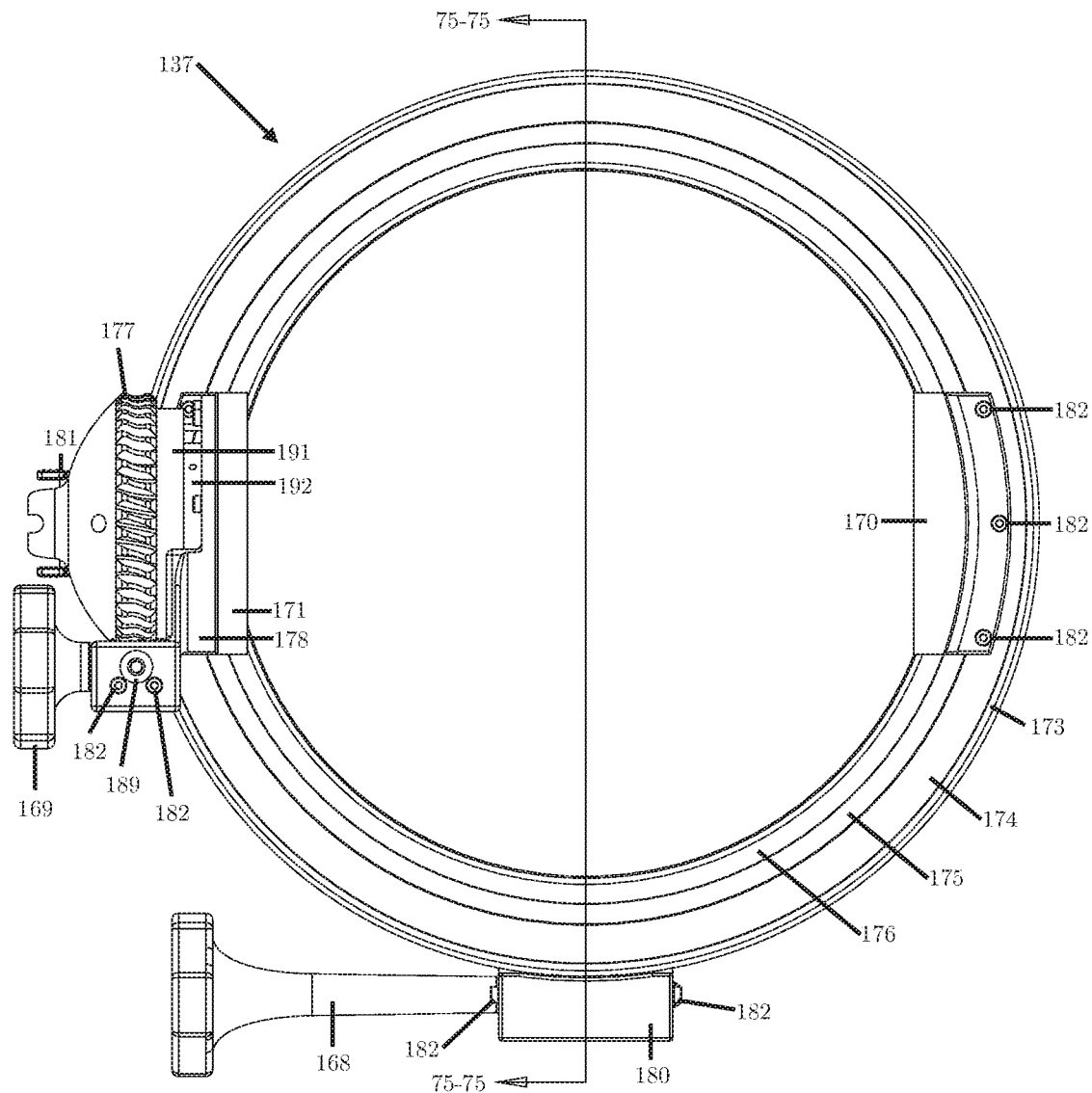
FIG. 75 is a right side view of the embodiment of the flexion-extension assembly shown in FIG. 69.
Figure 119:
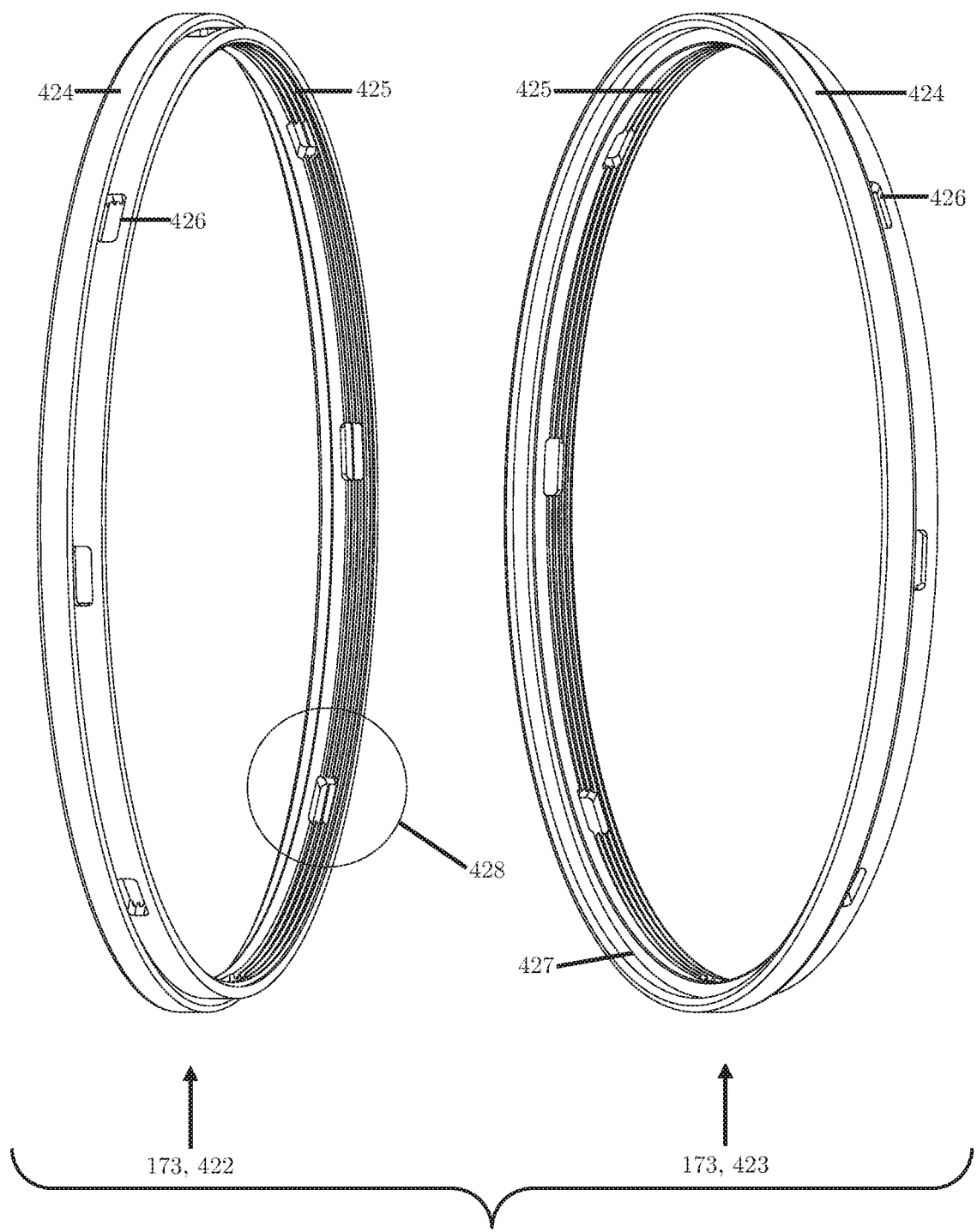
Figure 120:
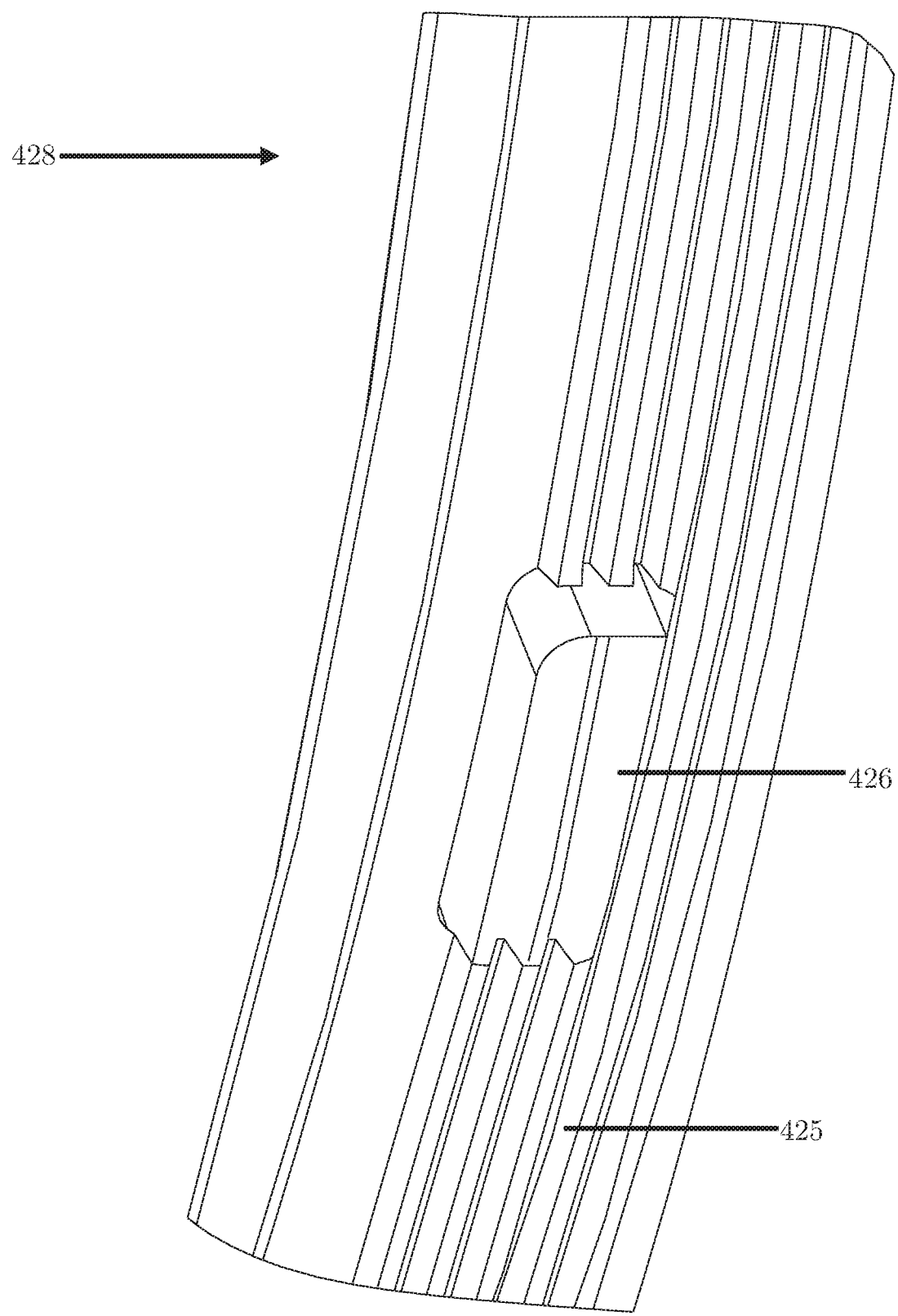
Figure 121:
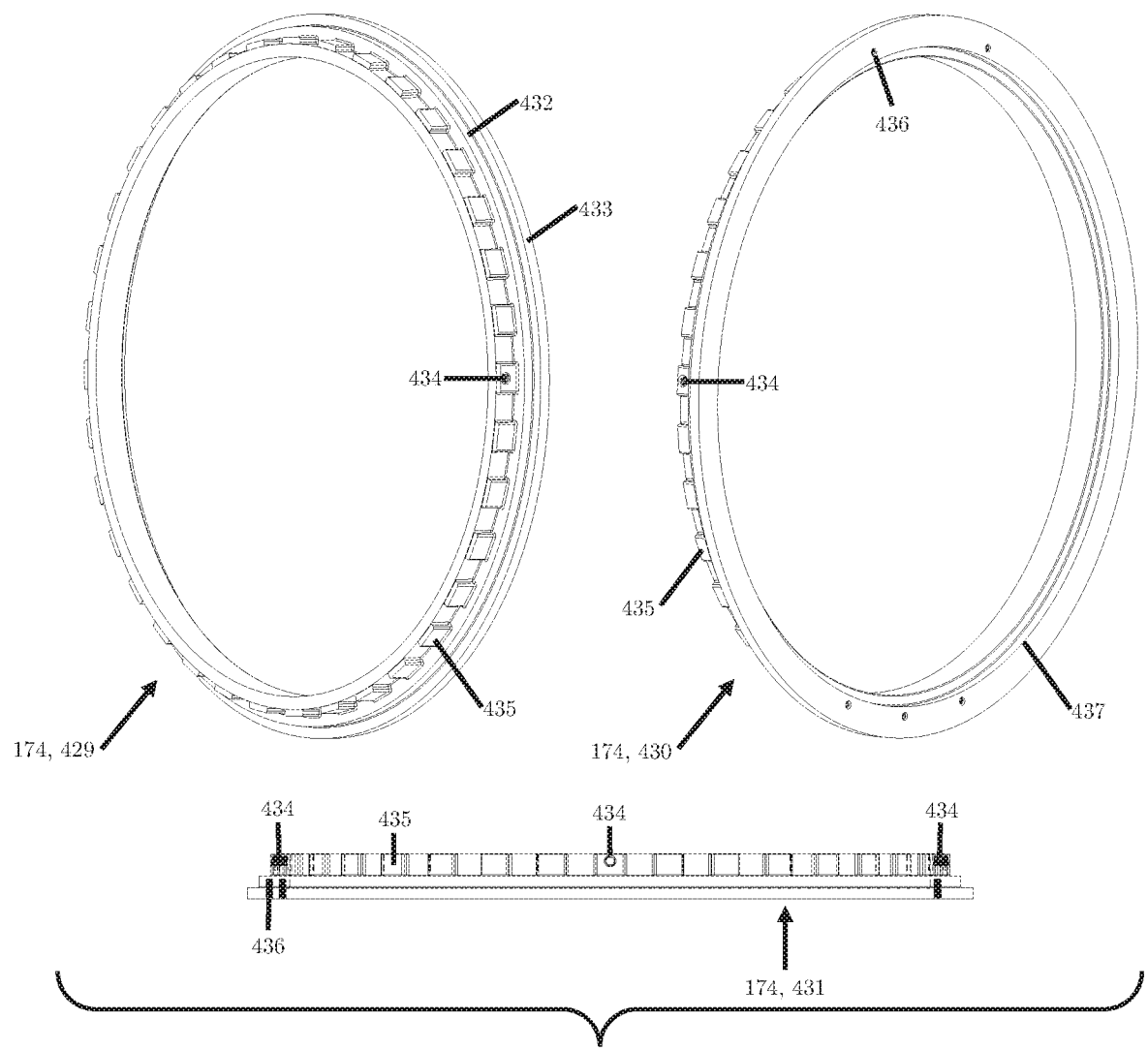
Figure 122:
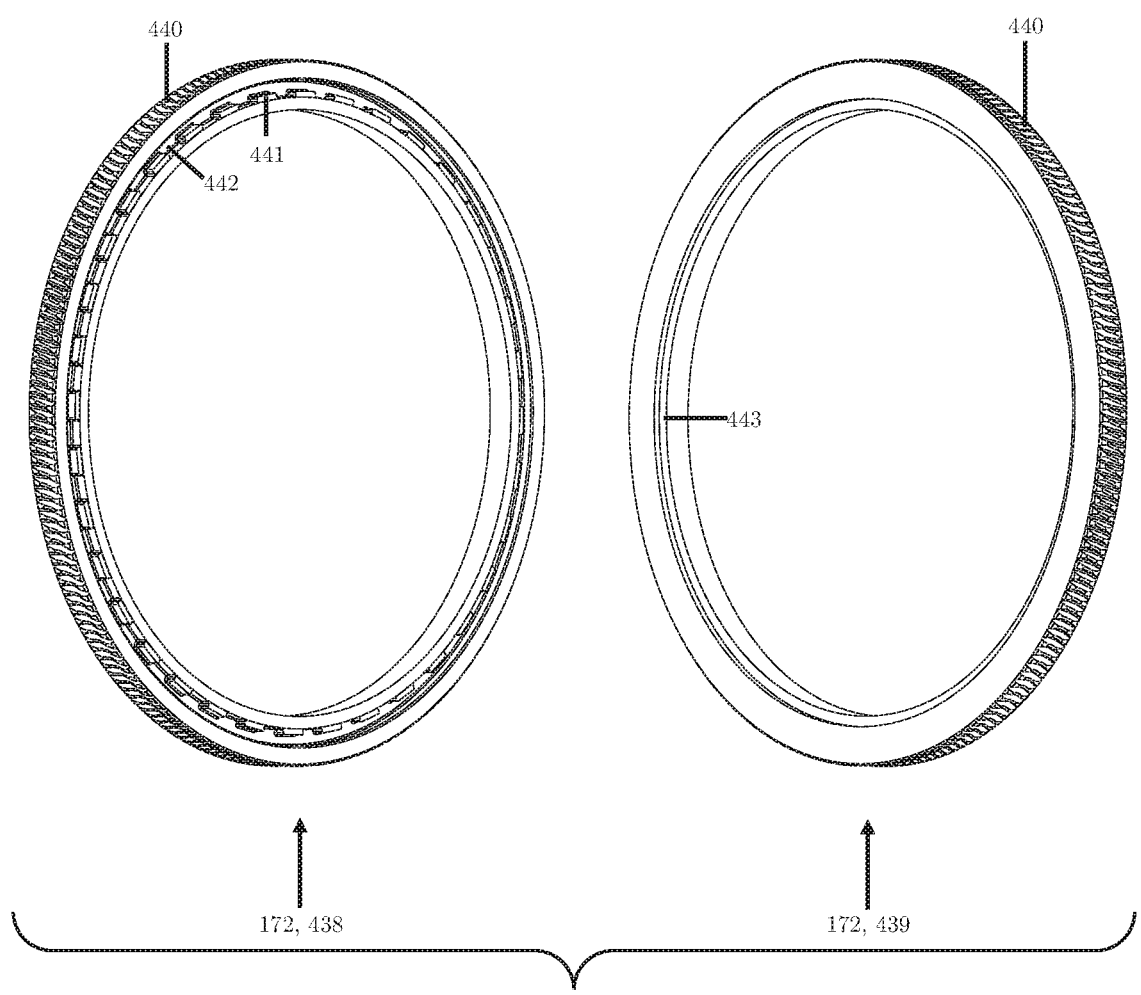
Figure 123:
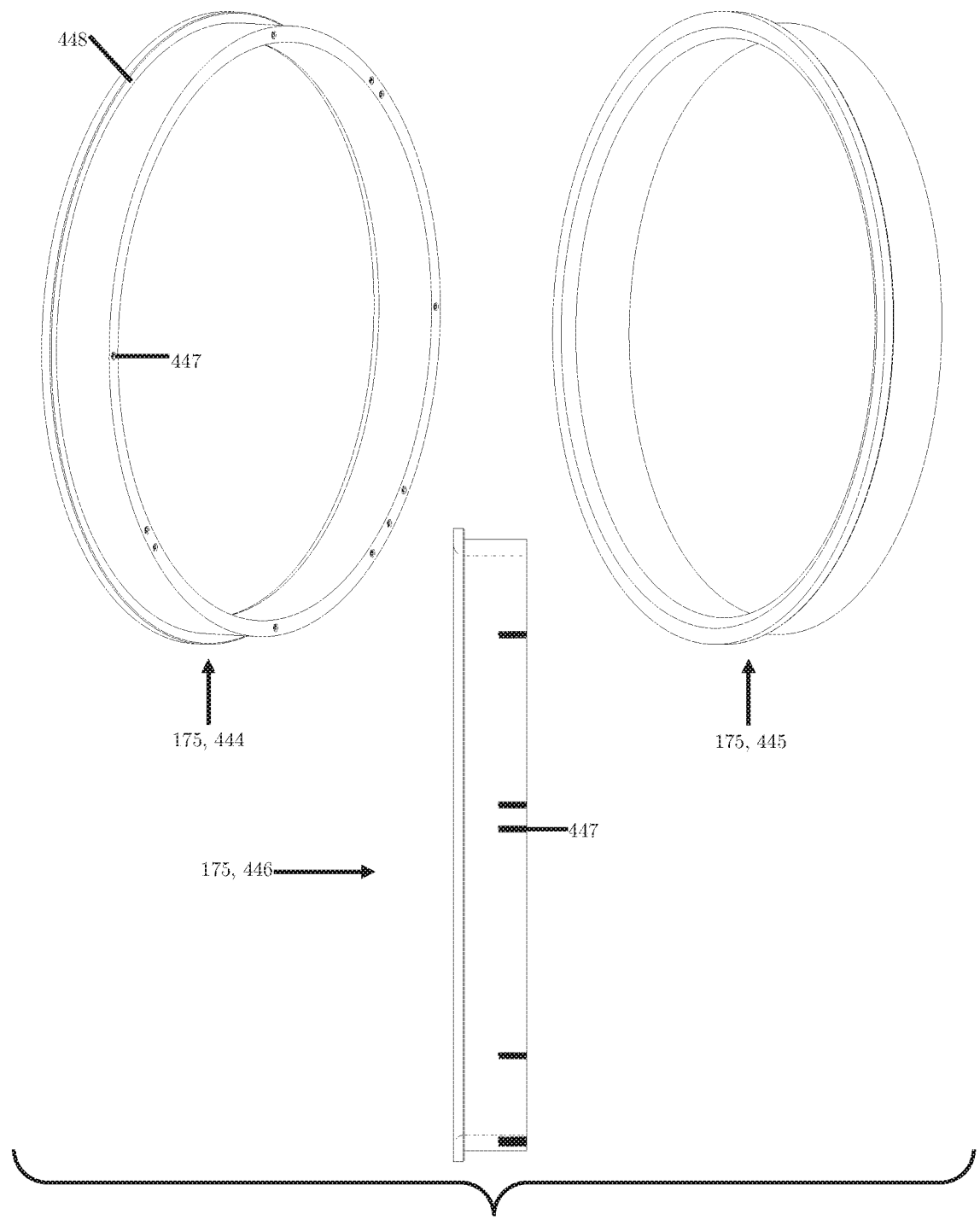
Figure 124:
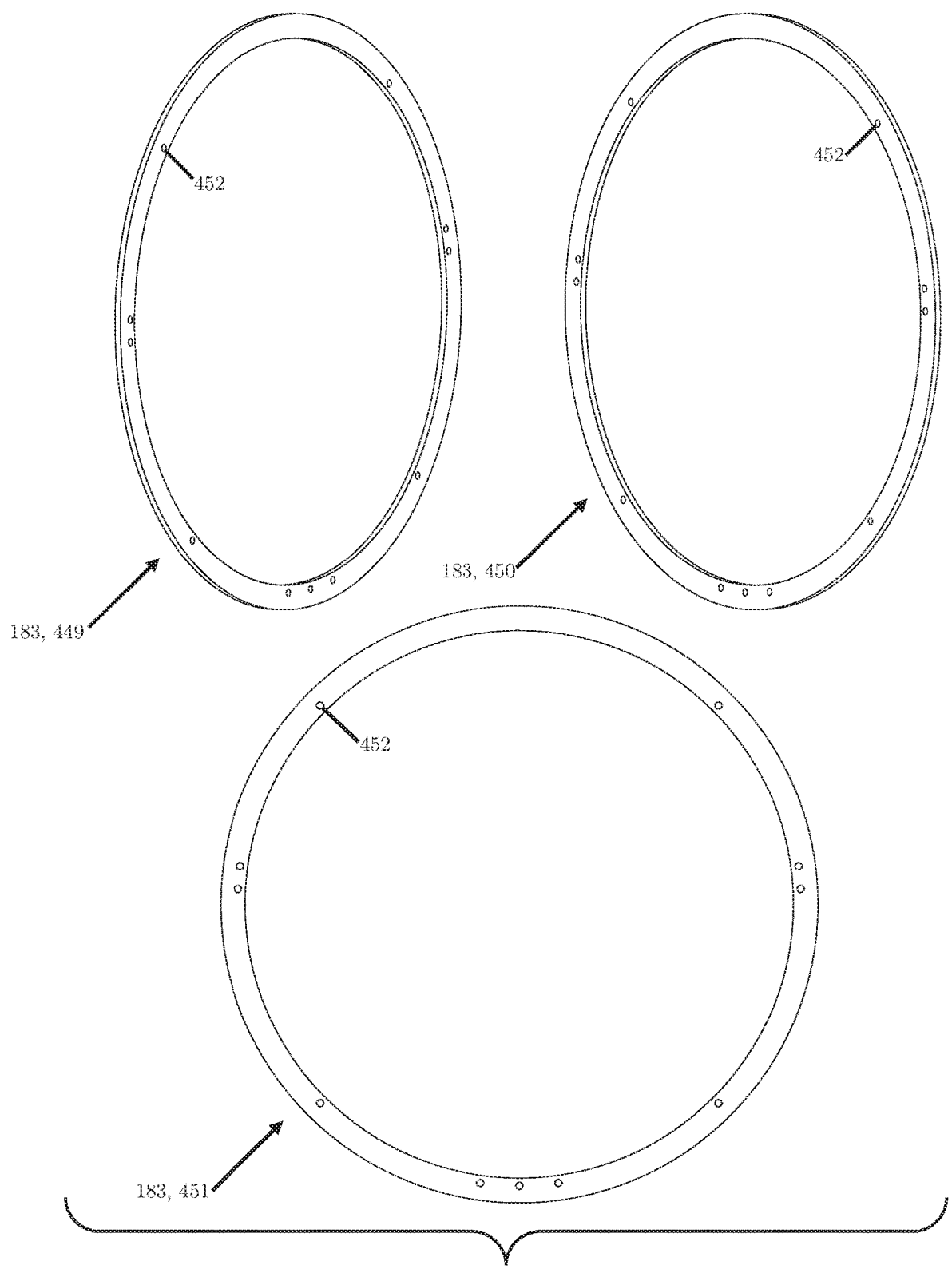
Figure 125:
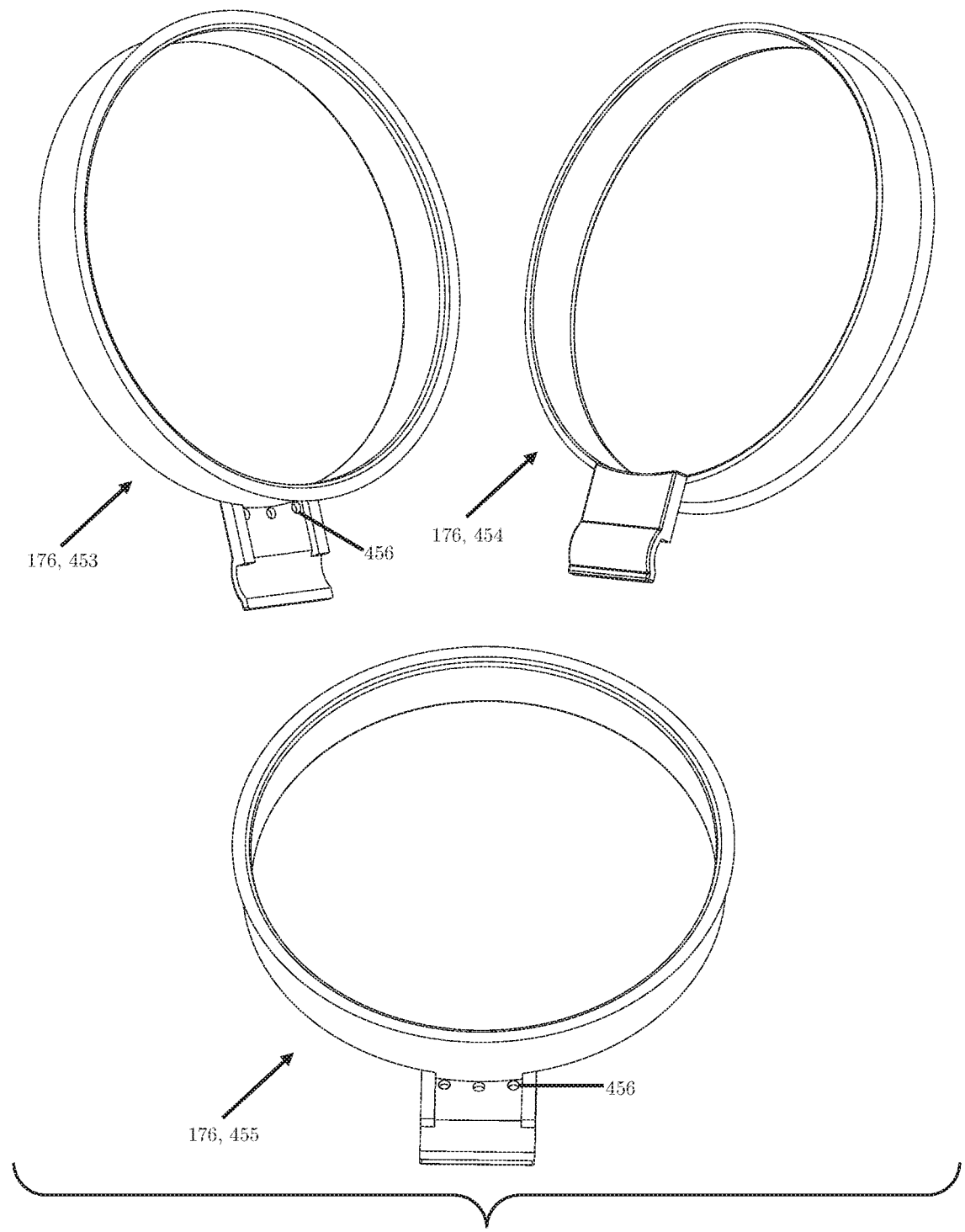
Figure 126:
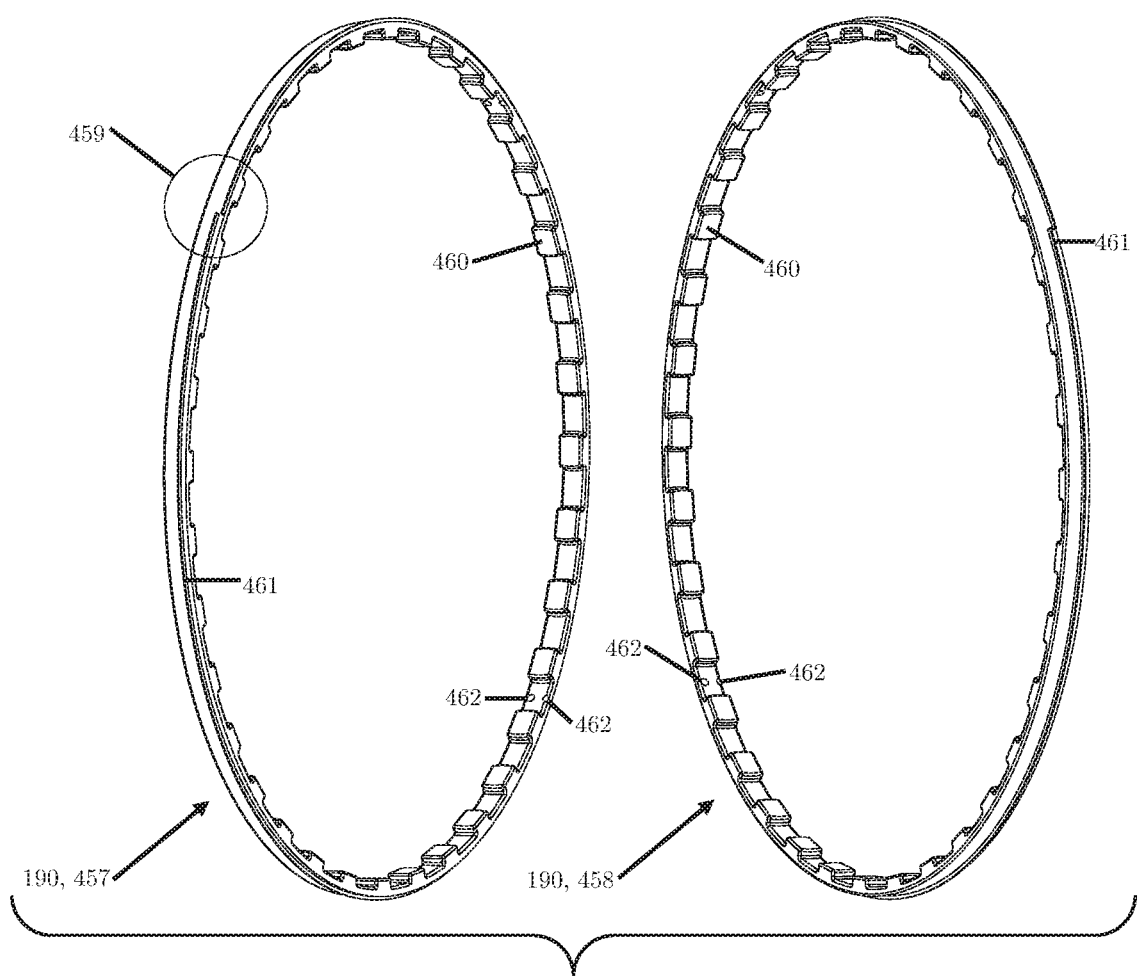
Figure 127:
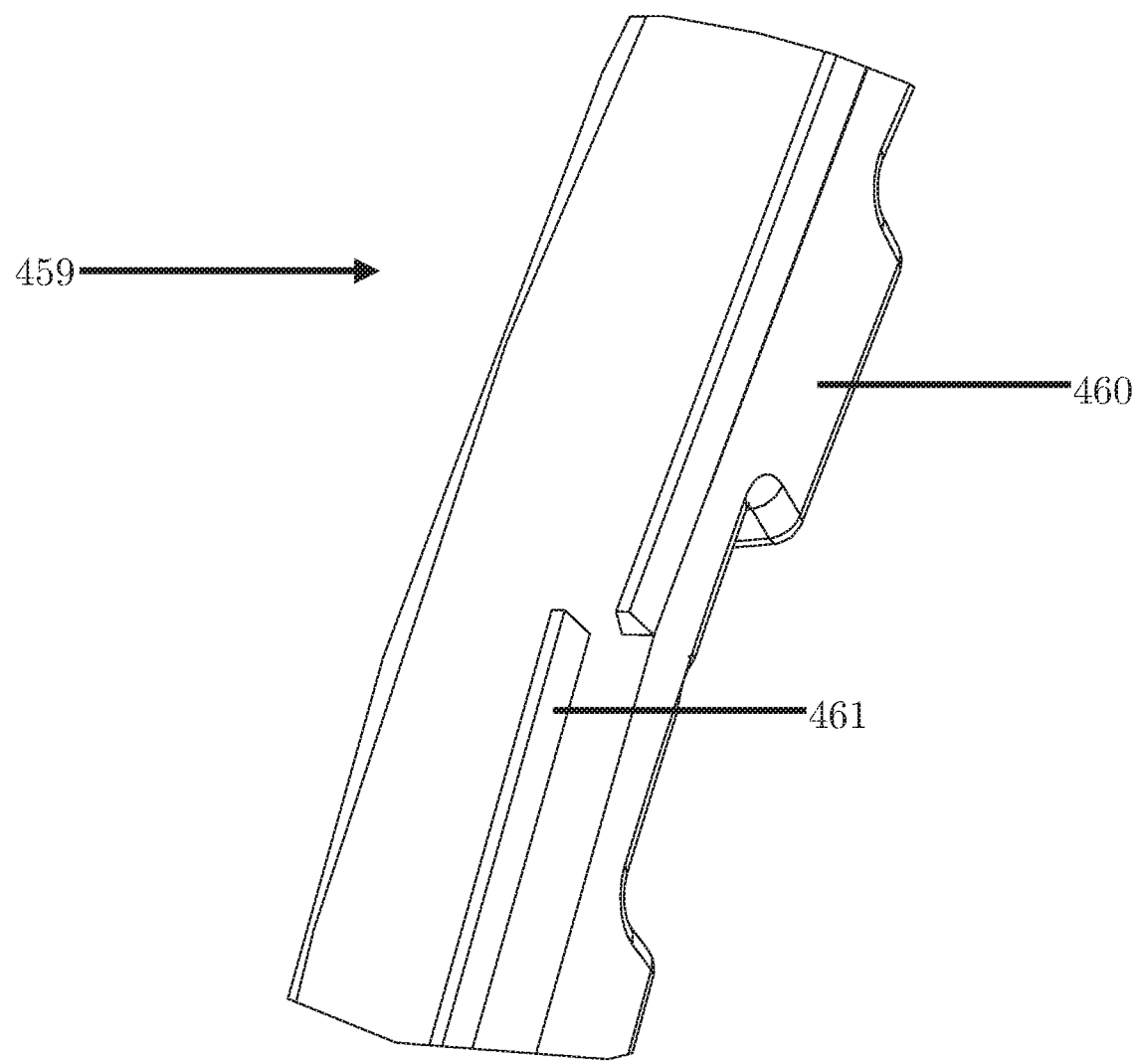
Figure 128:
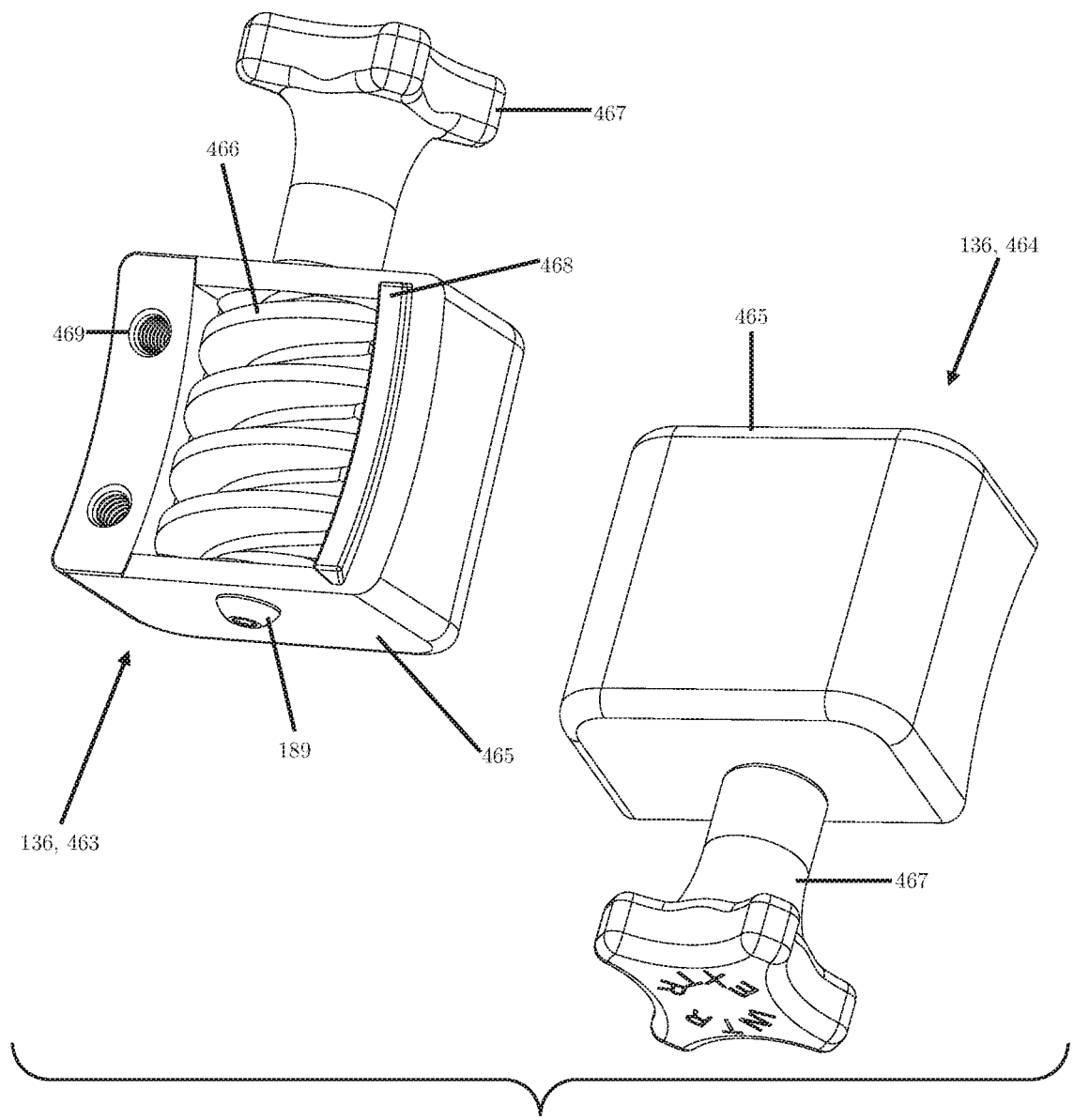
Figure 129:
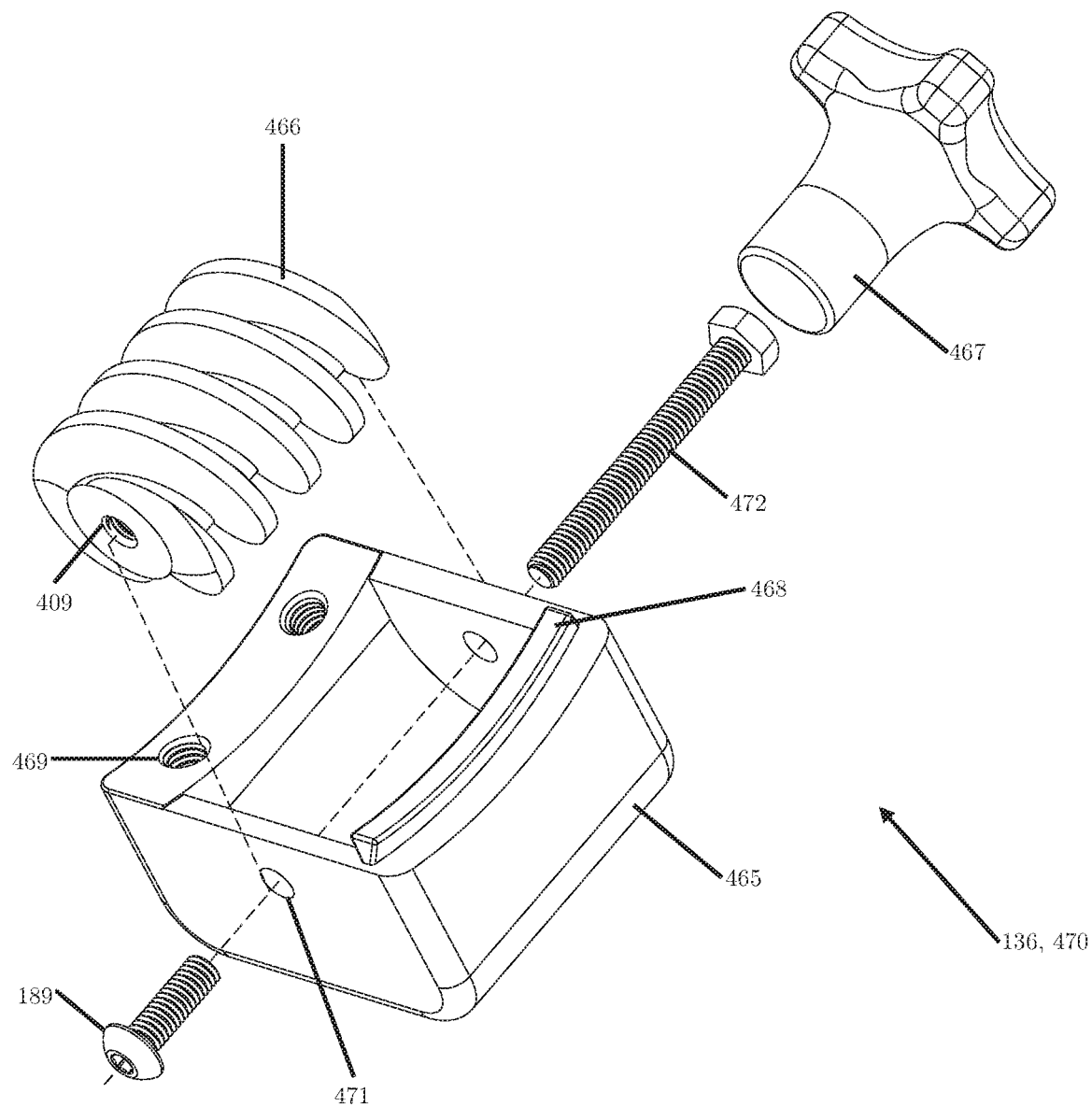
Figure 130:
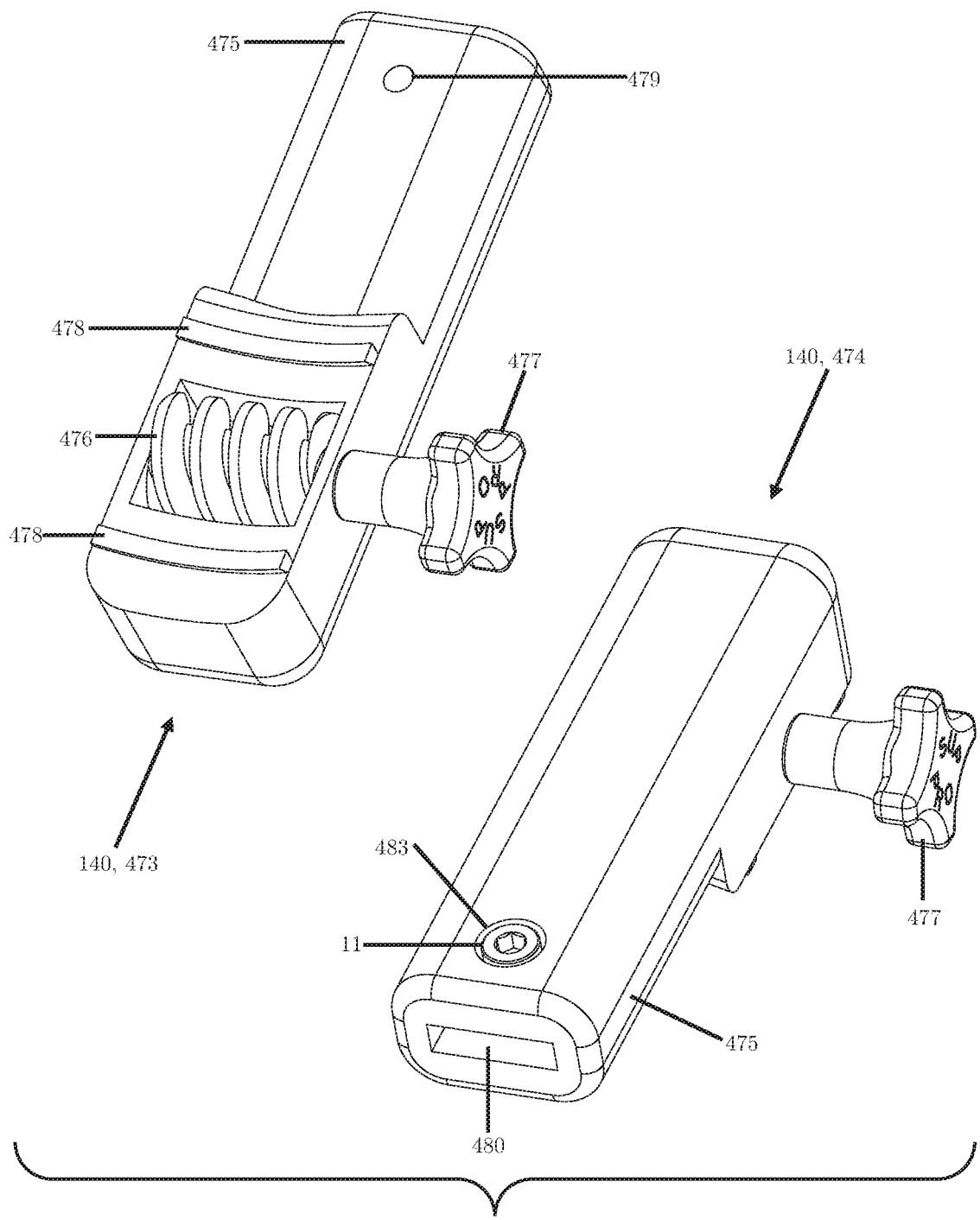
Figure 131:
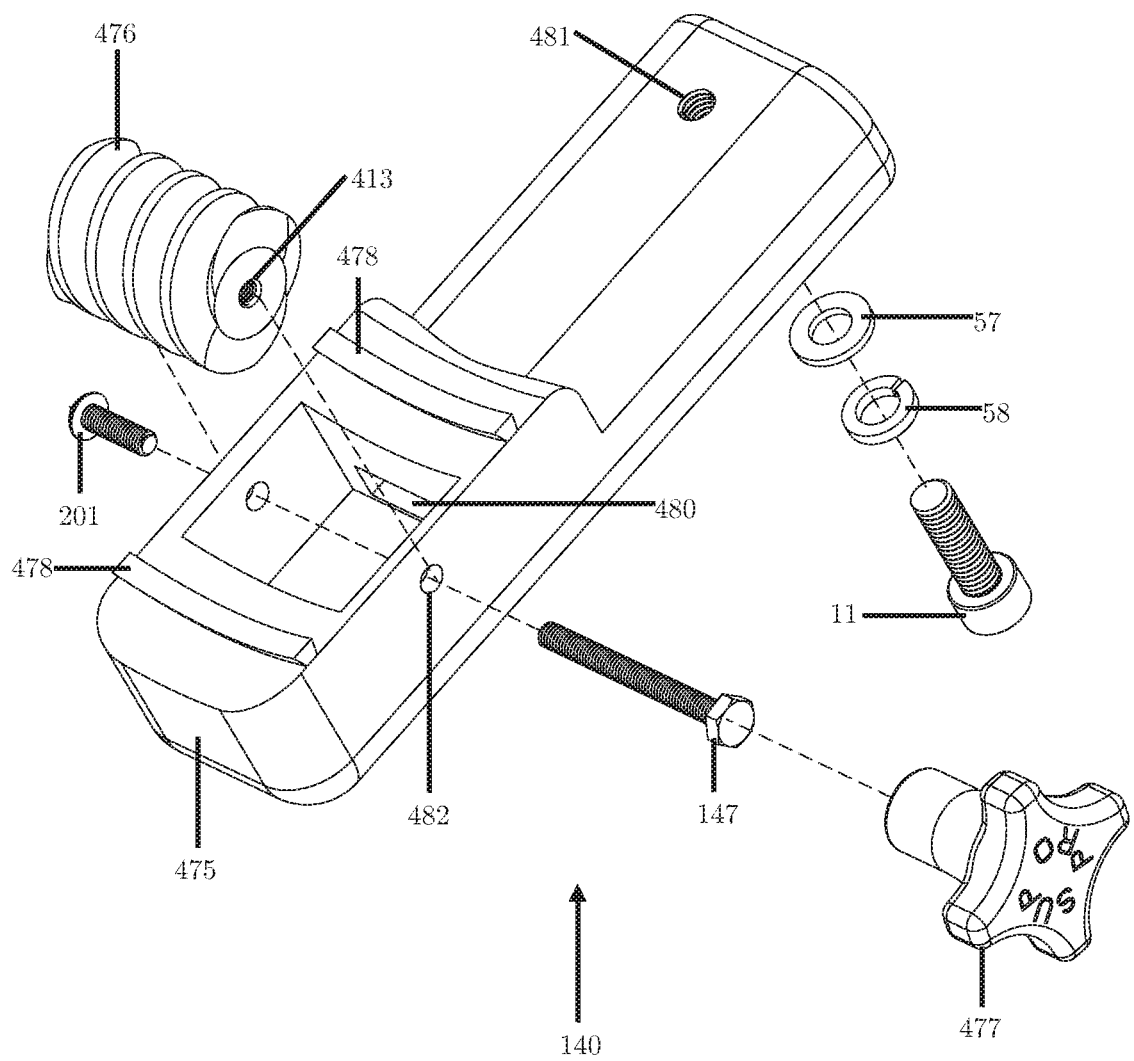
Figure 132:
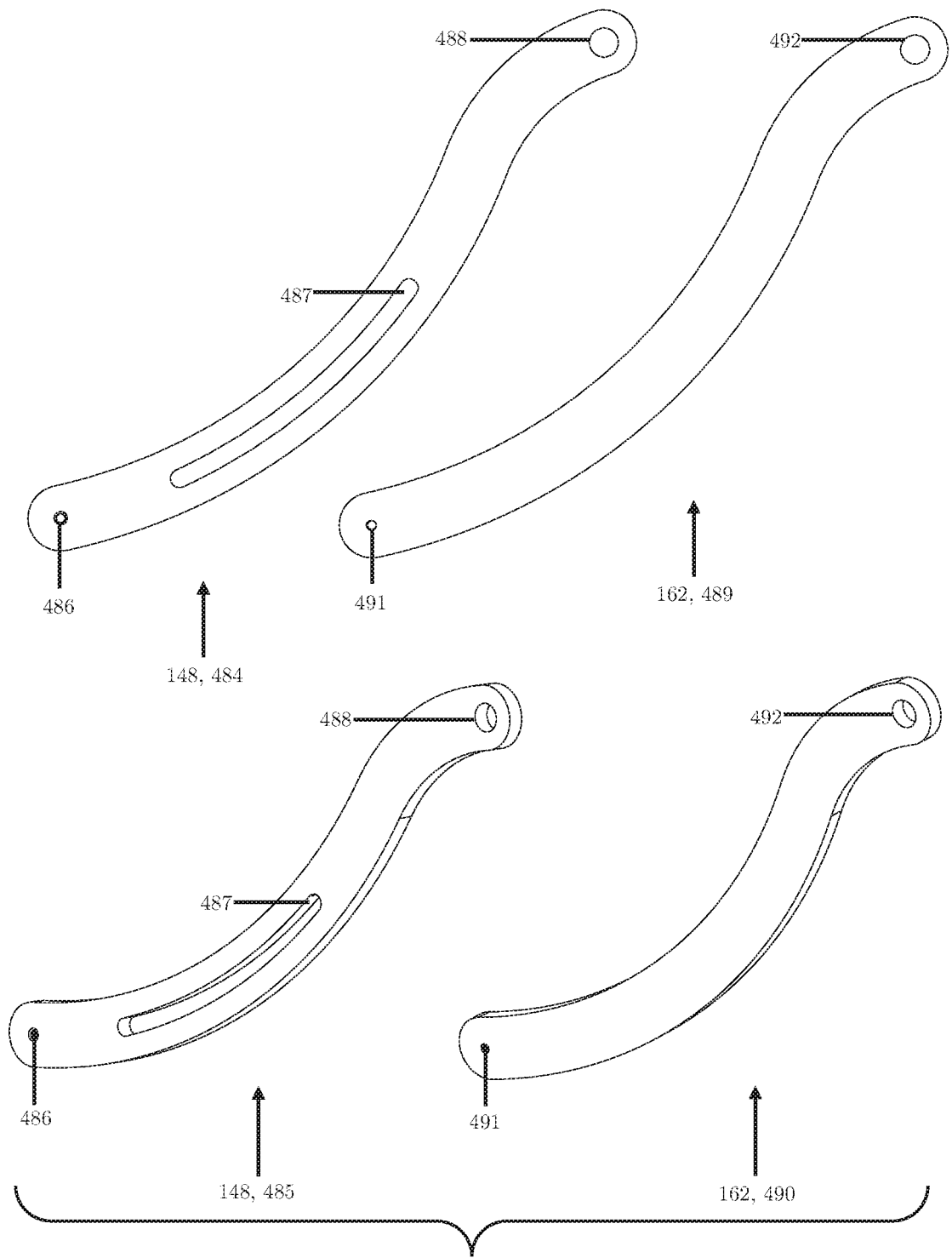
Figure 133:
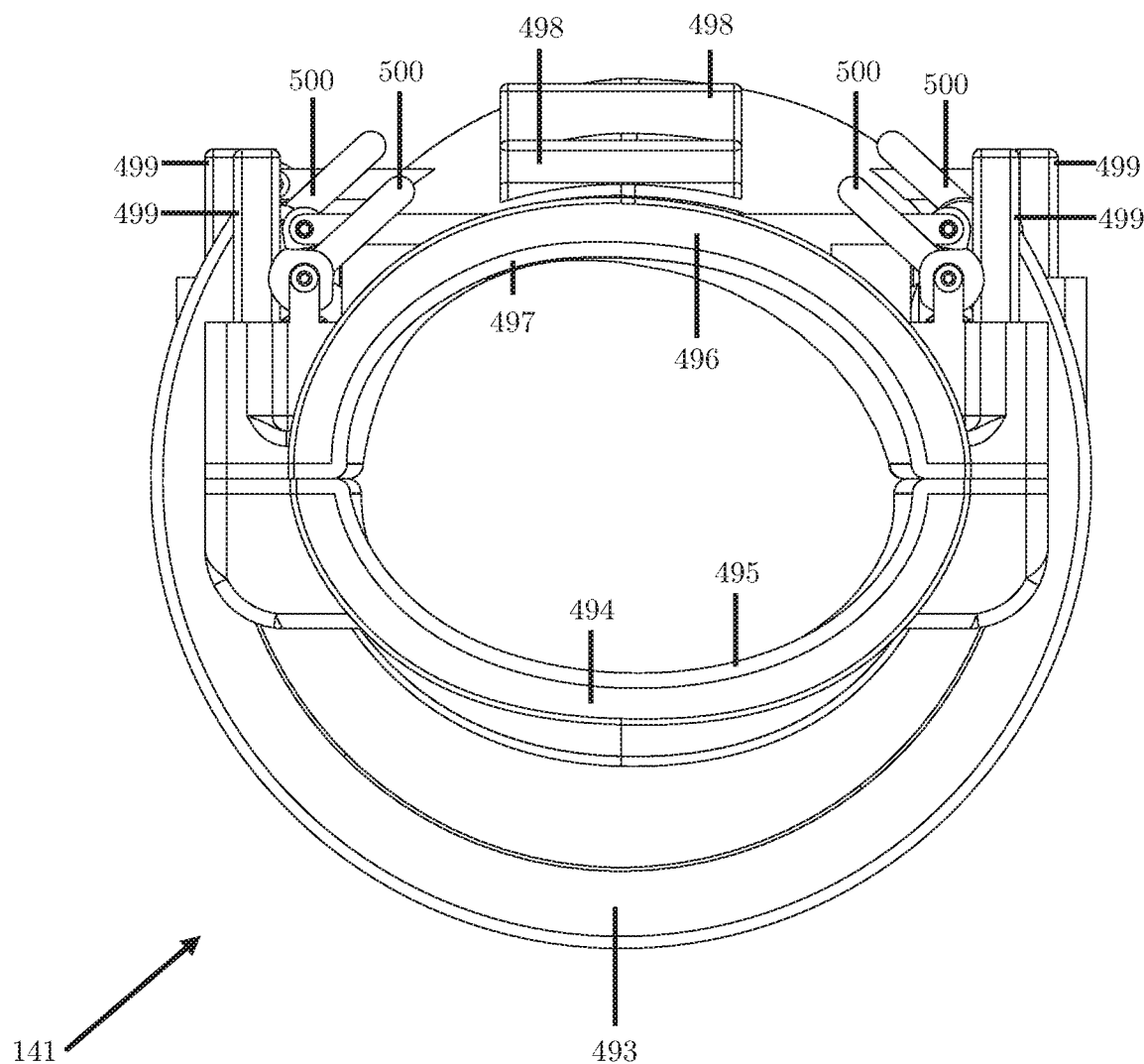
Figure 134:
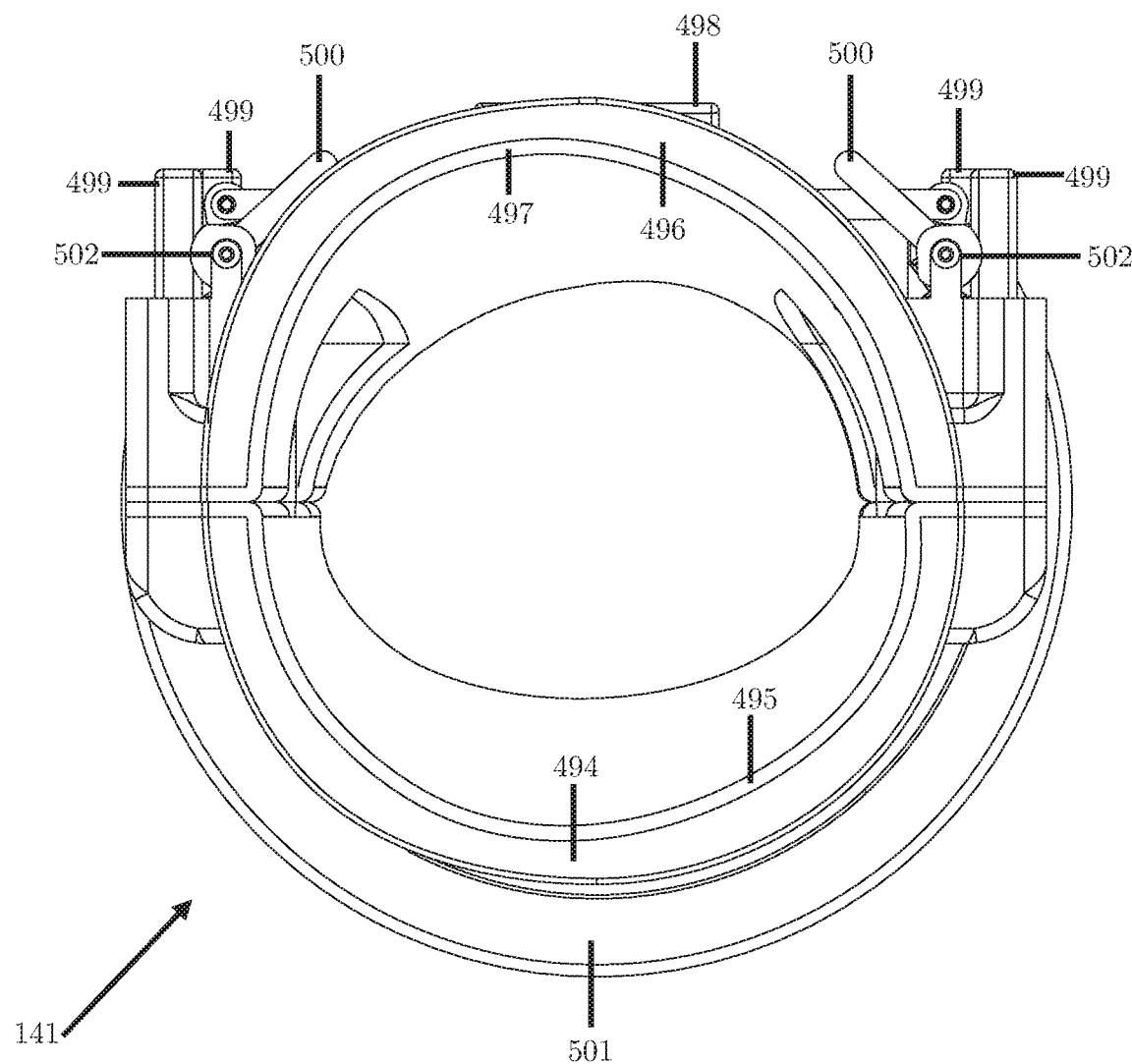
Figure 135:
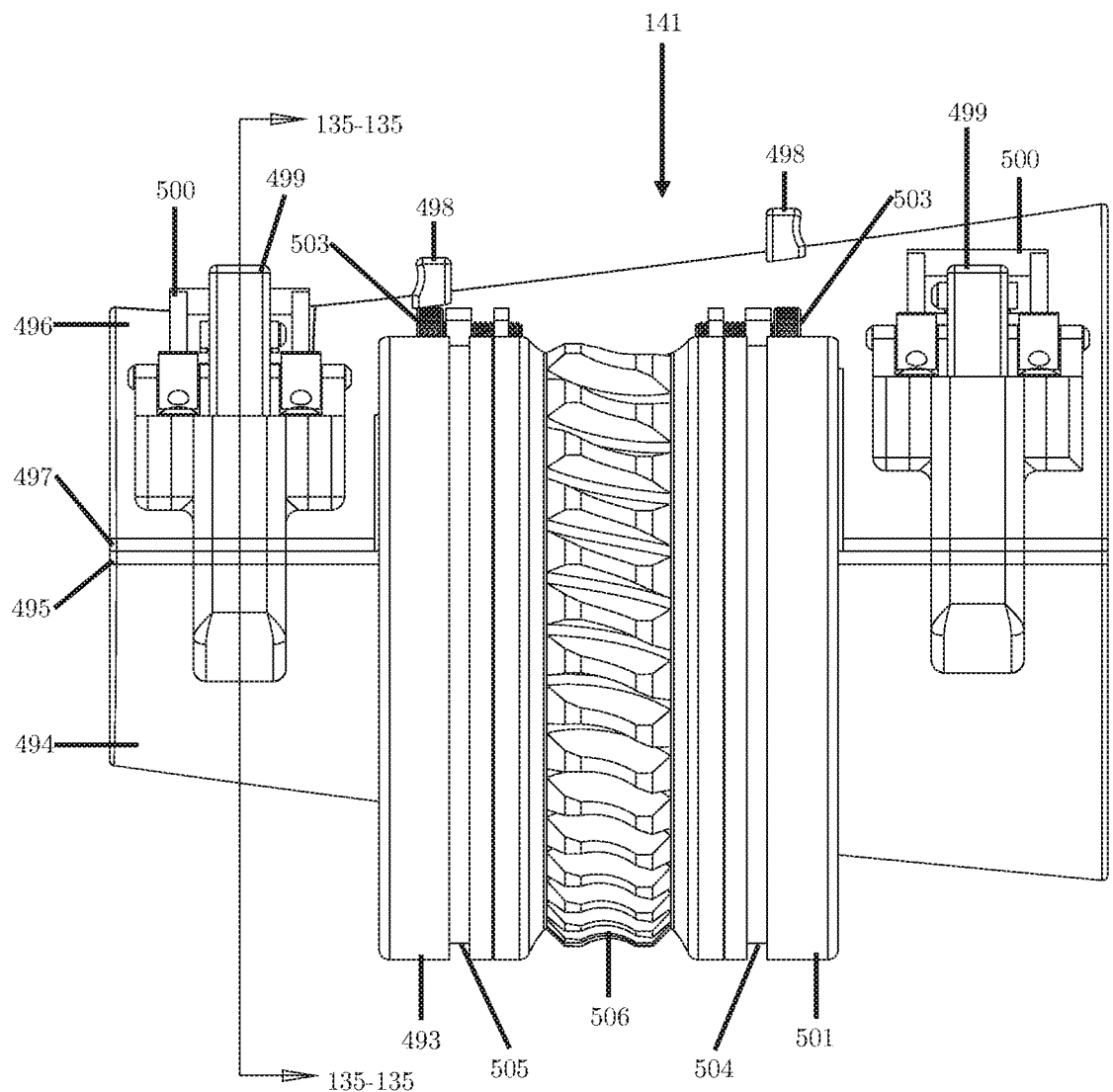
Figure 136:
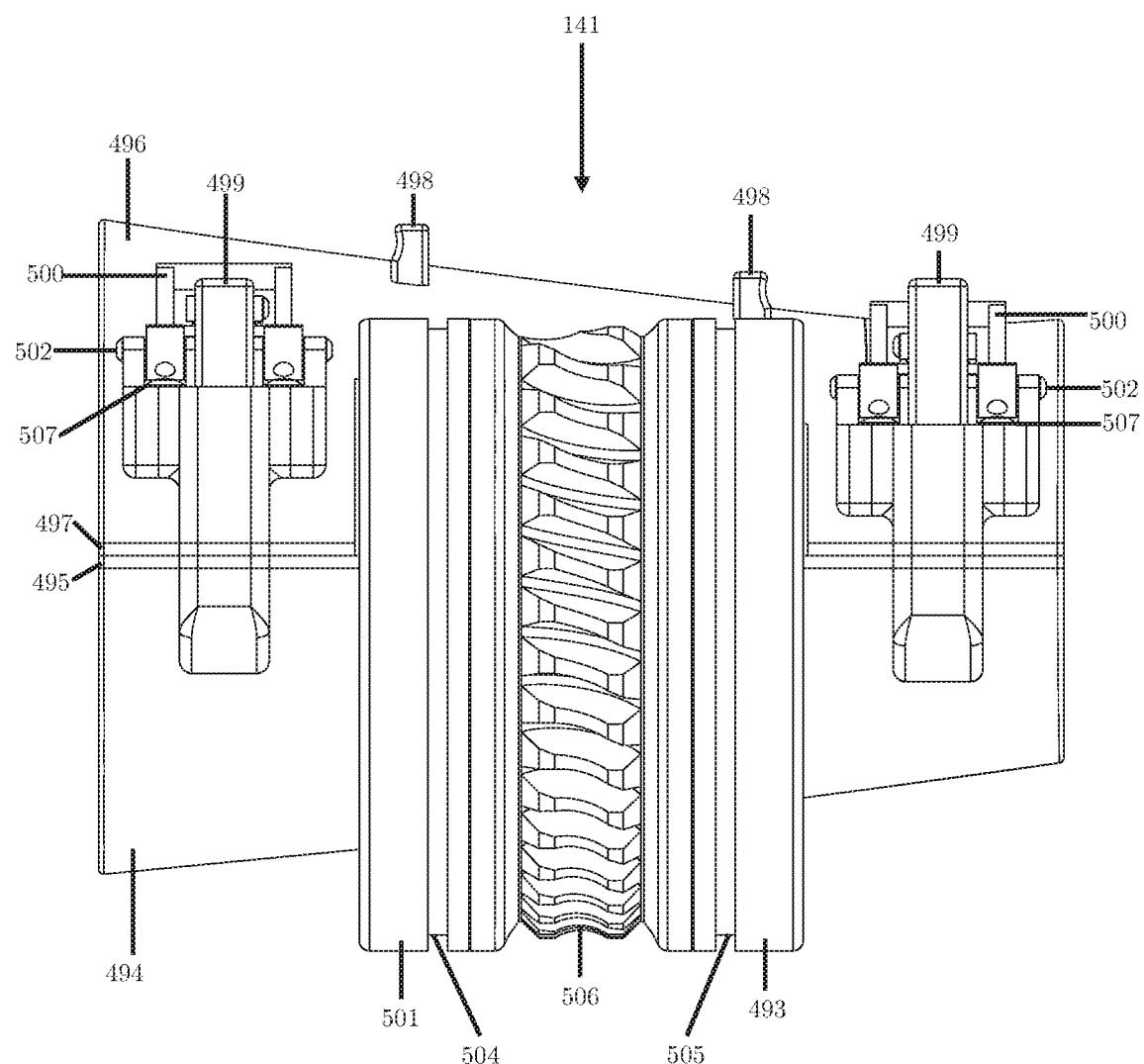
Figure 137:
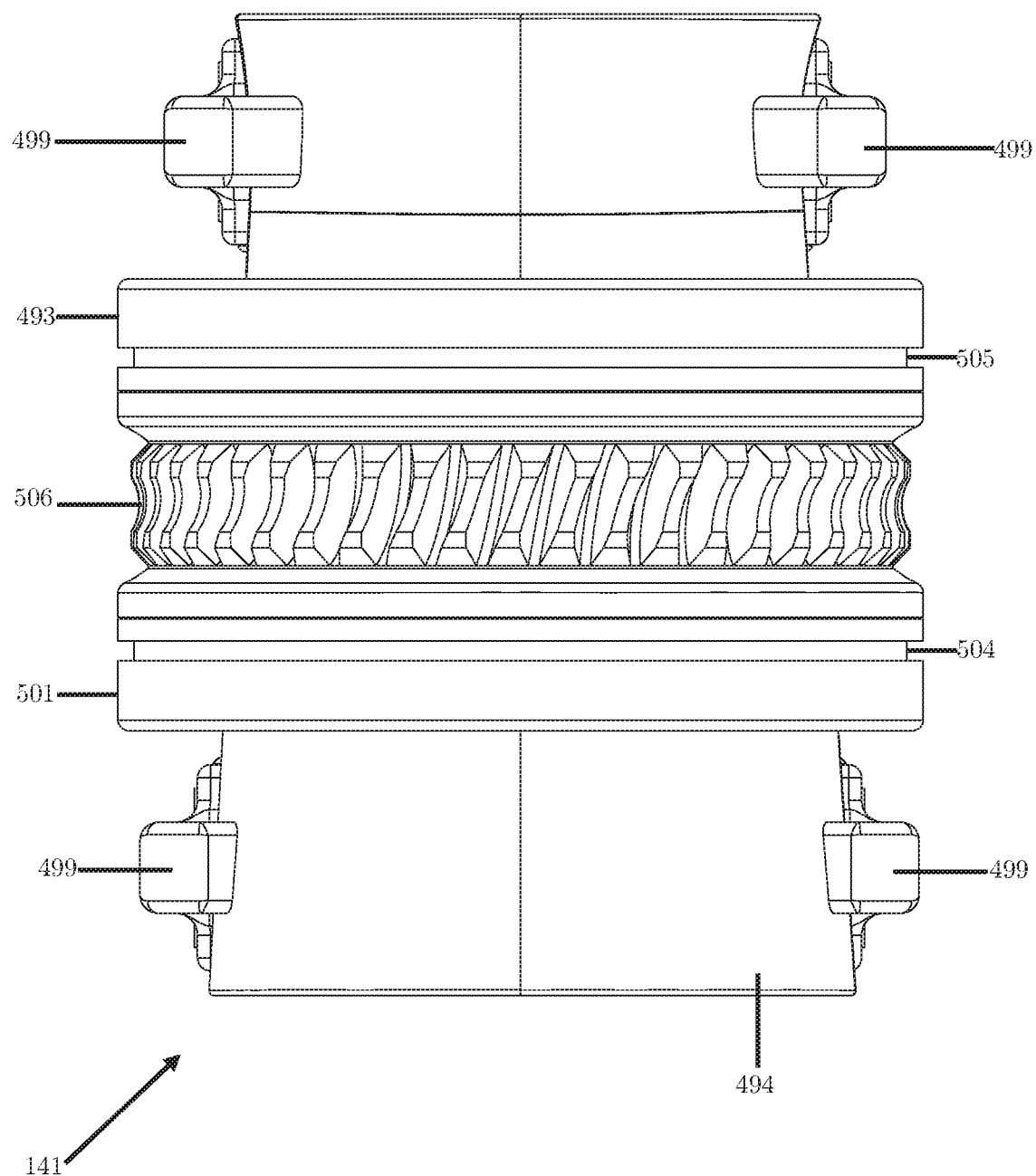
Figure 138:
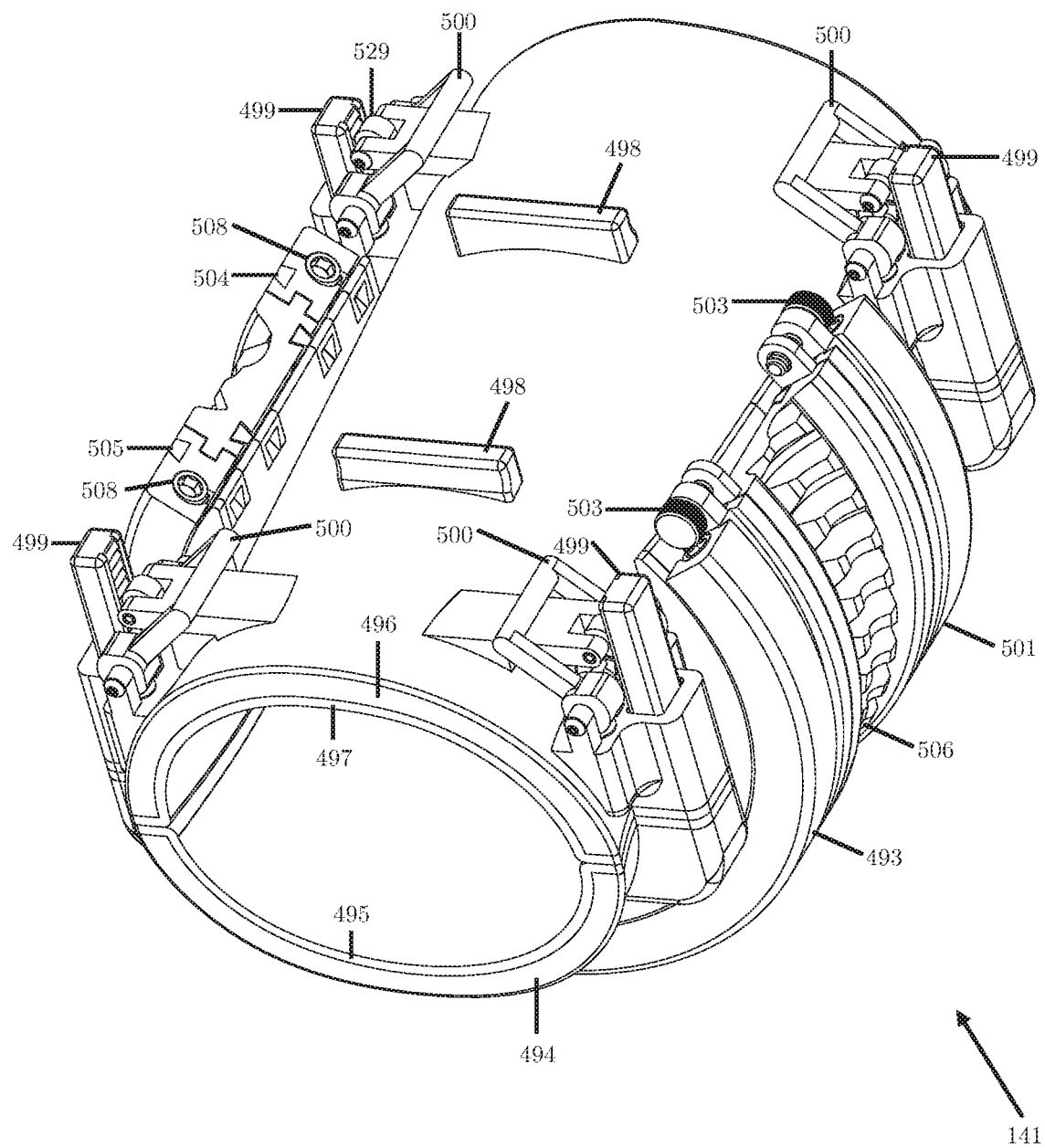
Figure 139:
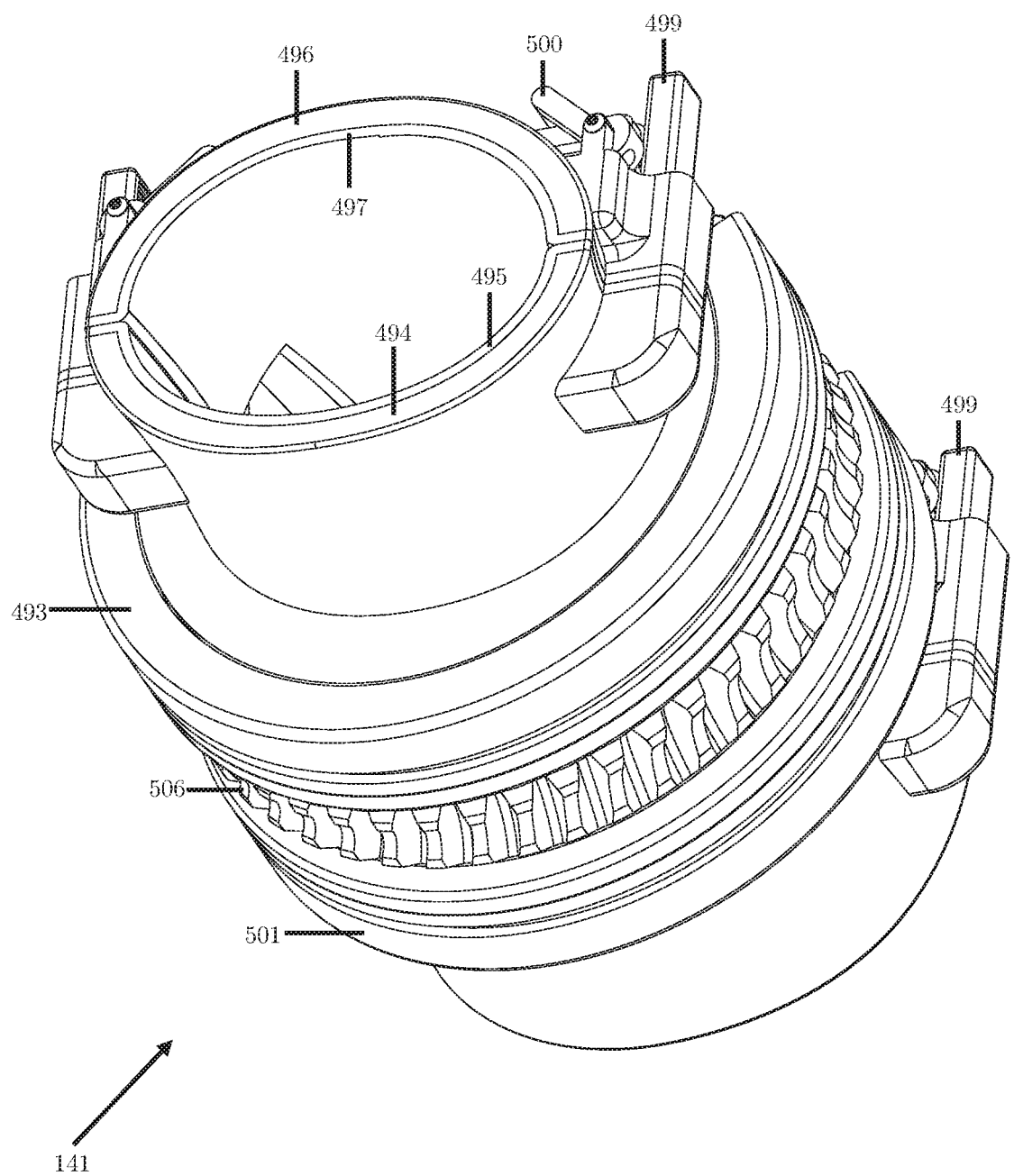
Figure 140:
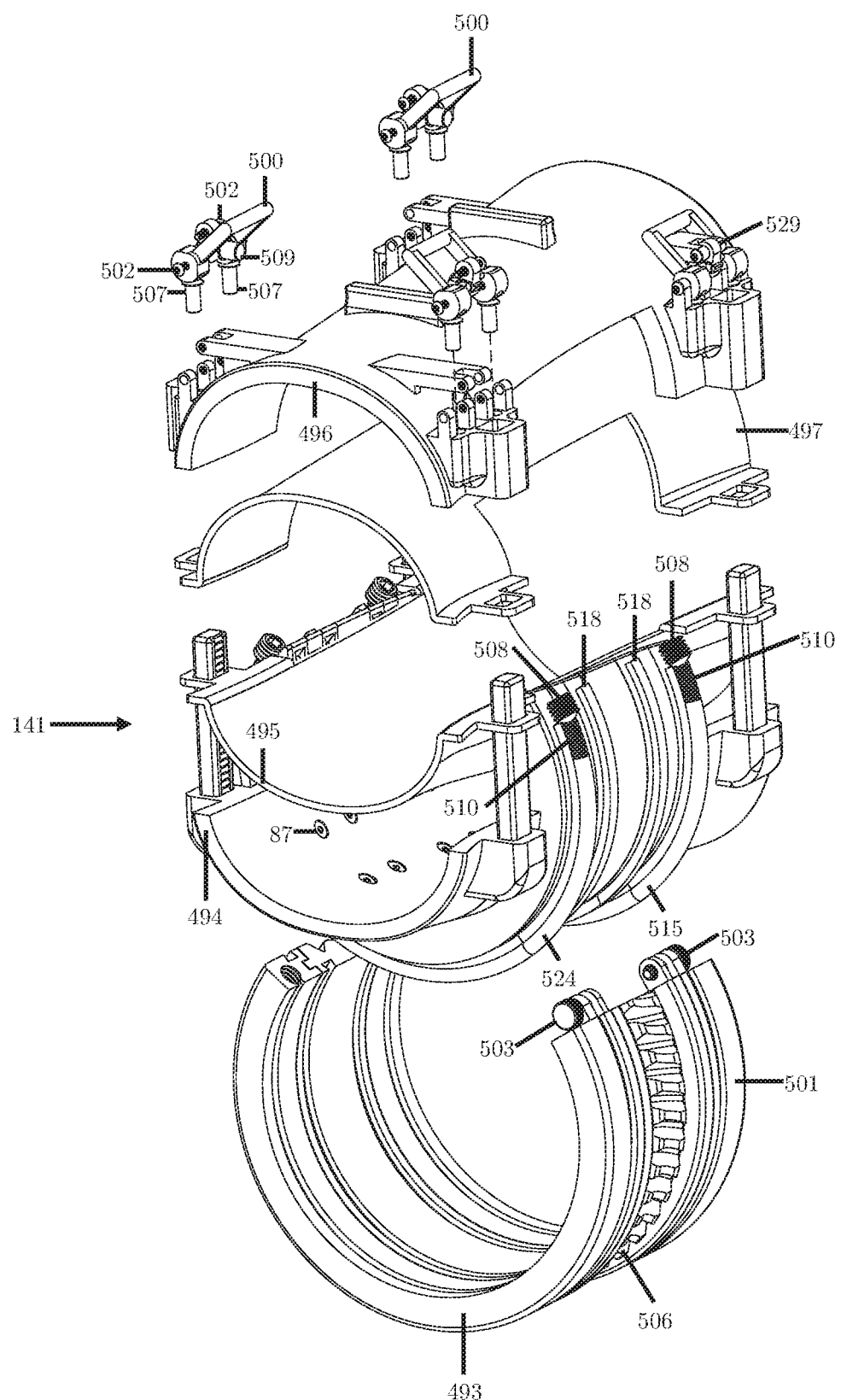
Figure 141:
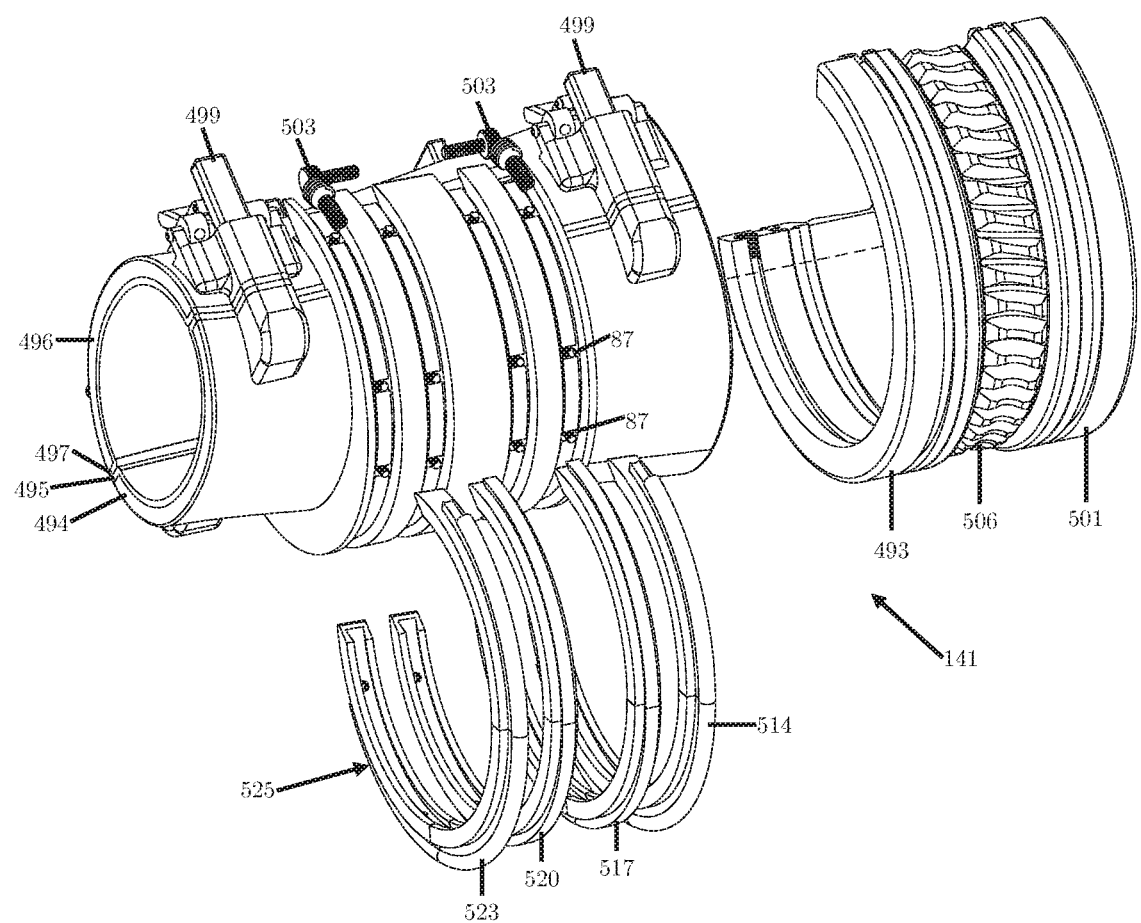
Figure 142:
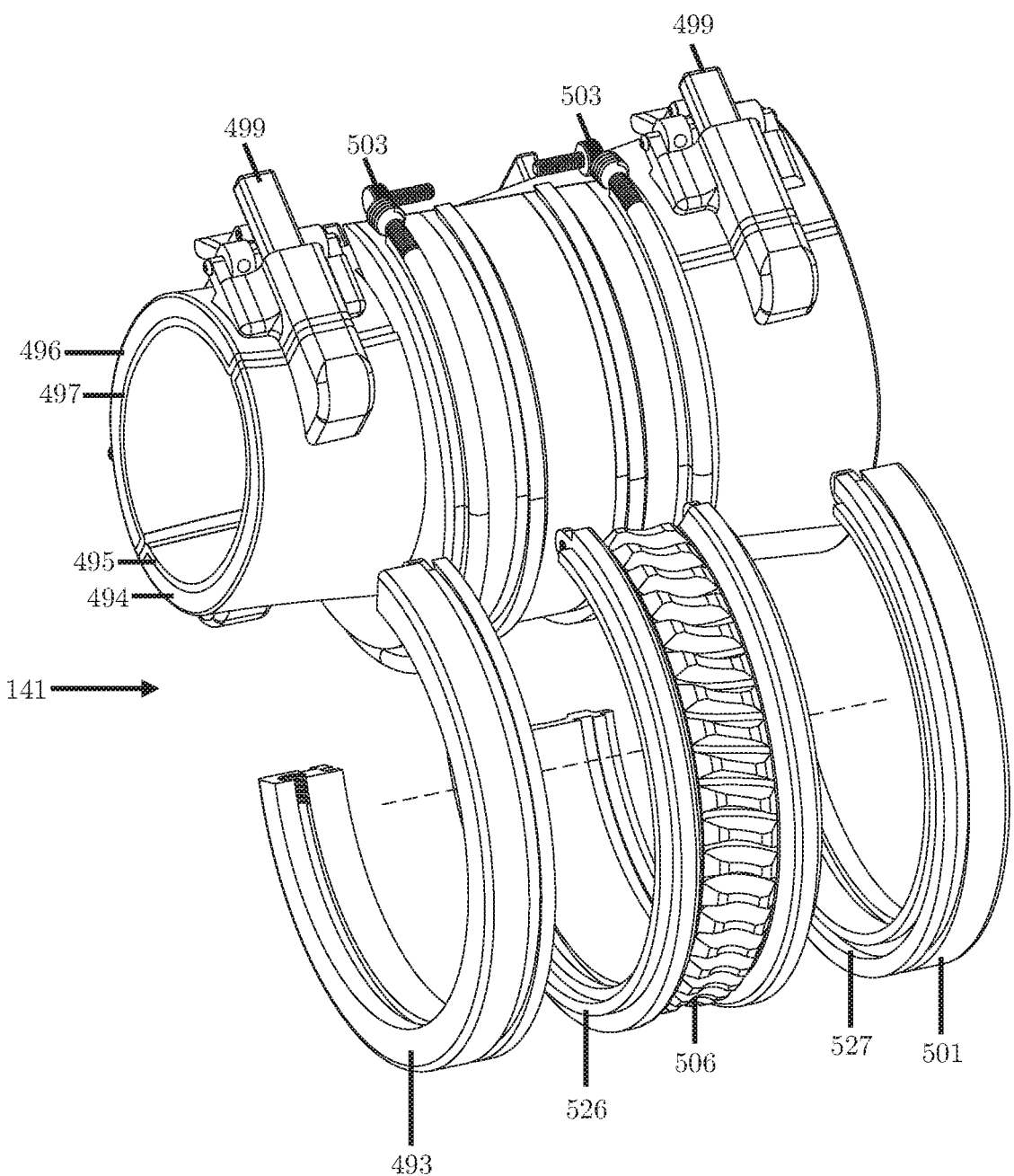
Figure 143:
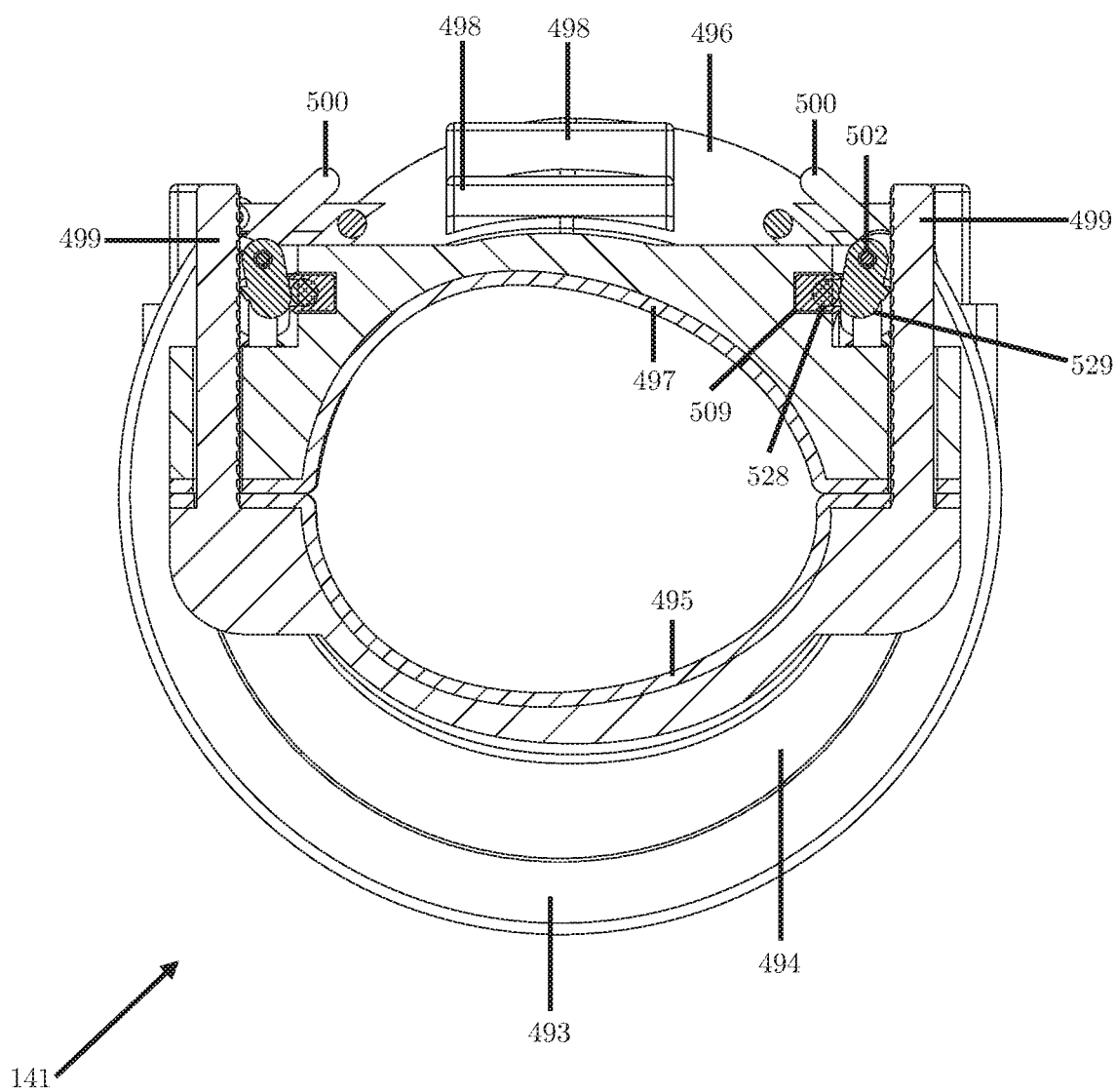
Figure 144:
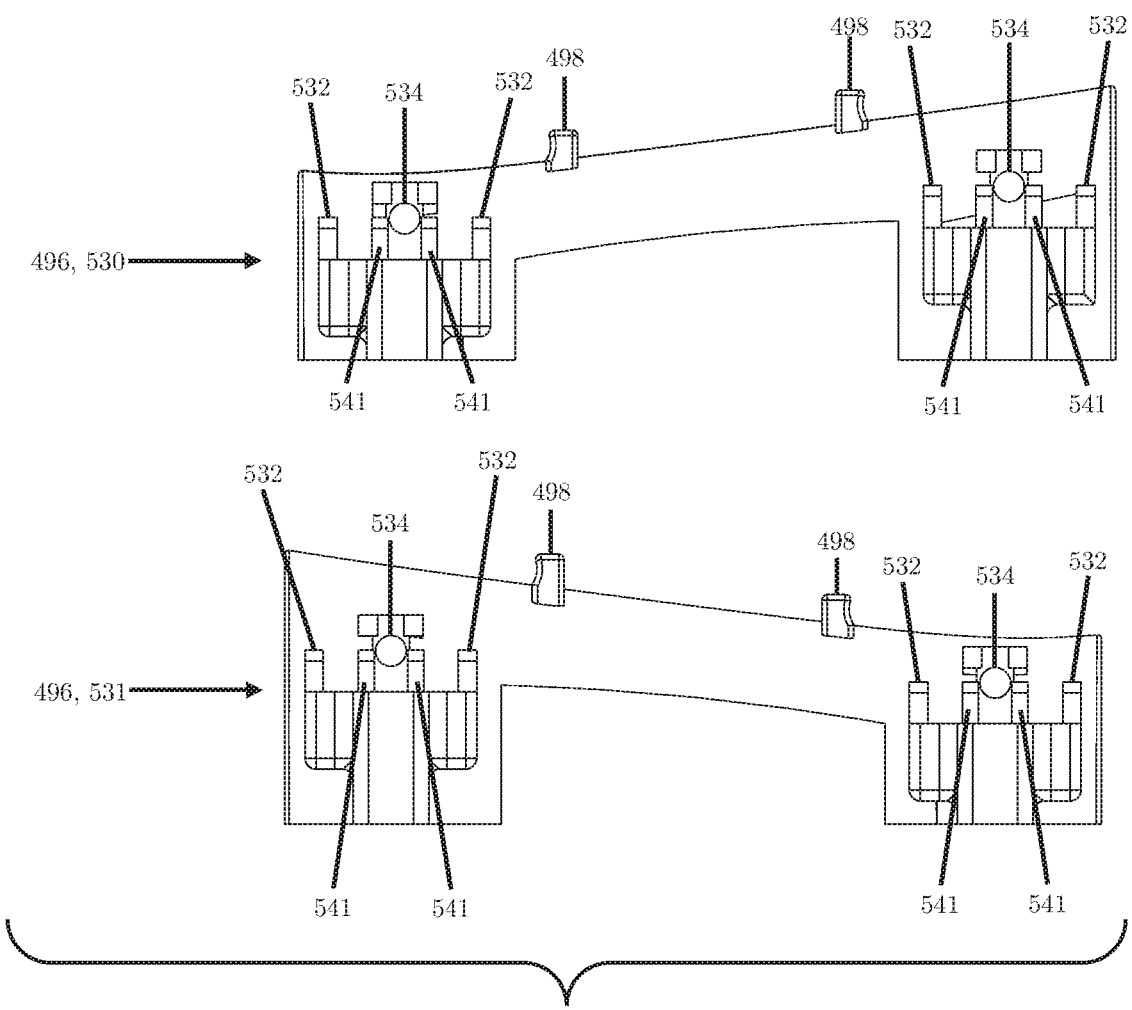
Figure 145:
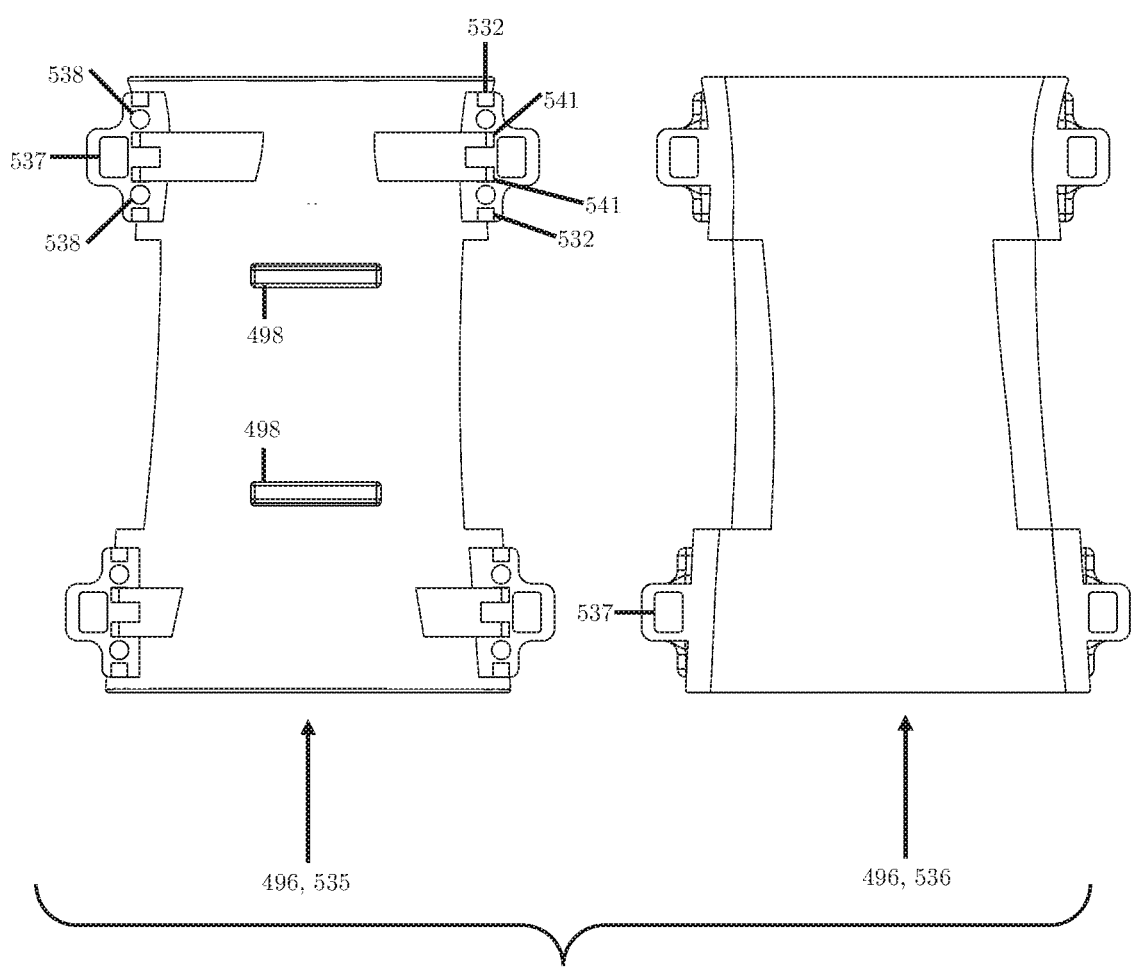
Figure 146:
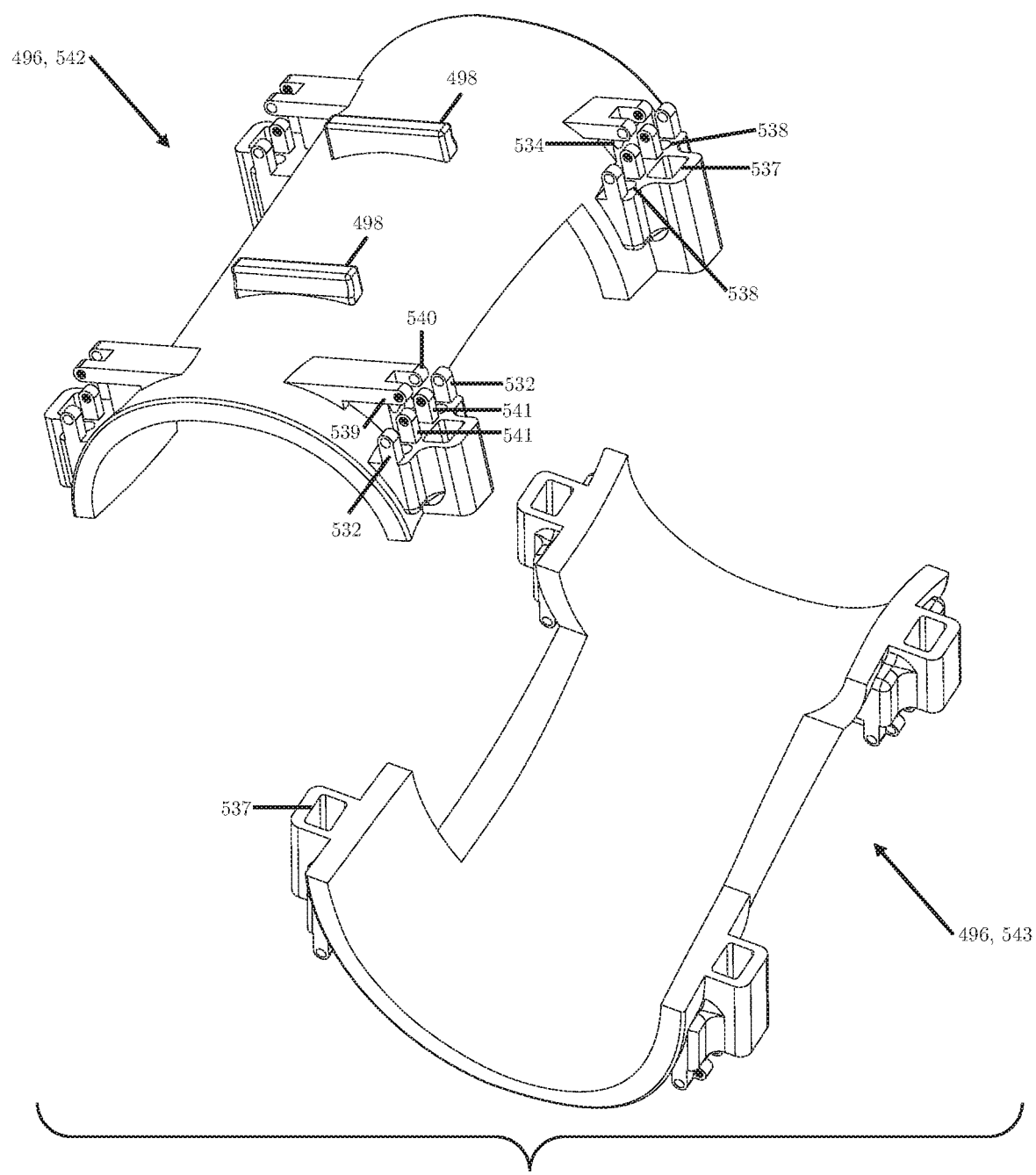
Figure 147:
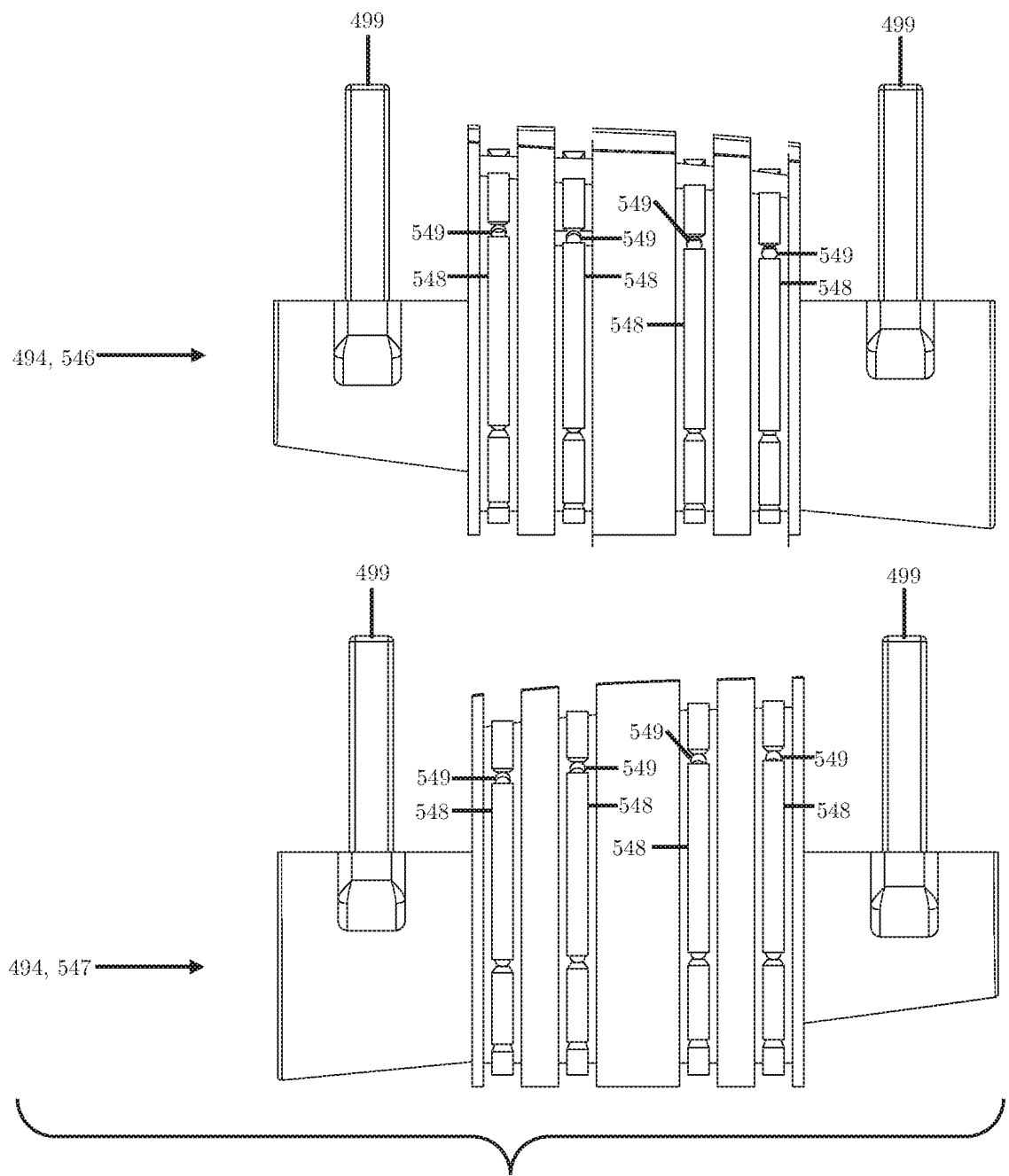
Figure 148:
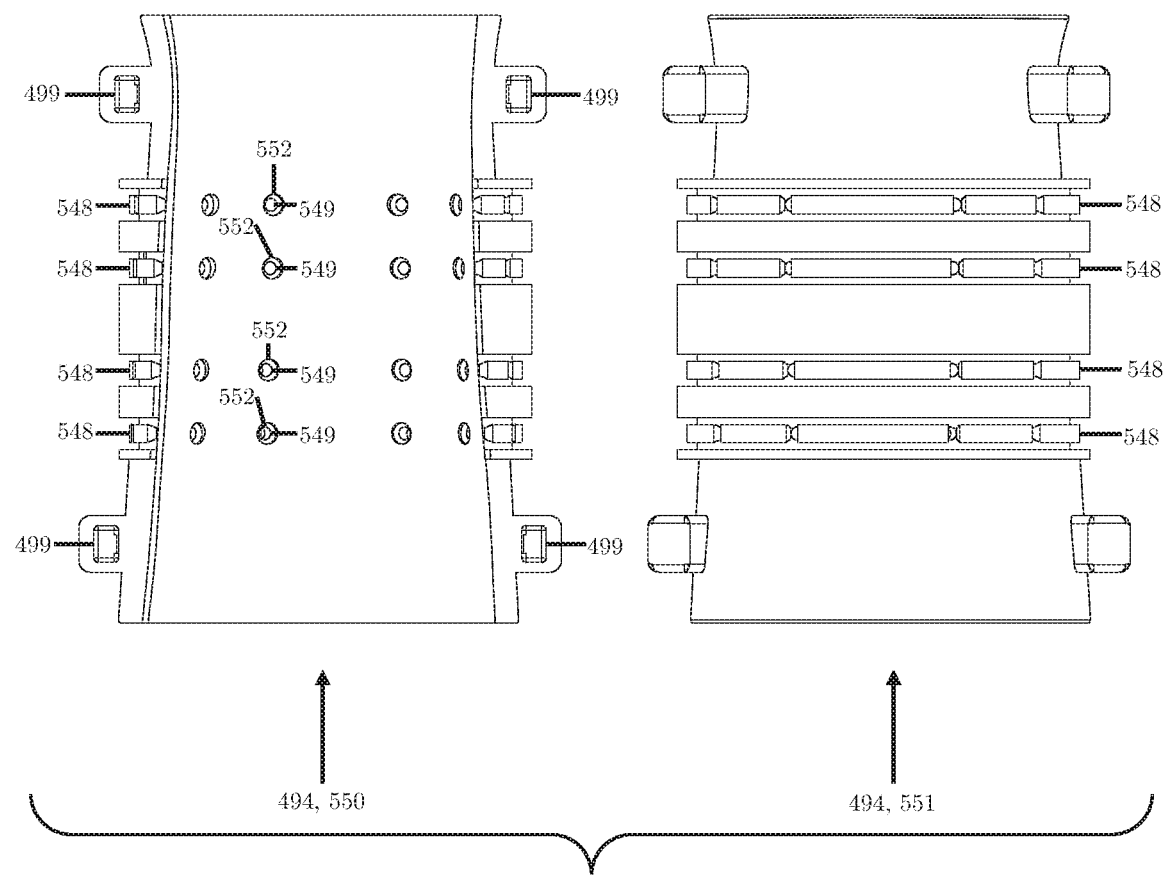
Figure 149:
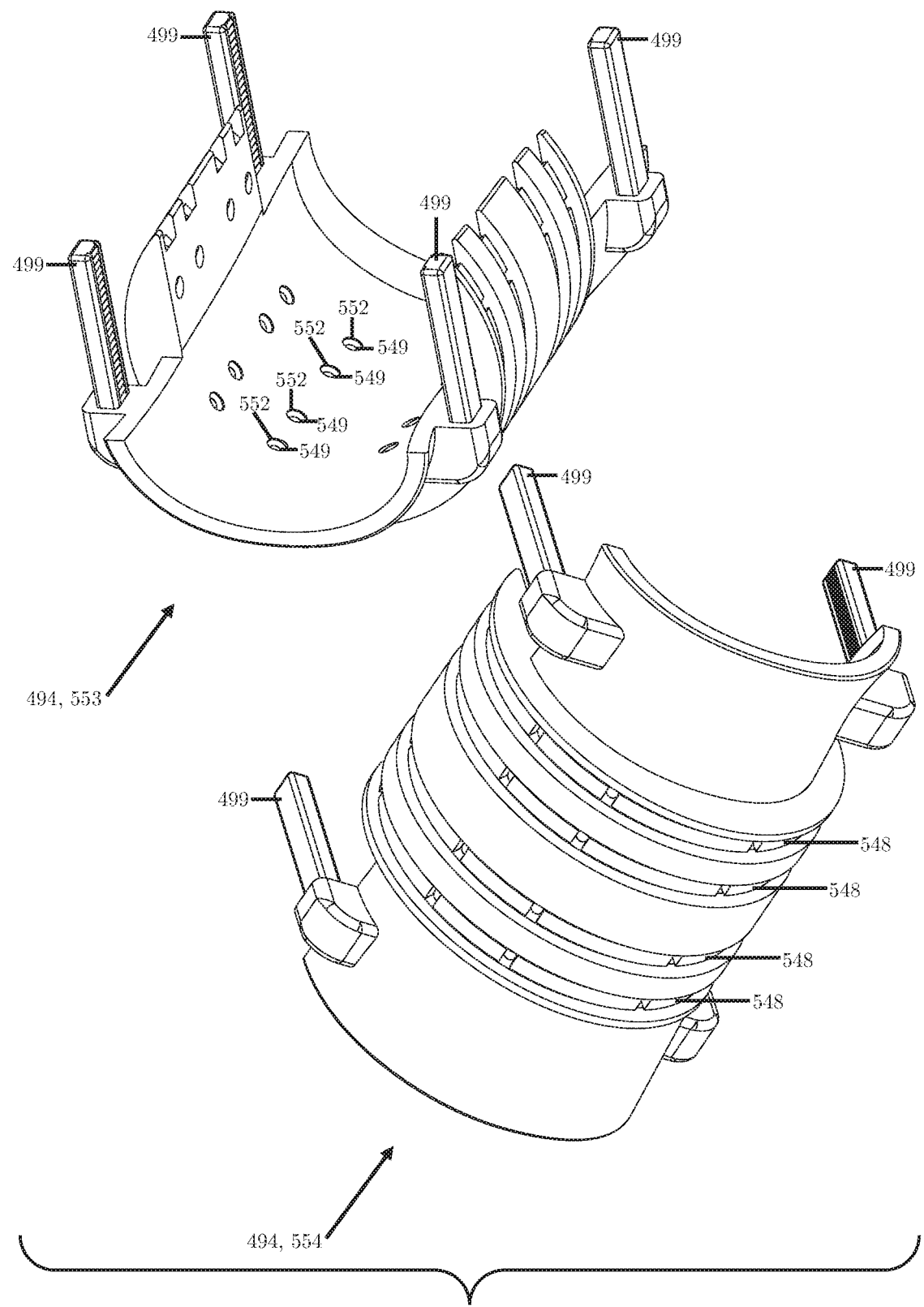
Figure 150:
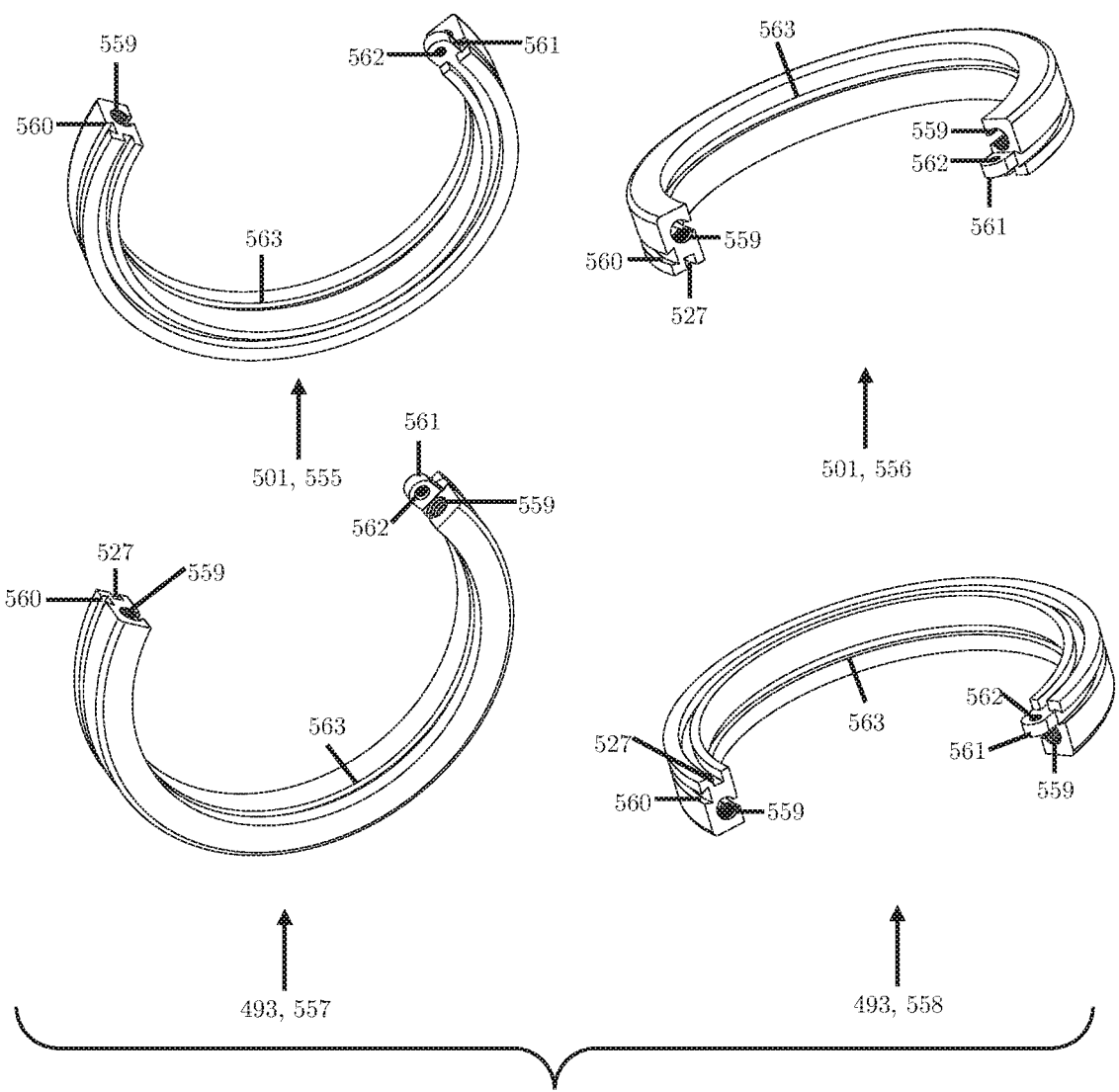
Figure 151:
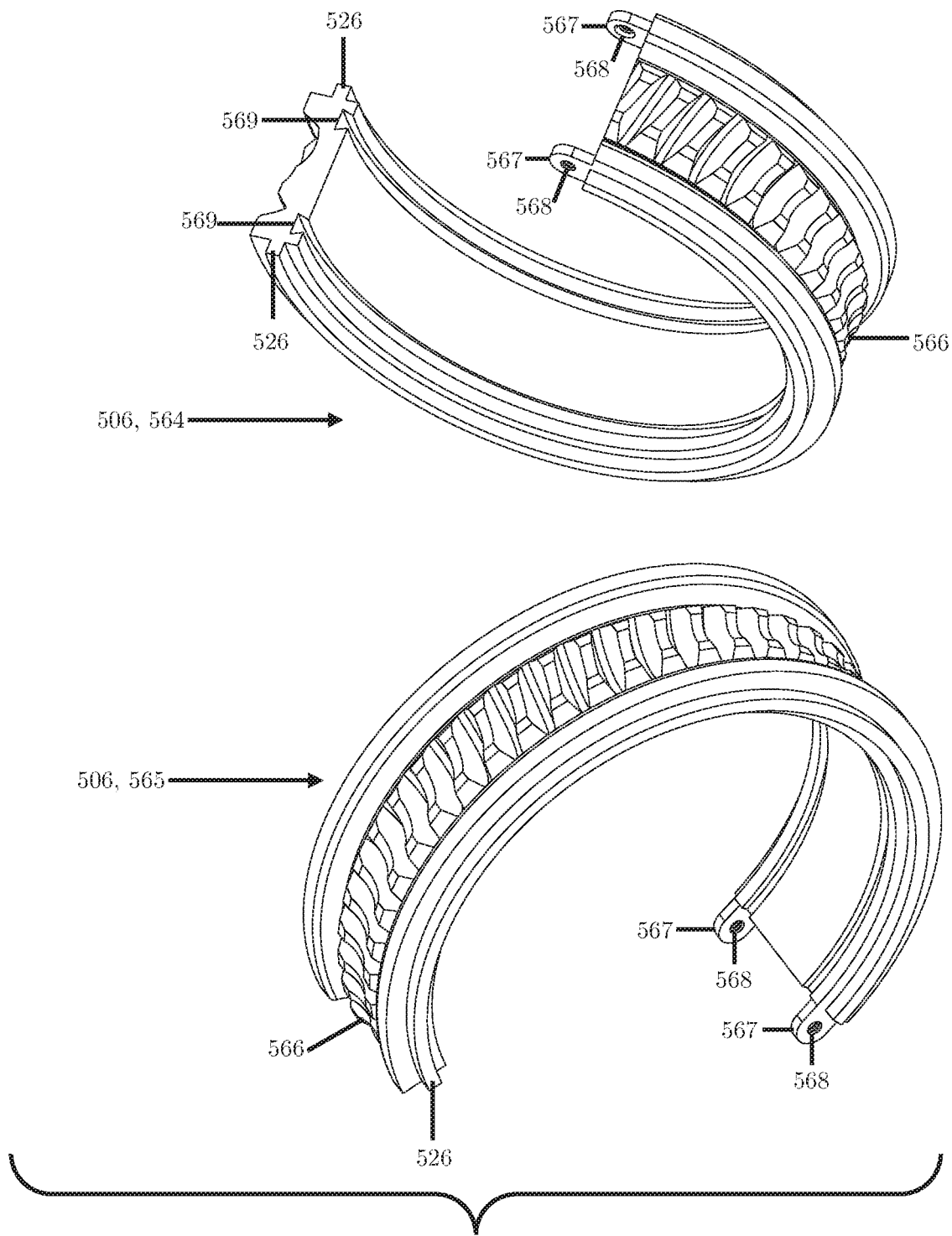
Figure 152:
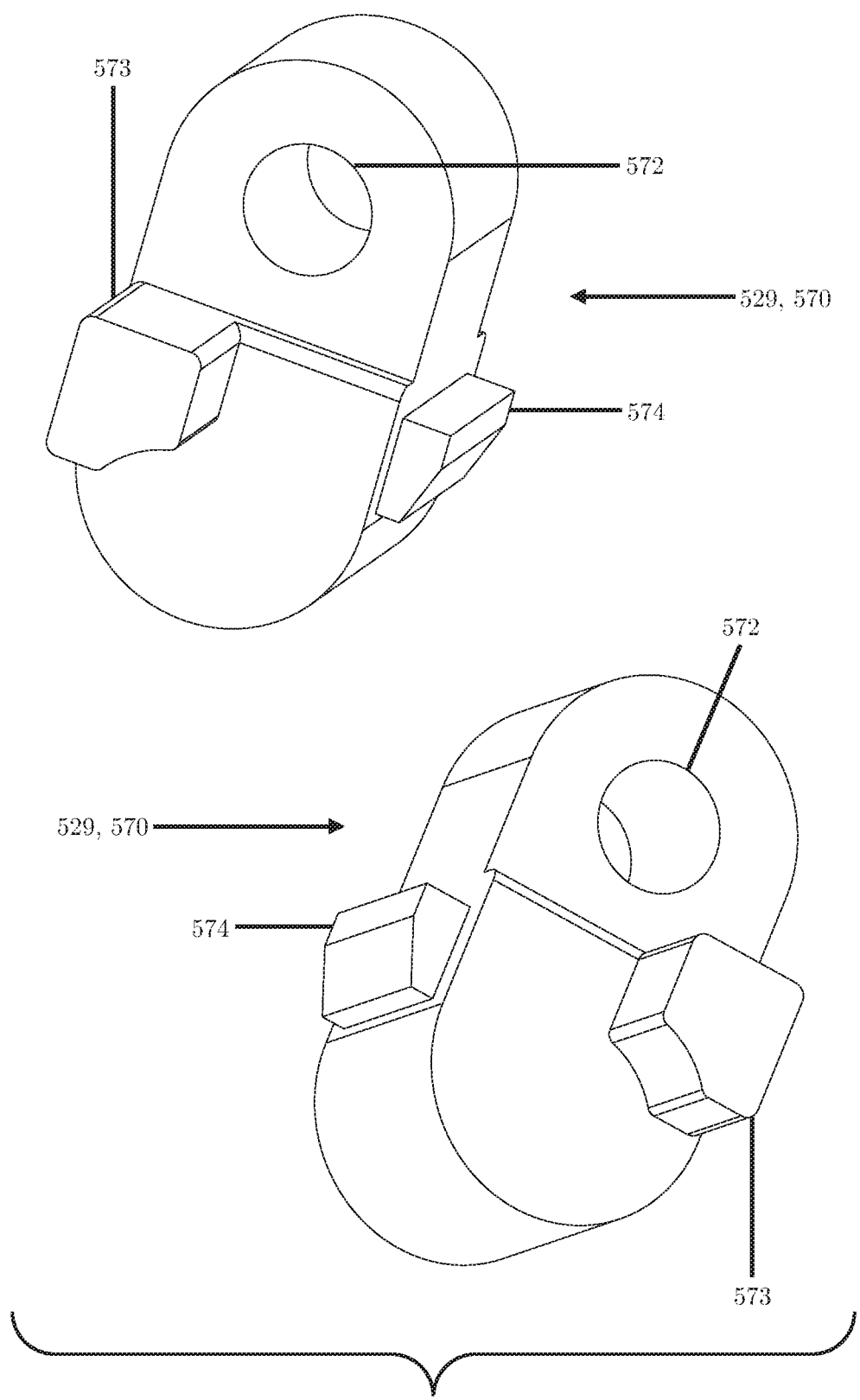
Figure 153:
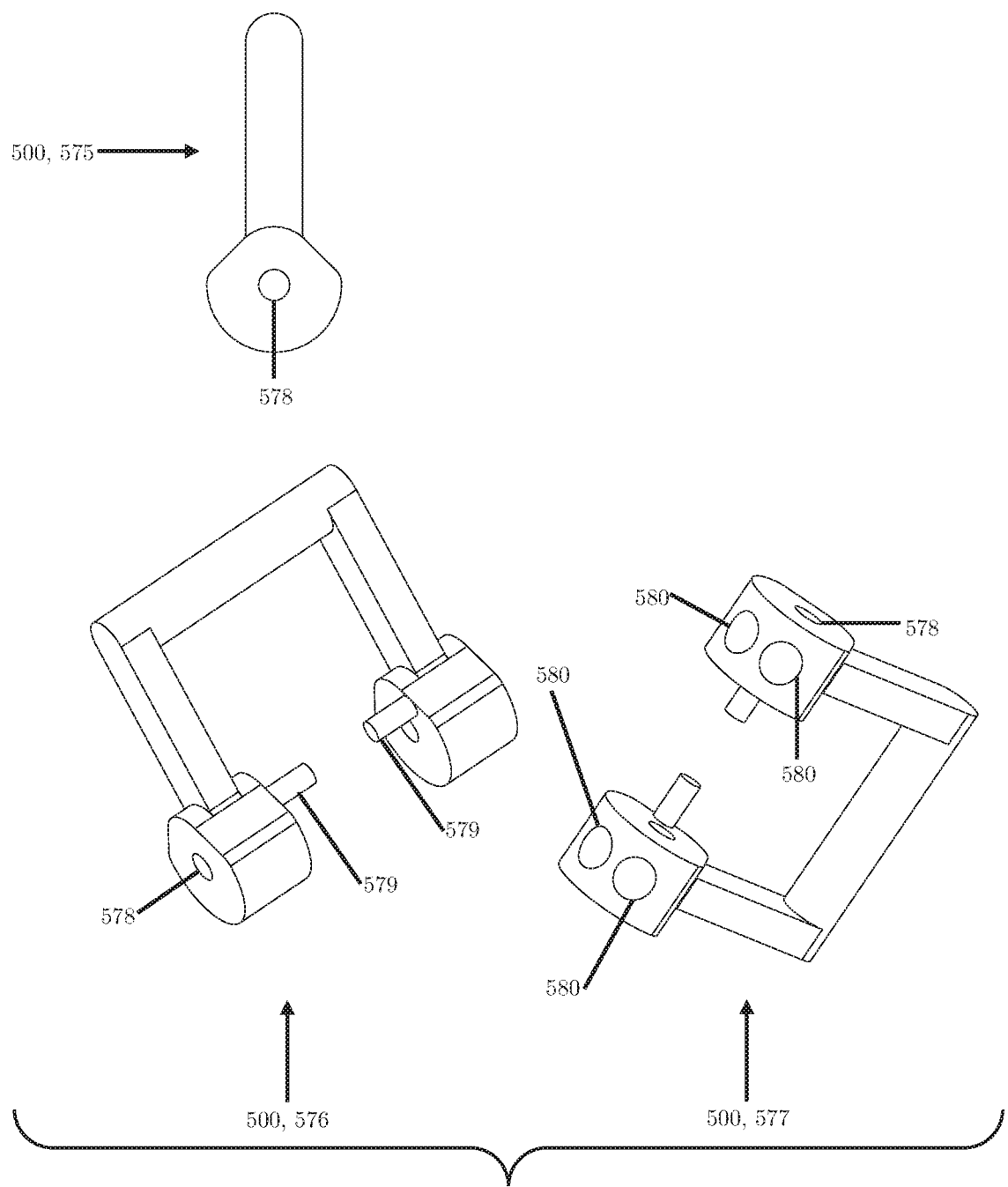
Figure 154:
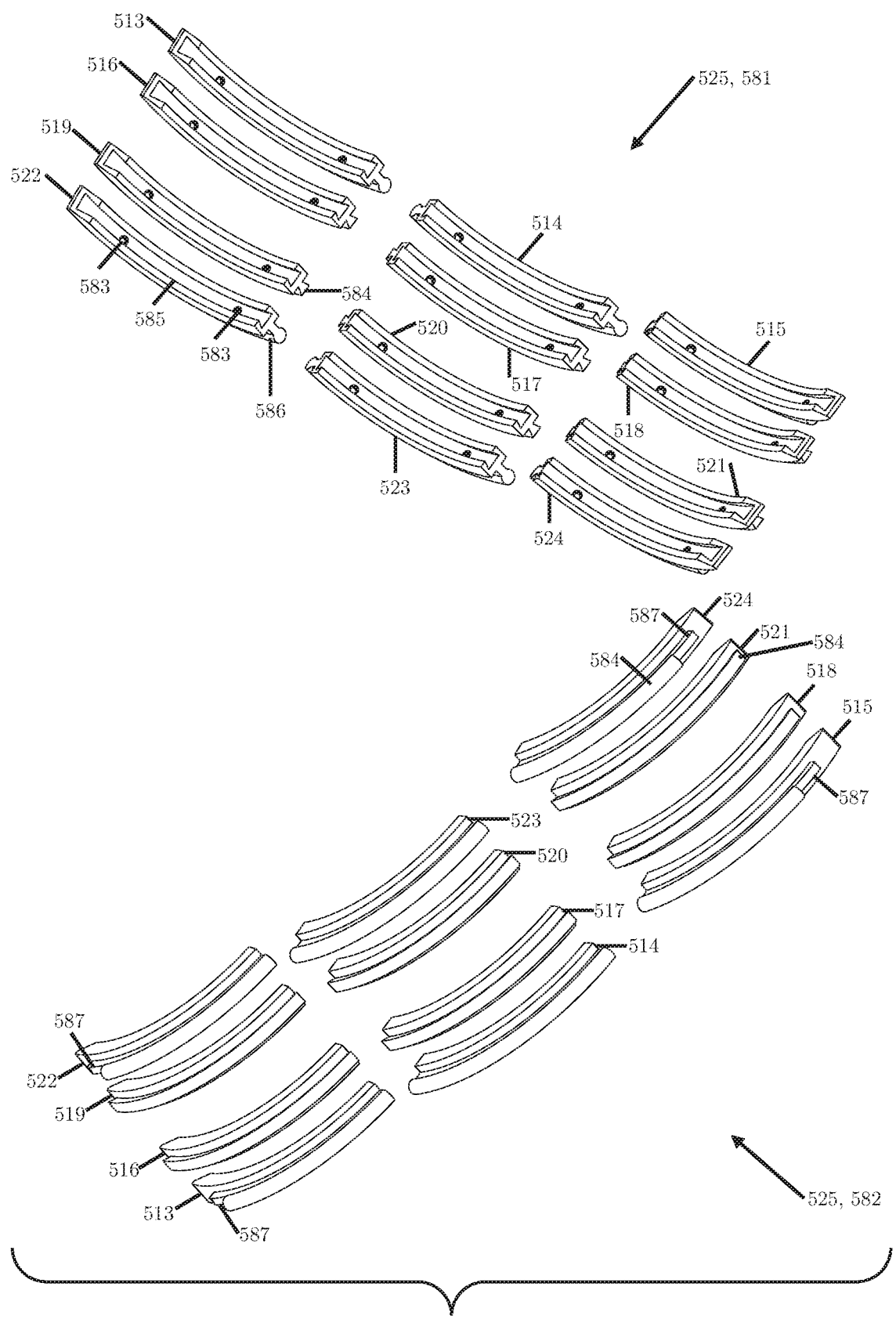

FIG. 119 contains a front right perspective view 422 and a front left perspective view 423 of one contemplated embodiment of the flexion-extension clutch handle of the present invention, with the way it's assembled within the flexion-extension assembly being shown in FIG. 73;

FIG. 120 is a detail view, encircled by the circle 428 in FIG. 119, that shows the thread geometry of the flexion-extension clutch handle;

FIG. 121 contains a front left perspective view 429, a front right perspective view 430, and a front view 431 of one contemplated embodiment of the flexion-extension wheel of the present invention, with the way it's assembled within the flexion-extension assembly being shown in FIG. 73;

FIG. 122 contains a front right perspective view 438 and a front left perspective view 439 of one contemplated embodiment of the flexion-extension worm gear of the present invention, with the way it's assembled within the flexion-extension assembly being shown in FIG. 73;

FIG. 123 contains a front right perspective view 444, a front left perspective view 445, and a front view 446 of one contemplated embodiment of the flexion-extension axle of the present invention, with the way it's assembled within the flexion-extension assembly being shown in FIG. 73;

FIG. 124 contains a front right perspective view 449, a front left perspective view 450, and a front view 451 of one contemplated embodiment of the flexion-extension retention disk of the present invention, with the way it's assembled within the flexion-extension assembly being shown in FIG. 73;

FIG. 125 contains a front right perspective view 453, a front left perspective view 454, and a right perspective view 455 of one contemplated embodiment of the flexion-extension pad of the present invention and is shown assembled within the flexion-extension assembly in FIG. 69;

FIG. 126 contains a front right perspective view 457 and a front left perspective view 458 of one contemplated embodiment of the rear flexion-extension clutch of the present invention, with the way it's assembled within the flexion-extension assembly being shown in FIG. 73;

FIG. 127 is a detail view, encircled by the circle 459 in FIG. 127, that shows the thread geometry of the flexion-extension clutch;

FIG. 128 contains a bottom rear perspective view 463 and a top front perspective view 464 of one contemplated embodiment of the internal-external rotation gearbox assembly of the present invention and is shown assembled to the orthosis in FIG. 59;

FIG. 129 is an exploded bottom rear perspective view of the embodiment of the internal-external rotation gearbox assembly shown in FIG. 128;

FIG. 130 contains a bottom rear perspective view 473 and a top front perspective view 474 of one contemplated embodiment of the supination-pronation gearbox assembly of the present invention, which is a second contemplated embodiment of the gearbox assembly shown in FIG. 22 and is shown assembled to the orthosis in FIG. 59;

FIG. 131 is an exploded bottom rear perspective view of the embodiment of the supination-pronation gearbox assembly shown in FIG. 130;

FIG. 132 contains a front view 484 and a front left perspective view 485 of one contemplated embodiment of the front scapular rotation rail of the present invention, and also contains a front view 489 and a front left perspective view 490 of one contemplated embodiment of the rear scapular rotation rail of the present invention, where the front scapular rotation rail is shown assembled to the orthosis in FIG. 59 and the rear scapular rotation rail is shown assembled to the orthosis in FIG. 60;

FIG. 133 is a front view of a third contemplated embodiment, of the wrist cuff assemblies of FIGS. 33 and 43—the ratchet lock wrist cuff assembly—which uses a ratchet, locking system to provide a clamping force, it is shown assembled to the supination-pronation gearbox assembly, and hence the orthosis, in FIG. 59;

FIG. 134 is a back view of the embodiment of the wrist cuff assembly shown in FIG. 133;

FIG. 135 is a right side view of the embodiment of the wrist cuff assembly shown in FIG. 133;

FIG. 136 is a left side view of the embodiment of the wrist cuff assembly shown in FIG. 133;

FIG. 137 is a bottom view of the embodiment of the wrist cuff assembly shown in FIG. 133;

FIG. 138 is a front right perspective view of the embodiment of the wrist cuff assembly shown in FIG. 133;

FIG. 139 is a bottom right perspective view of the embodiment of the wrist cuff assembly shown in FIG. 133;

FIG. 140 is an exploded front right perspective view of the embodiment of the wrist cuff assembly shown in FIG. 133;

FIG. 141 is an exploded bottom right perspective view, of the embodiment of the wrist cuff assembly shown in FIG. 133, that emphasizes how the wrist cuff rails, front spring ring, rear spring ring, and worm gear ring are assembled;

FIG. 142 is an exploded bottom right perspective view, of the embodiment of the wrist cuff assembly shown in FIG. 133, that emphasizes how the front spring ring, rear spring ring, and worm gear ring are assembled to the wrist cuff rails;

FIG. 143 is a cross-sectional view, taken along plane 135-135 of FIG. 135, of the embodiment of the wrist cuff assembly shown in FIG. 133, which shows the engagement of the components that comprise the ratchet lock mechanism;

FIG. 144 contains a right side view 530 and a left side view 531 of the upper ratchet lock wrist cuff from the embodiment of the wrist cuff assembly shown in FIG. 138;

FIG. 145 contains a top view 535 and a bottom view 536 of the upper ratchet lock wrist cuff from the embodiment of the wrist cuff assembly shown in FIG. 138;

FIG. 146 contains a top right perspective view 542 and a bottom right perspective view 543 of the upper ratchet lock wrist cuff from the embodiment of the wrist cuff assembly shown in FIG. 138;

FIG. 147 contains a left side view 546 and a right side view 547 of the lower ratchet lock wrist cuff from the embodiment of the wrist cuff assembly shown in FIG. 138;

FIG. 148 contains a top view 550 and a bottom view 551 of the lower ratchet lock wrist cuff from the embodiment of the wrist cuff assembly shown in FIG. 138;

FIG. 149 contains a top right perspective view 553 and a bottom left perspective view 554 of the lower ratchet lock wrist cuff from the embodiment of the wrist cuff assembly shown in FIG. 138;

FIG. 150 contains a top front perspective view 555 and a top rear perspective view 556 of the rear spring ring from the embodiment of the wrist cuff assembly shown in FIG. 138, and also contains a top front perspective view 557 and a top rear perspective view 558 of the front spring ring from the same assembly:

FIG. 151 contains a top right perspective view 564 and a bottom left perspective view 565 of the worm gear cradle from the embodiment of the wrist cuff assembly shown in FIG. 138;

FIG. 152 contains a top front perspective view 570 and a bottom front perspective view 571 of the pawl from the embodiment of the wrist cuff assembly shown in FIG. 138;

FIG. 153 contains a right side view 575, a front right perspective view 576, and a bottom right perspective view 577 of the ratchet lever from the embodiment of the wrist cuff assembly shown in FIG. 138; and FIG. 154 contains an exploded front top perspective view 581 and an exploded front bottom perspective view 582 of the wrist cuff rails from the embodiment of the wrist cuff assembly shown in FIG. 138.

DETAILED DESCRIPTION OF THE PREFERRED EMBODIMENTS

The present invention will now be described in connection with one or more embodiments. The discussion of any one embodiment is not intended to be limiting of the present invention. To the contrary, the discussion of various embodiments is intended to illustrate the scope and breadth of the present invention. After reading and understanding the discussion that follows, those skilled in the art may contemplate one or more variations and equivalents to the embodiments discussed herein. Those variations and equivalents are intended to be encompassed by the present invention as if specifically described herein.

Figure 1:
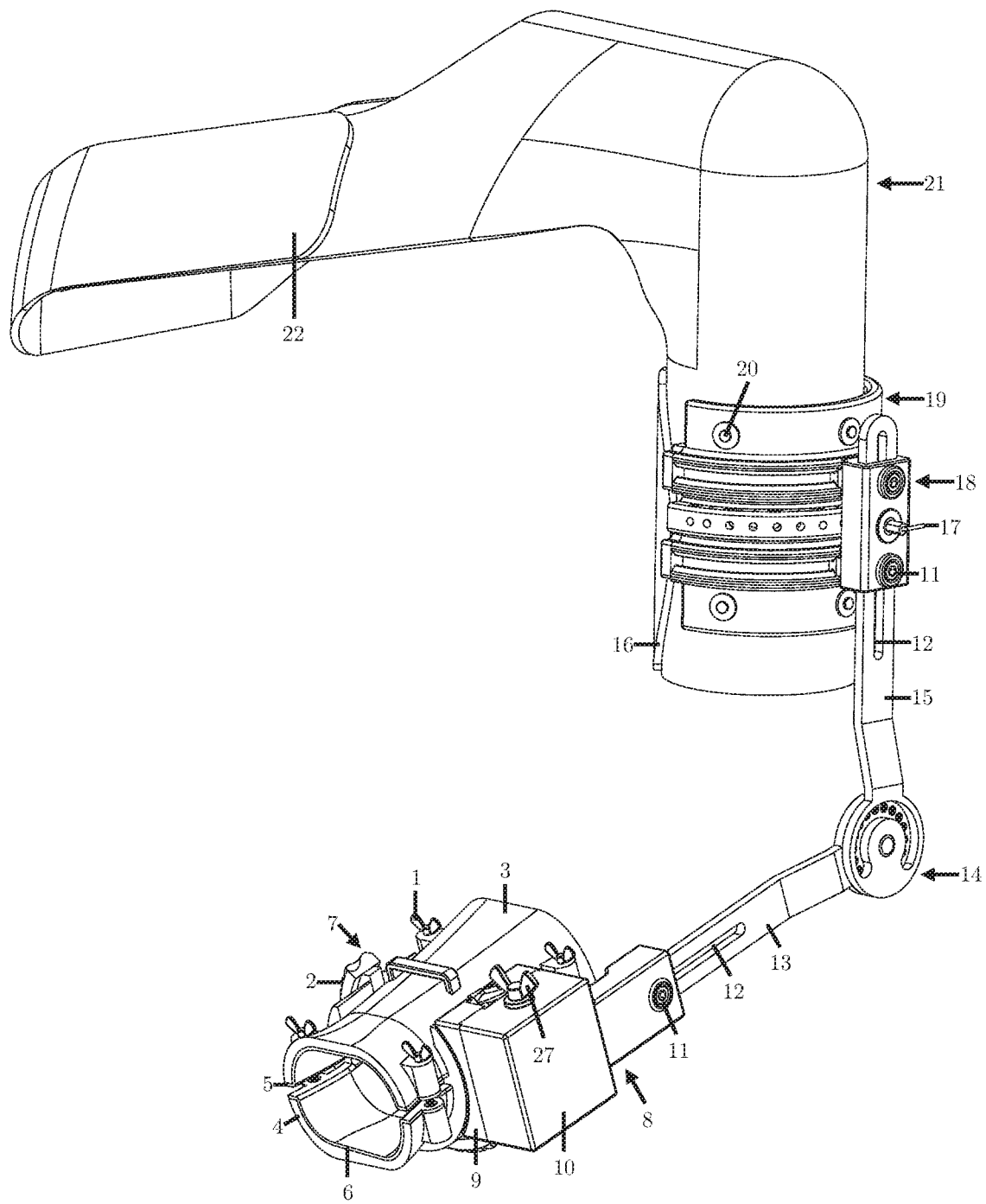
FIG. 1 is a perspective view of one contemplated embodiment of the present invention where the wrist cuff assembly is clamped to the wrist and lower forearm using thumbscrews.
Figure 2:
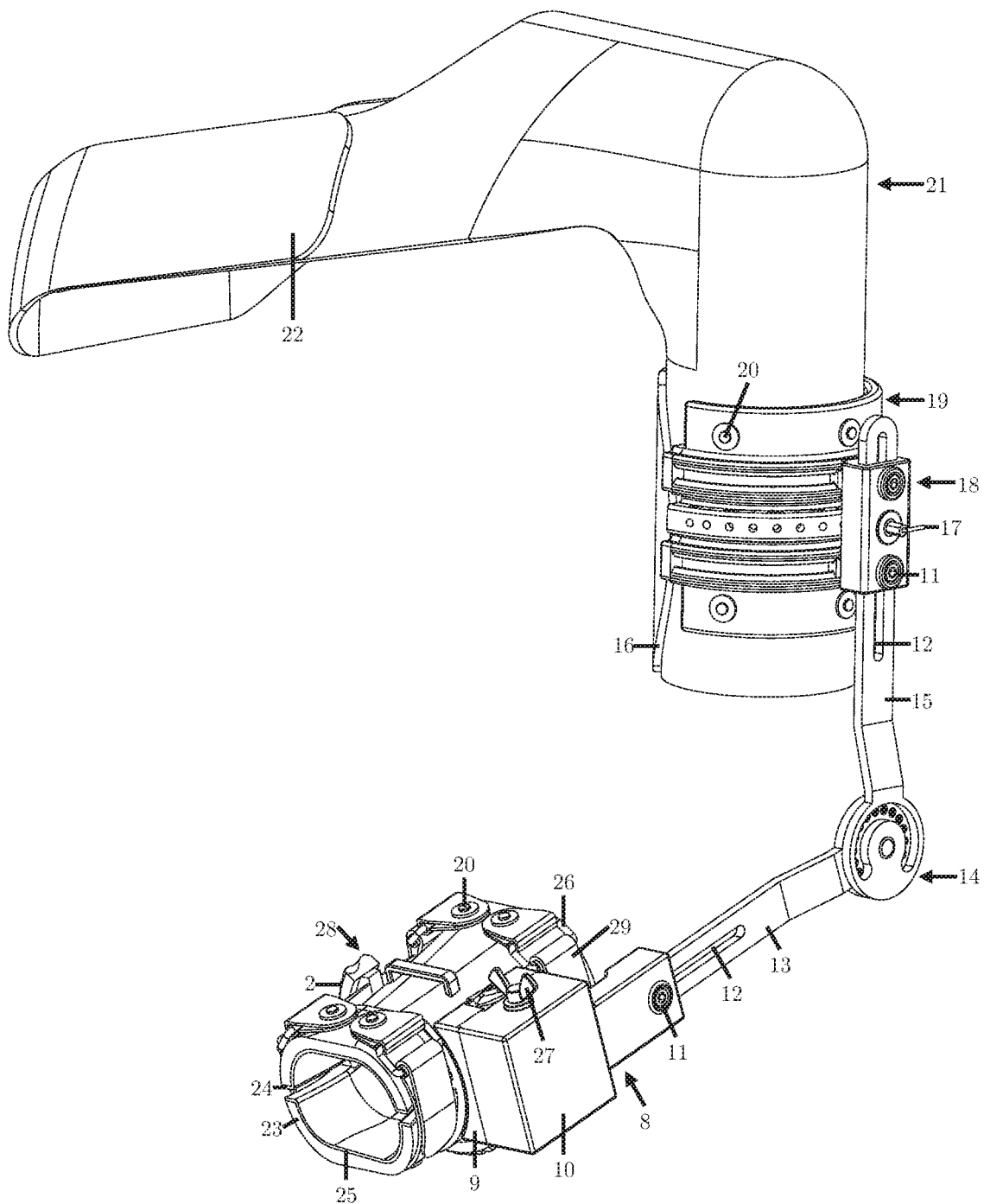
FIG. 2 is a perspective view of another contemplated embodiment of the present invention where the wrist cuff assembly is clamped to the wrist and lower forearm using straps. Apart from the wrist clamp assembly, it is identical to the embodiment depicted in FIG. 1.

Two embodiments of the orthosis of the present invention will be discussed throughout this section. They are identical except that each uses one of two contemplated embodiments for the wrist cuff assembly where one embodiment of the assembly uses thumbscrews to clamp the upper and lower wrist cuff to the forearm and the other uses hook and loop face straps. The first embodiment of the orthosis, orthosis-thumb, is illustrated in FIG. 1. For simplicity and conciseness, it is being referred to as orthosis-thumb because it uses the embodiment of the wrist cuff assembly that uses thumbscrews. The second embodiment of the orthosis, orthosis-strap, is illustrated in FIG. 2. For simplicity and conciseness, it is being referred to as orthosis-strap because it uses the embodiment of the wrist cuff assembly that uses hook and loop face straps.

For the sake of convenience, "orthosis" will be used to collectively refer to either embodiment of the orthosis, which includes orthosis-thumb and orthosis-strap. Similarly, "wrist cuff assembly" will be used to collectively refer to either embodiment of the wrist cuff assembly, which includes the wrist cuff assembly that uses thumbscrews and the wrist cuff assembly that uses straps.

Referring now to the invention in more detail, in FIG. 1 the orthosis-thumb includes one embodiment of a shoulder brace 21, a semicircular upper arm cuff assembly 19, a linear motion carriage assembly 18, a splint arm assembly 14, a worm gearbox assembly 8, and a thumbscrew wrist cuff assembly 7 all assembled together. The orthosis-strap of FIG. 2 includes the same components and assemblies except that instead of the thumbscrew wrist cuff assembly 7 it includes a strap wrist cuff assembly 28.

Figure 3:
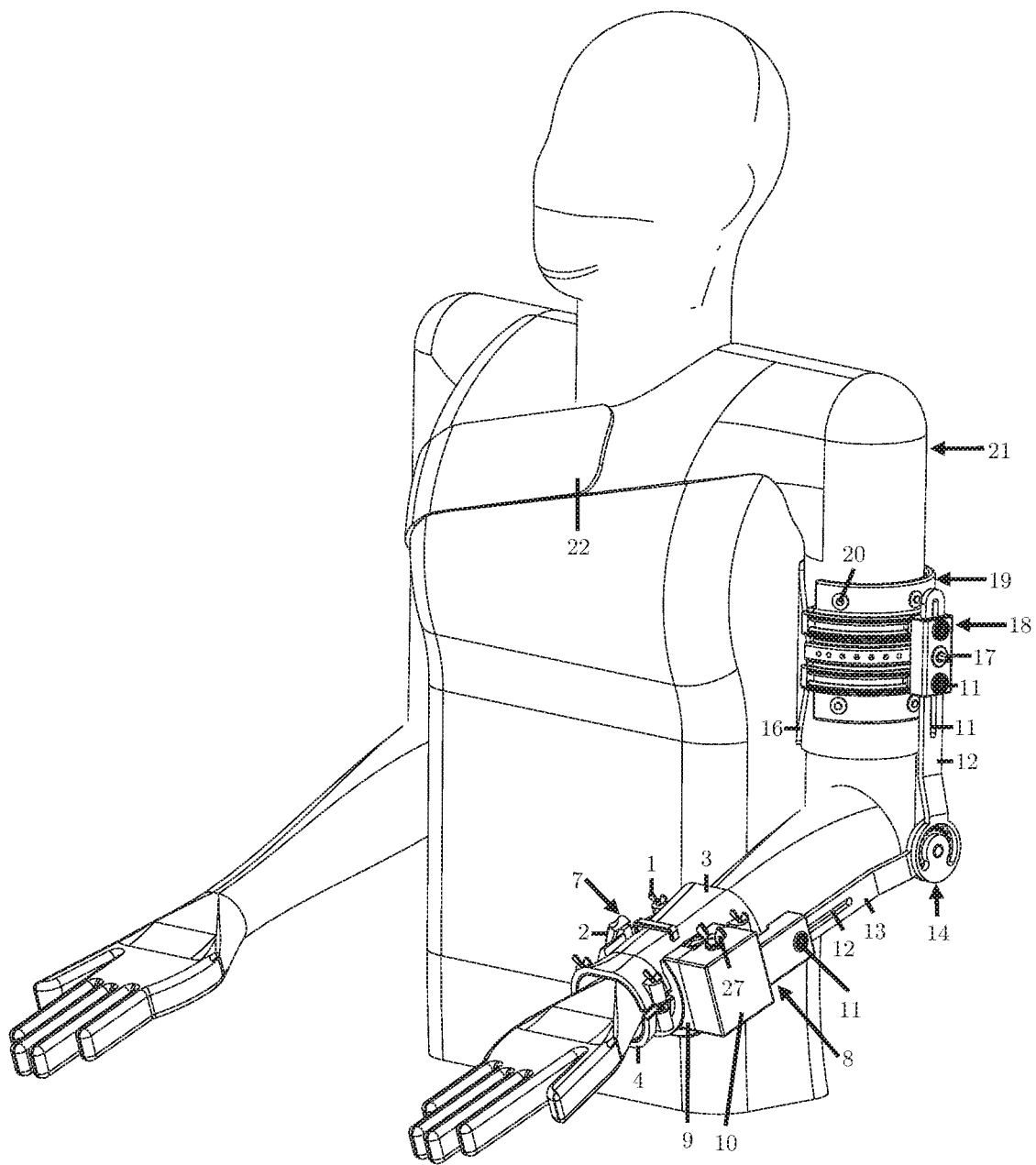
FIG. 3 is a perspective view of a person wearing the embodiment of the orthosis depicted in FIG. 1.
Figure 4:
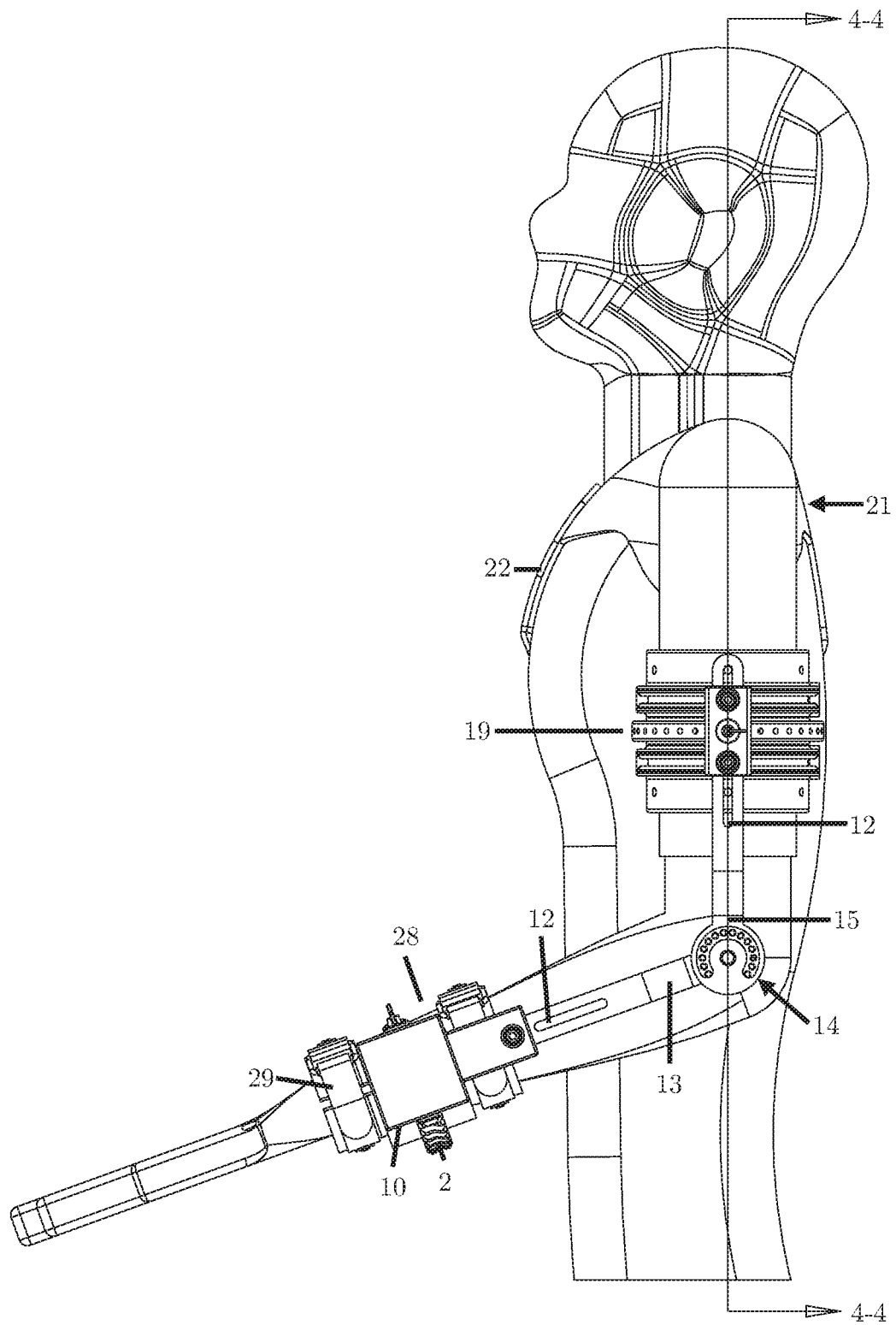
FIG. 4 is a right side view of a person wearing the embodiment of the orthosis shown in FIG. 2.
Figure 5:
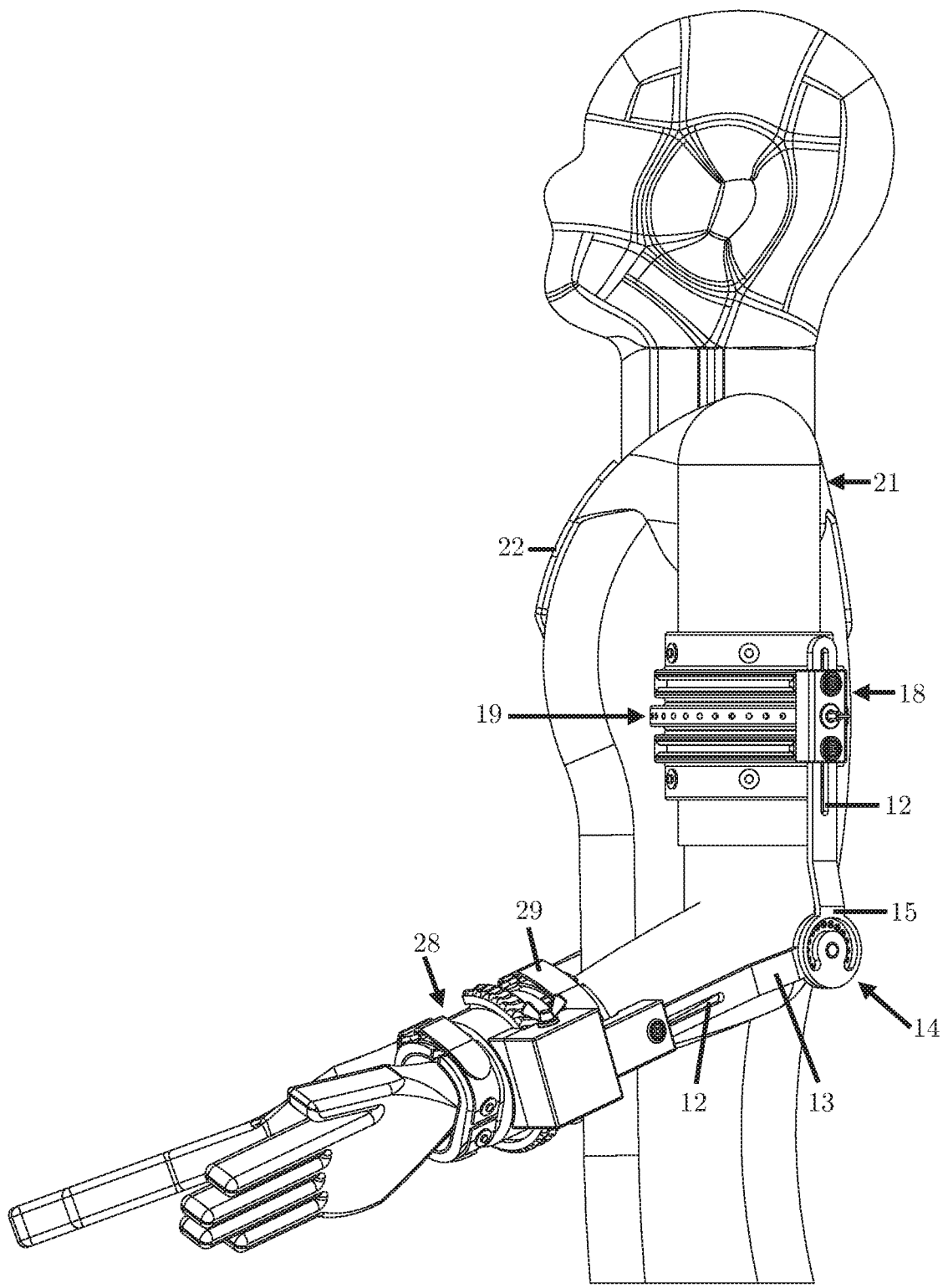
FIG. 5 is a right side view of a person wearing the embodiment of the orthosis shown in FIG. 2 with the person's arm externally rotated 130° from an internally rotated position parallel to the torso, the forearm being rotated a few degrees from the fully supinated position.

FIG. 3 shows a perspective view of how the orthosis-thumb is contemplated to be worn on the upper body of the user. The orthosis-strap is contemplated to be worn in an identical way except that the strap wrist cuff assembly 28 is worn in place of the thumbscrew wrist cuff assembly 7. FIG. 4 shows a right side view of a person wearing the orthosis-strap. FIG. 5 shows the same right side view of FIG. 4 but with the arm externally rotated 130° from an internally rotated position parallel to the torso and the forearm rotated a few degrees from the fully supinated position as an example of how the orthosis looks in a different anatomical position.

Figure 6:
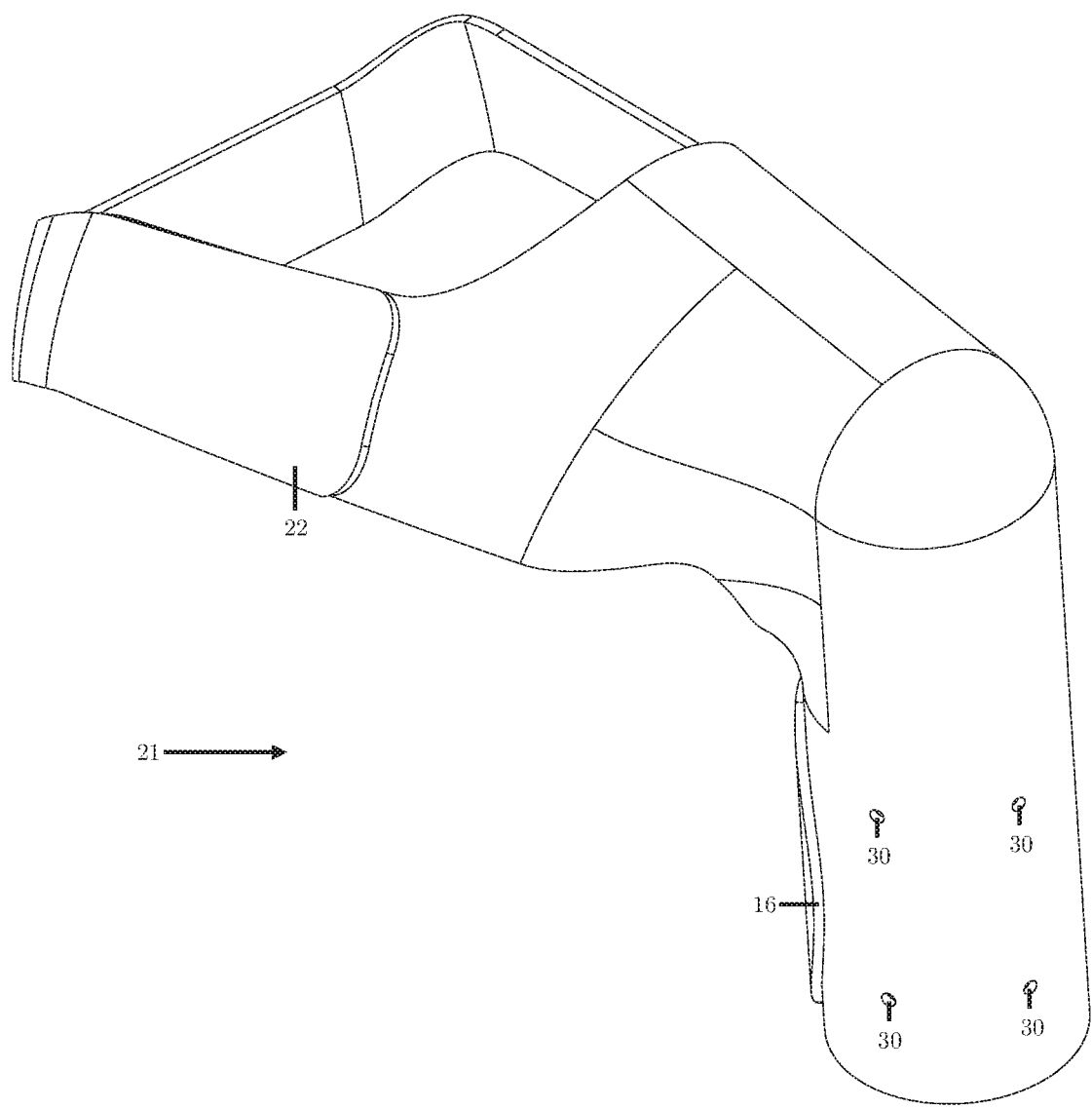
FIG. 6 is a perspective view of one contemplated embodiment of the shoulder brace of the present invention, which is shown assembled to the orthosis in FIGS. 1-5.
Figure 7:
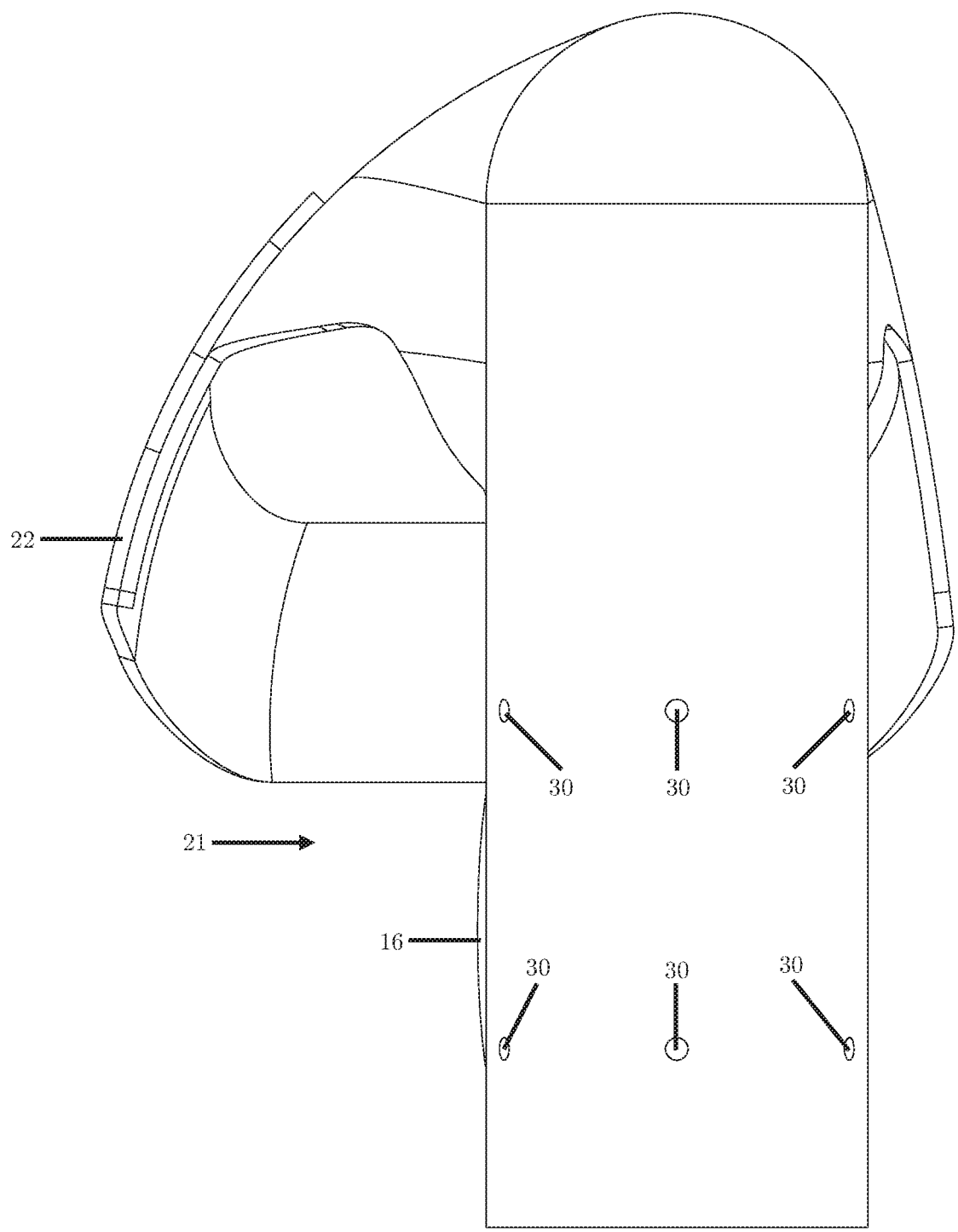
FIG. 7 is a right side view of the embodiment of the shoulder brace shown in FIG. 6.
Figure 8:
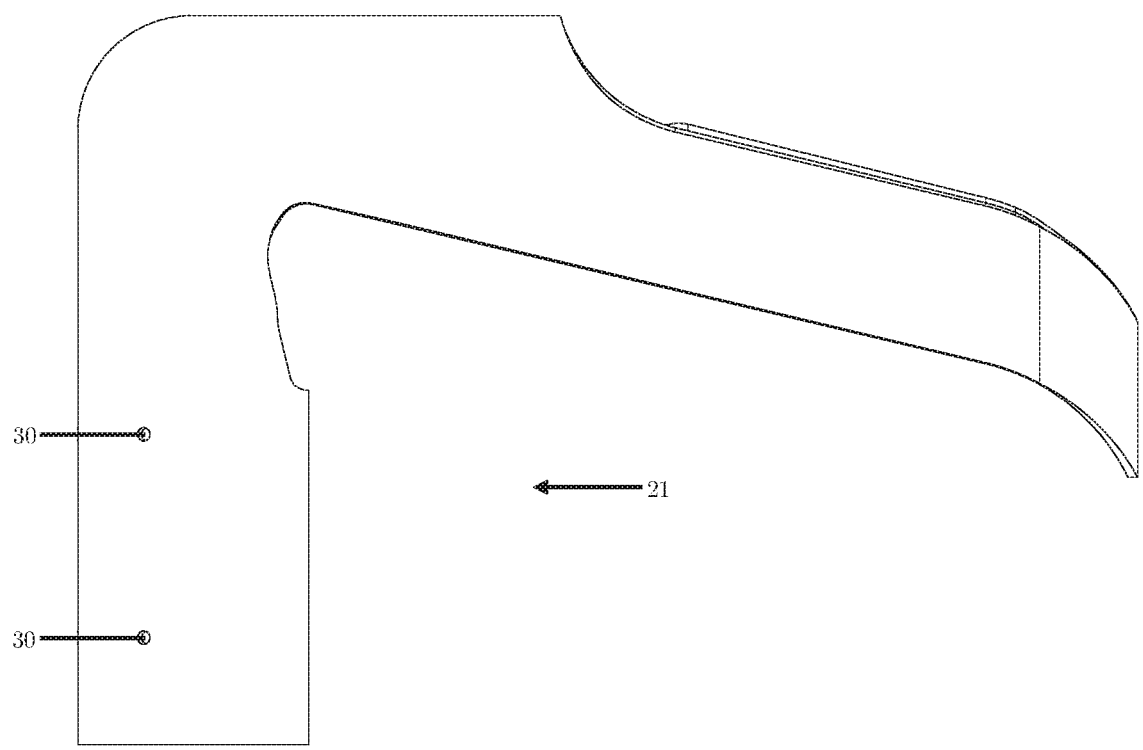
FIG. 8 is a rear view of the embodiment of the shoulder brace shown in FIG. 6.

As illustrated in FIGS. 6-8, the shoulder brace 21 includes an upper arm strap 16, a chest strap 22, and rivet holes 30.

As a preliminary matter, the shoulder brace 21 is contemplated to be flexible and therefore made of a fabric such as neoprene.

The orthosis is contemplated to be worn by putting on and securing the shoulder brace 21 and by securing the wrist cuff assembly to the wrist and adjacent forearm. The shoulder brace 21 is contemplated to be put on by securing the upper arm strap 16 and by securing the chest strap 22. In one embodiment of both straps 16, 22, it is contemplated that they be secured using hook and loop fasteners on the surfaces that contact each other. Alternatively, the straps 16, 22 may be secured using buckles, clips, ties, chafe loops with hook and loop fasteners, or another equivalent and satisfactory technique without departing from the scope of the present invention.

As illustrated in FIG. 3, the upper arm strap 16 wraps around the upper arm. As also illustrated in FIG. 3, the chest strap 22, starting from the backside of the shoulder of the same arm, wraps around the back, curves around the right side of the torso, and wraps around the chest, before being secured to a portion of the shoulder brace 21 that runs across the chest and stops just short of the right side of the torso. As shown in FIGS. 3-5, the shoulder brace 21 completely envelopes the shoulder of the same arm while leaving the other shoulder free. The upper arm strap 16 and chest strap 22 are pulled tightly enough to secure the shoulder brace 21 with minimal wiggle and slip.

It is contemplated that the shoulder brace 21 could either be worn directly on the skin or on top of clothing, depending on what the user finds to be more comfortable or secure. If worn on top of clothing, the clothing is presumed to be thin enough for the straps to be fully engageable and for the orthosis to be held securely.

It is one aspect of the shoulder brace 21 to be flexible so as not to hinder the range of motion of the shoulder while the orthosis is being worn. This is accomplished by the shoulder brace 21 being made of a fabric and, ideally, one that is elastic. Elasticity in the material would help create tension in the straps 16, 22 and thus a more secure fit. A few contemplated possibilities are neoprene, spandex, rubber, selvage, vinyl, velvet, denim, cotton, and polyester, among other materials that allow the shoulder brace 21 to serve its standard purpose while at the same time allowing the shoulder to move through all of its normal angular range. However, the shoulder brace 21 may be made from any suitable material without departing from the scope of the present invention. It is contemplated that the fabric be ⅛-¼ inches thick, but a thickness outside of this range may be established within the scope of the present invention.

The primary function of the shoulder brace 21 is to serve as an attachment point for the components and assemblies that comprise the orthosis. Because the shoulder brace 21 is secured to the chest, back, and shoulder, most of the weight of the orthosis, and any tugging forces that might be placed on it, is borne by the chest, back, and shoulder. In other words, the weight of the components and assemblies that attach to the shoulder brace 21, and any forces that might be placed on it—especially those that are expected to be encountered during resistance training—is distributed throughout the shoulder brace 21. These forces are then transferred from the shoulder brace 21 to the chest, back, and shoulder.

The use of the shoulder brace 21 as the primary means of wearing the orthosis and as an attachment point for the components and assemblies that comprise it is advantageous, for several reasons, over the way that arm orthoses are commonly worn, which is apparent to those skilled in the art. Arm orthoses are commonly worn by securing cuffs to the upper and lower arm, usually a padded thermoplastic, using chafe loops in conjunction with hook and loop straps. The orthosis stays on the arm because of the squeezing and friction forces of the cuffs and straps.

The first advantage is that when the shoulder brace 21 is used, the weight of the orthosis and any forces that might be placed on it is distributed to the chest, back, and shoulder, as was discussed in the previous paragraph. In contrast, with the more common arm orthosis, its weight and any forces that might be placed on it is distributed primarily to the upper and lower arm. The chest, back, and shoulder are collectively a much solider anchor point and can bear weight more comfortably than the upper and lower arm. This is because the weight of an external object added to the body is much easier to bear when it's spread over the relatively large area of the chest, back, and shoulders rather than being concentrated in the relatively small areas of the upper and lower arm. This is the same reason why a backpack of several pounds can be worn comfortably over the shoulders.

Additionally, the shoulder brace 21 should be much more comfortable and secure because of the way the common arm orthosis relies on the squeeze to the upper and lower arm and on friction. Such a squeeze may reduce circulation and cause heat and perspiration to build up around the arm, in addition to possible marking on the arm from the cuff rubbing against it. This may be especially uncomfortable when the orthosis is being worn for long periods of time. There is also a potential for the cuffs to slip, causing the orthosis to come out of alignment and lose some of its effectiveness. Instead of a squeezing force and friction, the shoulder brace 21 relies on the internal strength of the bones and muscles of the chest, back, and shoulder. There is no way for an upper arm cuff attached to the shoulder brace 21 to slip unless the shoulder brace 21 itself slips, which is unlikely because it could not slide past the shoulders without ripping.

A third advantage of the shoulder brace 21 over the common arm orthosis is that with the upper arm strap 16 of the shoulder brace 21 pulled taught and secured, it easily permits the upper arm to rotate while remaining secure because of it being anchored to the chest, back, and shoulder rather than directly to the upper arm. In contrast, because the common arm orthosis is strapped to the upper arm itself there is no way for the upper arm to rotate within the cuff and still be secure. When the arm dangles from the shoulder or is raised away from the body, at any angle, and the forearm is actively rotated, the upper arm rotates with it, through a number of degrees, at certain points in the forearm rotation (i.e. forearm rotation and shoulder internal/external rotation are coupled to each other). This upper arm rotation is therefore permitted by the shoulder brace 21 but prohibited by the common arm orthosis. In other words, with the shoulder brace 21, rotation can occur with respect to the shoulder but, with the common arm orthosis, rotation can only occur with respect to the upper arm. This means that a common arm orthosis configured to provide supination and pronation could not do it fully, as it would fall short of the degrees through which the upper arm rotates. It would be successful, however, at providing full supination or pronation when the elbow is fixed, which could occur, for example, with the elbow propped up on a table and the forearm flexed at the elbow.

In addition to the shoulder brace's 21 main function as a point of attachment for the assemblies and components of the orthosis, it is contemplated that it would also, simultaneously, serve the purpose of a standard shoulder brace, which is familiar to those skilled in the art. This purpose is to alleviate pain and discomfort to the shoulder area by providing support to the rotator cuff. Causes of such pain and discomfort include but are not limited to sprains, tendonitis, arthritis, and subluxations.

Figure 9:
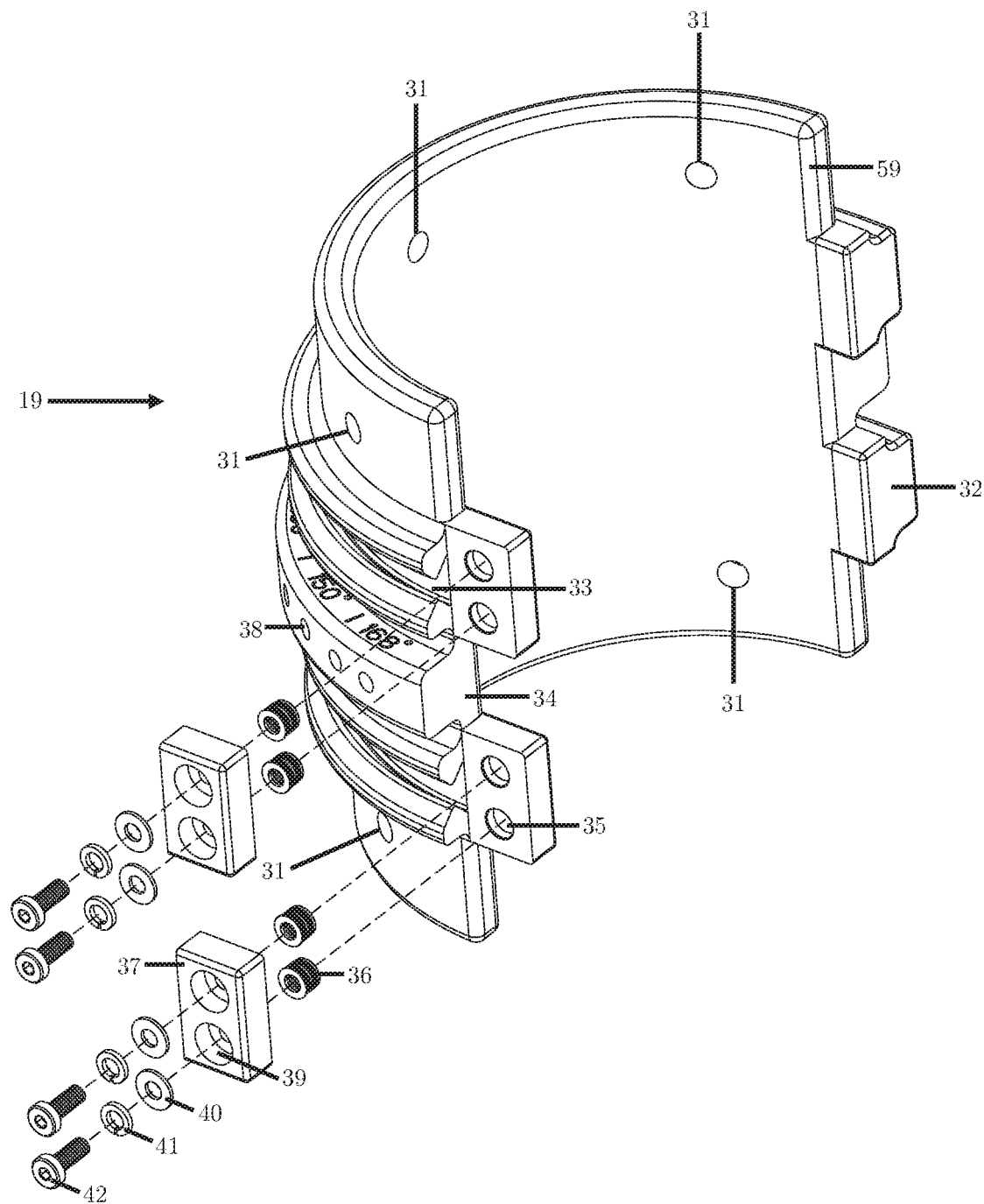
FIG. 9 is an exploded view of one contemplated embodiment of the semicircular upper cuff assembly of the present invention, which is shown assembled to the orthosis in FIGS. 1-5 and FIGS. 14-16.

The exploded view of FIG. 9 shows a contemplated upper arm cuff assembly 59 19. A semicircular upper arm cuff 59 is the main body in the assembly. It has six contemplated rivet holes 31 for attachment to the shoulder brace 21. One diameter contemplated for each hole 31 is that which is suitable for a No. 8 belt rivet, or 0.2 inches. More or less holes 31 may be used without departing from the scope of the present invention. Additionally, any diameter hole that can reasonably fit on the face of the upper arm cuff 59 without it losing its rigidity may be used without departing from the scope of the present invention. The six rivet holes 31 of the upper arm cuff 59 mate with the six rivet holes 30 of the shoulder brace 21, which are shown in FIGS. 6-8. Since the shoulder brace 21 is made of fabric, the diameter of the rivet holes 30 should be less than or equal to that of the rivet holes 31 of the upper arm cuff 59. This is because the rivet holes 30 of the shoulder brace 21 can stretch and therefore need only be large enough to allow for stretching, without ripping, when the rivet is poked through.

Figure 58:
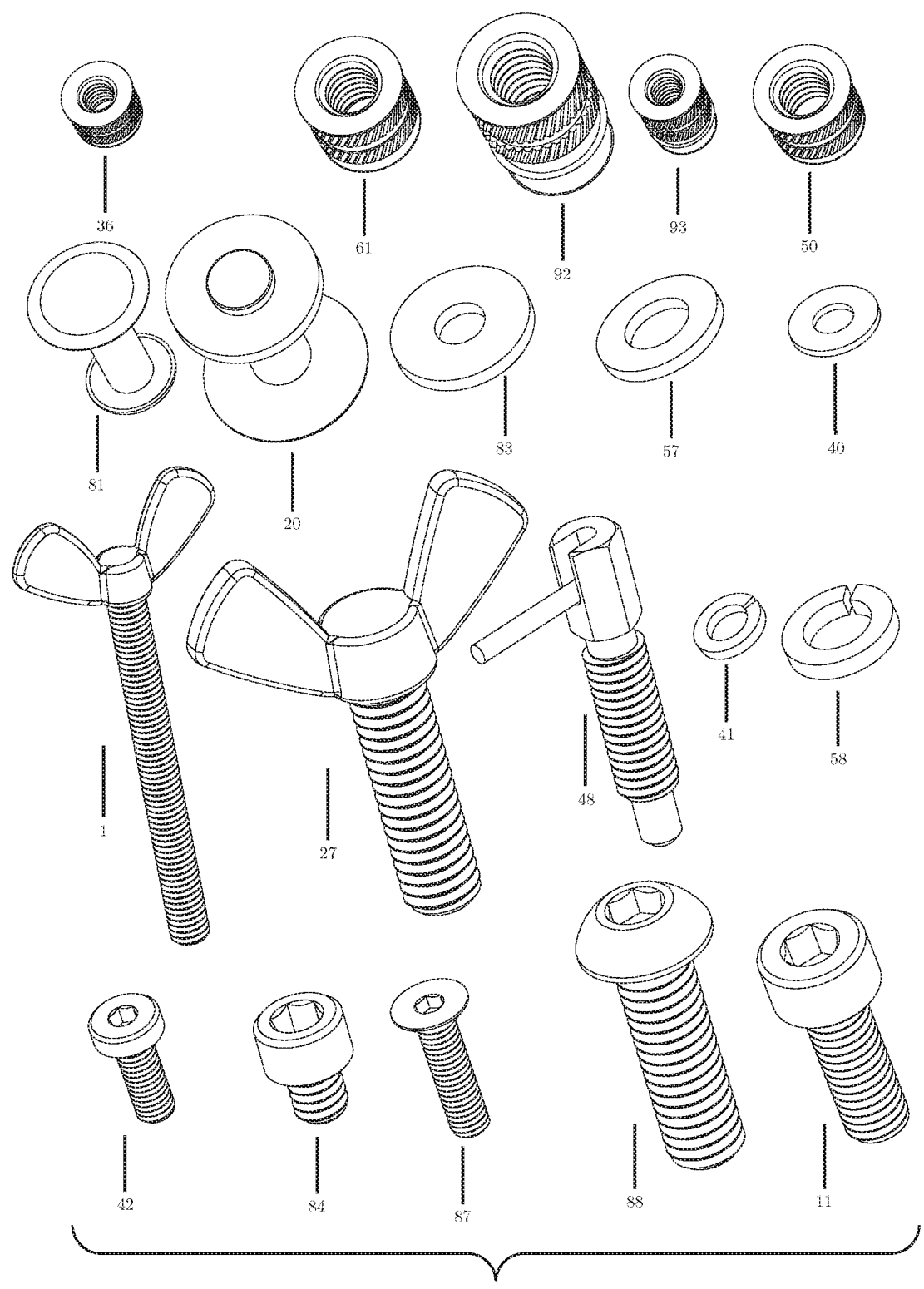
FIG. 58 contains front perspective views of all the hardware used in the contemplated embodiments of the orthosis of the present invention at the same scale (but not to scale), which includes heat-set threaded inserts, rivets, washers, screws, thumbscrews, and the retractable spring plunger.

It is contemplated that the upper arm cuff assembly 19 is fastened to the shoulder brace 21 using No. 8 belt rivets, which are more formally known as flush-mount solid rivets with washers, with one rivet used for each mated pair of rivet holes. With the rivet installed, the washer sits flush with the surface of the upper arm cuff 59 and the head sits flush with the surface of the shoulder brace 21. FIG. 58 shows what the rivet 20 looks like, after it has been set and peened, in relative size to the other hardware used throughout the embodiment of the orthosis being presented in this section, although the length may vary depending on the thickness of the materials being fastened.

FIGS. 1-3 and FIGS. 15-16 show the upper arm cuff assembly 19 installed to the shoulder brace 21 with the rivets 20. It is contemplated that the rivets 20 may be made of copper, as copper is the material most commonly used for belt rivets, but any other material, including but not limited to plastics and other metals, may be used without departing from the scope of the present invention. The size of the rivets 20 also need not be No. 8. Without departing from the scope of the present invention, they may be any size, so long as the shoulder brace rivet holes 30 and upper arm cuff rivet holes 31 are sized accordingly, and so long as the surface of the upper arm cuff 59 can accommodate the washer without its integrity being compromised. Additionally, it is not necessary for the upper arm cuff assembly 19 to be fastened to the shoulder brace 21 using the rivets 20. Other suitable fastening methods, such as other rivet types, stitching, tapes, or epoxy, may be used without departing from the scope of the present invention.

When installed, the axis of the upper arm cuff assembly 19 is coincident with the rotational axis of the humerus. Additionally, the upper arm cuff assembly 19 is rotated so that the tangent lines to the end of the semicircular arc are parallel to the torso. The locations of the rivet holes 30 on the shoulder brace 21 are chosen so that these conditions are satisfied. The inner diameter of the upper arm cuff 59 is chosen to be equal to or slightly larger than the outside diameter of the portion of the shoulder brace 21 that loops around the upper arm. The thickness of the upper arm cuff 59 is contemplated to be ¼ inch, but any thickness that does not compromise the rigidity of the upper arm cuff 59 can be chosen without departing from the scope of the present invention. As will be delineated in further sections, the coincidence of the axis of the upper arm cuff assembly 19 and the rotational axis of the humerus means that anything that moves along the surface of the upper arm cuff 59, and that's coupled to the forearm, will move with the arm as it rotates internally or externally.

Figure 15:
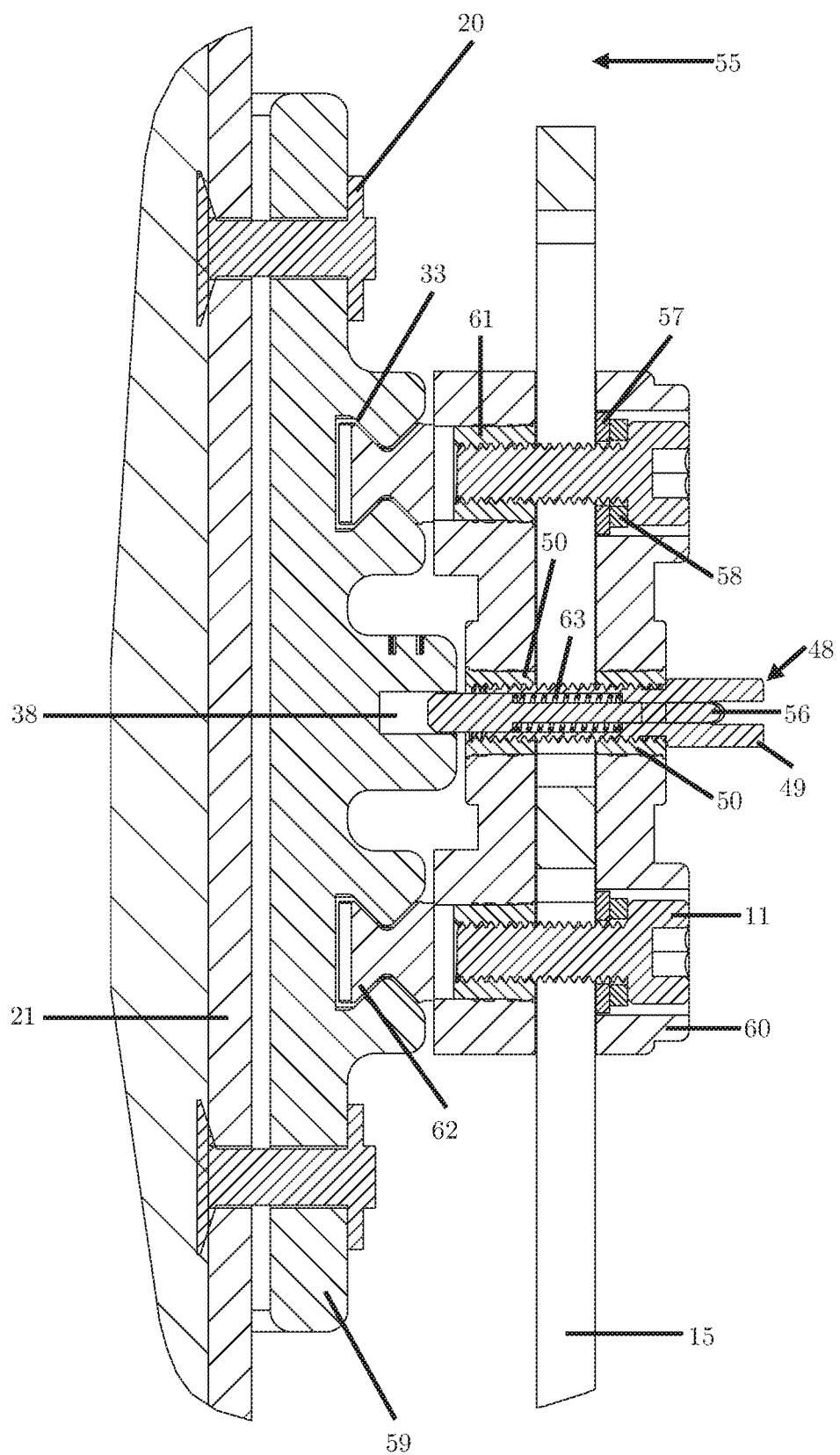
FIG. 15 is a cross-sectional detail view, taken along plane 4-4 in FIG. 4 and encircled by the circle 55 in FIG. 14, that shows the engagement of the upper arm cuff with the linear motion carriage assembly, the nose of the retractable spring plunger being shown engaged in the 90° index hole of the upper arm cuff.
Figure 16:
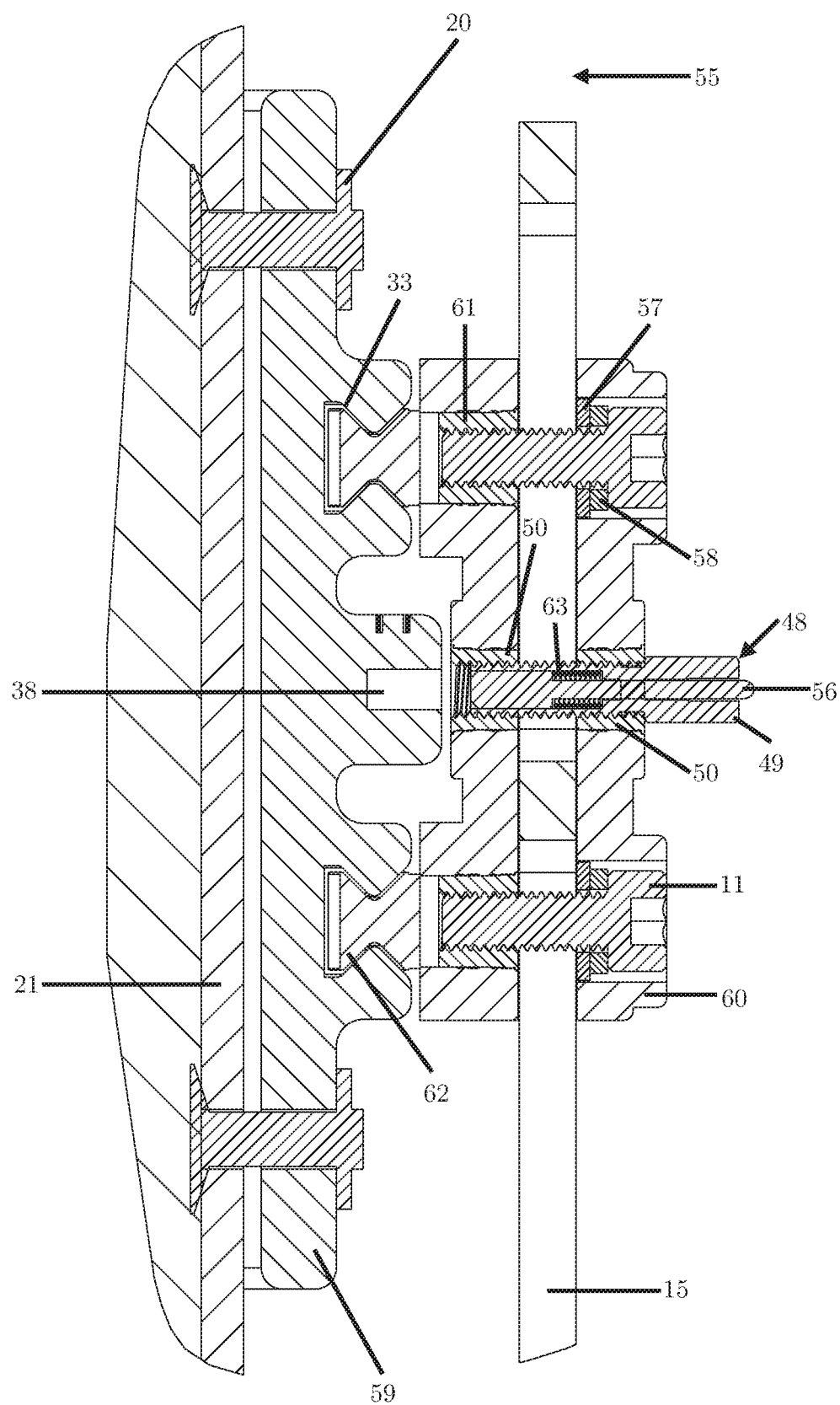
FIG. 16 is a cross-sectional detail view, taken along plane 4-4 in FIG. 4 and encircled by the circle 55 in FIG. 14, that shows the engagement of the upper arm cuff with the linear motion carriage assembly, the nose of the retractable spring plunger being shown in the retracted and locked position.

As shown in FIGS. 9-12 and in FIGS. 15-16, an upper and lower curvilinear, semicircular, guide track 33 is molded to the upper arm cuff 59. The profile of the track 33 is easily seen in the cross-sectional views of FIGS. 15-16. It is contemplated that the profile of the track 33 be such that a linear motion carriage bearing would be slidingly disposed to and would ride along the inside rather than outside. This helps to minimize the buildup of dust and other debris that might hinder the motion of the linear motion carriage.

It is also contemplated that the profile of each track 33 be such that a single bearing riding along one of the tracks 33 only has the freedom to follow the arc and not to roll, pitch, or yaw about a set of three perpendicular axes through a point in the center of the bearing. This means that the linear motion carriage would be highly stable in its motion along the track 33. As shown in FIGS. 15-16, the track 33 is generally "X" shaped and is effective at preventing rolling, pitching, or yawing of the linear motion carriage.

While an "X" shape is used for the tracks 33 of the upper arm cuff 59 embodiment of the present invention, there are many other profiles that could achieve the objective of roll, pitch, and yaw prevention and any such profile may be used without departing from the scope of the present invention. Additionally, a track profile that does not satisfy the roll prevention objective for a single bearing and carriage might satisfy it when two identical tracks are used with one connected carriage. This is the case, for example, with a round profile. A round profile, or any profile that satisfies the roll, pitch, and yaw prevention objectives through the use of two identical tracks, but fails to meet one of the objectives when a single track is used, may be used without departing from the scope of the present invention. Additionally, the two tracks may have different profiles and fall within the scope of the present invention. Furthermore, while the upper arm cuff 59 embodiment uses tracks 33 with an internal profile, where the bearing of a linear motion carriage is intended to travel along the inside surfaces of the track, a rail in which the carriage travels along the outside surfaces could be used instead without departing from the scope of the present invention.

It is contemplated that each track 33 would have the bearing of a linear motion carriage traveling along it but that there would be a single carriage for both bearings. In other words, rather than each bearing having its own carriage and separate areas where a load can be attached, the two carriages would be connected together to form one carriage to which a load can be attached. The use of such a dual carriage assembly decreases the likelihood of the carriages rolling compared to that in a single carriage configuration and increases the distance from the carriage that a load can safely be carried without failure.

As shown in FIG. 9, the end of each track 33 on one side of the upper arm cuff 59 is open so that a linear motion carriage can be slid on. Molded to the upper arm cuff 59 at the end of each track 33, on the opposite side of the upper arm cuff 59, is an end cap 32 that prevents the linear motion carriage from sliding off. On the open end of each track 33, it is contemplated that a removable end cap 37 can be installed, after the linear motion carriage has been slid on, to prevent the carriage from sliding off the end.

The removable end cap 37 is installed using a set of hardware that includes an M3 socket cap screw 42, an M3 split lock washer 41, and M3 flat washer 40, and an M3 heat set threaded insert 36. This hardware is shown in FIG. 58 in contemplated relative scale to the other hardware used throughout the orthosis. The heat set threaded insert 36 is installed into a molded pocket 35 so that the top is flush with the adjacent surface. Once the removable end cap is put in place 37, the M3 flat washer 40. M3 split, lock washer 41, and M3 socket cap screw 42 are installed in the order shown in FIG. 9.

Figure 10:
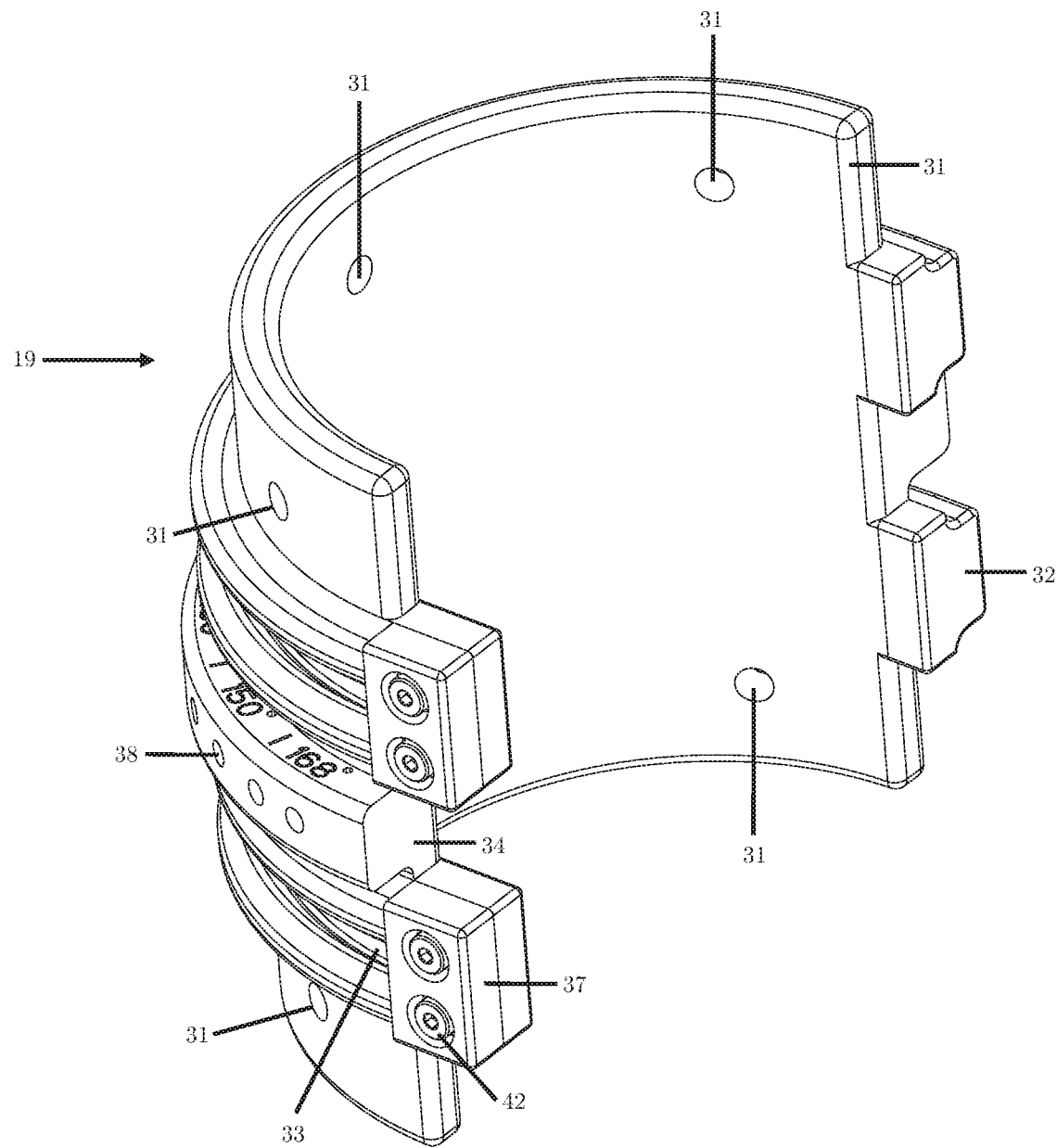
FIG. 10 is an unexploded view of the embodiment of the semicircular upper cuff assembly shown in FIG. 9.
Figure 11:
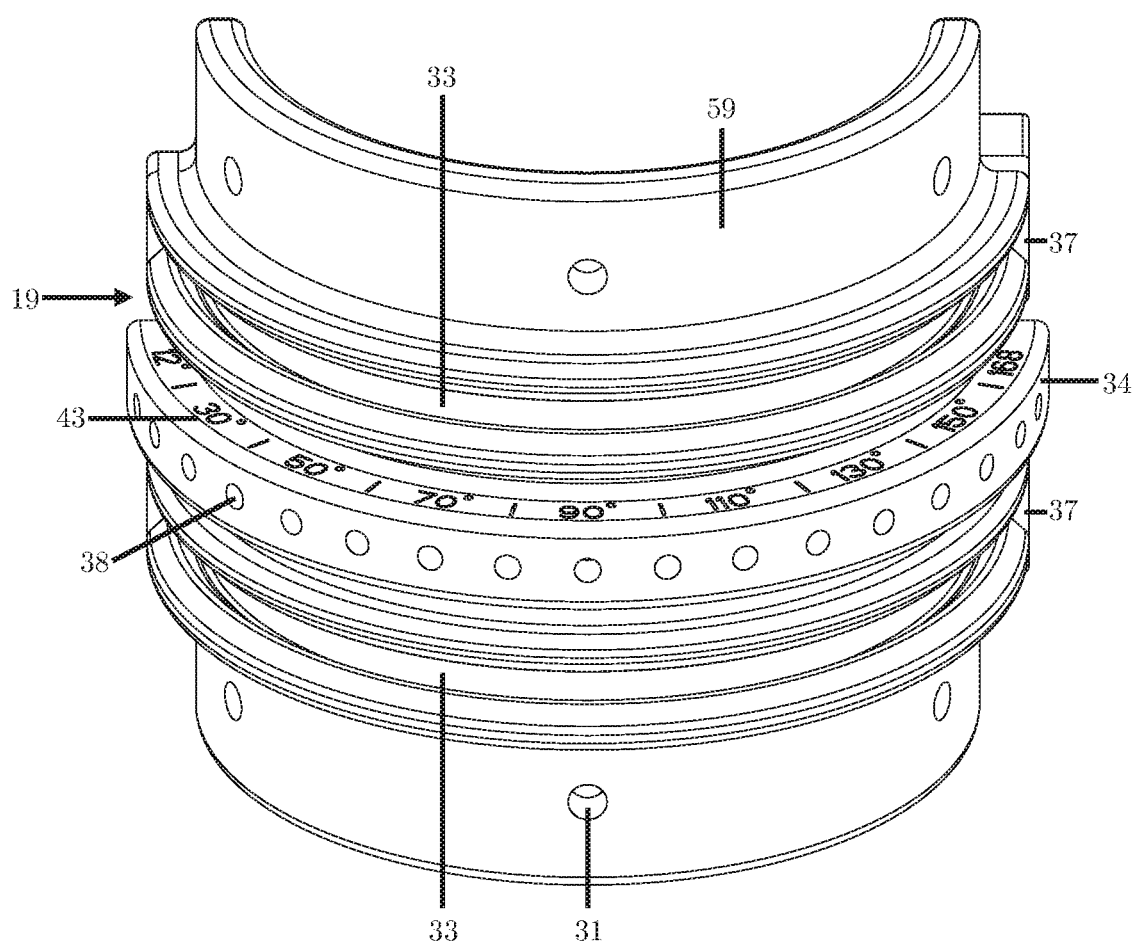
FIG. 11 is a right perspective view of the embodiment of the semicircular upper cuff assembly of FIG. 9.
Figure 12:
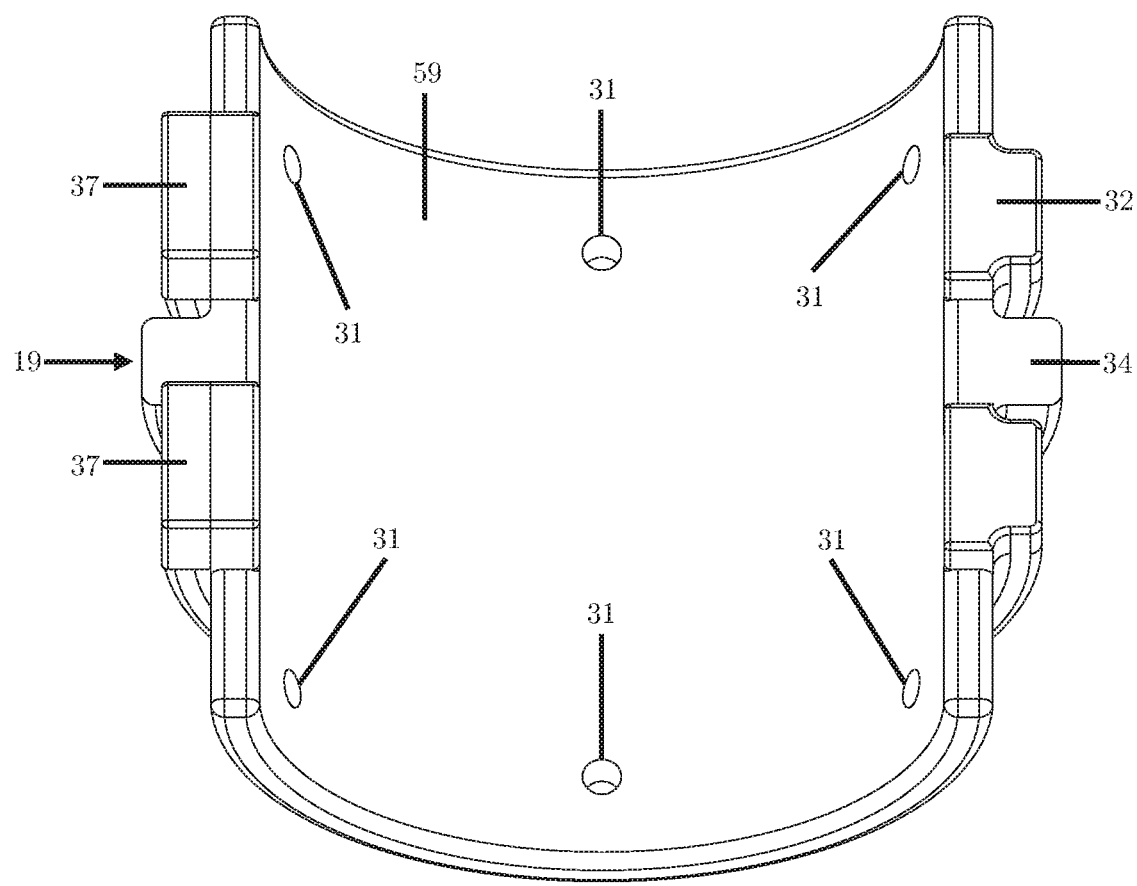
FIG. 12 is a left perspective view of the embodiment of the semicircular upper cuff assembly of FIG. 9.

FIG. 10 shows how the assembly looks with the hardware installed. The M3 flat washer 40 serves to spread the load from the M3 socket cap screw 42 and prevent the underlying material from getting damaged. The M3 split lock washer 41 serves to help prevent the M3 socket cap screw 42 from loosening.

It is contemplated that the upper arm cuff 59 and removable end caps 37 be made of thermoplastic material but any other rigid material may be used without departing from the scope of the present invention.

Figure 13:
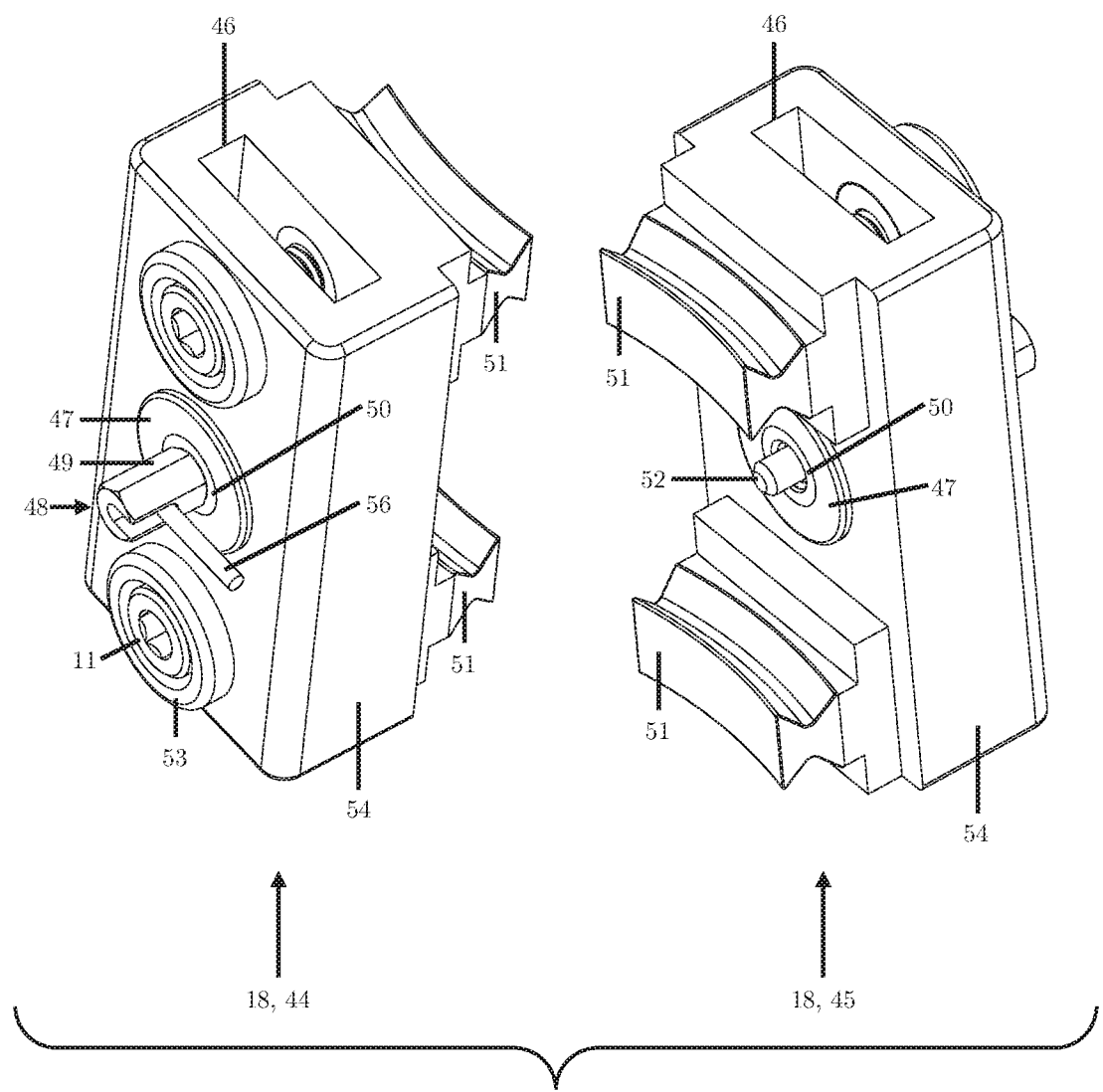
FIG. 13 contains a back right perspective view 44 of one contemplated embodiment of the linear motion carriage assembly on the left and a front left perspective view 45 of the assembly on the right, shown assembled to the orthosis in FIGS. 1-5 and FIGS. 14-16.
Figure 14:
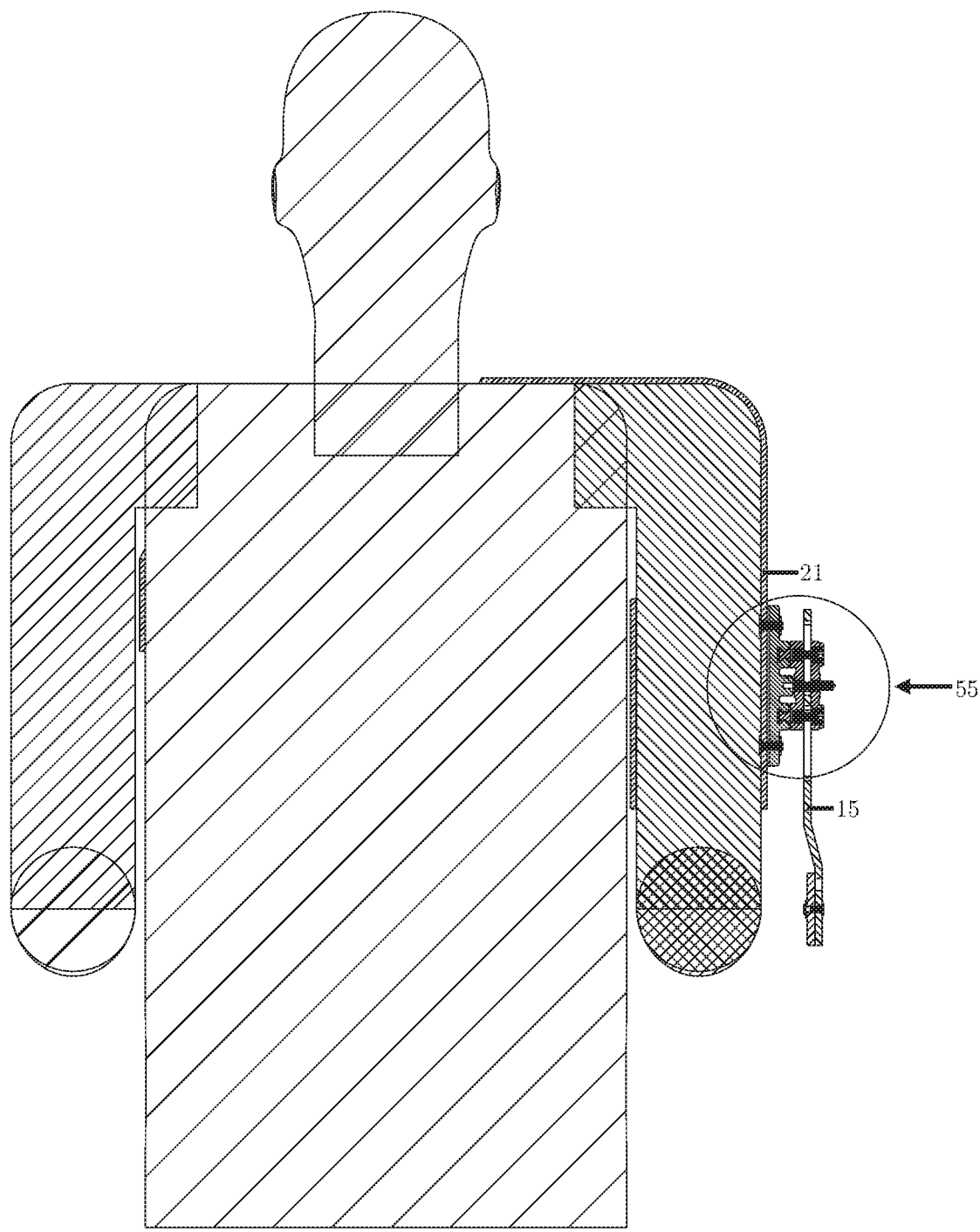
FIG. 14 is a front cross-sectional view of a person wearing the orthosis, taken along plane 4-4 of FIG. 4. The circle 55 encloses the area of the detail views shown in FIGS. 15 and 16.

FIG. 13 shows a back right perspective view 44 of the embodiment of the linear motion carriage assembly 18 and a front left perspective view 45 of the embodiment of the linear motion carriage assembly 18. It is shown assembled to the orthosis in FIGS. 1-5 and FIGS. 14-16. A linear motion carriage 54 is the main body of the assembly. A rectangular hole 46 runs from the top to the bottom of linear motion the carriage. Two bearings 51 are molded to one side of the linear motion carriage. They have an "X" shaped profile that corresponds to and fits, with a sliding disposition, into the tracks 33 of the upper arm cuff 59. They are arc shaped with a radius of curvature selected that makes the center of the arc circle coincident with the rotational axis of the humerus and makes the bearing 51 line up appropriately to engage in the track 33. The cross-sectional views of FIGS. 15-16 show the engagement of the linear motion carriage assembly 18 with the upper arm cuff 59. A small amount of clearance between the inner surfaces of the track 33 and the surfaces of the bearing 51 allow it to slide smoothly.

It is contemplated that the linear motion carriage 54 is made of a thermoplastic but any other sufficient material may be used without departing from the scope of the present invention.

The bearings 51 may either slide due to a sufficiently low coefficient of friction between the bearing surfaces and the inner surfaces of the tracks 33 or with the help of lubrication from a grease or oil, such as silicon-based greases or oils. The bearings 51 may also roll, rather than slide, by means of an embedded ball or roller bearing system, such as one that could be found on many traditional linear motion carriages, which is familiar to those skilled in the art. The medium through which the bearings 51 travel along the track 33, lubrication or no lubrication (low surface friction coefficient), embedded bearings or no embedded bearings, is immaterial to the scope of the present invention. A sliding medium with lubrication is selected for this embodiment because of the relative ease of manufacture, low number of required moving parts, low noise, decreased coefficient of friction, and increased part life. Additionally, because the bearing 51 is not intended to rotate constantly, as does a wheel for example, the use of embedded bearings is not perceived to be essential.

Referring back to FIG. 11, it is contemplated that a number of index holes 38 are molded into a protrusion 34 on the side of the upper arm cuff 59 and that the axis of each hole 38 is perpendicular to the cuff's axis. The holes 38 are spaced at angular positions that represent the angles at which the arm of the user can be locked in internal or external rotation. In the embodiment shown, there are 17 holes 38 and each hole, except for the holes on the end, is spaced 10° from the adjacent hole. To appropriately accommodate the width of the linear motion carriage 54, the holes 38 on the end are only spaced 80 from the adjacent hole. There is an embossed angular marking 43 on top of the protrusion 34 and above each hole 51 to indicate what angle is represented by the hole. The 0° reference plane passes through the ends of the semicircular arc. It is noted that any number of holes 38 and corresponding angular positions may be used without departing from the scope of the present invention.

Figure 17:
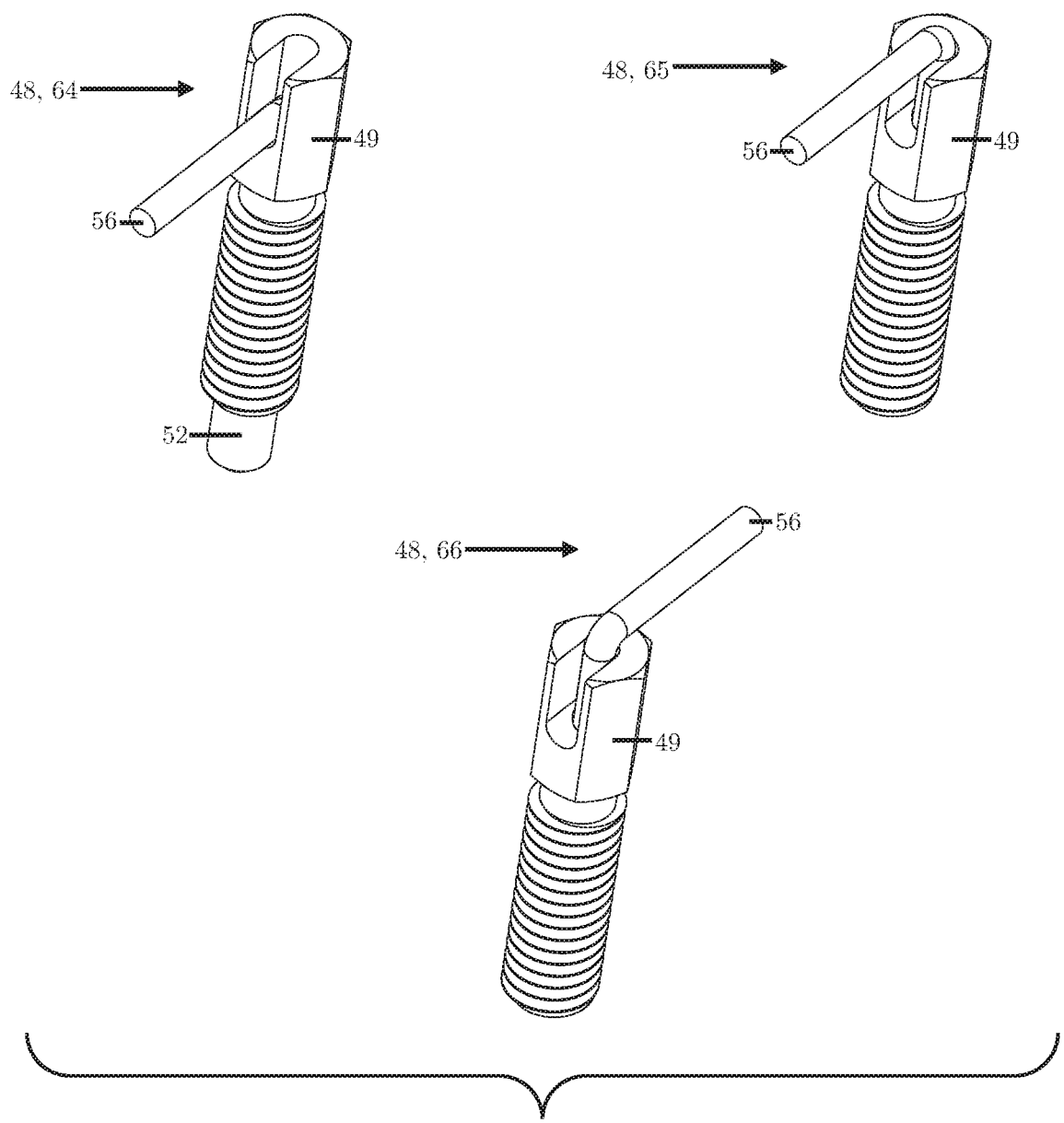
FIG. 17 contains a view 64 of the retractable spring plunger with the nose in the extended position, a view 65 of the retractable spring plunger with the nose in the retracted position, and a view 66 of the retractable spring plunger with the nose in the retracted and locked position, the retractable spring plunger being shown assembled to the orthosis in FIGS. 1-5 and FIGS. 14-16.

FIG. 17 shows a view 64 of one contemplated embodiment of a retractable spring plunger 48 with the nose 52 in the extended position, a view 65 of the retractable spring plunger 48 with the nose 52 in the retracted position, and a view 66 of the retractable spring plunger 48 with the nose 52 in the retracted and locked position. The nose 52 and handle 56 of the retractable spring plunger 48 are one solid shaft. The retractable spring plunger 48 is locked by retracting the nose 52 to the max position and rotating the handle 56 so that it rests on the body 49. The body 49 of the retractable spring plunger 48 has threads on it so that it may be installed by screwing it into a threaded hole.

Referring back to FIG. 13, it is contemplated that the retractable spring plunger 48 is installed in the center of the linear motion carriage 54. As shown in FIGS. 15-16, the retractable spring plunger 48 is screwed into two No. 10 heat set threaded inserts 50 that are embedded into the linear motion carriage 54 on each side of the rectangular hole 46. The No. 10 heat set threaded insert 50 is shown in FIG. 58 in relative scale with the other hardware used throughout the orthosis of the present invention.

FIG. 16 shows the nose 52 in the retracted position. A ground spring 63, disposed between the nose 52 and body 49 of the retractable spring plunger 48, is shown in a compressed position. The retracted position may be held by locking the handle 56 of the retractable spring plunger 48, as shown in view 66 of FIG. 17. When the nose 52 is retracted, the linear motion carriage 54, and therefore the connected lower assemblies of the orthosis, is free to rotate within the tracks 33 of the upper arm cuff 59.

FIG. 15 shows the nose 52 in the extended position and shows the spring 63 at equilibrium. When the nose 52 of the retractable spring plunger 48 is coincident with one of the angularly positioned holes 46 of the upper arm cuff 59, the nose 52 can be extended to its resting position so that it protrudes into the selected hole 46. In that instance, the nose 52 locks the linear motion carriage 54 in place at that angle. This is the case in FIG. 15 with the angle being 90°. The angular hole 46 is sized to be, at minimum, deep enough for the nose 52 not to hit the bottom of it when in the extended position and slightly larger in diameter than the nose 52—just large enough for it to smoothly slide when indexed but not so large that it wobbles when engaged.

It is noted that, instead of a plunger and index hole system where the linear motion carriage 54 can be locked at discrete angular positions, a different system for locking the position of the linear motion carriage could be used without, departing from the scope of the present invention. The system could be, for example, one that uses a set screw or clamping mechanism in lieu of the retractable spring plunger 48. Additionally, instead of a discrete set of selectable angles, the angles may vary continuously between the minimum and maximum and fall within the scope of the present invention.

Figure 18:
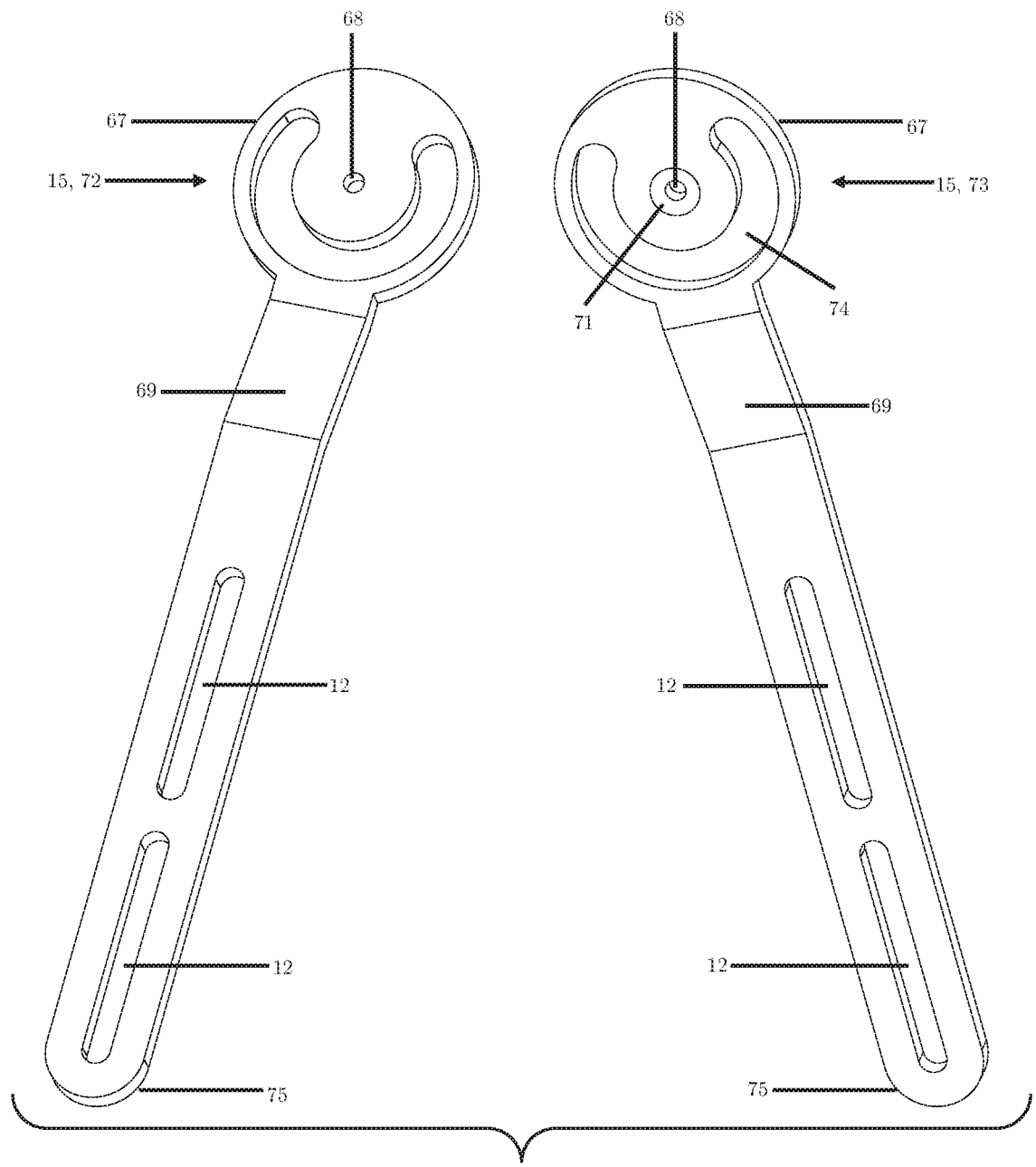
FIG. 18 contains a front perspective view 72 and a rear perspective view 73 of one contemplated embodiment of the upper splint arm, which is shown assembled to the orthosis in FIGS. 1-5.

FIG. 18 shows a front perspective view 72 and a rear perspective view 73 of one contemplated embodiment of an upper splint arm 15. The upper splint arm 15 is contemplated to be a rectangular bar with a bend 69 between the ends, a circular disk 67 at one end, and a semicircular arc 75 at the other. There are two obround slots 12 near the end of the bar with the semicircular arc 75 and an arced obround slot 74 centered on the circular disk 67 at a defined radial distance. A hole 68 for a rivet sits at the center of the circular disk 67 and is surrounded by a countersink 71 so that the head of the rivet may sit flush with the adjacent surface.

The semicircular arc end 75 of the upper splint arm 15 is slidingly disposed with respect to the rectangular hole 46 on the linear motion carriage 54 and is slid up and down for height adjustment. The height is selected so that the axis of the elbow is coincident to the axis of the circular disk 67, which ensures that the arm can be flexed at the elbow without hindrance. The bend 69 ensures that the circular disk 67 has sufficient clearance from the elbow of the user. The upper splint arm 15 is clamped against the inner back wall of the hole 46 by passing two screws 11 through either obround slot 12 and torquing them down. The screws 11 are shown installed in FIG. 13. As shown in the cross-sectional views of FIGS. 15-16, the screws 11 are screwed into an M5 heat set threaded insert 61 that is embedded in the linear motion carriage 54 and are preceded by an M5 flat washer 57 and an M5 split lock washer 58. The M5 flat washer 57 serves to spread the load from the M5 socket cap screw 11 to the upper splint arm 15. The M5 split lock washer 58 serves to help prevent the M5 socket cap screw 11 from loosening. In FIG. 58, the M5 socket cap screw 11, M5 heat set threaded insert 61, M5 flat washer 57, and M5 split lock washer 58 are shown in in contemplated relative scale to the other hardware used throughout the orthosis of the present invention. A cylindrical disk protrusion 53 on the surface of the linear motion carriage 54 allows the head of the screw 11 to be completely countersunk and is for aesthetic purposes. Without it, the linear motion carriage 58 might have to be exceedingly thick for the head of the screw 11 to be completely countersunk (which may arise when only certain screw lengths are available). Additionally, the set of hardware chosen for the linear motion carriage assembly 18 might obviate the need for the protrusion 53.

Figure 19:
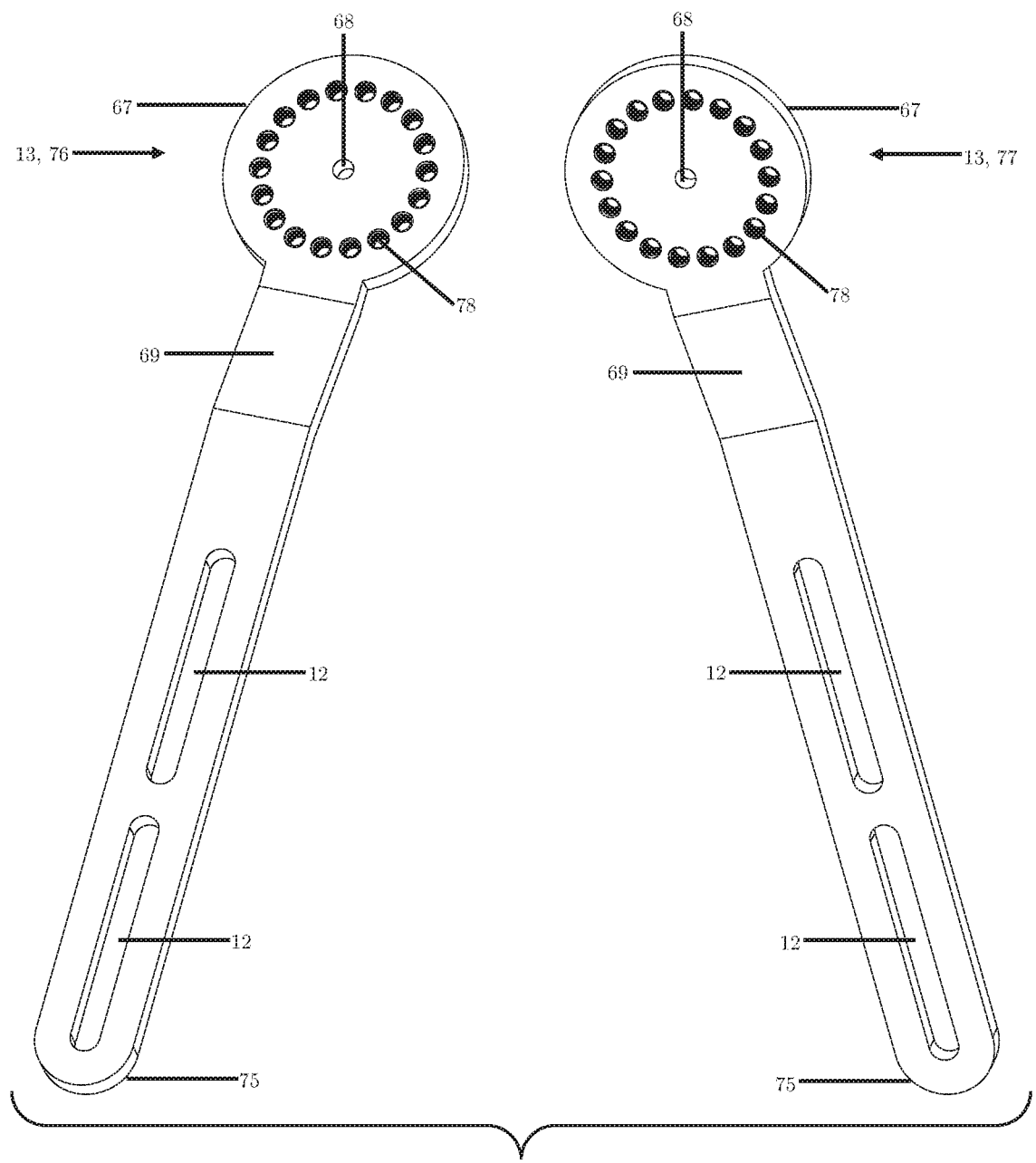
FIG. 19 contains a front perspective view 76 and a rear perspective view 77 of one contemplated embodiment of the lower splint arm which is shown assembled to the orthosis in FIGS. 1-5.

FIG. 19 shows a front perspective view 76 and a rear perspective view 77 of one contemplated embodiment of a lower splint arm 13. It is identical to the upper splint arm 15 except that it has a different set of features on the circular disk. The lower splint arm 13 is contemplated to be a rectangular bar with a bend 69 between the ends, a circular disk 67 at one end, and a semicircular arc 75 at the other. There are two obround slots 12 near the end of the bar with the semicircular arc 75. There are 18 equally-circumferentially-spaced No. 8 threaded holes 75 at a defined radial distance from the center of the circular disk. A hole 68 for a rivet sits at the center of the circular disk 67.

Figure 20:
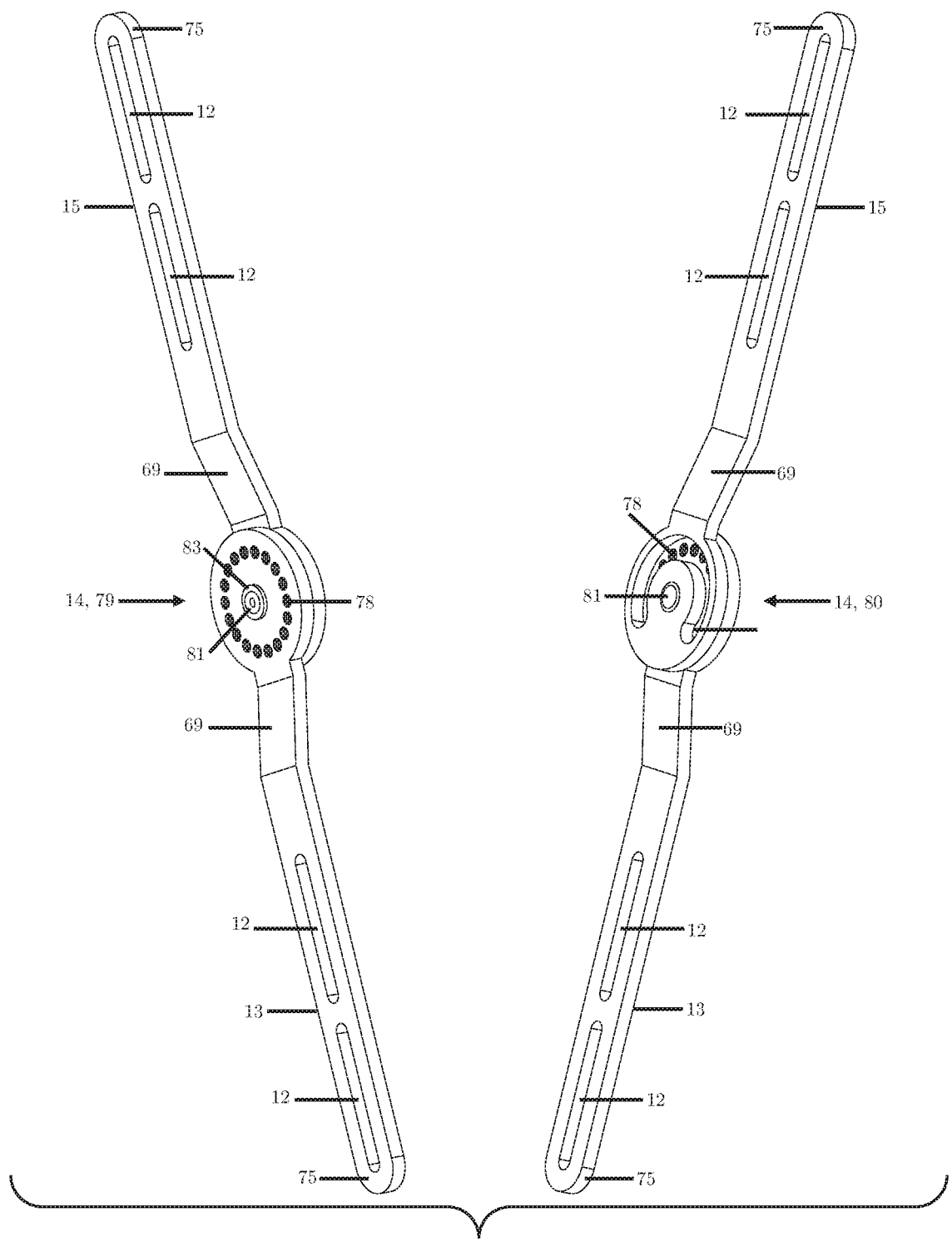
FIG. 20 contains a left perspective view 79 and a right perspective view 80 of the embodiment of the splint arm assembly, which is shown assembled to the orthosis in FIGS. 1-5.

FIG. 20 shows a left perspective view 79 of the splint arm assembly 14 and a right perspective view 80 of the splint arm assembly 14. It is contemplated that the upper splint arm 15 is riveted to the lower splint arm 13 at the center of the circular disks 67. A semitubular rivet 81 is installed in the rivet hole 68 and the hollow end is preceded by a washer 83 before being clinched.

Figure 21:
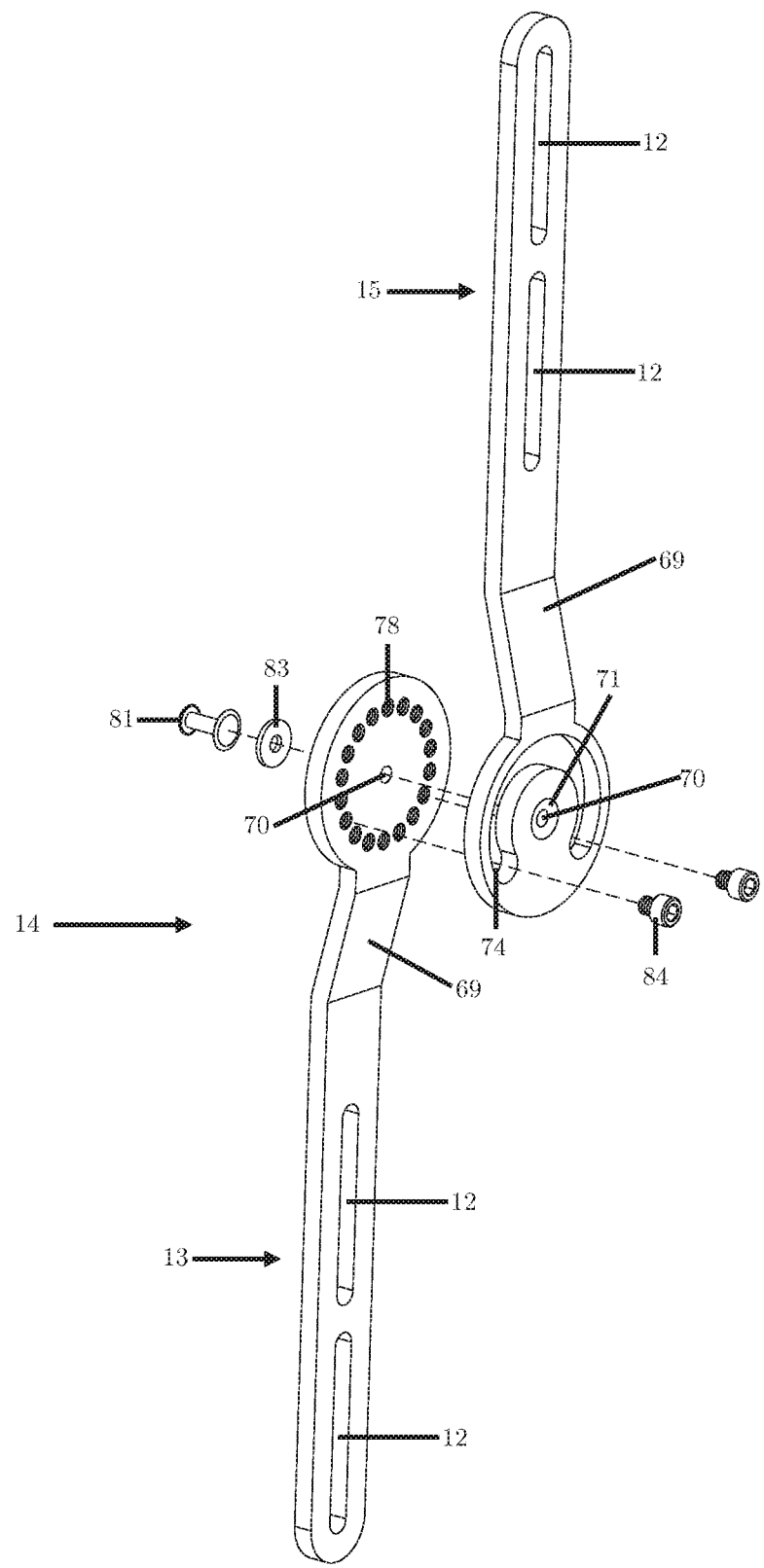
FIG. 21 is an exploded view of the embodiment of the splint arm assembly, which is shown assembled to the orthosis in FIGS. 1-5.

FIG. 21 shows an exploded view of the splint arm assembly 14. The countersink end of the rivet 81 sits in the countersink 71 of the upper splint arm 15. The splint arm assembly 14 is shown assembled to the orthosis in FIGS. 1-5.

It is of the nature of semitubular rivets to resist swelling during installation. The semitubular rivet 81 therefore creates a joint tight enough for the surfaces of the circular disks 67 to be flush against one another yet loose enough (with possible lubrication) for it to serve as a bearing about which the upper splint arm 15 and lower splint arm 13 can be rotated with respect to each other.

FIG. 21 shows two No. 8 screws 84. It is contemplated that by placing one or both of the screws 84 through the arced obround slot 74 of the upper splint arm 15 and threading one or both into select threaded holes 78 on the lower splint arm 13 that the elbow flexion range of motion can either be limited or locked. The screw(s) 84 hitting against the end(s) of the arced obround slot 74 prevent the splint arms 13, 15 from rotating with respect to each other. The capacity to limit or lock the range of motion potentially serves to allow the user to complete certain resistance exercises, to achieve certain stretches, or to achieve certain positions of comfort, among other uses. In the configuration shown in the figure, the splint arms 13, 15 would be locked in a position that would force the arm of the user to be straight. This configuration could, for example, allow the user to complete a dumbbell raise without expending muscular effort on keeping the arm straight.

While the semitubular rivet 81 is used to join the upper splint arm 15 and lower splint arm 13 and to act as a bearing, other fastening methods that permit the two arms to rotate with respect to one another may be used without departing from the scope of the present invention. Such methods include but are not limited to other rivet types, a nut and bolt, or a press-fitted shaft. Additionally, a bearing, such as a roller bearing, may be used on each of the circular disks 67 without departing from the scope of the present invention.

In regard to the upper splint arm and lower splint arm, it is noted that the size of the obround holes, length and and angle of the bend, and number of threaded holes can be varied, as long as the objective of each respective feature is still achieved, without departing from the scope of the present invention.

Figure 23:
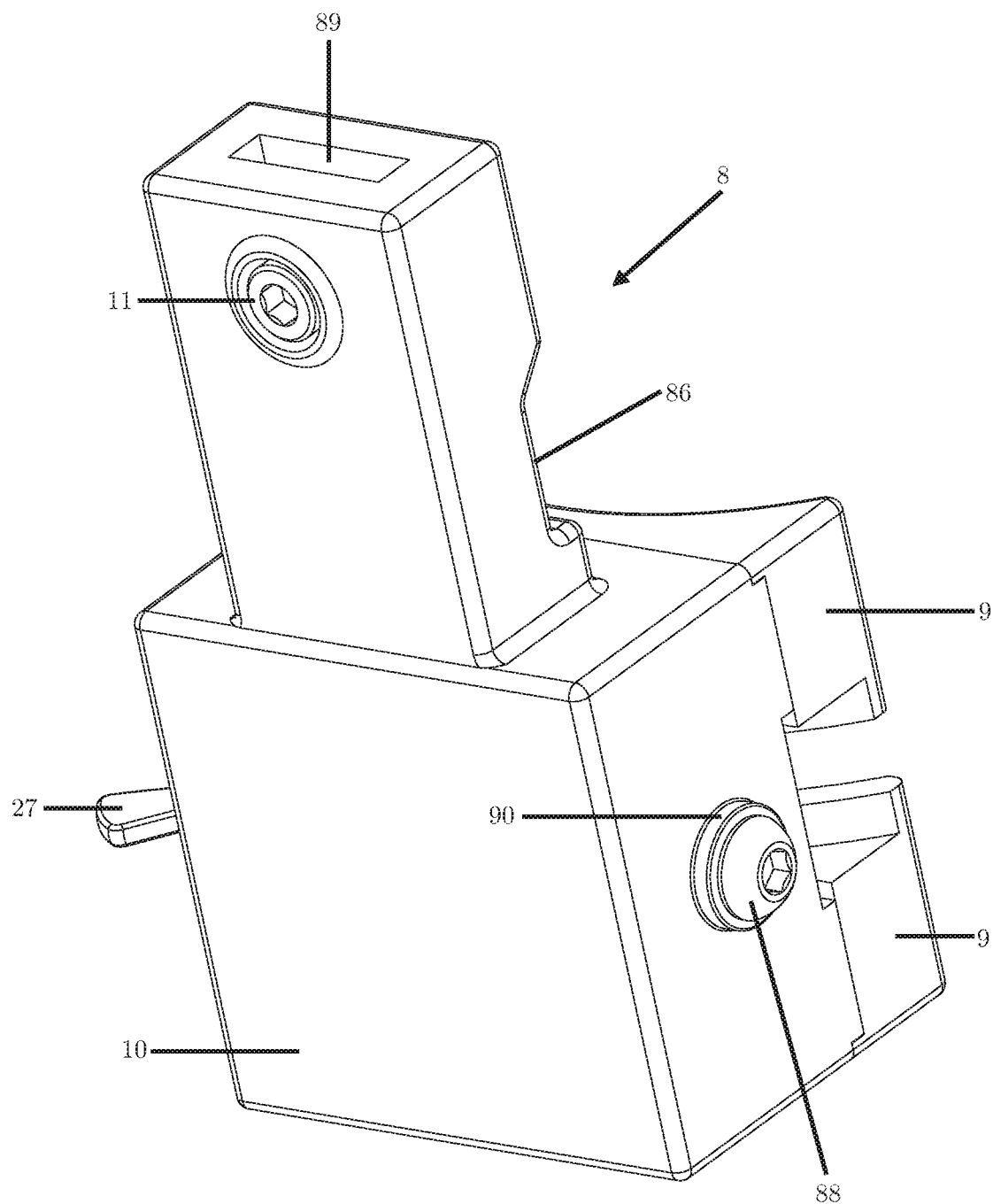
FIG. 23 is a rear right perspective view of the embodiment of the gearbox assembly shown in FIG. 22.
Figure 24:
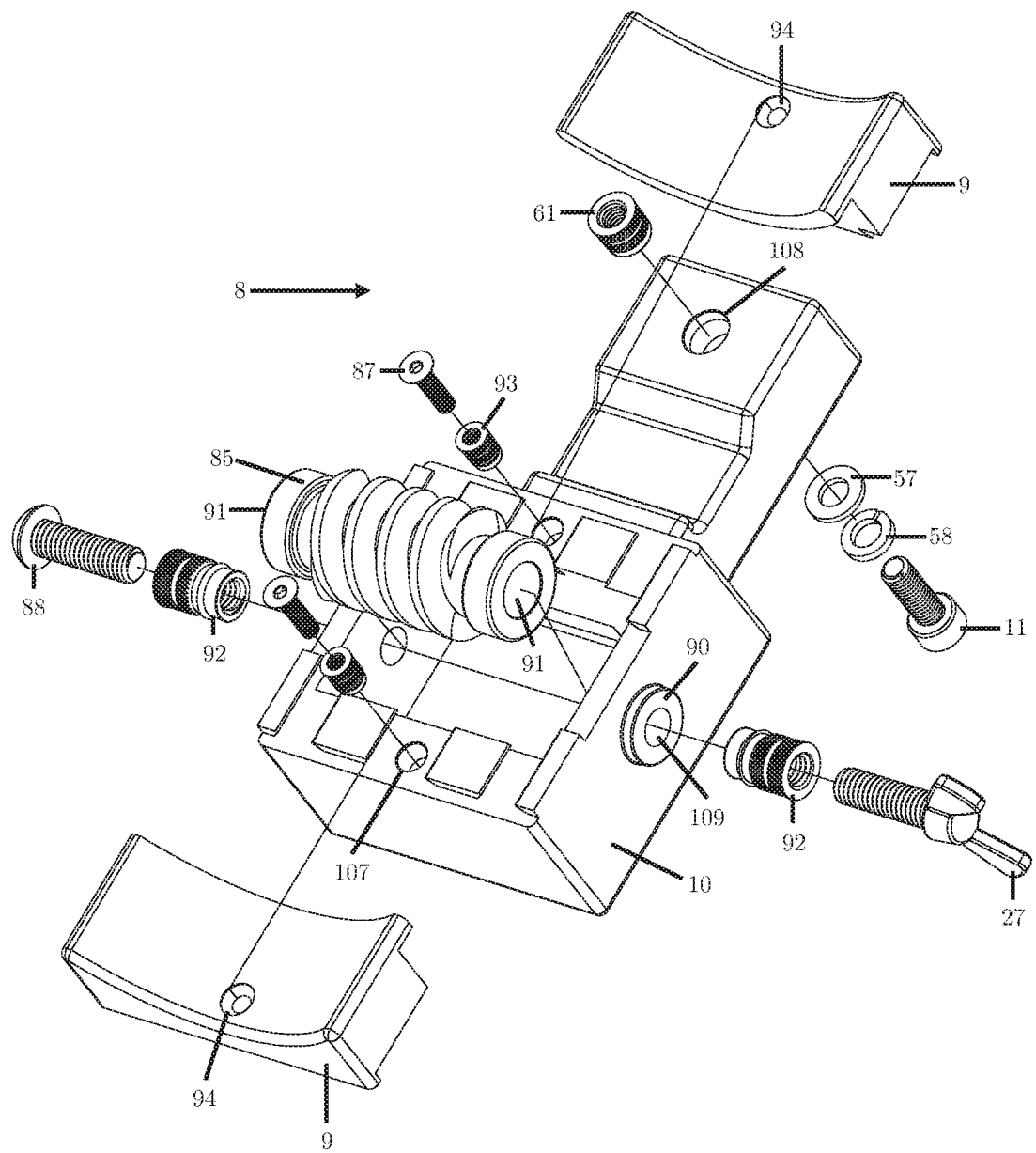
FIG. 24 is an exploded view of the embodiment of the gearbox assembly shown in FIG. 22.

FIG. 22 shows a front left perspective view of one contemplated embodiment of the gearbox assembly 8, FIG. 23 a back right perspective view, and FIG. 24 an exploded view. The gearbox 10 is the main component of the assembly and is shown in FIGS. 29-32. It is contemplated to be made from a thermoplastic but any material may be used without departing from the scope of the present invention.

Figure 29:
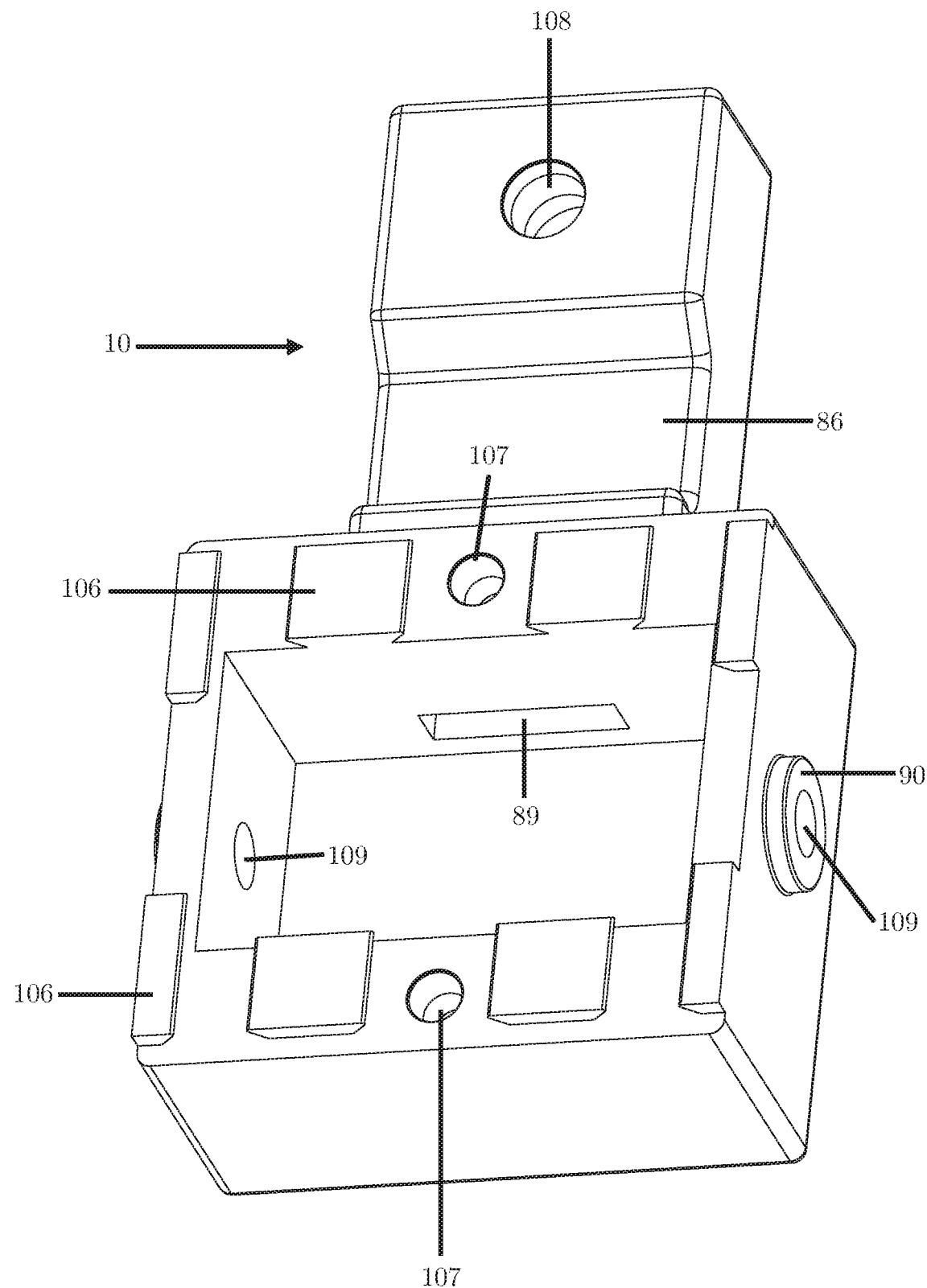
FIG. 29 is a front left perspective view of the gearbox from the contemplated embodiment of the gearbox assembly shown in FIG. 22.
Figure 30:
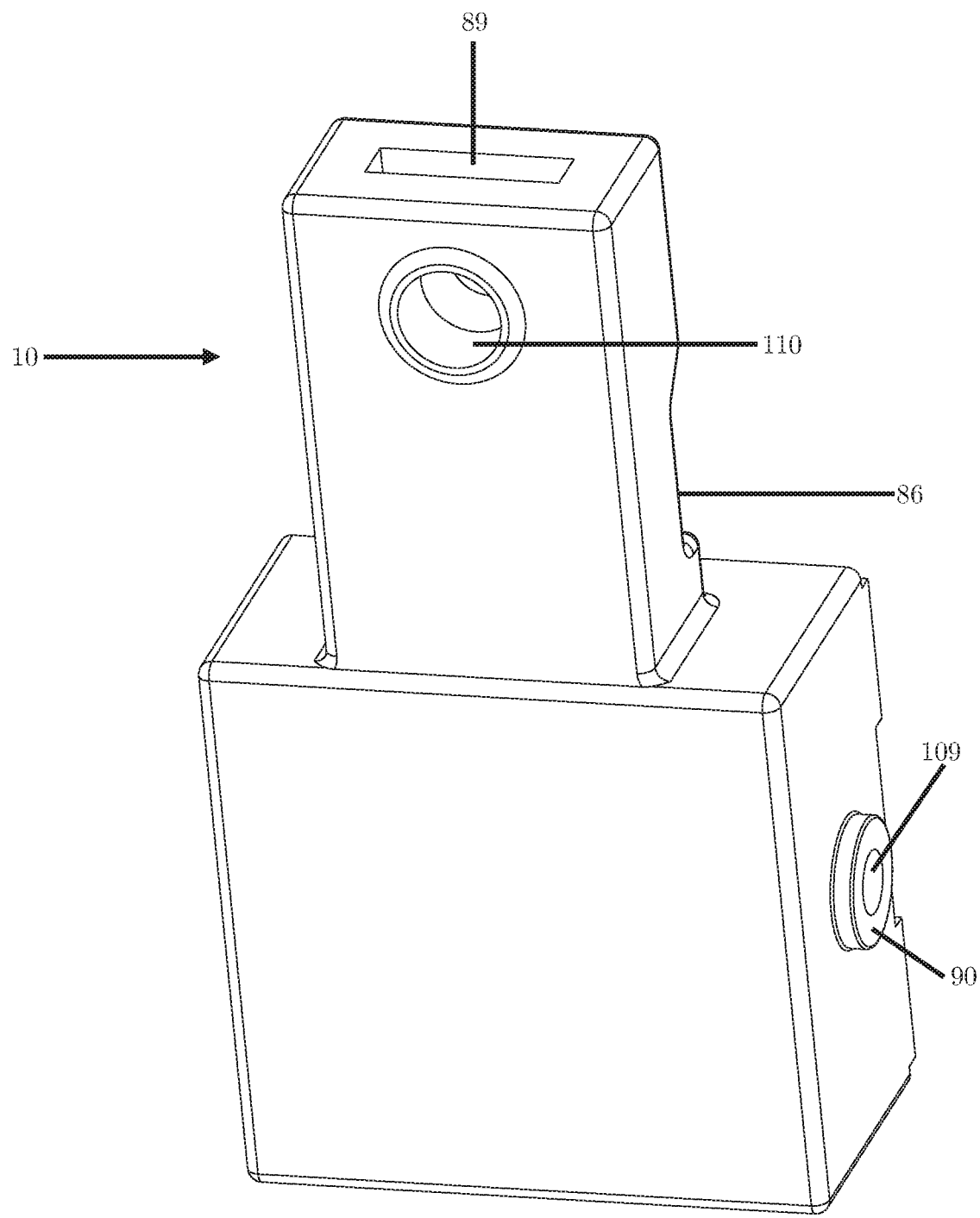
FIG. 30 is a rear right perspective view of the gearbox from the contemplated embodiment of the gearbox shown in FIG. 29.
Figure 31:
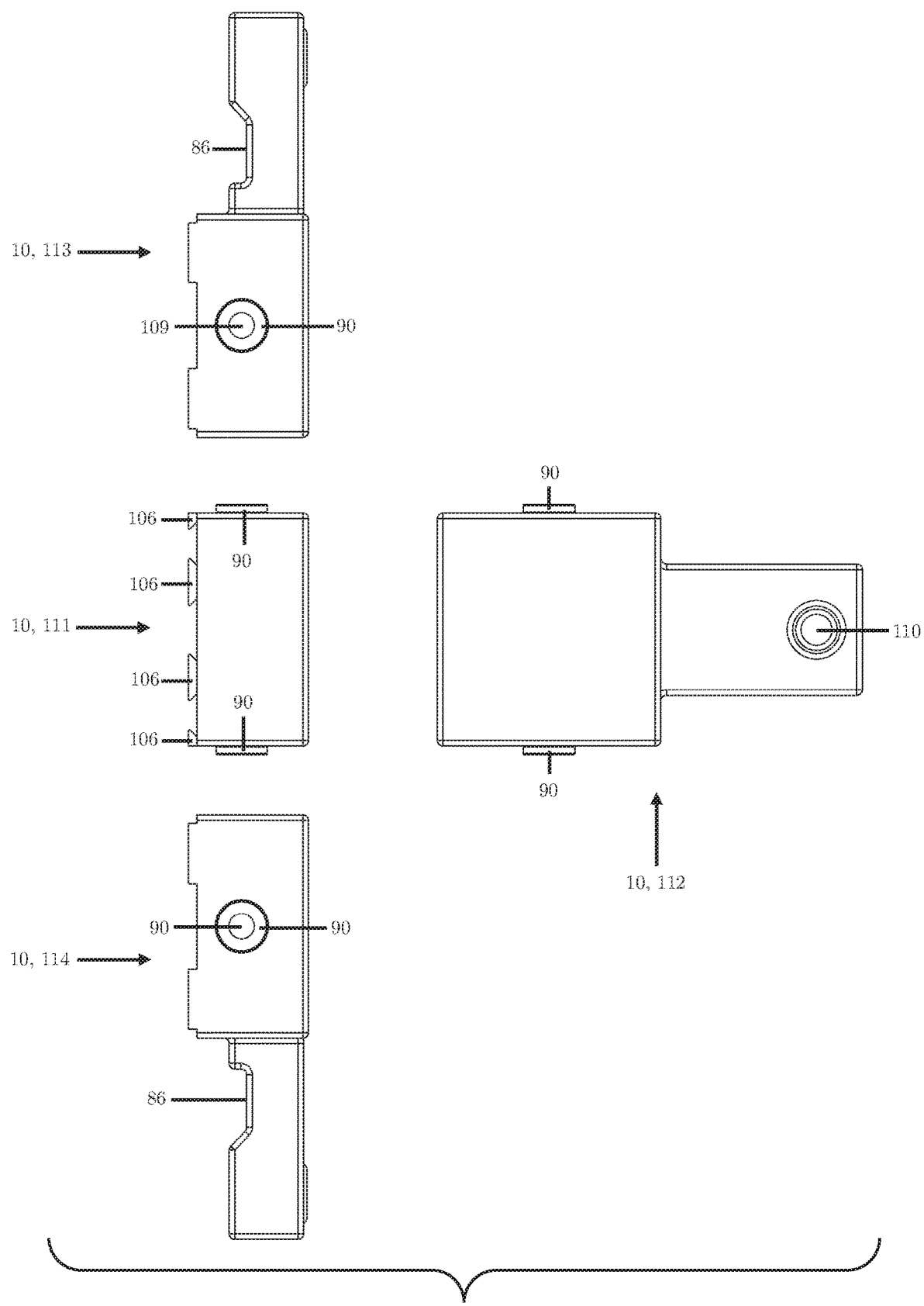
FIG. 31 is a view that contains a front view 111 of the embodiment of the gearbox shown in FIG. 29, an orthographically projected right side view 112, an orthographically projected top view 113, and an orthographically projected bottom view 114.
Figure 32:
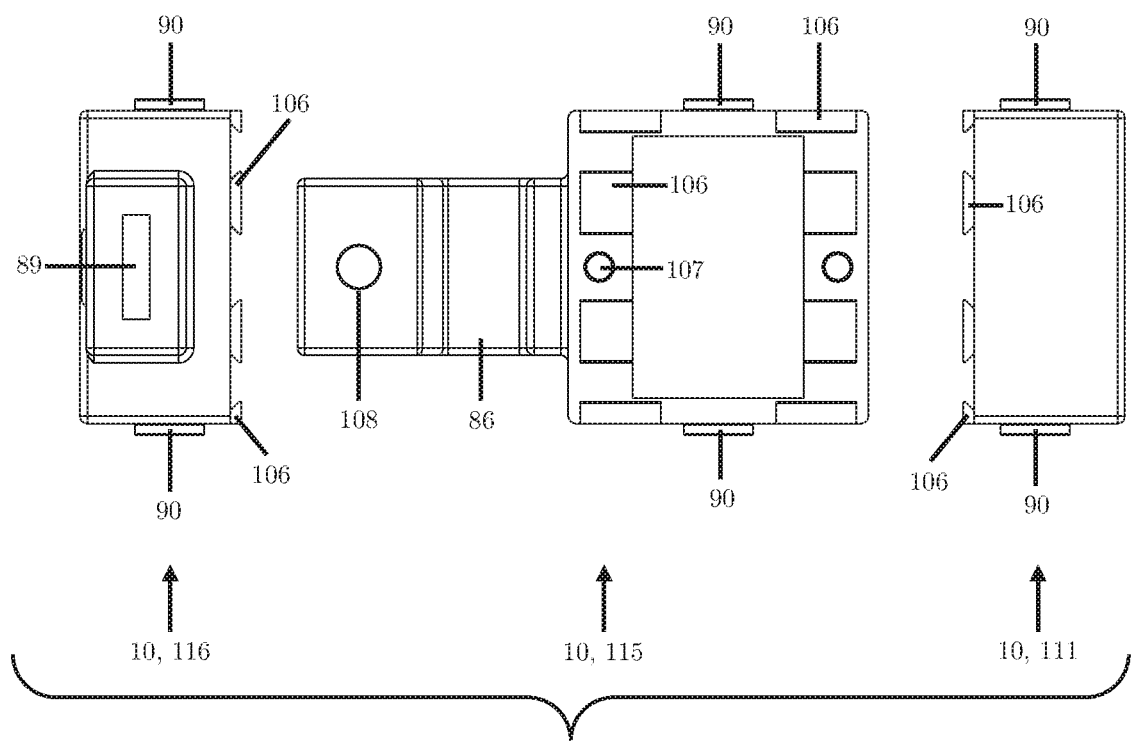
FIG. 32 contains a front view 111 of the embodiment of the gearbox shown in FIG. 29, an orthographically projected left side view 115, and an orthographically projected rear view 116.

Referring now to FIG. 29 some of the features will be described. Within the "box" area of the gearbox 10, a rectangular hole 89 begins and runs the length of the body. The rectangular hole 89 is seen more clearly in FIG. 27, which shows a cross-sectional side view, taken along plane 26-26A of FIG. 26, of the gearbox assembly 8. Two pockets 107 are molded to accept an M3 heat set threaded insert. A pocket 108 is molded to accept an M5 heat set threaded insert. Two holes 109 accept the shaft of a worm gear. A recessed area 86 prevents the wrist cuff assembly from hitting the gearbox 10 when rotated to certain positions. A set of rails 106 allows a gearbox cap to be slid on and locked in place on each side of the worm gear.

Referring now to the exploded view of FIG. 24, the features will be described. A symmetrical worm 85 sits in the gearbox 10 with its axis coincident with that of the hole 109. It is contemplated to be made of a thermoplastic but any material may be used without departing from the scope of the present invention. The worm 85 has a pocket 91 molded to each end for an M6 heat set threaded insert. An M6 heat set threaded insert 92 is installed into each pocket 91 so that the top sits flush with the adjacent surface. An M6 pan-head screw 88 is passed through the hole 109 and threaded into the M6 heat set threaded insert 92 on one side of the worm

85. The threads of the screw 88 and insert 92 are contemplated to be locked to each other using a permanent threadlocker, such as Loctite Threadlocker Red 271. On the opposite side of the worm 85, a thumb screw 27 is passed through the hole 109, threaded into the M6 heat set threaded insert 92, and locked with a permanent threadlocker. Together the M6 pan-head screw 88 and the M6 thumbscrew 27 form the shaft of the worm 85 so that it can rotate in the hole 109. The worm 85 is turned with the thumbscrew 27. A pair of cylindrical protrusions 90 help accommodate for the lengths of the M6 pan-head screw 88 and thumbscrew 27 by acting as a surface against which the underside of the heads rotate. Since a portion of the pan-head screw 88 and thumbscrew 27 may stick out past the sides of the gearbox 10, the protrusions 90 obviate the need to make the walls of the gearbox 10 thicker.

Figure 26:
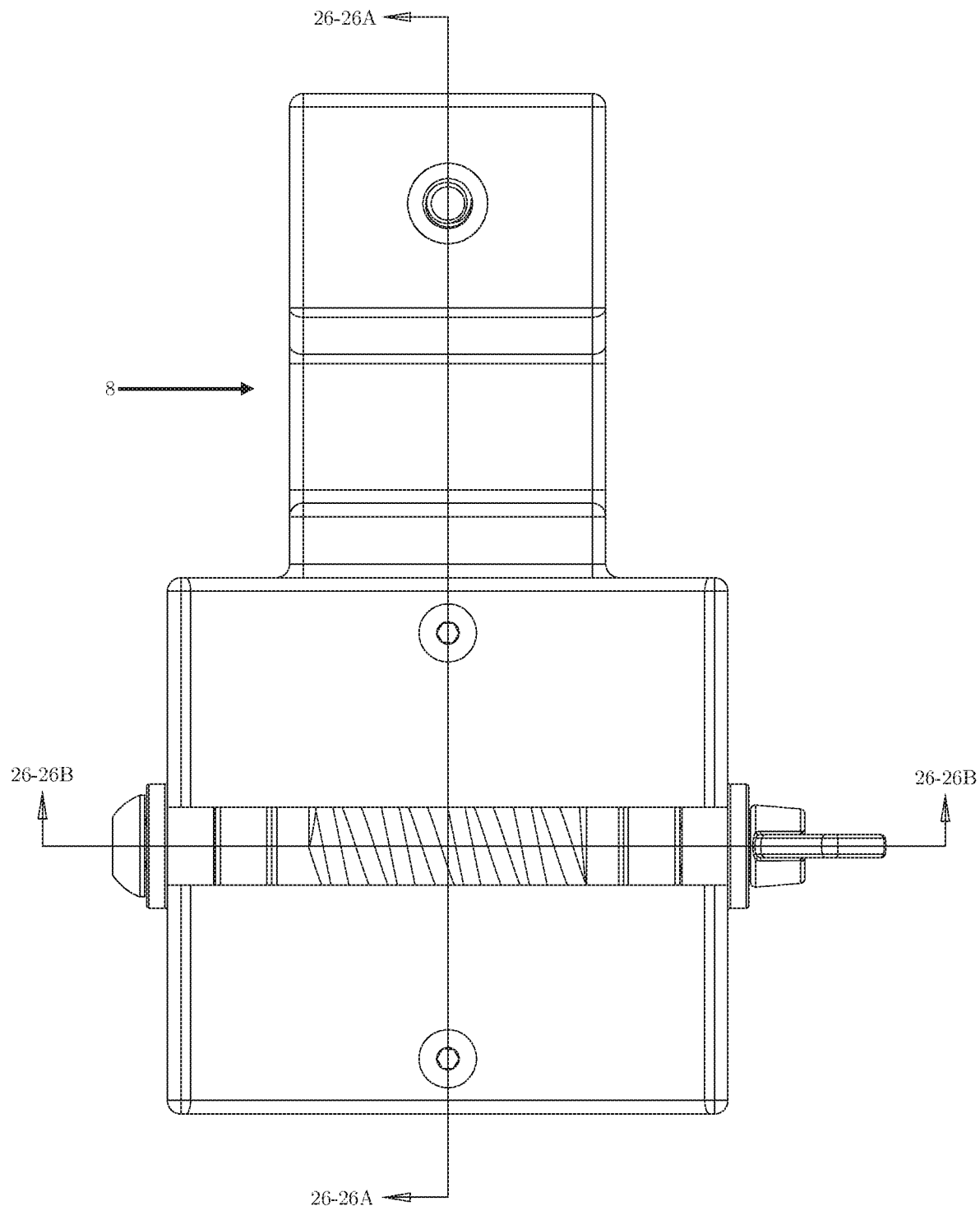
FIG. 26 is a top view of the embodiment of the gearbox assembly shown in FIG. 22.
Figure 27:
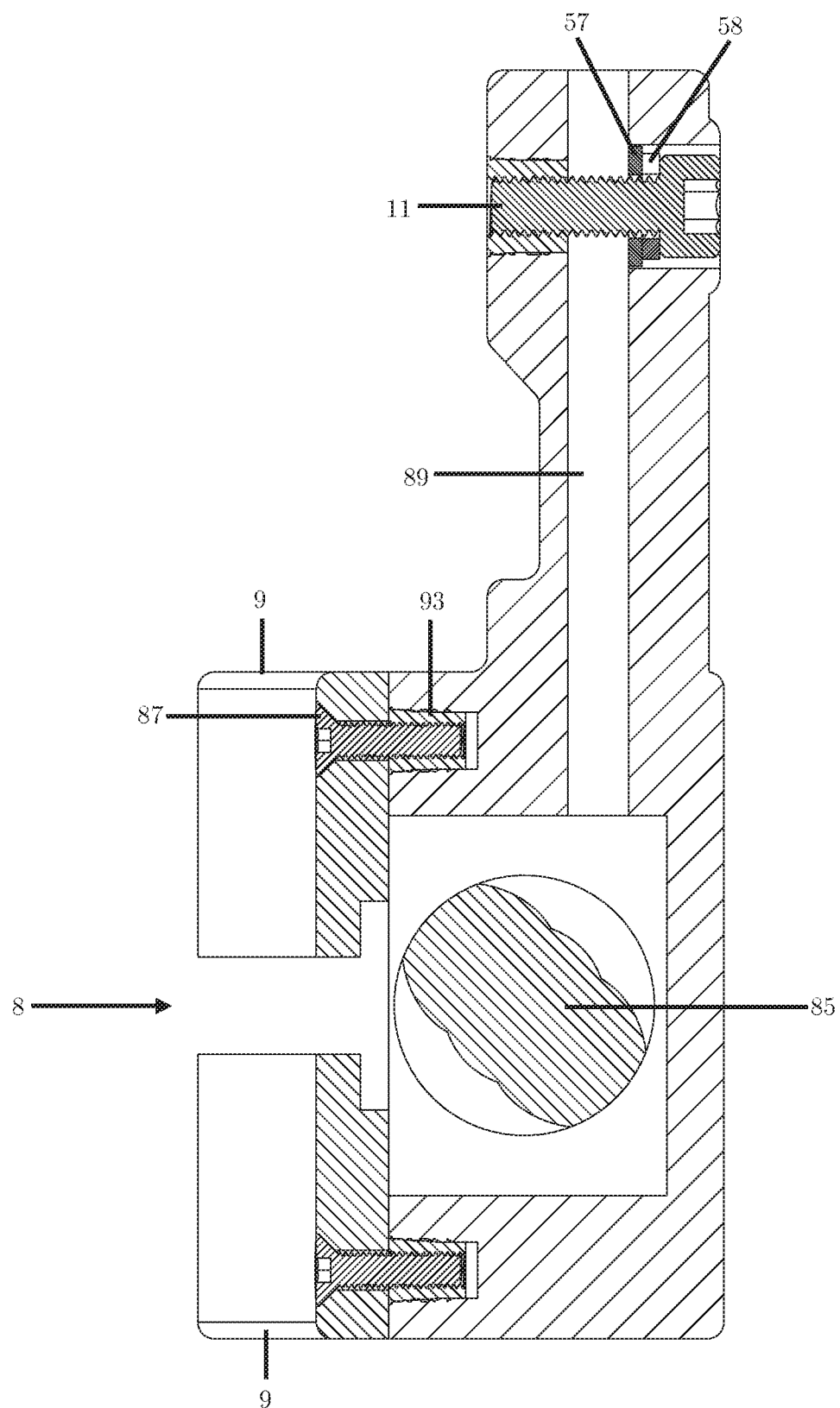
FIG. 27 is a cross-sectional side view, taken along plane 26-26A of FIG. 26, of the embodiment of the gearbox assembly shown in FIG. 22.
Figure 28:
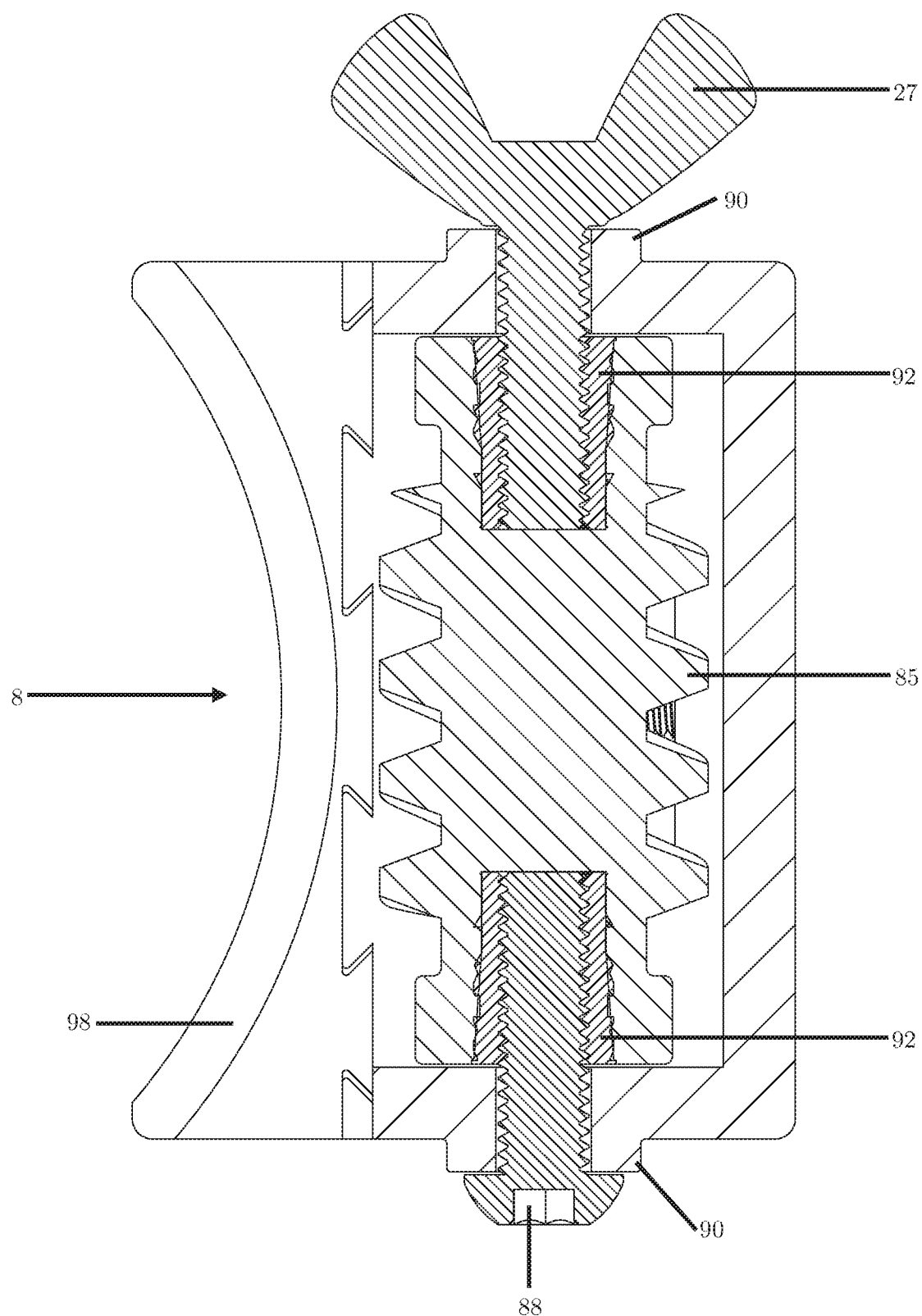
FIG. 28 is a cross-sectional front view, taken along plane 26-26B of FIG. 26, of the embodiment of the gearbox assembly shown in FIG. 22.

FIG. 28 shows a cross-sectional front view, taken along plane 26-26B of FIG. 26, of the gearbox assembly 8. It illustrates how the worm 85 is installed in the gearbox 10 with the inserts 92, pan-head screw 88, and thumbscrew 27 and clarifies why the protrusions 90 may be needed.

It is noted that other possible techniques for implementing the shaft of the worm 85 may be used without departing from the scope of the present invention. Such techniques include but are not limited to installation of the worm 85 on a milled shaft with a key or setscrew, or manufacturing the worm 85 and shaft together as one piece. Additionally, a bearing, such as a roller bearing, may be used without departing from the scope of the present invention. Also, any type of head or handle may be used for the thumbscrew 27 without departing from the scope of the present invention. Its purpose is to serve as the instrument through which the worm 85, and hence wrist cuff assembly, is rotated.

Figure 25:
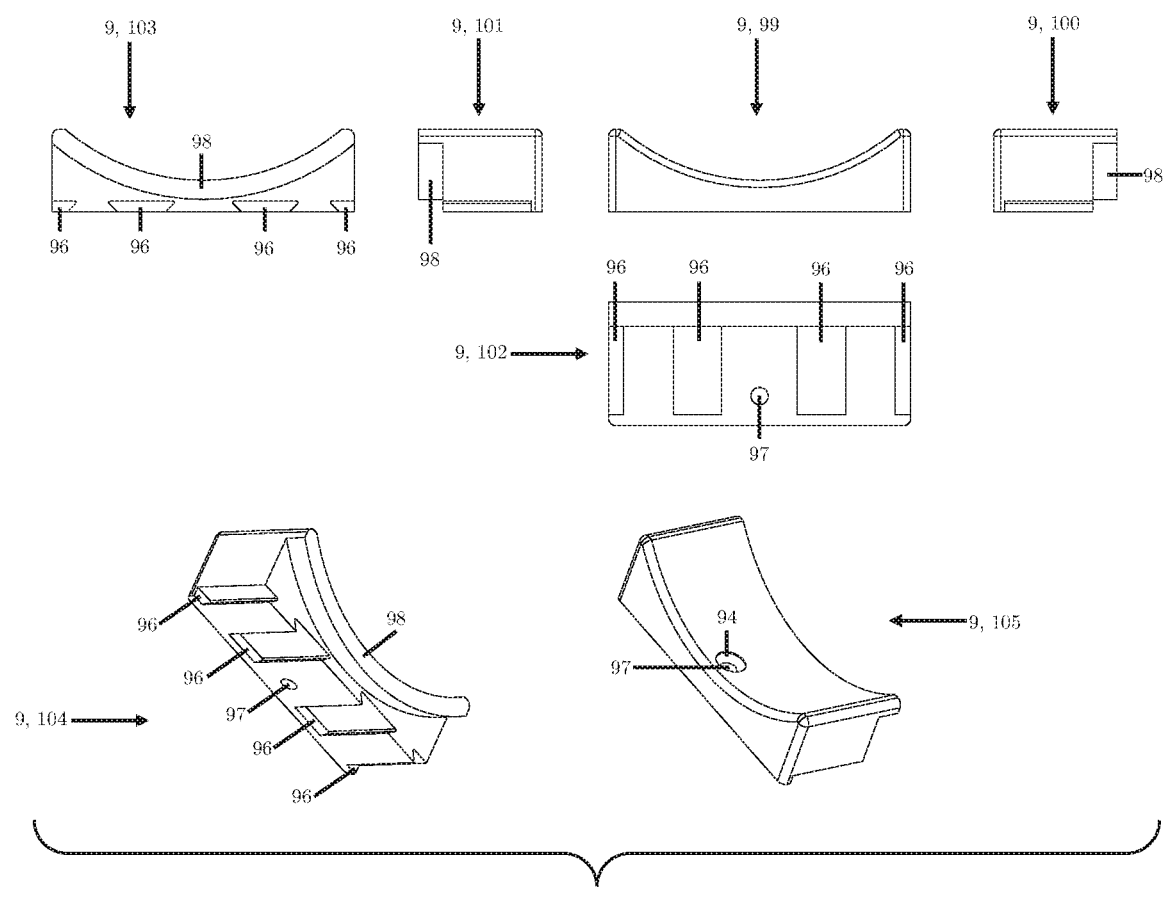
FIG. 25 is a view containing a front view 99 of the gearbox cap from the embodiment of the gearbox assembly shown in FIG. 22, an orthographically projected right side view 100, an orthographically projected left side view 101, an orthographically projected bottom view 102, an orthographically projected rear view 103, a rear bottom perspective view 104, and a front top perspective view 105.

As illustrated in the views of FIG. 25, a gearbox cap 9 has 4 slots 96 on its underside, a hole 97, and a molded pocket 94 for a screw chamfer. The cap 9 is contemplated to be made of a thermoplastic but any other suitable material may be used without departing from the scope of the present invention. The cap 9 is installed on the gearbox 10 by sliding the 4 slots 96 over the corresponding rails 106 that are molded to the top of the gearbox 10. Shown in FIG. 24, an M3 heat set threaded insert 93 is installed into the molded pocket 107 so that the top sits flush with the adjacent surface. Once the gearbox cap 9 is slid in place, an M3 flat head screw 87 is placed through the hole 97 and threaded into the insert 93. The interlocking of the slots 96 of the cap 9 and rails 106 of the gearbox 10 serves to resist vertical forces on the cap 9 while the screw 87 resists forces that tend to slide the cap 9 off the rails 106.

Figure 55:
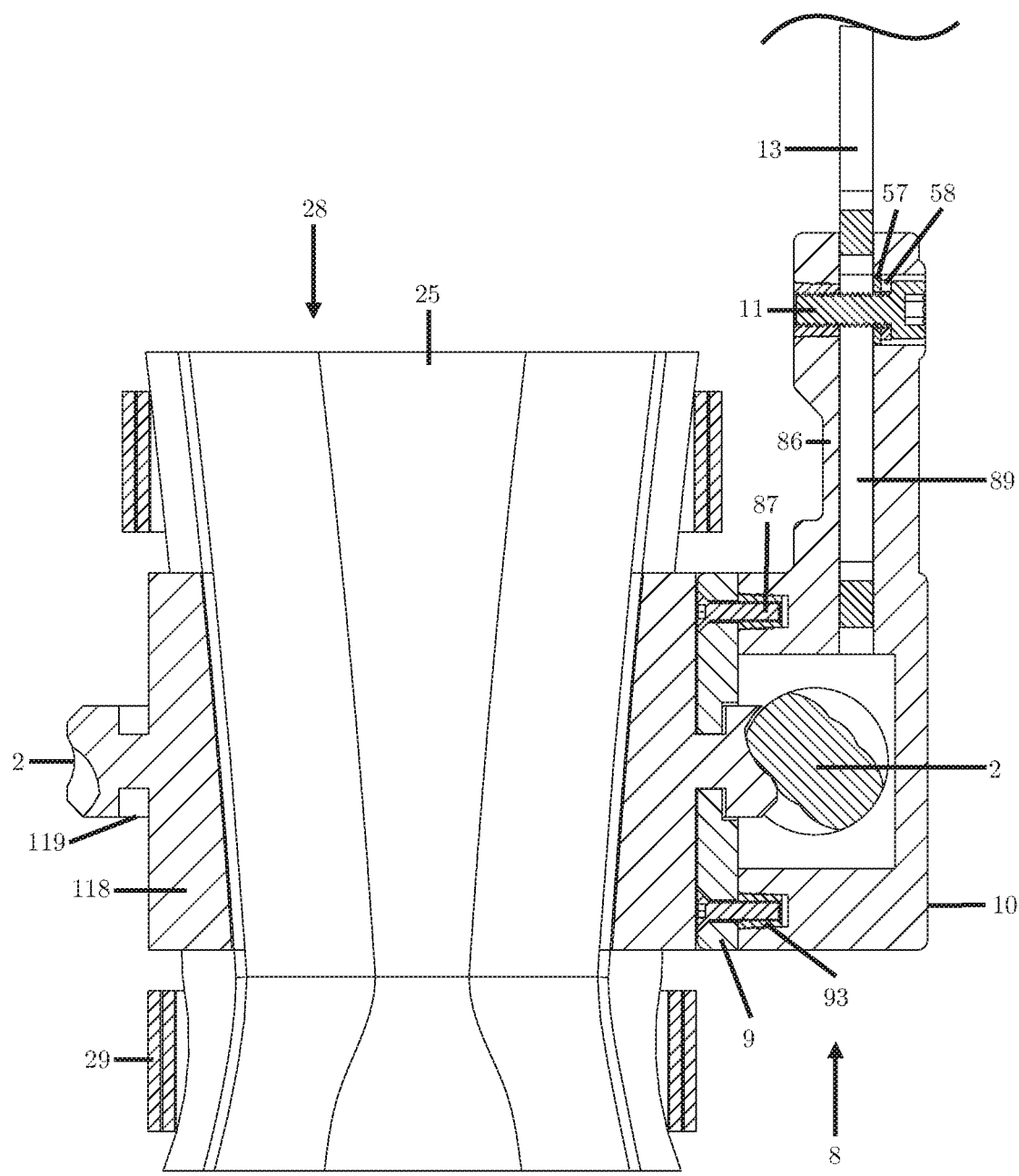
FIG. 55 is a cross-sectional top view of the strap wrist cuff assembly of FIG. 43 assembled to the gearbox assembly of FIG. 22 and assembled to the lower splint arm of FIG. 19, the cross-section being taken along plane 26-26A of FIG. 26.

An M5 heat set threaded insert 61 is installed into the molded pocket 108 on the gearbox 10 so that the top sits flush with the adjacent surface. It is contemplated that the end of the lower splint arm 13 with the obround slot 12 is slid into the rectangular hole 89 of the gearbox 10 so that the gearbox assembly 8 is slidingly disposed to the arm 13. The capacity to slide the gearbox assembly 8 back and forth allows the position of the wrist cuff assembly 7 along the wrist and forearm to be adjusted. When the desired position is reached, the gearbox assembly 8 is clamped in place with a socket cap screw 11, which passes through a hole 110 on the gearbox 10, passes through the obround slot 12 of the lower splint arm 13, and is preceded by an M5 split lock washer 58 and M5 flat washer 57. The M5 flat washer 57 serves to help spread the load from the M5 socket cap screw 11 to the lower splint arm 13. The M5 split lock washer 58 serves to help prevent the M5 socket cap screw 11 from loosening. The screw 11 is countersunk into the hole 110 so that, when torqued, the top of the head sits flush with the adjacent surface. FIG. 55 shows how the gearbox assembly 8 is slidingly disposed and clamped to the lower splint arm 13 at one position of translational adjustment.

The hardware shown in FIG. 24 is shown in FIG. 58 in relative scale to the other hardware used throughout the orthosis.

Figure 34:
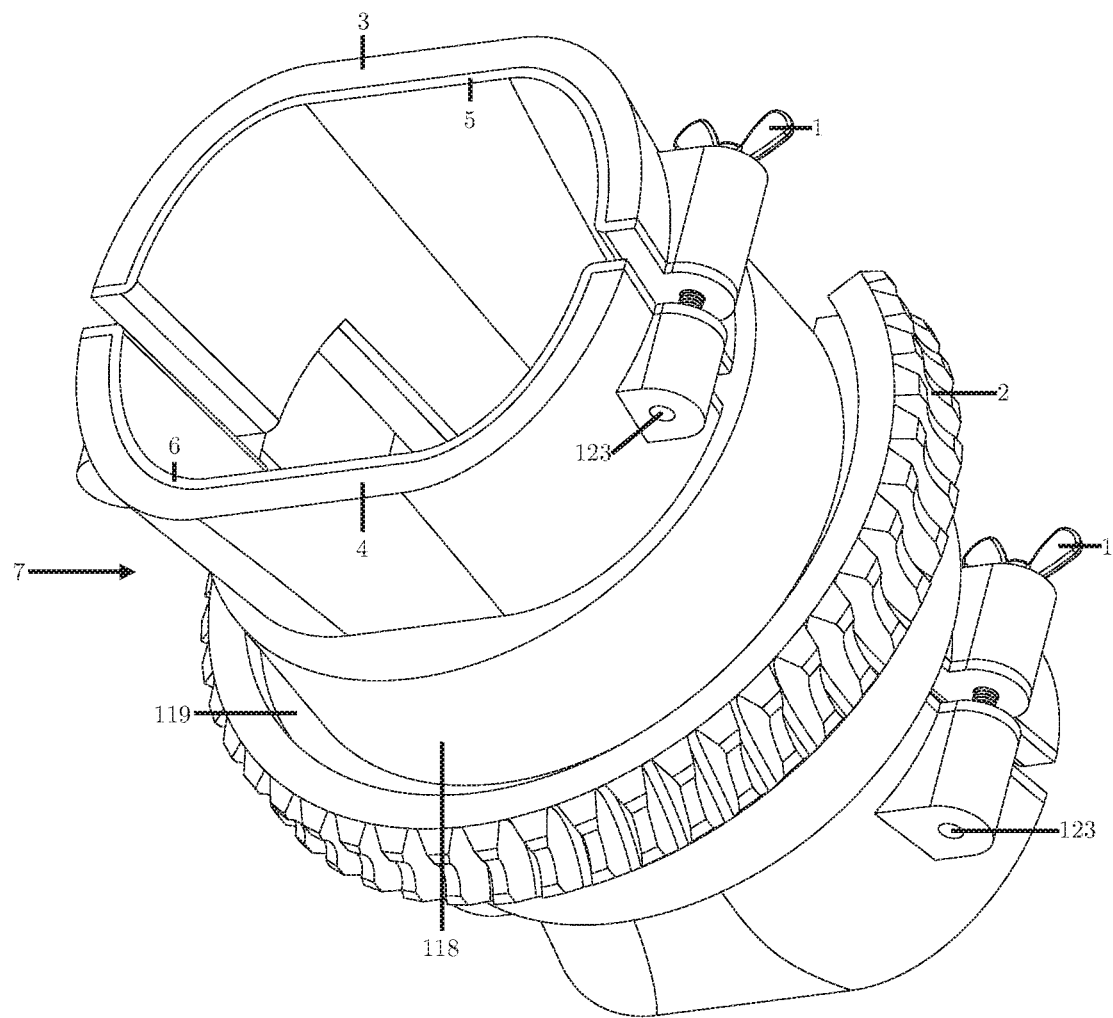
FIG. 34 is a front bottom perspective view of the embodiment of the wrist cuff assembly shown in FIG. 33.
Figure 35:
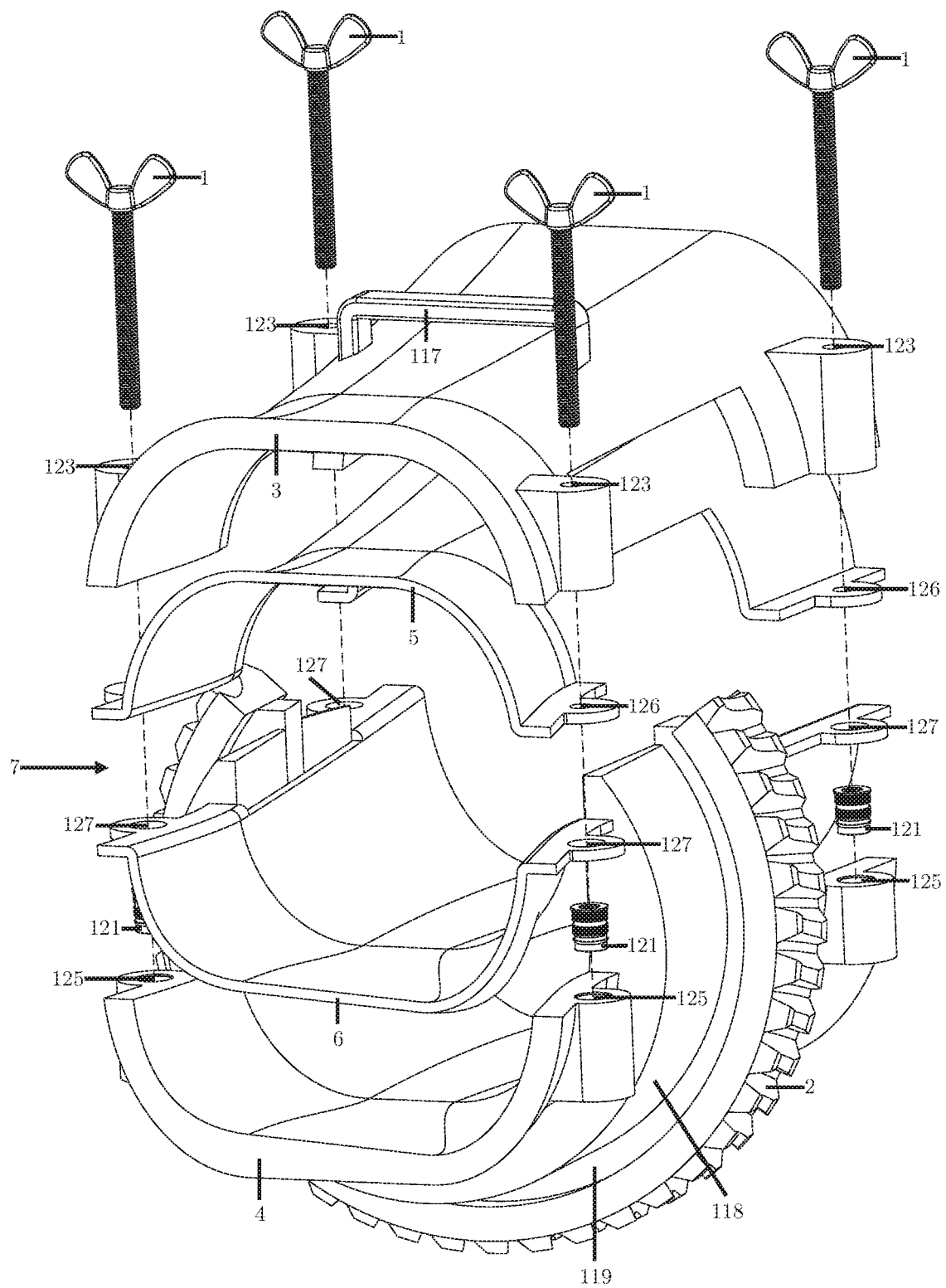
FIG. 35 is an exploded view of the embodiment of the wrist cuff assembly shown in FIG. 33.
Figure 36:
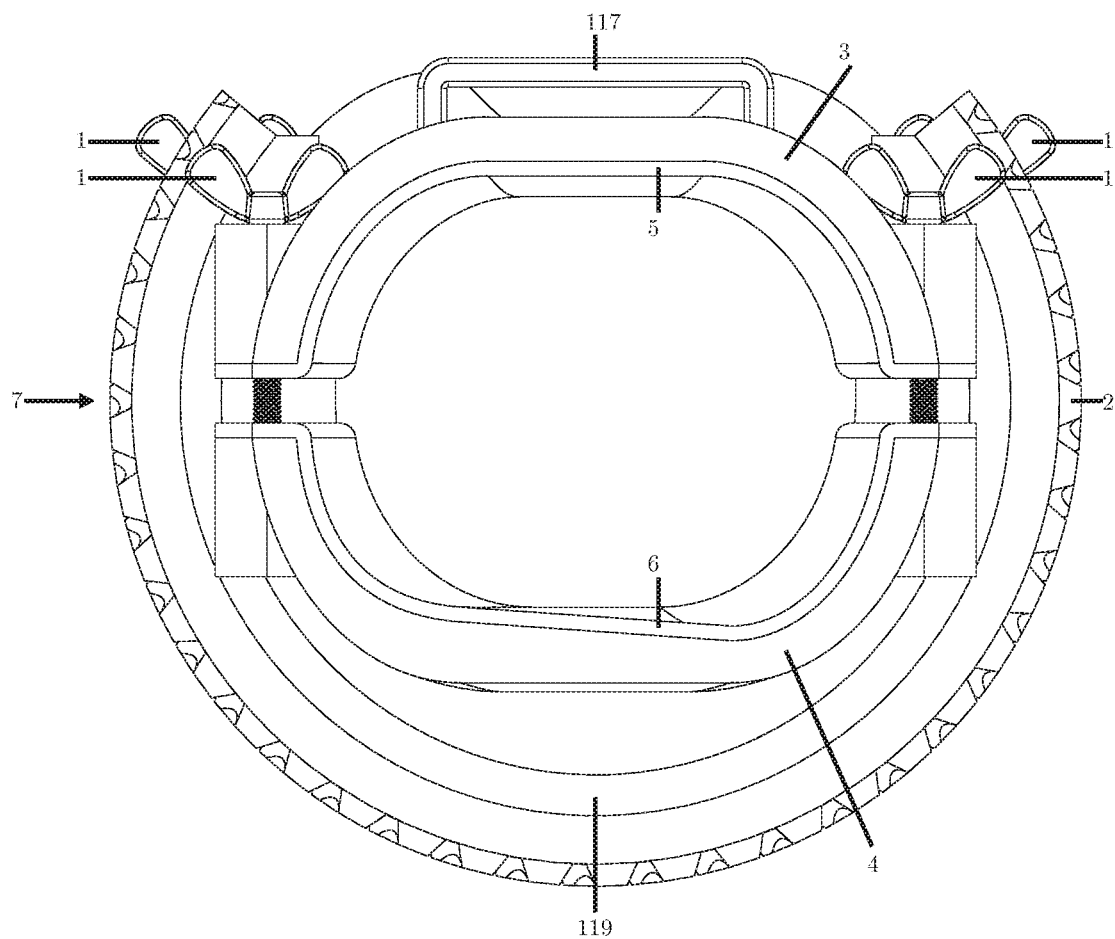
FIG. 36 is a front view of the embodiment of the wrist cuff assembly shown in FIG. 33.
Figure 37:
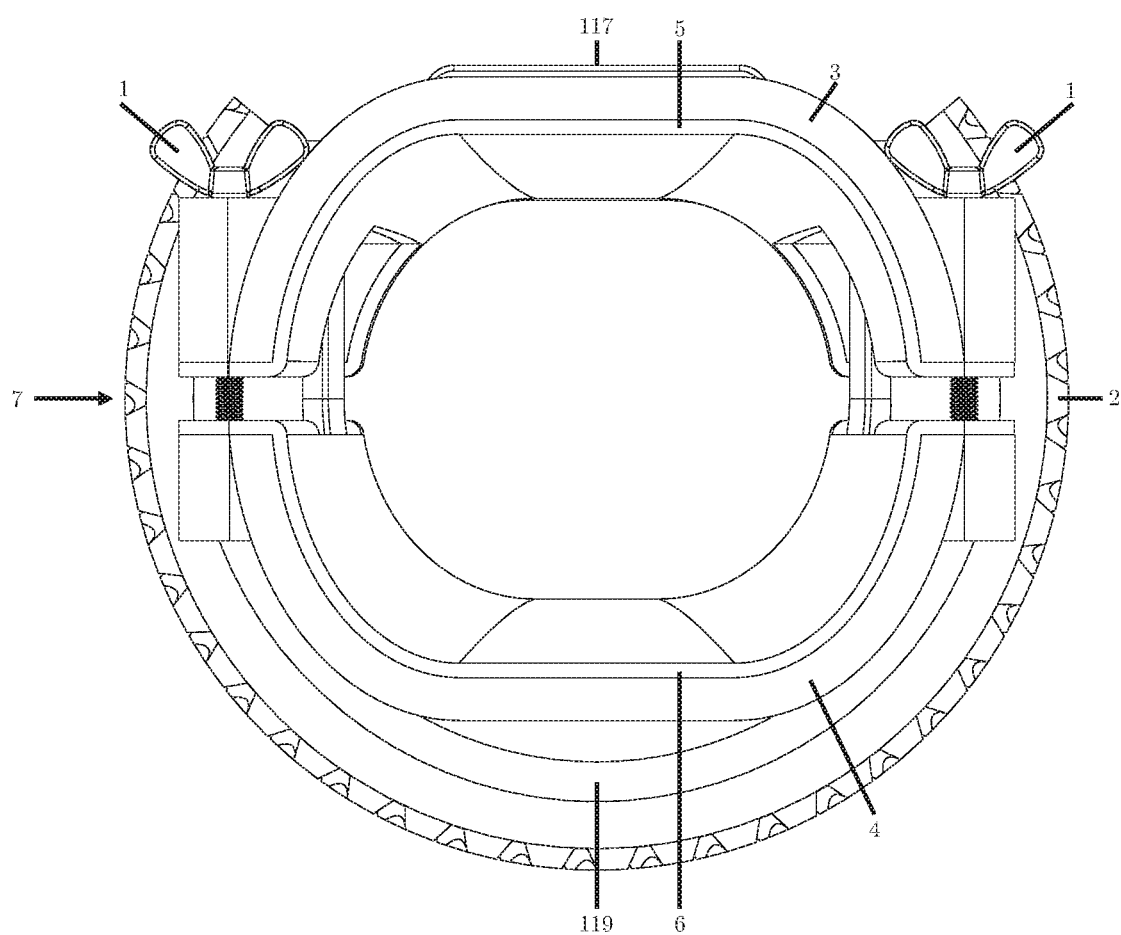
FIG. 37 is a rear view of the embodiment of the wrist cuff assembly shown in FIG. 33.
Figure 38:
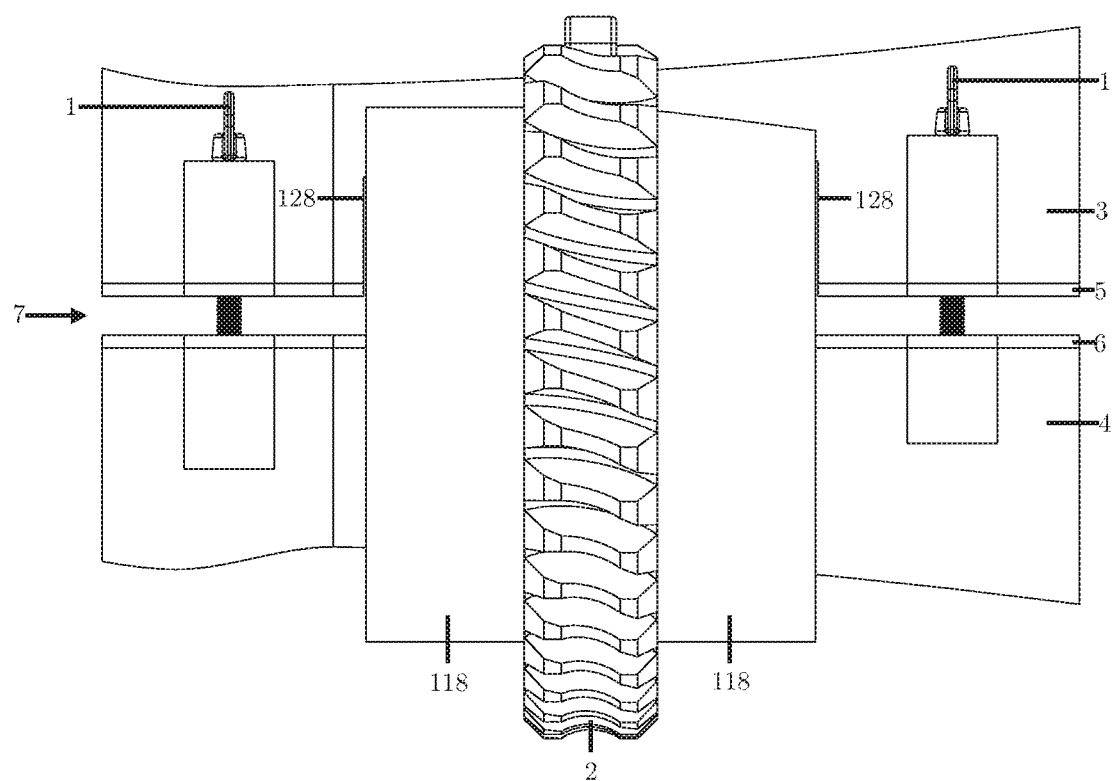
FIG. 38 is a right side view of the embodiment of the wrist cuff assembly shown in FIG. 33.
Figure 39:
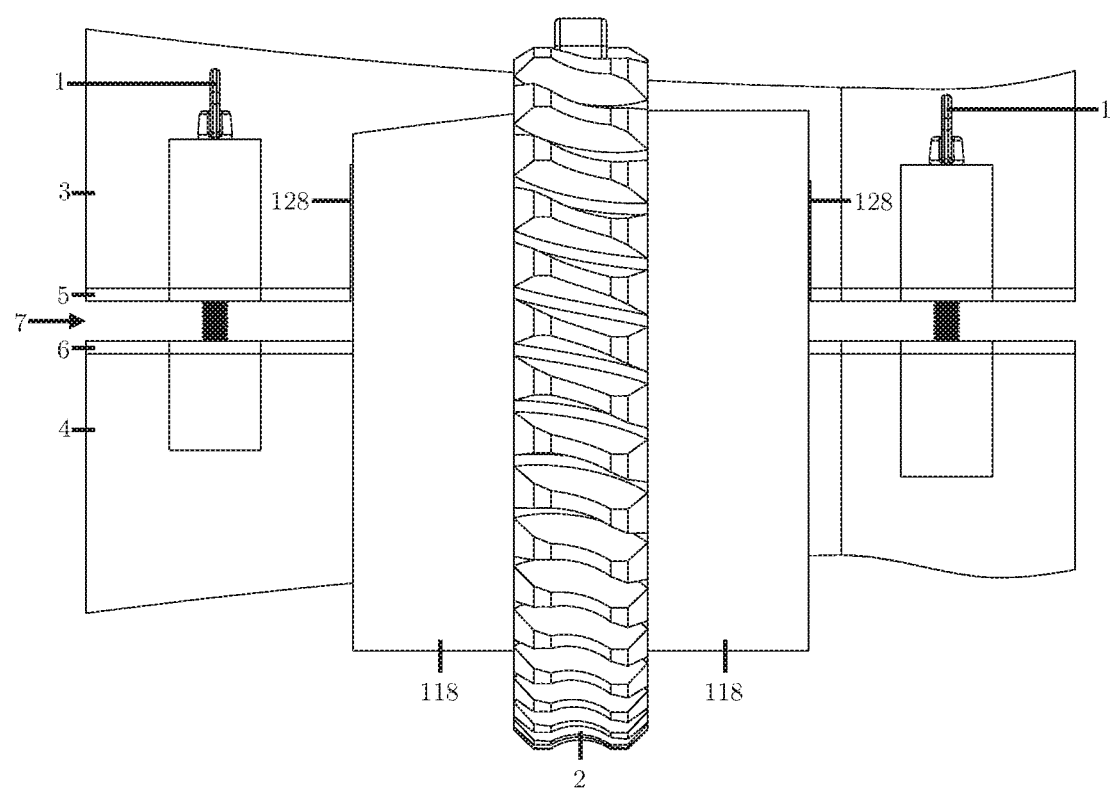
FIG. 39 is a left side view of the embodiment of the wrist cuff assembly shown in FIG. 33.
Figure 40:
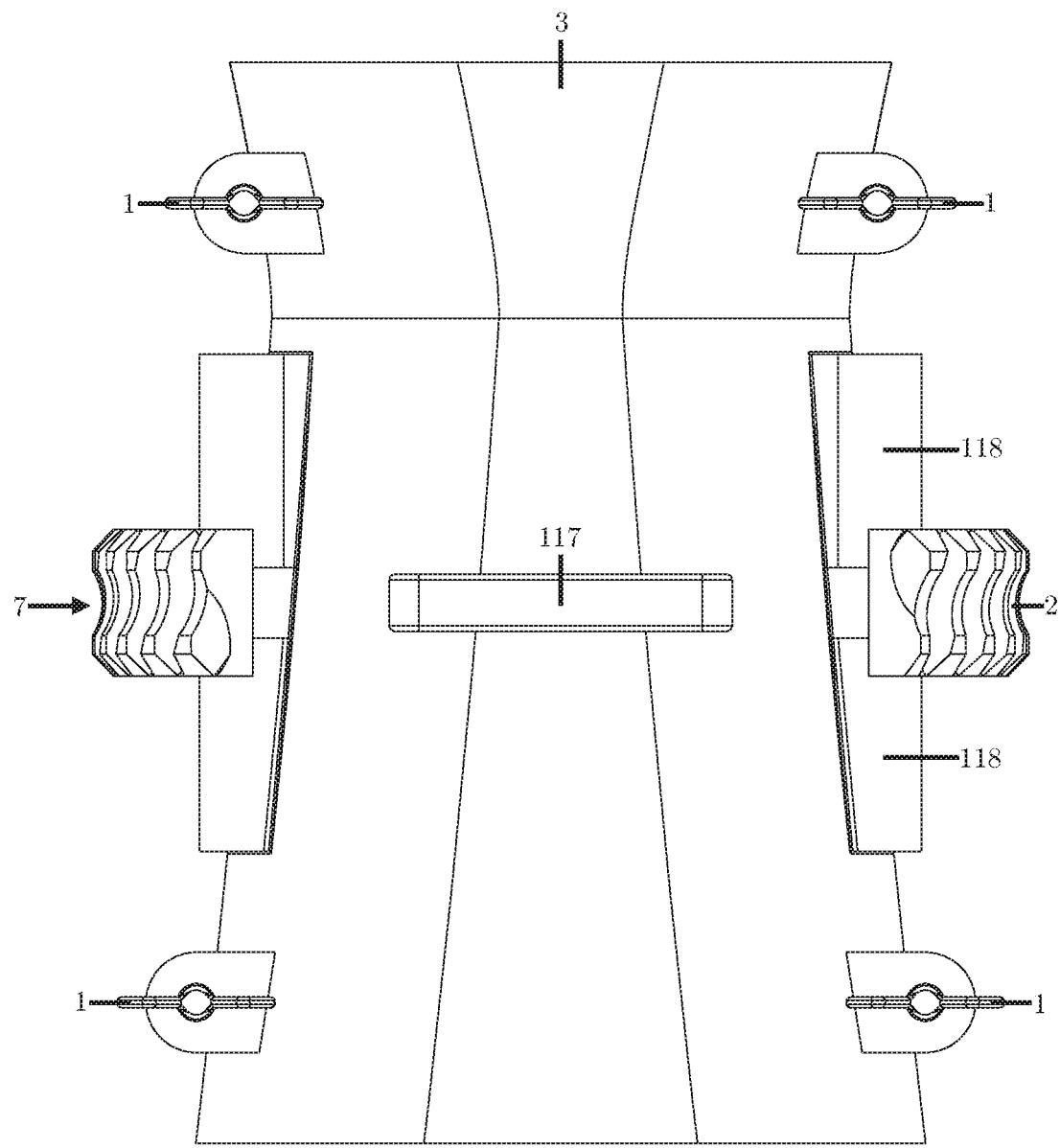
FIG. 40 is a top view of the embodiment of the wrist cuff assembly shown in FIG. 33.

It is contemplated that a wrist cuff assembly 7 is clamped to the wrist and forearm of the user and coupled with the gearbox assembly 8. Two contemplated embodiments of the assembly are presented herein, including a thumbscrew wrist, cuff assembly 7 and a strap wrist cuff assembly 28. Several views of the thumbscrew wrist cuff assembly 7 are presented in FIGS. 33-40 so that the features may be fully divulged and understood. FIG. 33 is a front top perspective view, FIG. 34 is a front bottom perspective view, FIG. 35 is an exploded view, FIG. 36 is a front view, FIG. 37 is a rear view, FIG. 38 is a right side view, FIG. 39 is a left side view, and FIG. 40 is a top view. Referring now to the exploded view of FIG. 35, it is seen that the thumbscrew wrist cuff assembly 7 includes a thumbscrew upper wrist cuff 3, a thumbscrew lower wrist cuff 4, a thumbscrew upper pad 5, a thumbscrew lower pad 6, 4 M3 heat set threaded inserts 121, and 4 M3 thumbscrews 1. The upper and lower wrist cuffs 496, 494 are contemplated to be made of a thermoplastic but any suitable material may be used without departing from the scope of the present invention. The thumbscrew upper pad 5 and thumbscrew lower pad 6 are contemplated to be made from a foam, such as EVA, and ⅛ inch thick, but any suitable foam of any suitable thickness may be used without departing from the scope of the present invention.

Figure 41:
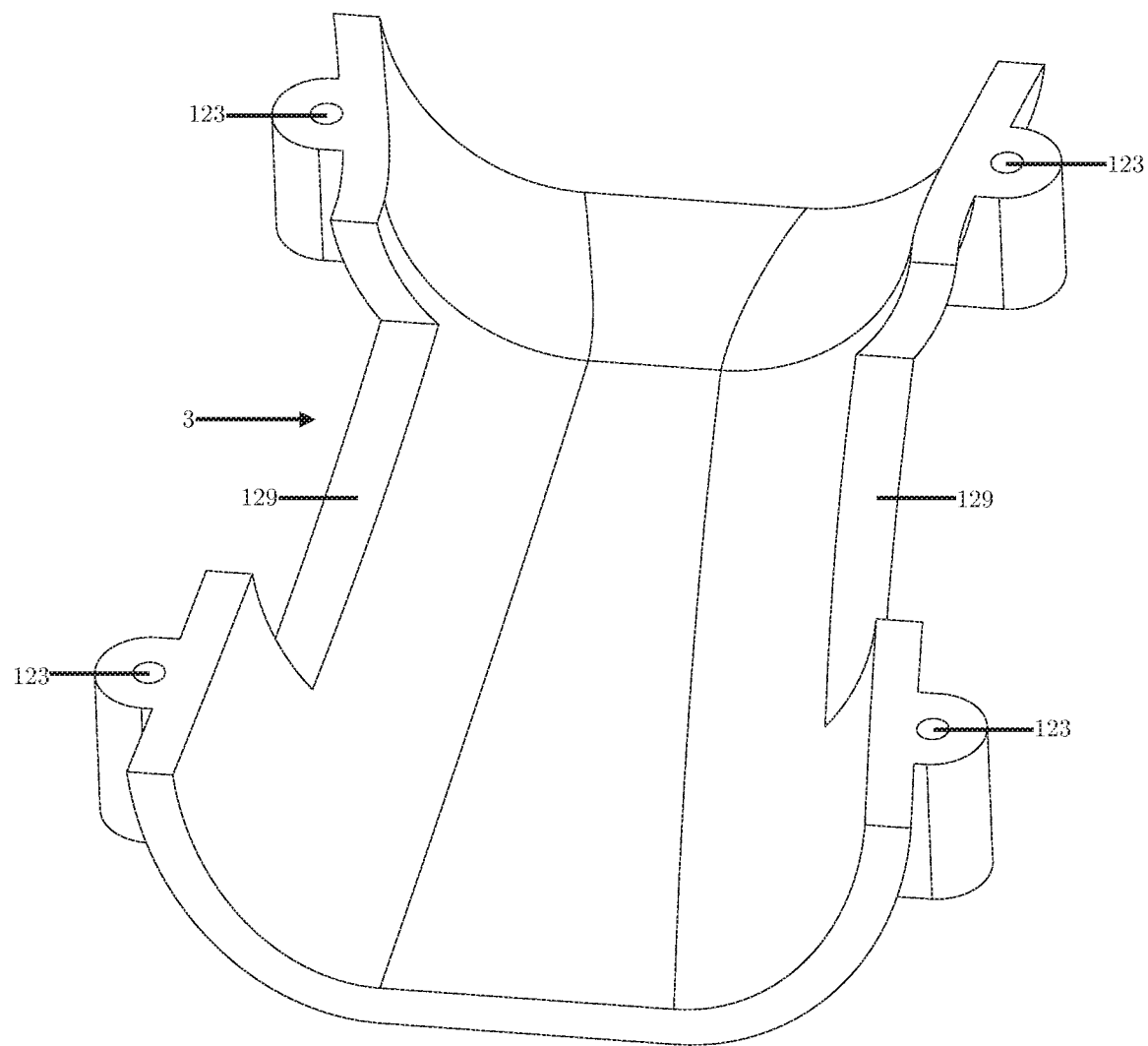
FIG. 41 is a perspective view of the inside of the thumbscrew upper wrist cuff from the embodiment of the wrist cuff assembly shown in FIG. 33.

FIG. 41 shows a perspective view of the inside of the thumbscrew upper wrist cuff 3. It has 4 holes 123 through which the thumbscrews 1 pass. Two grooves 129 allow it to engage with the thumbscrew lower wrist cuff 4 with a sliding disposition.

Figure 42:
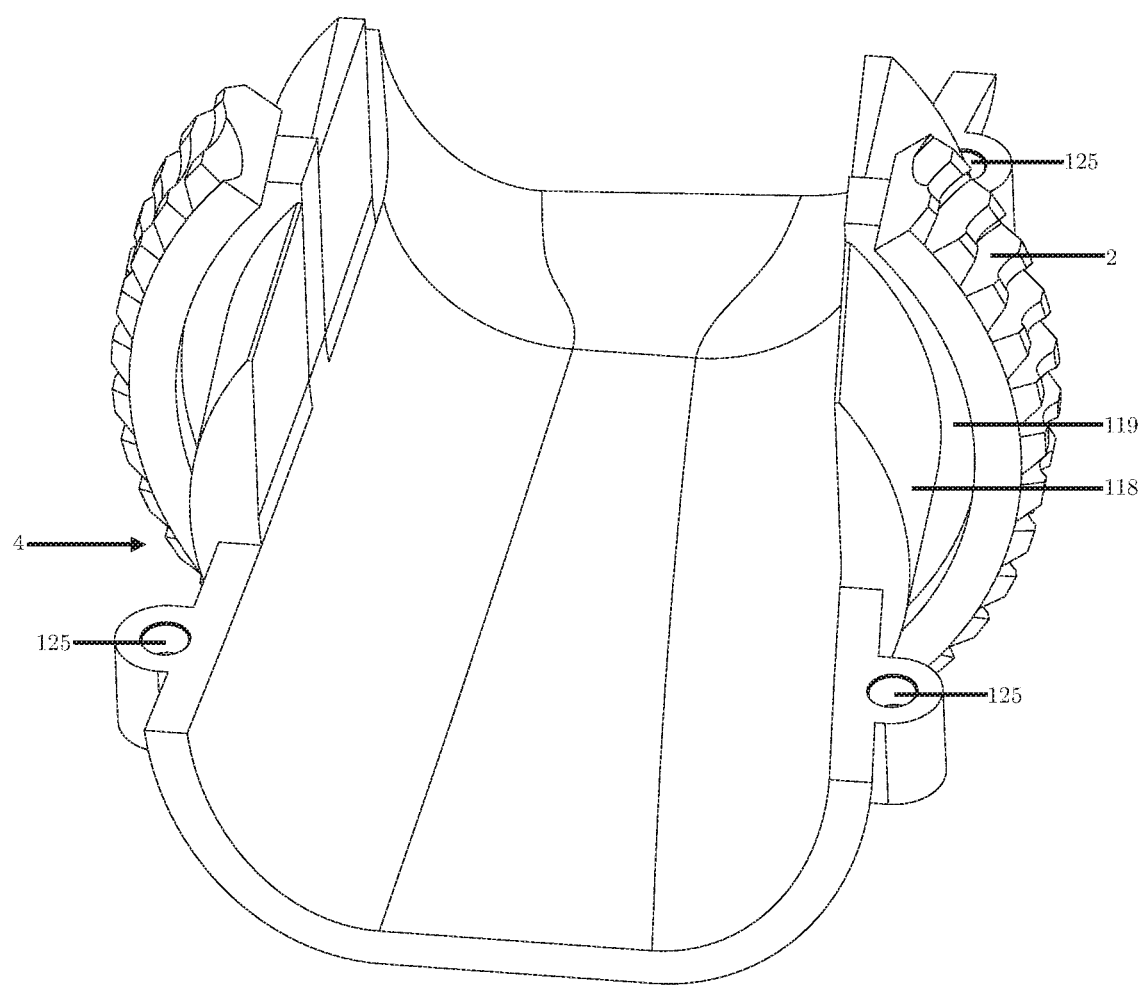
FIG. 42 is a perspective view of the inside of the thumbscrew lower wrist cuff from the embodiment of the wrist cuff assembly shown in FIG. 33.
Figure 54:
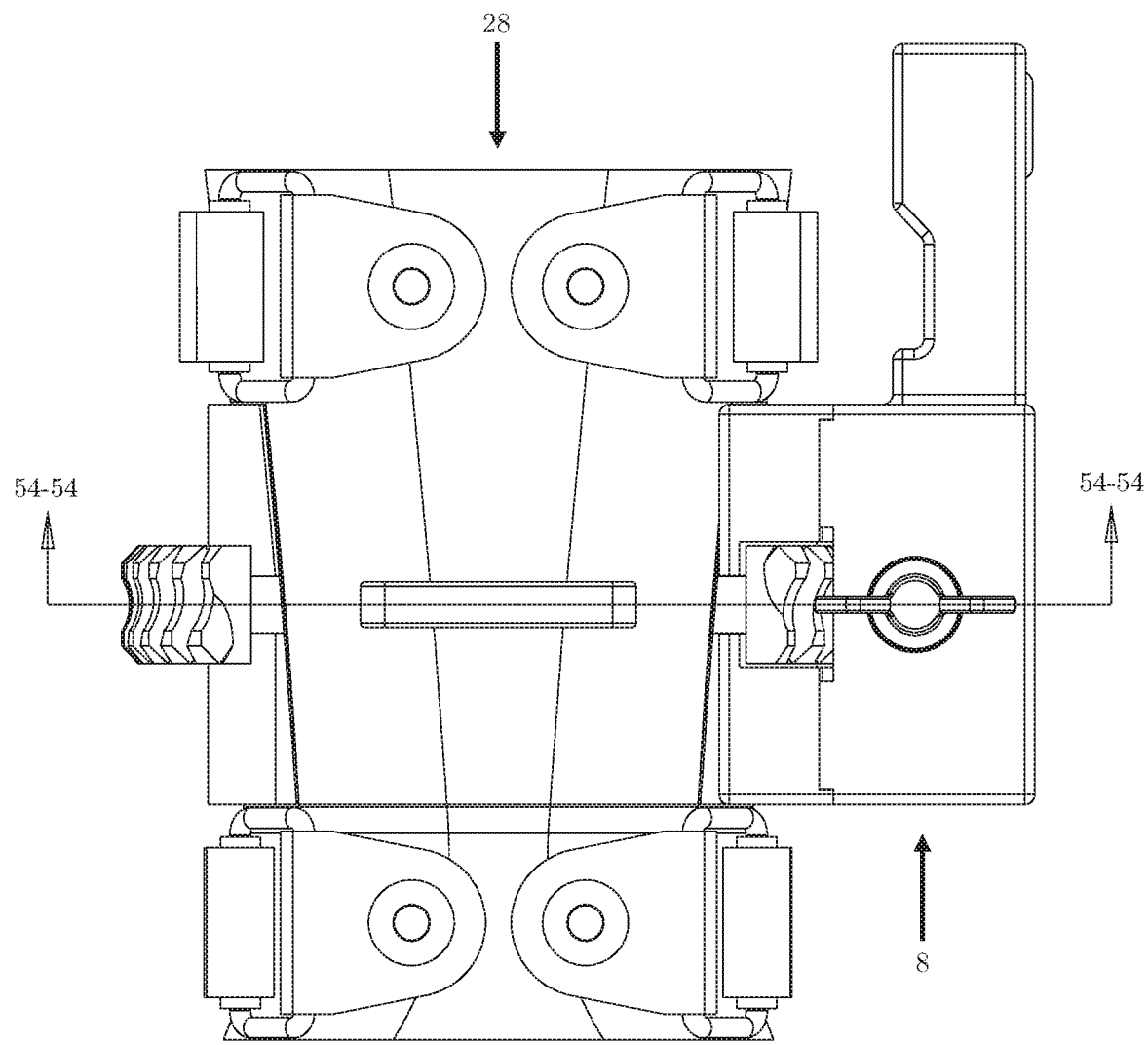
FIG. 54 is a top view of the strap wrist cuff assembly of FIG. 43 assembled to the gearbox assembly of FIG. 22.

FIG. 42 shows a perspective view of the inside of the thumbscrew lower wrist cuff 4. It has 4 molded pockets 125 for M3 heat set threaded inserts to be installed into. A worm gear 2 is molded to the underside of the lower wrist cuff 4. It does not revolve completely around but leaves an opening at the top for the forearm to slip in and rest in the bottom of the lower wrist cuff 4. The are of the worm gear 2 is contemplated to be approximately 260°, which is greater than the approximately 180° of possible forearm rotation. The extra arc length helps to stretch the forearm slightly past the fully pronated or fully supinated position when needed. An arced rectangular slot 119 is molded into both sides of the worm gear 2 and revolves completely around the gear. The worm gear 2, and hence the thumbscrew lower wrist cuff 4, is held against the worm 85 by the gearbox caps 9 so that the axes of the worm gear 2 and worm 85 are at the appropriate distance for them to engage properly. When the caps 9 are screwed to the gearbox 10 and the thumbscrew lower wrist cuff 4 coupled to the worm gear 2, an arced protrusion 98, on each cap 9, of the same radius as the worm gear 2, is slidingly engaged to the slots 119 on the worm gear 2. FIGS. 54-55 show this engagement with clarity (FIGS. 54-55 are for the strap wrist cuff assembly 28 but the engagement is identical). It is noted that a lubricant, such as a silicon-based oil or grease, or a bearing configuration may be used to facilitate the rotation of the thumbscrew lower wrist cuff 4 without departing from the scope of the present invention.

The worm gear 2 to the worm 85 ratio is contemplated to be approximately 22.5, but any ratio may be used without departing from the scope of the present invention. A ratio of 22.5 means that it would take 11.25 (half of 22.5) turns of the thumbscrew 1 to rotate the forearm from a position of full pronation to full supination and vice versa.

The coupling of the worm gear 2 to the worm 85 is contemplated to be self-locking. This is ensured when the following inequality is satisfied:

$$\mu_s < \cos(\phi)\tan(\psi) \qquad (1)$$

where $\mu_s$ is the coefficient of static friction between the worm gear 2 and worm 85 surfaces, $\phi$ is the pressure angle, and $\psi$ is the helix angle of the worm. The coefficient of static friction $\mu_s$ can be calculated from:

$$\mu_s = \tan(\theta_s) \qquad (2)$$

(1) and (2) are familiar to those skilled in the art. As an example, for 3D printed PLA plastic printed with a resolution of 0.2 mm, the coefficient of static friction might be $\mu_s = 0.2$. If the pressure angle is $\phi = 20°$ then a helix angle of 86° would satisfy (1).

Because the coupling of the worm gear 2 to the worm 85 is self-locking, the angle of forearm rotation with respect to the lower splint arm 13 is held. The worm 85 can drive the worm gear 2 in both directions but the worm gear 2 cannot backdrive the worm 85. Additionally, the need for an extraneous clutch or locking mechanism is obviated. If enough backdriving force is applied to the worm gear 2 it is expected that the teeth on the gears may actually fail rather than backdriving occurring.

It is noted that any worm gear 2 to worn 85 ratio may be used without departing from the scope of the present invention but that the ideal configuration is, generally, one in which the diametral difference between the worm gear 2 and worm 85 is not too large and the number of revolutions of the worm 85 required to take the forearm from full supination to full pronation is not too many. Additionally, a double-enveloping, or globoid, worm gear and worm pair may be used without departing from the scope of the present invention.

Referring back to FIG. 42, it is contemplated that a cylinder 118 is adjacent to the slot 119 on each side and is "circumscribed" about the body of the thumbscrew lower wrist cuff 4. The radius of the cylinder 118 is equal to the inner radius of the slot 119. The interior of the cylinder 118 extends from the outer wall to the side walls of the thumbscrew lower wrist cuff 4 but leaves free the space that the forearm needs to be lowered into the cuff. When the thumbscrew lower wrist cuff 4 is assembled to the gearbox assembly 8, the arced surface formed by the cap 9 is slidingly disposed to the cylinder 118. This serves to help prevent the wrist cuff assembly from pitching or yawing and therefore keeps it more stable. This is especially important when a load, such as that which may be experienced during resistance training, is placed on the hand and causes torsional stresses to be placed on the wrist cuff assembly that could deviate its axis and ruin the worm gear's 2 alignment with the worm 85. Such torsional stresses could also otherwise cause the cap protrusion 98 to fail. The cross-sectional view of FIG. 55 shows the cylinder's 118 geometry more clearly (it is shown for the strap wrist cuff assembly 28 but the geometry is identical to that of the thumbscrew wrist cuff assembly 7).

Referring back to FIG. 35, it is noted that the thumbscrew upper wrist cuff 3 and the thumbscrew lower wrist cuff 4 are ideally molded to the shape of the wrist and forearm and that the thumbscrew upper pad 5 and the thumbscrew lower pad 6 are ideally molded to the shape of their respective cuffs 496, 494. It is contemplated that the padding be attached to the cuffs using an adhesive, such as a high-strength spray adhesive, an epoxy, contact cement, glue, or tape, but any suitable adhesive may be used without departing from the scope of the present invention. If the thumbscrew upper wrist cuff 3 and thumbscrew lower wrist cuff 4 are instead molded to the general shape of a wrist and forearm that matches closely to that of the user then sufficiently dense and thick padding may accommodate for any discrepancies in shape.

4 M3 heat set threaded inserts 121 are installed into the molded pockets 125 of the thumbscrew lower wrist cuff 4 so that the tops are flush with the adjacent surfaces. After the forearm contacts the thumbscrew lower padding 6, the thumbscrew upper wrist cuff 3 is lowered by the handle 117 to slidingly engage the cylinder 118 of the thumbscrew lower wrist cuff 4. It is contemplated that each M3 thumbscrew 1 is passed through the corresponding hole 123 on the thumbscrew upper wrist cuff 3, the hole 126 on the thumbscrew upper pad 5, and the hole 127 on the thumbscrew lower padding 6 before being screwed into the M3 heat set insert 121. Each thumbscrew 1 is torqued until a comfortable clamping pressure at each corner of the thumbscrew wrist cuff assembly 7 is reached. The better the thumbscrew wrist cuff assembly 7 conforms to the forearm and the higher the clamping pressure, the greater the coupling between the two and the more efficient the transfer of torque from one to the other.

It is noted that the wrist cuff assembly is contemplated to grip the carpal bones of the wrist, up to and including the pisiform, because they are a solider and stabler location to grip than the radius and ulna of the forearm alone. This is because the radius and ulna cross over each other as the forearm is rotated. Additionally, by stopping at the pisiform, the wrist, is free to flex and the hand is left open to grip objects. The need to grip objects with the hand could arise, for example, during resistance training when the user needs to grip a dumbbell. It is therefore expected that the gearbox assembly 8 be adjusted transversely until the top edge of the wrist cuff assembly rests just above the pisiform. It is noted that because there is no locking mechanism to prevent the thumbscrew wrist cuff assembly 7 from sliding off the ends of the gearbox caps 9 that the forearm of the user may be coupled to the orthosis either by putting on the thumbscrew wrist cuff assembly 7 and then sliding it onto the caps 9 or by sliding the thumbscrew lower wrist cuff 4 onto the caps 9 first, resting the forearm in the cuff 4, and then engaging the thumbscrew upper wrist cuff 3.

Figure 53:
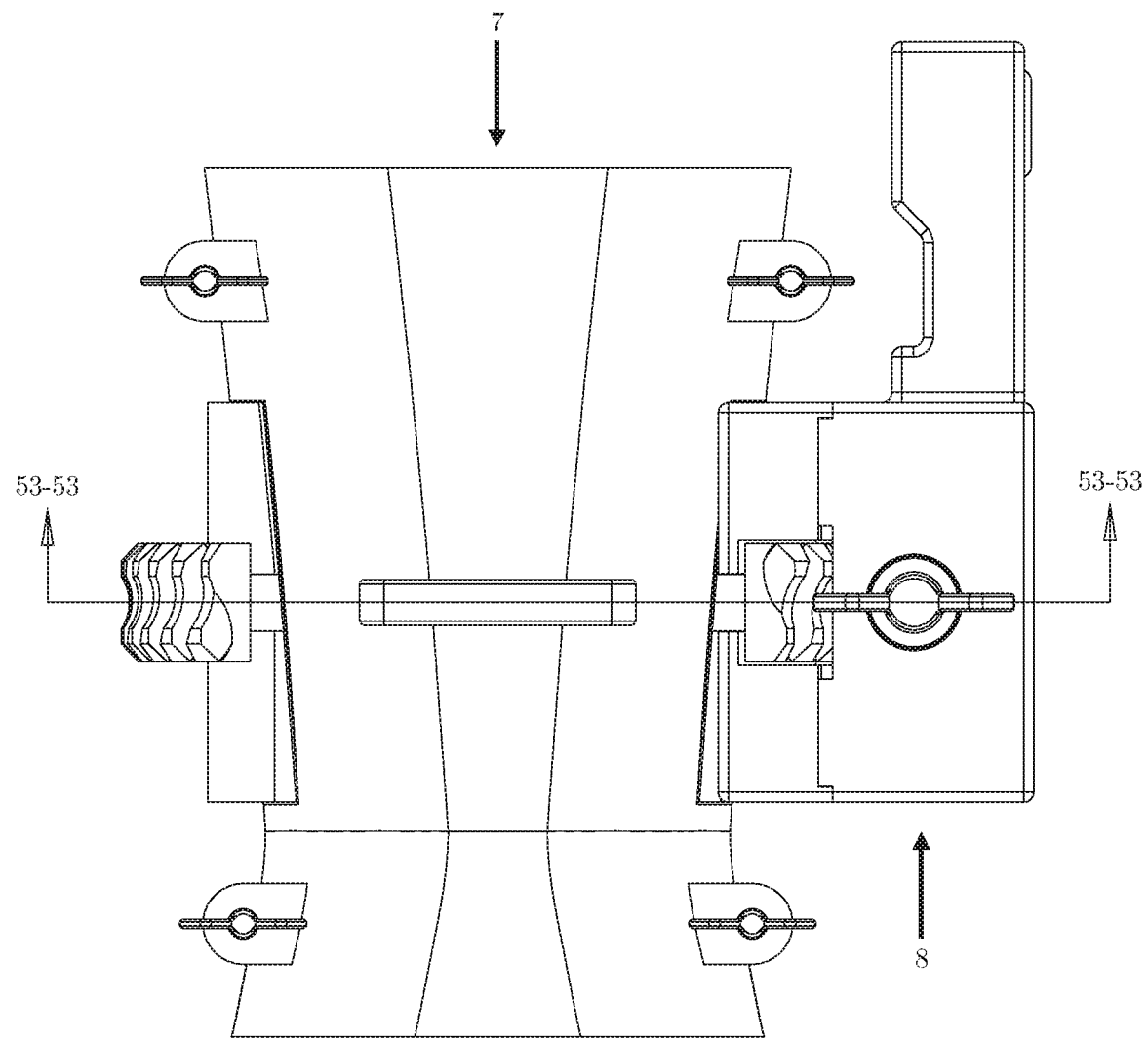
FIG. 53 is a top view of the thumbscrew wrist cuff assembly of FIG. 33 assembled to the gearbox assembly of FIG. 22.
Figure 56:
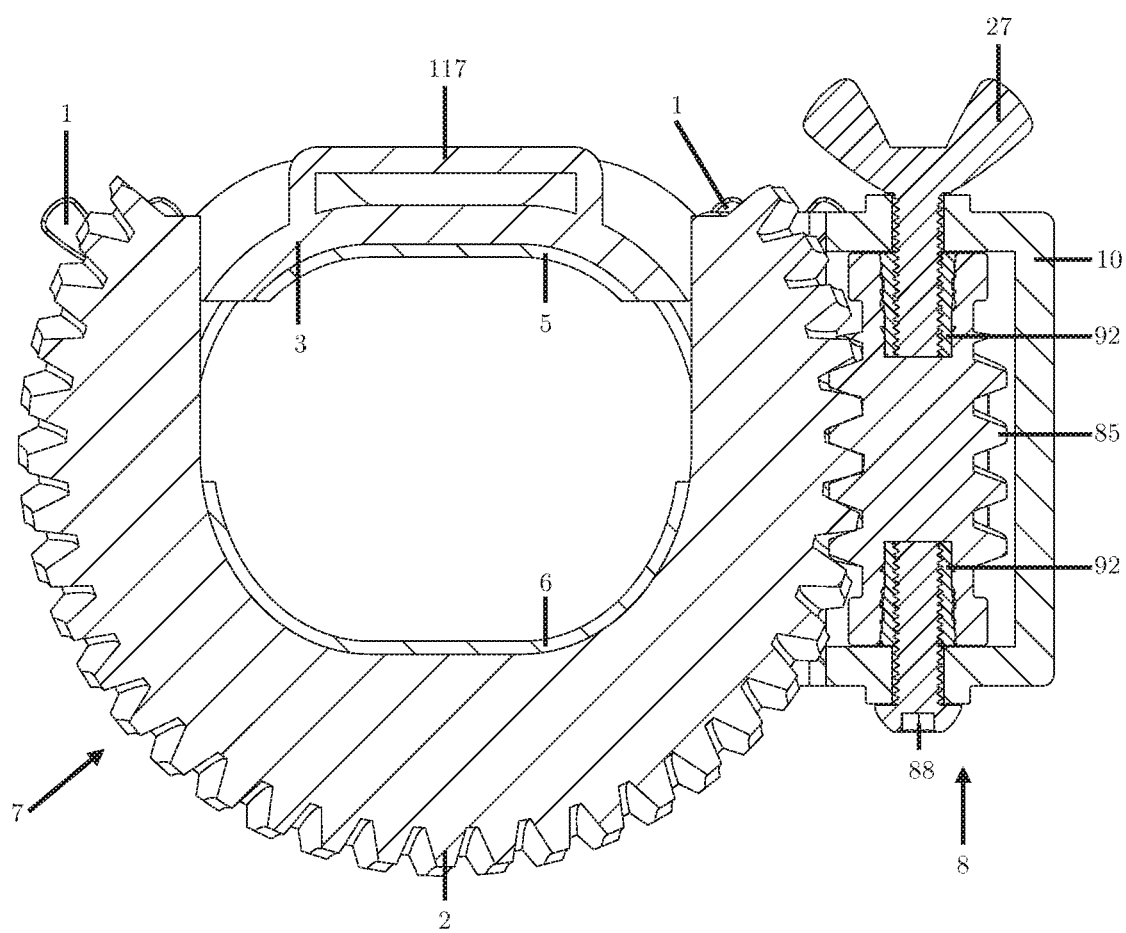
FIG. 56 is a cross-sectional front view, taken along plane 53-53 of FIG. 53, of the thumbscrew wrist cuff assembly of FIG. 33 assembled to the gearbox assembly of FIG. 22, both of which are shown assembled to the orthosis in FIG. 1 and FIG. 3.

FIG. 56 is a cross-sectional front view, taken along plane 53-53 of FIG. 53, of the thumbscrew wrist cuff assembly 7 and shows how the worm gear 2 and the worm 85 are coupled.

Figure 44:
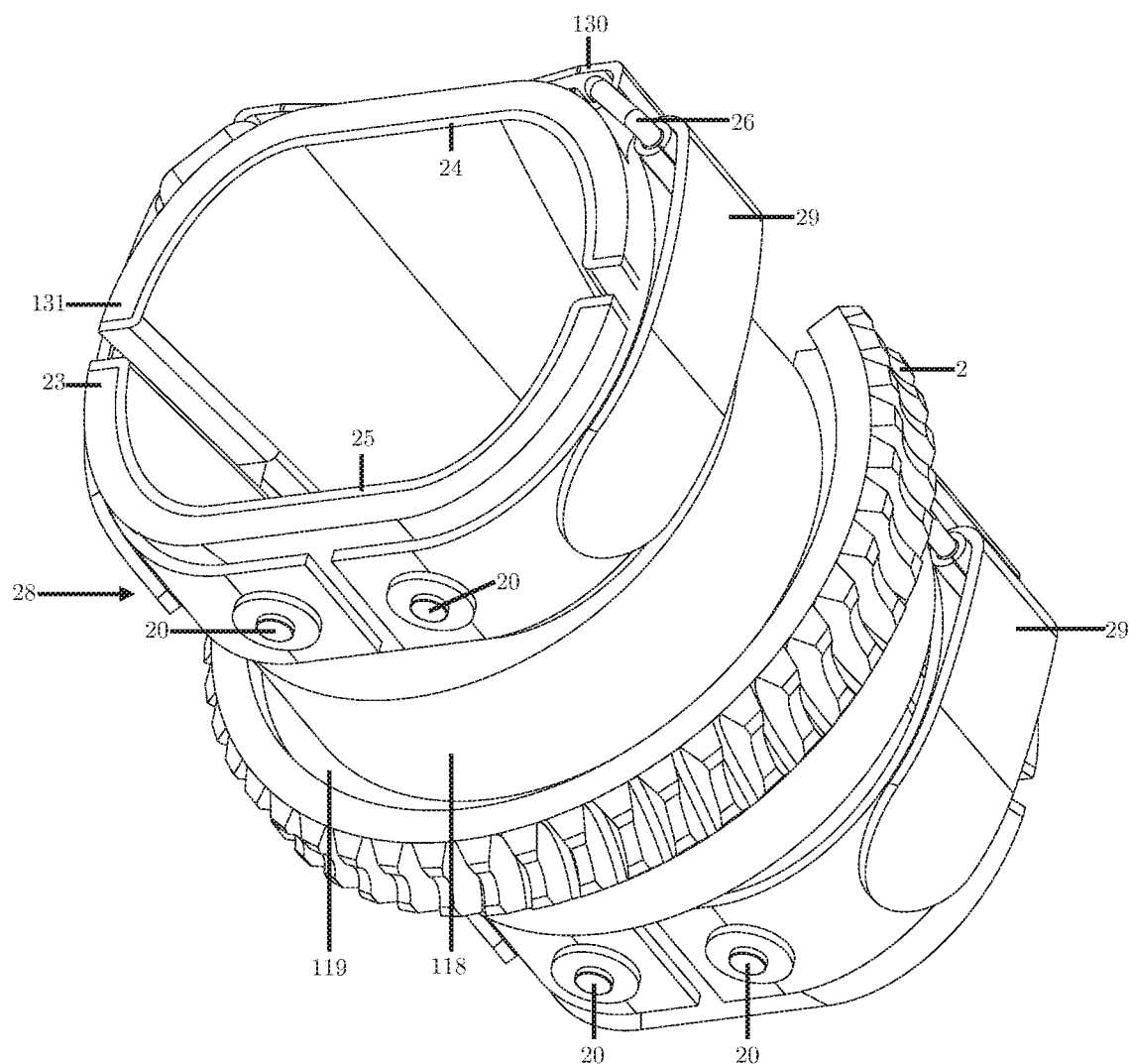
FIG. 44 is a front bottom perspective view of the embodiment of the wrist cuff assembly shown in FIG. 43.
Figure 45:
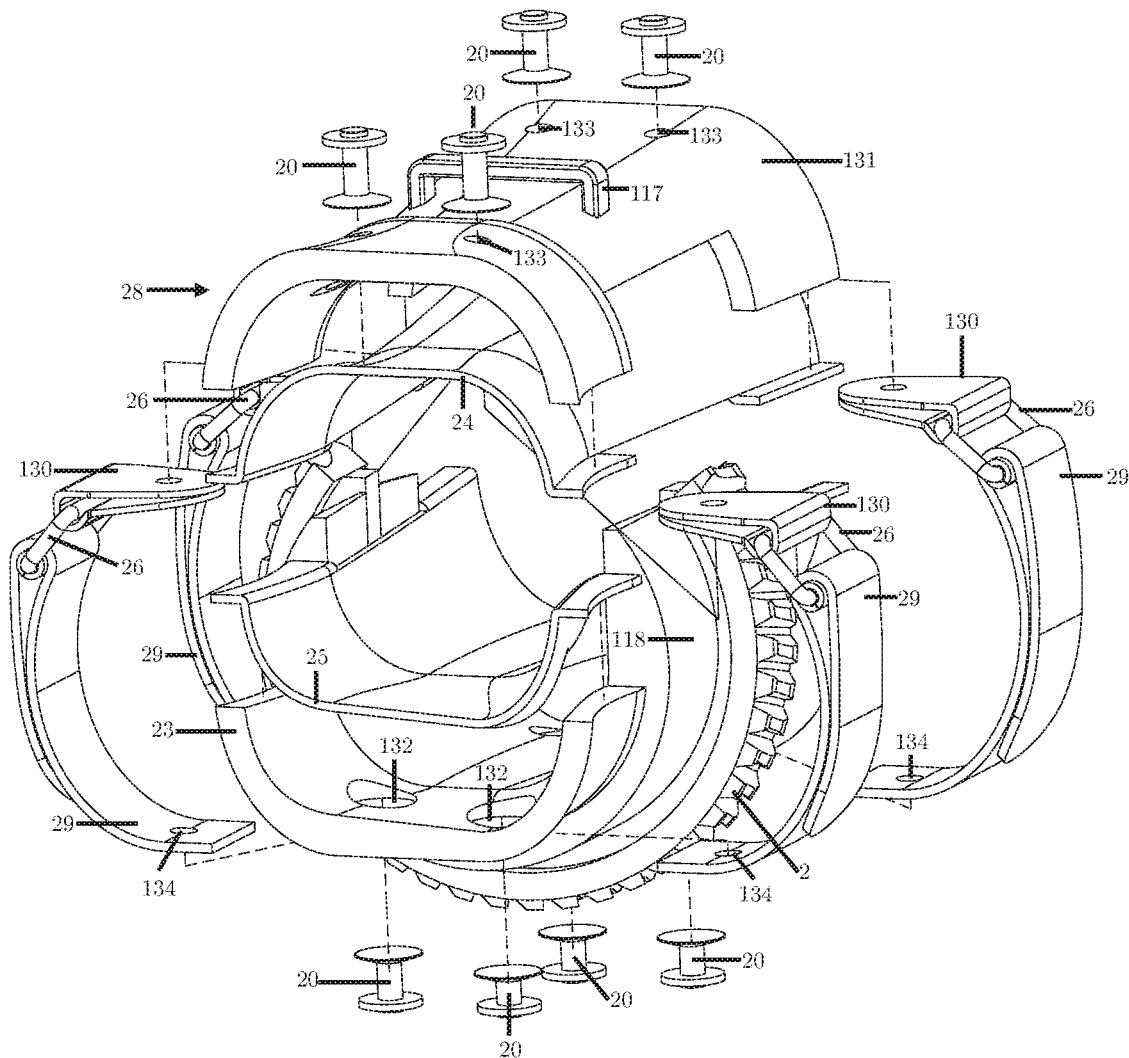
FIG. 45 is an exploded view of the embodiment of the wrist cuff assembly shown in FIG. 43.
Figure 46:
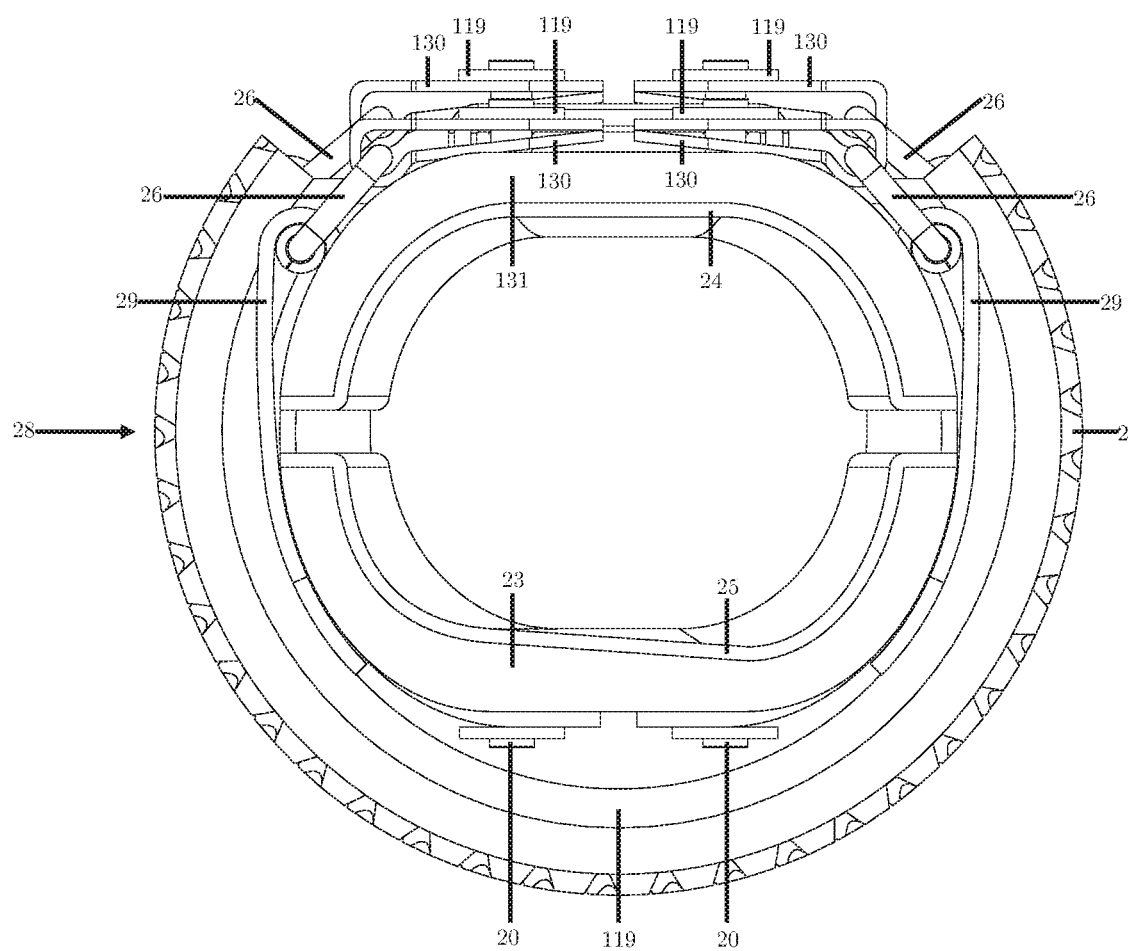
FIG. 46 is a front view of the embodiment of the wrist cuff assembly shown in FIG. 43.
Figure 47:
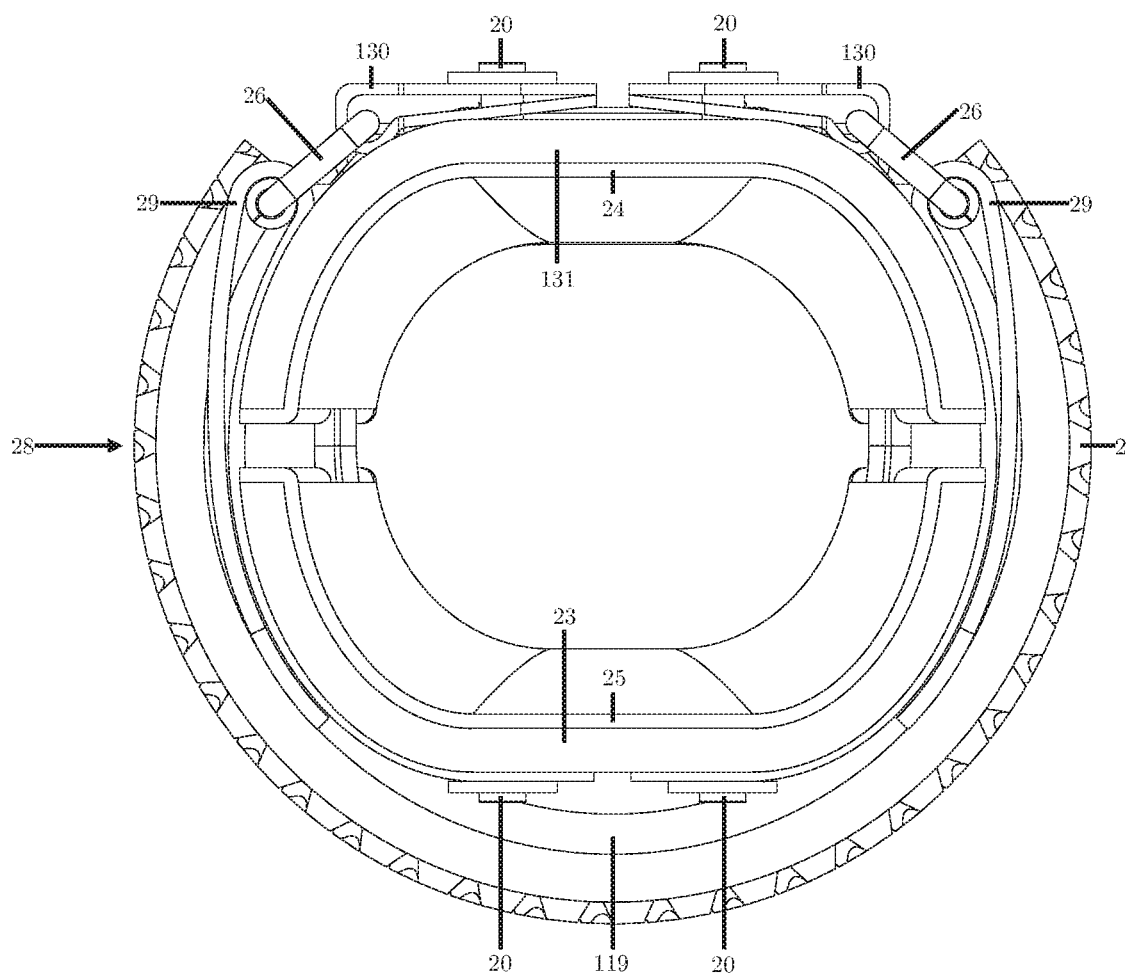
FIG. 47 is a rear view of the embodiment of the wrist cuff assembly shown in FIG. 43.
Figure 48:
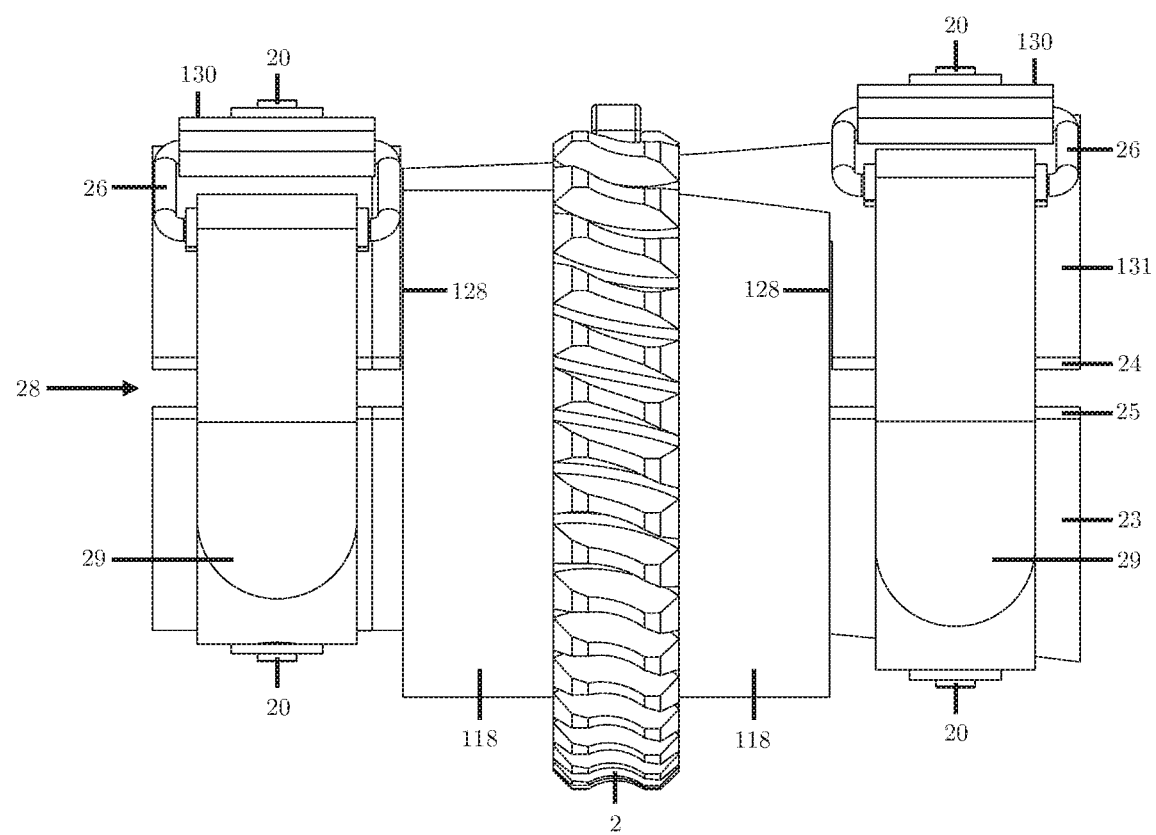
FIG. 48 is a right side view of the embodiment of the wrist cuff assembly shown in FIG. 43.
Figure 49:
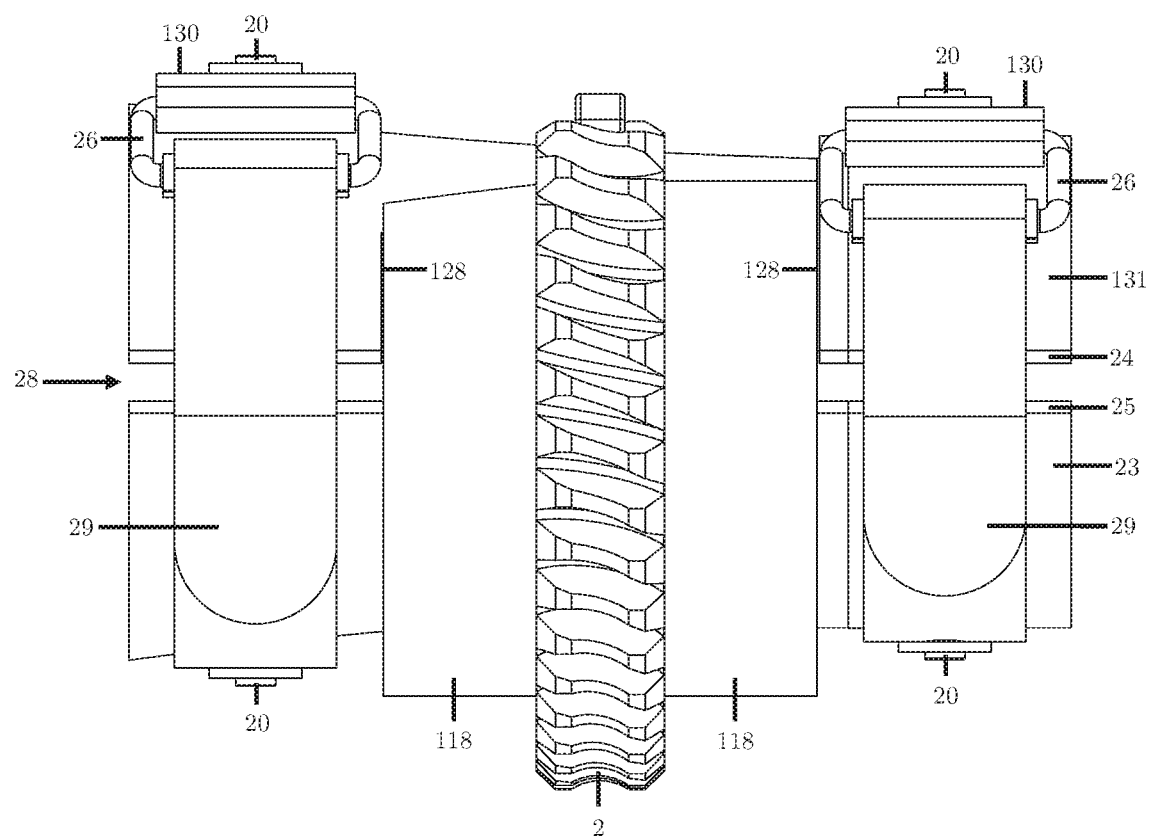
FIG. 49 is a left side view of the embodiment of the wrist cuff assembly shown in FIG. 43.
Figure 50:
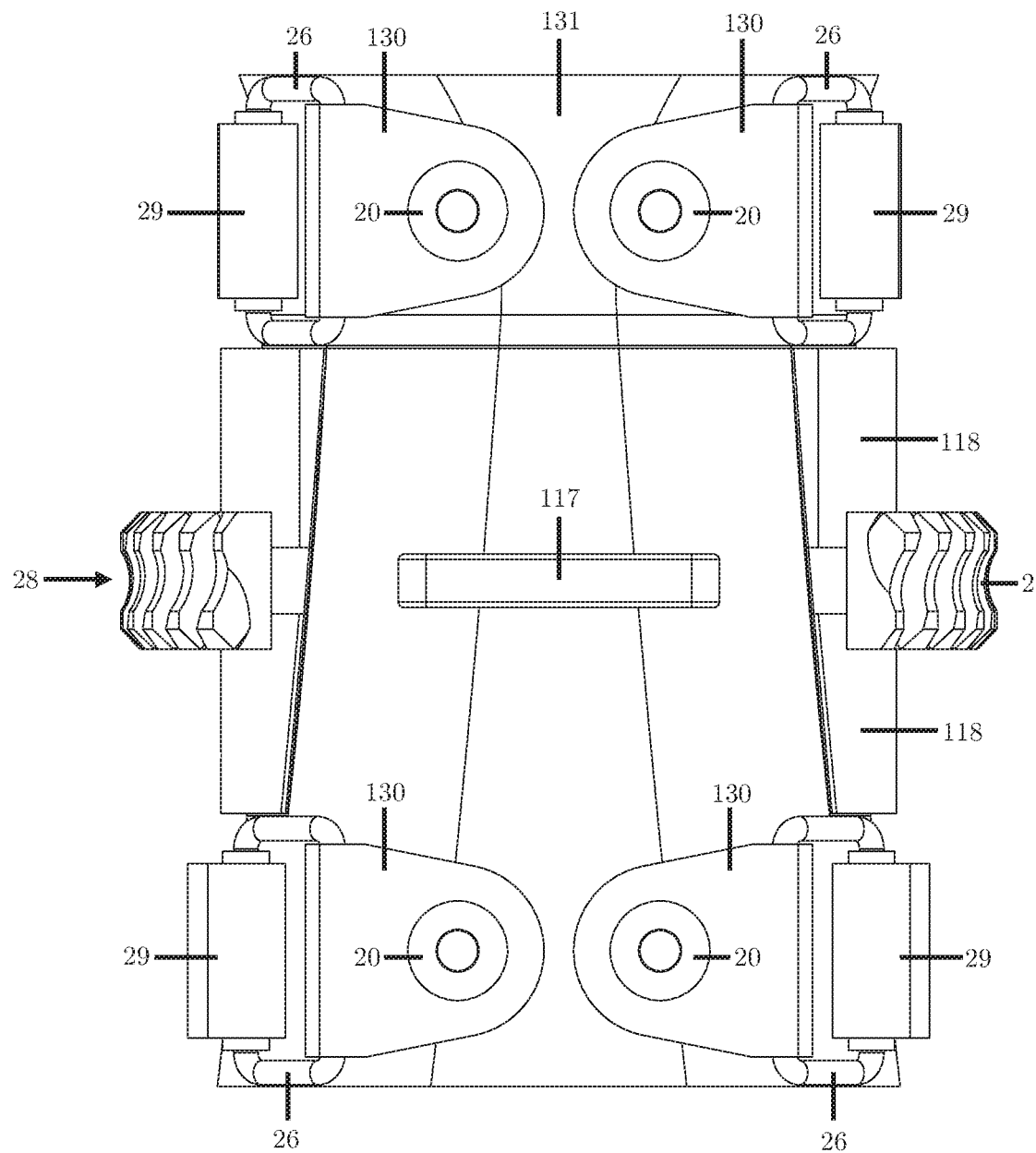
FIG. 50 is a top view of the embodiment of the wrist cuff assembly shown in FIG. 43.

Several views of the strap wrist cuff assembly 28 are presented in FIGS. 43-50 so that the features may be fully and understood. FIG. 43 is a front top perspective view, FIG. 44 is a front bottom perspective view, FIG. 45 is an exploded view, FIG. 46 is a front view, FIG. 47 is a rear view. FIG. 48 is a right side view, FIG. 49 is a left side view, and FIG. 50 is a top view. Referring now to the exploded view of FIG. 45, it is seen that, the strap wrist cuff assembly 28 includes a strap upper wrist cuff 131, a strap lower wrist cuff 23, a strap upper pad 24, a strap lower pad 25, 4 chafe loops 130, 4 metal loops 26, 4 hook and loop straps 29, and 8 No. 8 belt rivets 20.

Figure 51:
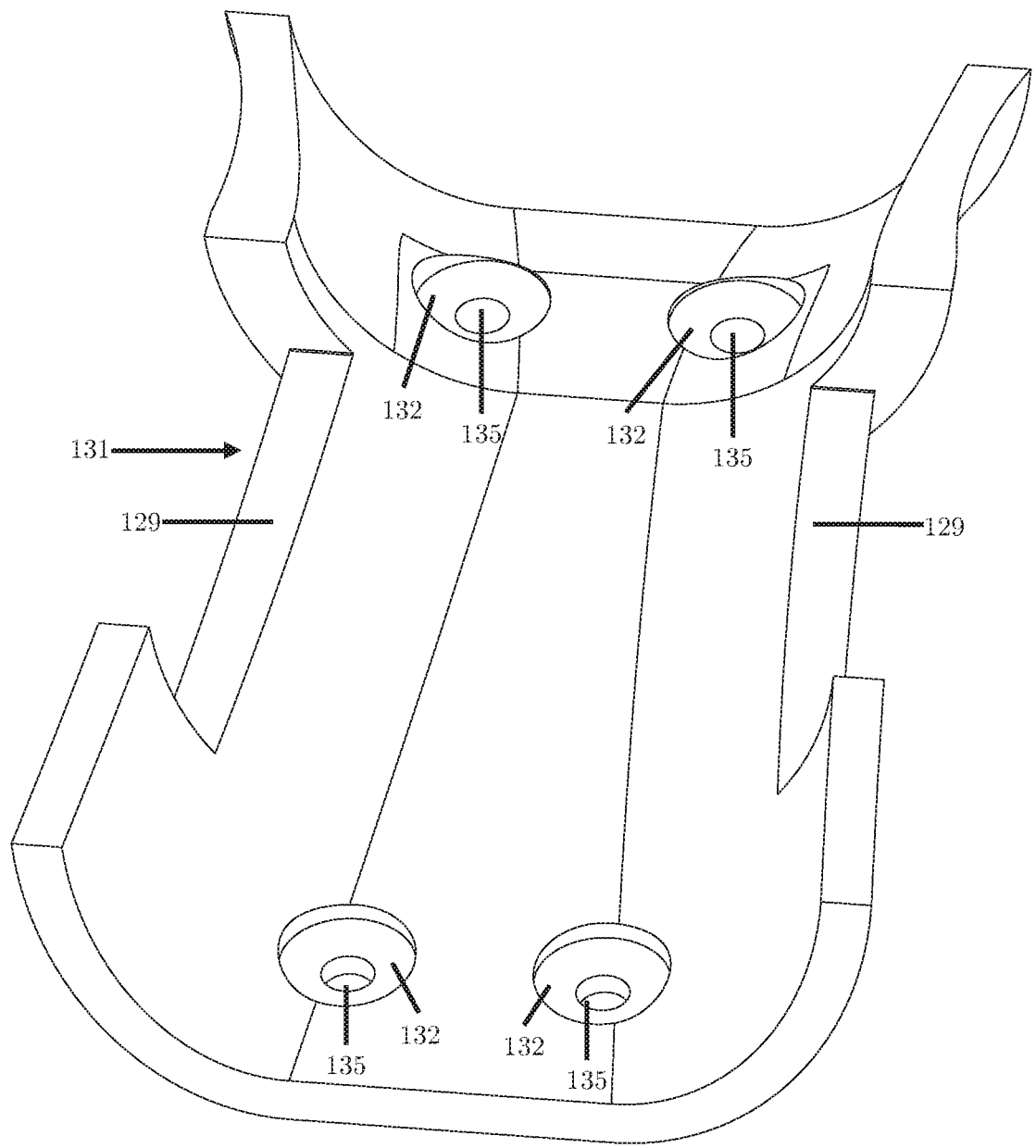
FIG. 51 is a perspective view of the inside of the strap upper wrist cuff from the embodiment of the wrist cuff assembly shown in FIG. 43.

FIG. 51 shows a perspective view of the inside of the strap upper wrist cuff 131. It has 4 holes 135 through which rivets are placed and 4 molded chamfer pockets 132 for the rivet heads to sit in. All the other features on the cuff 131, and their corresponding functions, are identical to those of the thumb upper wrist cuff 3 except for the thumbscrew holes 123 (shown in FIG. 41).

Figure 52:
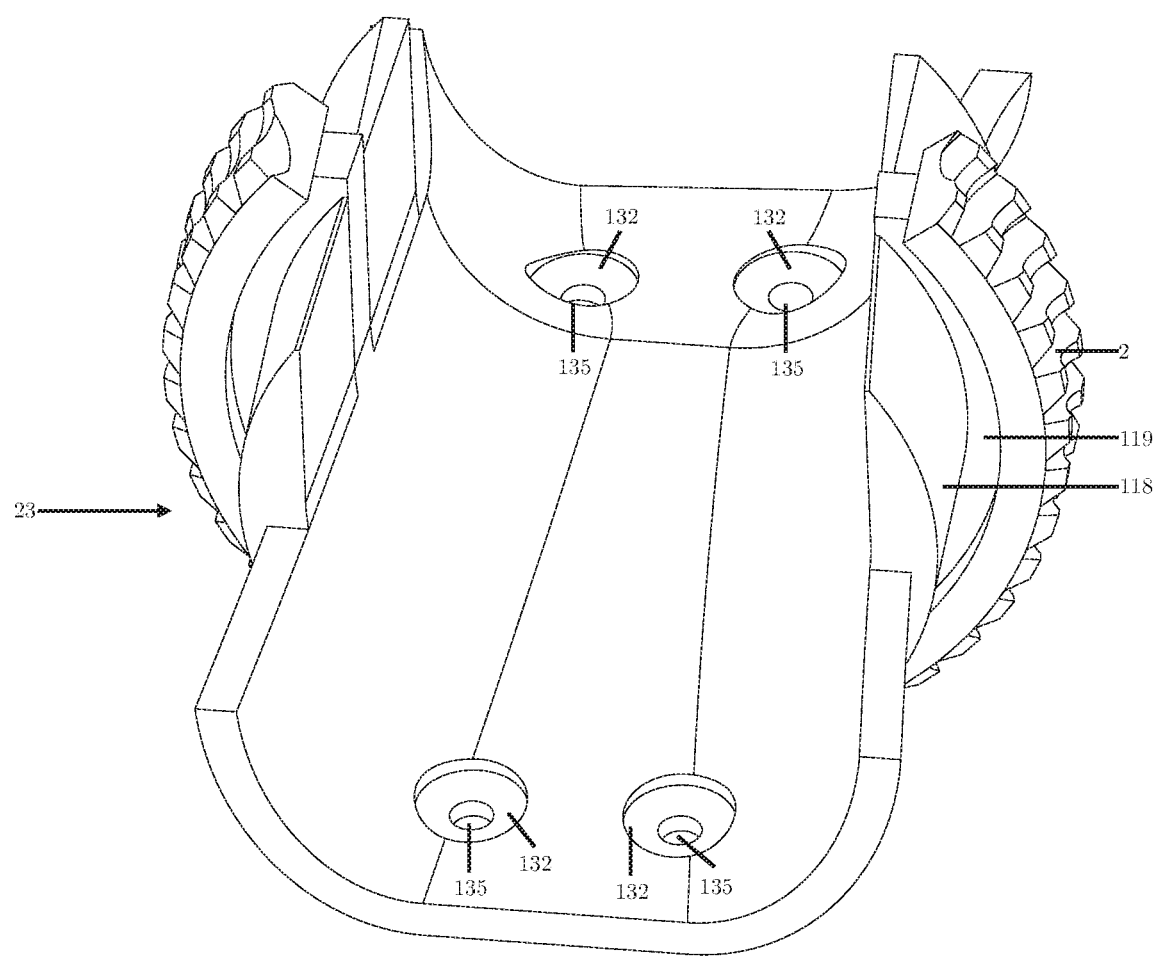
FIG. 52 is a perspective view of the inside of the strap lower wrist cuff from the embodiment of the wrist cuff assembly shown in FIG. 43.

FIG. 52 shows a perspective view of the inside of the strap lower wrist cuff 23. It has 4 holes 135 through which rivets are placed and 4 molded chamfer pockets 132 for the rivet heads to sit in. All the other features on the cuff 23, and their corresponding functions, are identical to those of the thumb lower wrist cuff 4 except for the molded heat set insert, pockets 125 (shown in FIG. 42).

Referring to the exploded view of FIG. 45, it is contemplated that the 4 chafe loops 130, together with their metal loops 26, are riveted to the strap upper wrist cuff 131 with the No. 8 belt rivets 20. The heads of each rivet 20 are countersunk into the molded pockets 132 so that the top is flush with the lowest point of the adjacent surface. This allows the strap upper wrist pad 131 to be installed over the rivets 20 without them poking through. The 4 hook and loop straps 29 are riveted to the strap lower wrist cuff 23 with No. 8 belt rivets 20. Similarly to the strap upper arm cuff 131, the heads of each rivet 20 are countersunk into the molded pockets 132 so that the top is flush with the lowest point of the surrounding surface, which allows the strap lower wrist pad 23 to be installed over the rivets 20 without them poking through. After the forearm has been rested in the strap lower cuff 23, each strap 29 is looped through the corresponding metal loop 26 of the chafe loop 130 and fastened to itself. The tension is adjusted based on how much of the end of the strap 29 is pulled through the metal loop 26. In an analogous manner to the use of the thumbscrews with the thumbscrew wrist cuff assembly 7, the placement of a strap 29 at each corner of the assembly 7 allows the optimal level of clamping pressure and comfort to be achieved.

Figure 57:
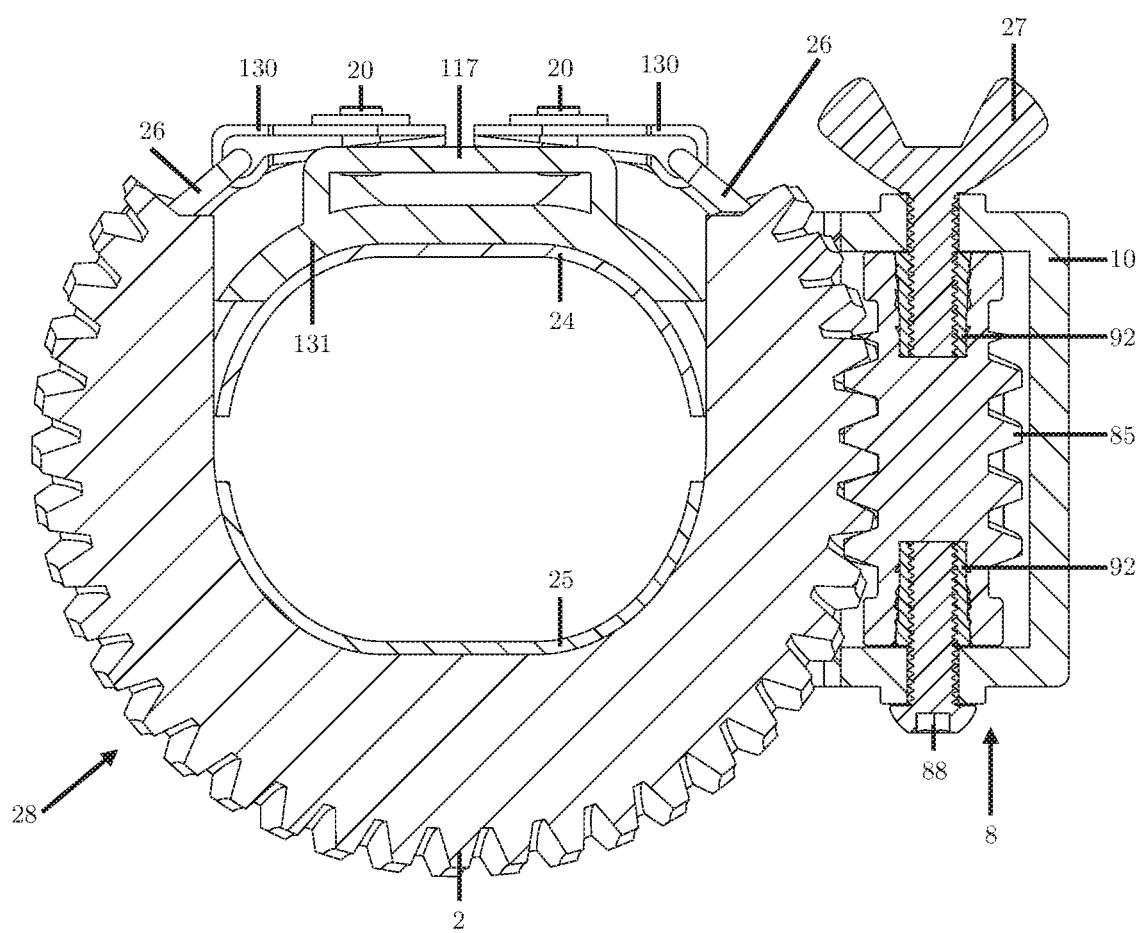
FIG. 57 is a cross-sectional front view, taken along plane 54-54 of FIG. 54, of the strap wrist cuff assembly of FIG. 43 assembled to the gearbox assembly of FIG. 22, both of which are shown assembled to the orthosis in FIGS. 2-5 and FIG. 4.

FIG. 57 is a cross-sectional front view, taken along plane 54-54 of FIG. 54, of the strap wrist cuff assembly 28 and shows how the worm gear 2 and worm 85 are coupled.

It is noted that while a chafe loop 130 with a hook and loop strap configuration is contemplated, other strap fastening methods, such as buckles or clips, may be used without departing from the scope of the present invention.

The strap wrist cuff assembly 28 is identical to the thumbscrew wrist cuff assembly 7 except that one is fastened using thumbscrews and the other is fastened using straps 29. Apart from this difference, everything in the previous discussion regarding the thumbscrew wrist cuff assembly 7 applies to the strap wrist cuff assembly 28.

The upper splint arm and lower splint arm must be highly resistant to bending forces along their lengths and to torsional forces about a central axis that runs down the length. It is therefore contemplated that they be made from a tempered steel approximately ¼ inch thick, but any material or thickness may be used without departing from the scope of the present invention.

It is noted that the heat set threaded inserts 36, 61, 92, 93, 50, shown in the top row of FIG. 58, are contemplated to be made of brass, but any suitable material may be used without departing from the scope of the present invention. The rivet 81 used in the splint arm assembly 14 is contemplated to be made out of steel and the belt rivet 20 is contemplated to be made out of copper. Again, in both cases, any suitable material may be used without departing from the scope of the present invention. Both rivets are shown in the second row of FIG. 58. The remaining hardware in FIG. 58 is contemplated to be made out of steel but any suitable material may be used without departing from the scope of the present invention.

It is also noted that while the heat set threaded inserts 36, 61, 92, 93, 50 were used throughout the embodiments of the orthosis as anchors for certain screws, other methods may be used to anchor the screws without departing from the scope of the present invention. Such methods include but are not limited to threads molded directly into the material, molding the material around a hexagonal nut, and embedding a hexagonal nut into a molded hexagonal pocket.

A third embodiment of the orthosis of the present invention will be now be discussed. While the embodiments of the orthosis described above allow for forearm supination/pronation and shoulder internal/external rotation to be controlled, this third embodiment of the orthosis of the present invention extends this functionality by allowing the arm and shoulder's full range of motion to be controlled. More specifically, this third embodiment provides an adjustable amount of forced forearm pronation or supination, shoulder internal or external rotation, shoulder adduction or abduction, and shoulder flexion or extension. Each of these four rotational degrees of freedom can be switched back and forth between a state of being locked and a state of being free to move. Similarly to the first two embodiments, this third embodiment allows the elbow's range of motion to be limited or locked. Additionally, the third embodiment of the orthosis permits scapular elevation/depression and allows the motion to be locked and unlocked. All of this is accomplished using a number of assemblies and components, some of which are second or third contemplated embodiments of the assemblies and components from the first embodiment of the orthosis.

The third embodiment of the orthosis, orthosis-ROM, is illustrated in FIG. 59. For simplicity and conciseness, it is being referred to as orthosis-ROM (where ROM stands for range of motion) because it is the embodiment that allows the arm and shoulder's full range of motion to be controlled.

Once again, for the sake of convenience, "orthosis" will be used to collectively refer to either embodiment of the orthosis, which includes orthosis-thumb, orthosis-strap, and orthosis-ROM. Similarly, "wrist cuff assembly" will be used to collectively refer to either embodiment of the wrist cuff assembly, which includes the wrist cuff assembly that uses thumbscrews, the wrist cuff assembly that uses straps, and a wrist cuff assembly that uses ratchets and pawls. The wrist cuff assembly that uses ratchets and pawls is a third embodiment that's being introduced and will be referred to as the ratchet lock wrist cuff assembly.

Referring now to the third embodiment of the present invention in more detail, in FIG. 59 the orthosis-ROM includes one embodiment of a torso vest 142, a flexion-extension assembly 137, a shoulder sleeve assembly 138, an internal-external rotation gearbox assembly 136, a splint arm assembly 139, a supination-pronation gearbox assembly 140, and a ratchet lock wrist cuff assembly 141 all assembled together. The flexion-extension assembly 137 and shoulder sleeve assembly 138 replace the upper arm cuff and linear motion carriage assemblies 19, 18 of FIGS. 9 and 13, a second embodiment of the splint arm assembly 14 of FIG. 20 is attached to the shoulder sleeve assembly 138, a second embodiment of the gearbox assembly 8 of FIG. 22 is attached to the splint arm assembly 14, and a third embodiment of the wrist cuff assemblies 7, 28 of FIGS. 33 and 43 is attached to the supination-pronation gearbox assembly 140. FIG. 60 shows the embodiment of the orthosis depicted in FIG. 59 but from a rear perspective.

Figure 61:
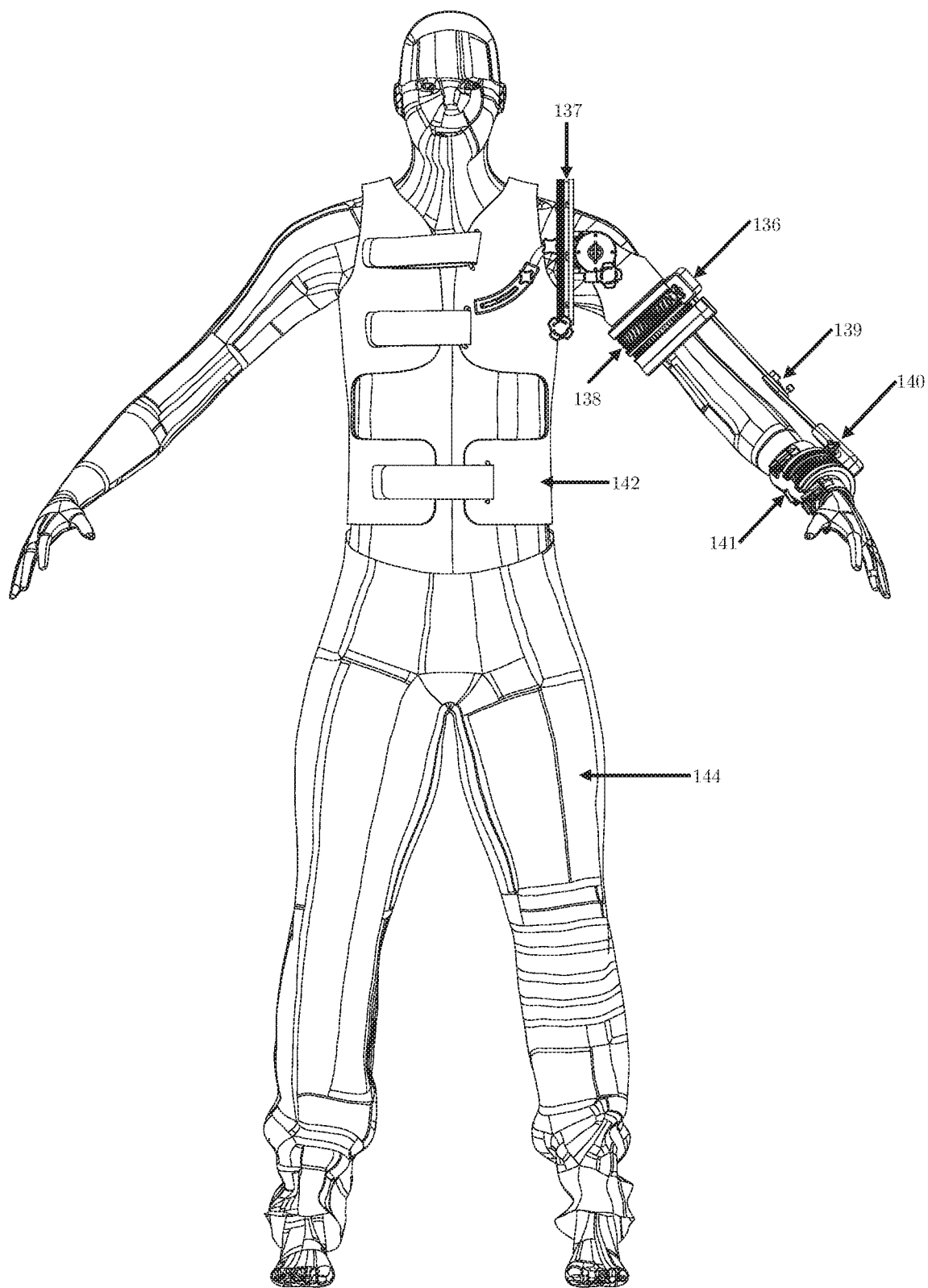
FIG. 61 is a front view of a person wearing the embodiment of the orthosis depicted in FIG. 59.
Figure 62:
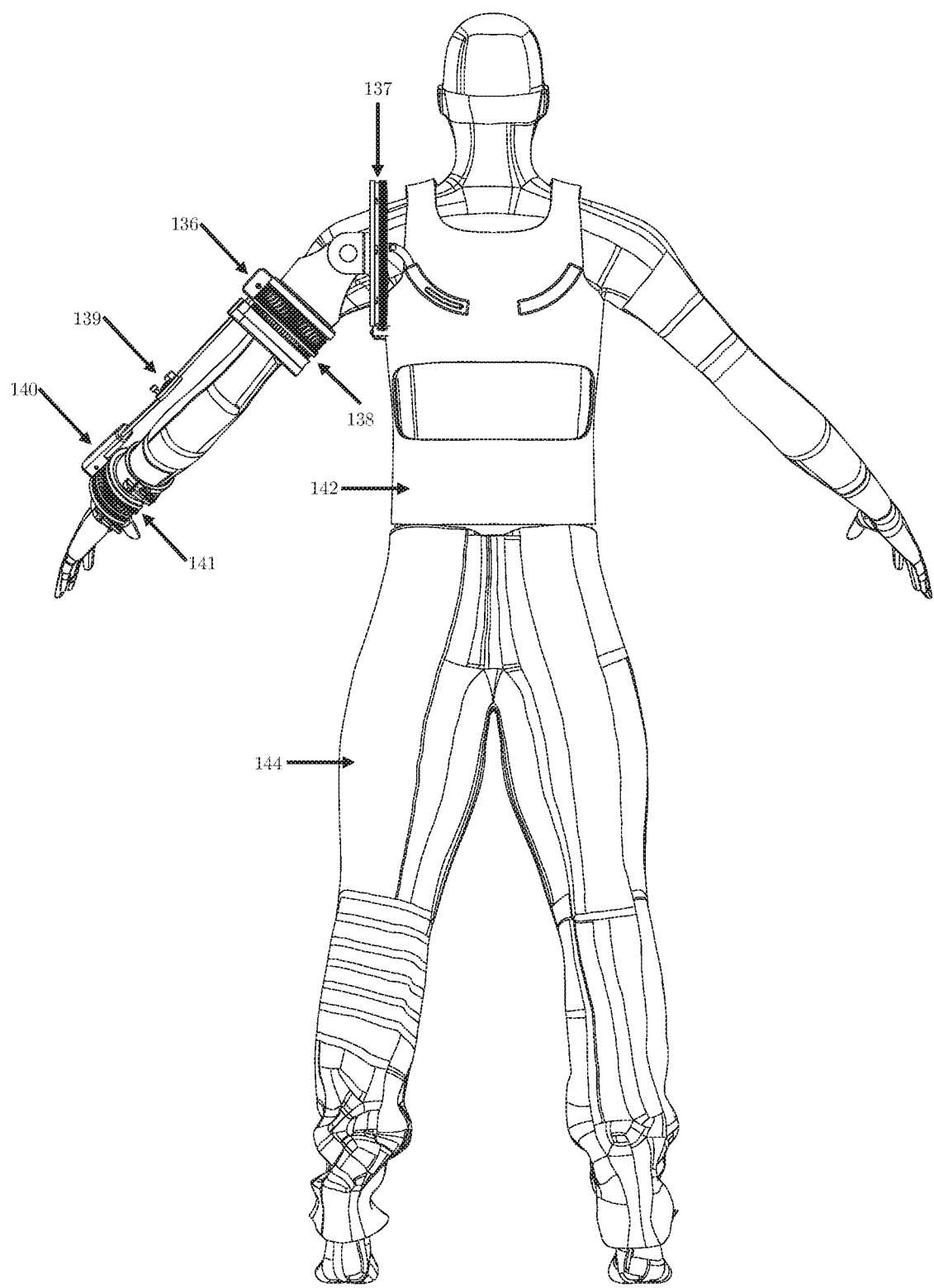
FIG. 62 is a rear view of a person wearing the embodiment of the orthosis depicted in FIG. 59.
Figure 63:
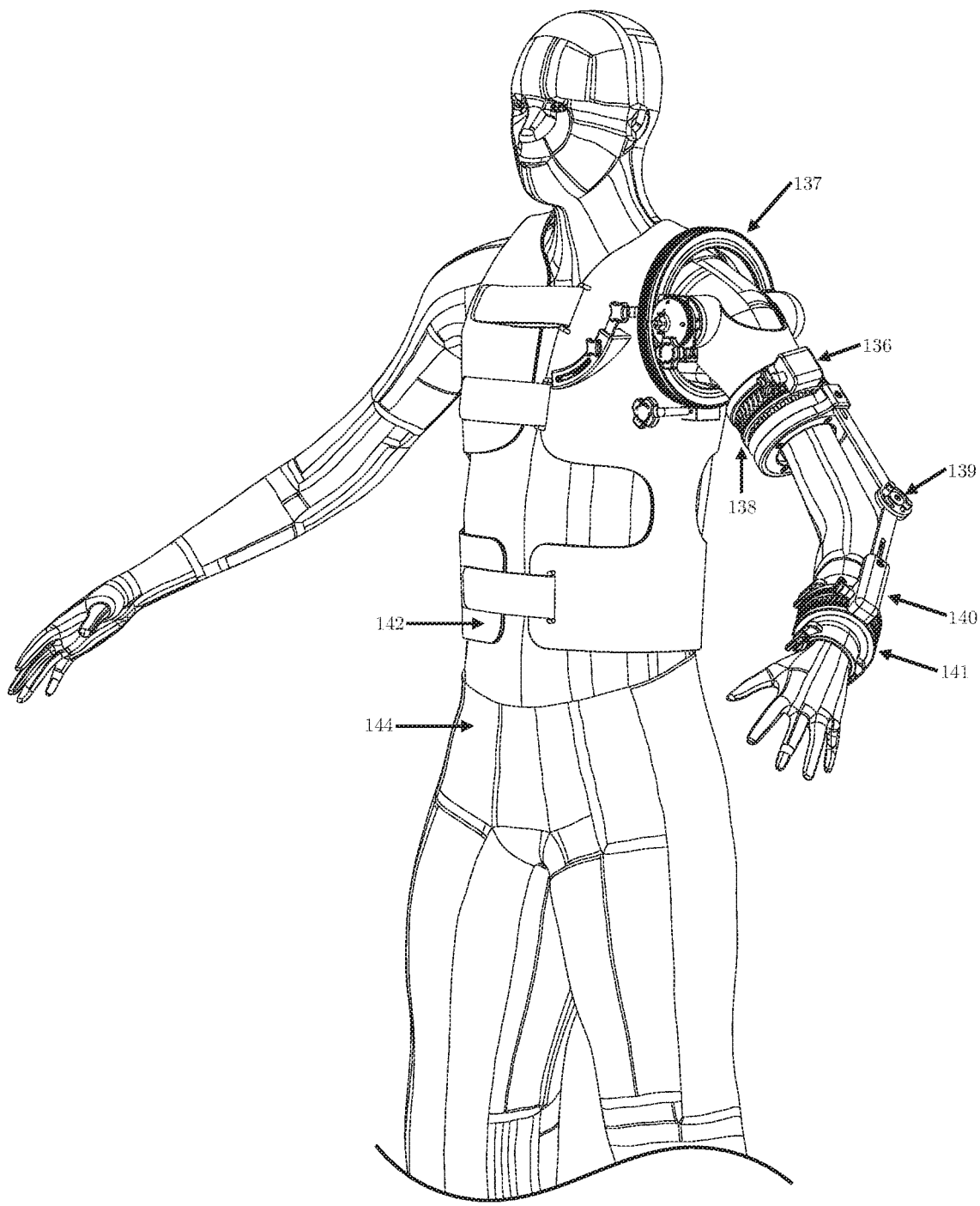
FIG. 63 is a broken front right perspective view of a person wearing the embodiment of the orthosis depicted in FIG. 59.

FIG. 61 is a front view of a person 144 wearing the embodiment of the orthosis depicted in FIG. 59. The orthosis is contemplated to be worn by putting on and securing the torso vest 142. In addition, as the effected arm is inserted through the armhole of the torso vest 142, it is also inserted through the opening of the flexion-extension assembly 137, the sleeve of the shoulder sleeve assembly 138, and the opening of the ratchet lock wrist cuff assembly 141 before finally securing the ratchet lock wrist cuff assembly 141 to the wrist and lower forearm. The torso vest 142 is a second contemplated embodiment of the shoulder brace 21. The components that comprise orthosis-ROM are anchored to it. FIGS. 62 and 63 show a back view and a front perspective view, respectively, of a person 144 wearing the embodiment of the orthosis depicted in FIG. 59.

Figure 67:
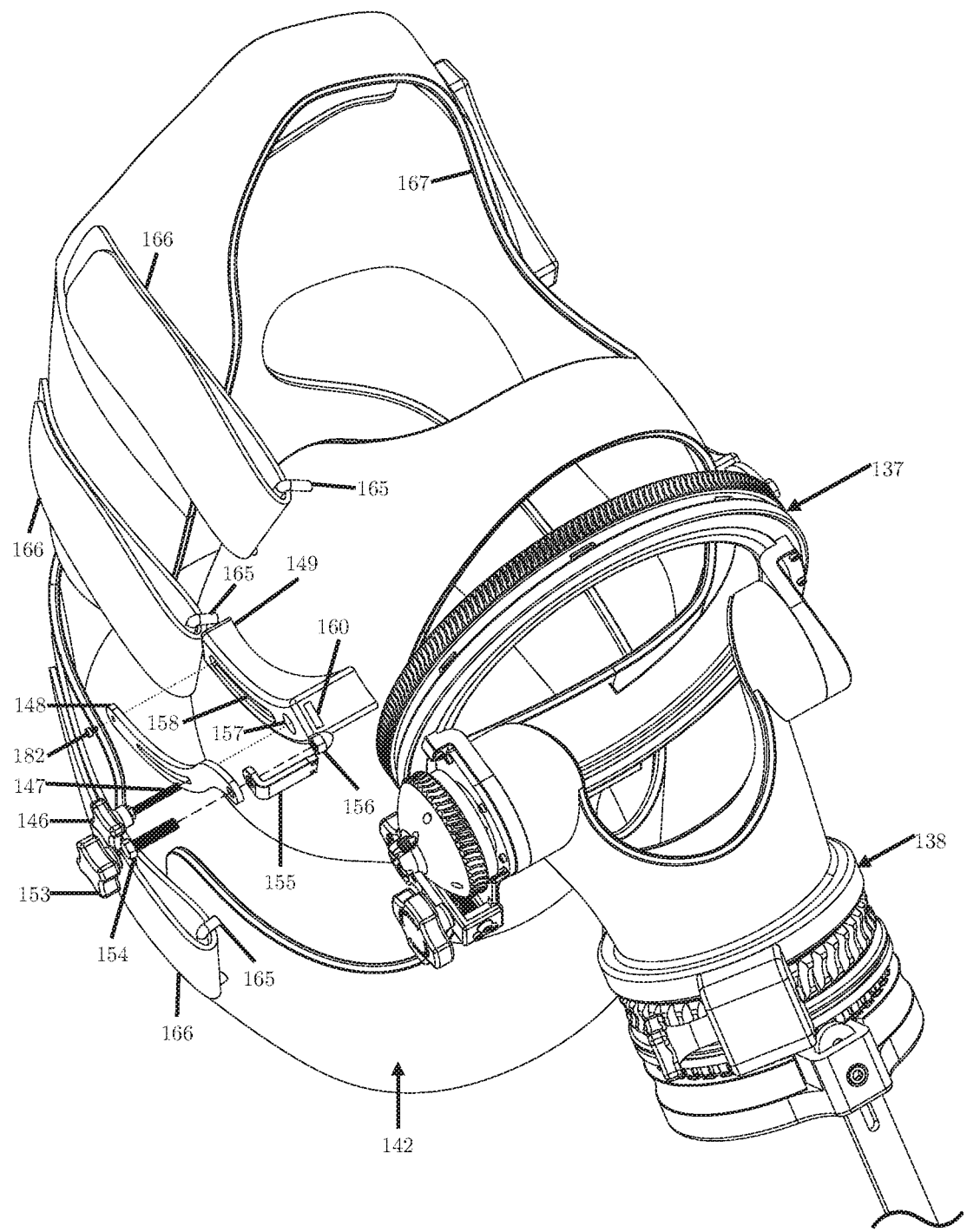
FIG. 67 is a broken, exploded, top front perspective view, of the embodiment of the orthosis depicted in FIG. 59, with the front components exploded that attach the flexion-extension assembly to the torso vest.
Figure 68:
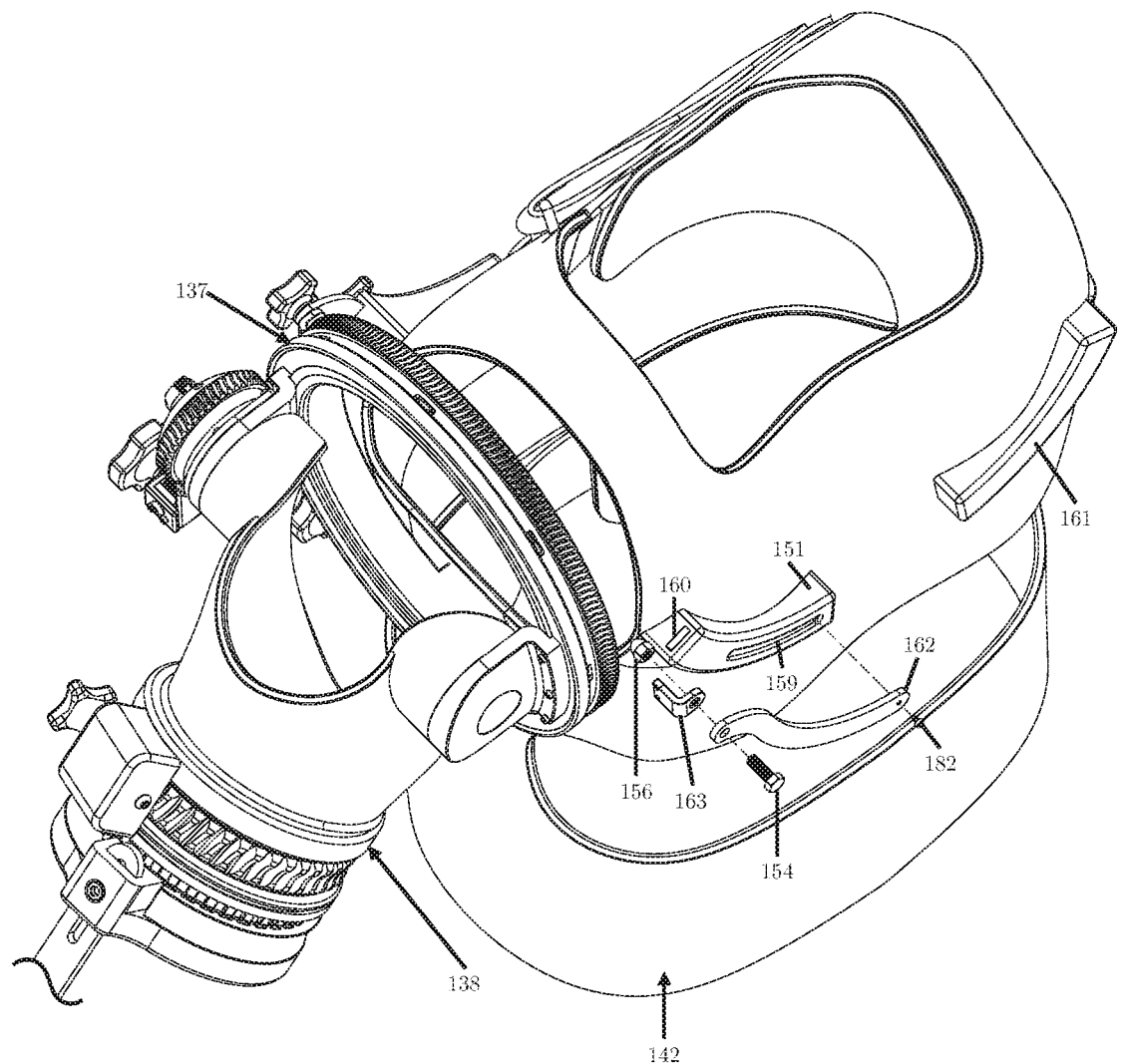
FIG. 68 is a broken, exploded, top rear perspective view, of the embodiment of the orthosis depicted in FIG. 59, with the rear components exploded that attach the flexion-extension assembly to the torso vest.

As illustrated in FIGS. 67-68, the torso vest 142 has three straps 166, three molded D-loops 165, a torso vest pad 167, a front scapular rotation rail housing 149, a rear scapular rotation rail housing 151, and a dummy scapular rotation rail housing 161. It has a traditional vest shape with no sleeves and a split down the middle front. It is put on by securing the straps 166 two of which are for the chest and one of which is for the abdomen. In one embodiment of the straps 166, it is contemplated that each is secured using hook and loop fasteners. Each strap 166 is affixed to the right side of the vest. 142 and passes through a loop 165 molded to the left side of the vest 142 before being pulled back to the right side and secured to itself. The straps 166 are pulled tightly enough to secure the vest 142 with minimal wiggle and slip and so that anything attached to it can be considered rigid. Because the vest 142 sits on the shoulders and wraps around the torso, the shoulders primarily, and the torso, bear the weight of anything attached to the vest 142 and do so in a way that spreads the load throughout. The straps 166 are contemplated to be attached to the vest using epoxy but may be attached using other methods, such as stitching, without departing from the scope of the present invention. And while a strap and loop fastening system was used in this embodiment, any type of fastening system, such as buckles or buttons, may be used without departing from the scope of the present invention.

It is one aspect of the torso vest 142 to be flexible enough to conform to the shape of the torso and to accommodate small changes in the shape of the areas surrounding the shoulder as the arm is being moved. In particular, movements such as scapular protraction and retraction would be permissible. This is accomplished by the torso vest 142 being made of a semi-rigid urethane or any material that allows the vest 142 to serve as a rigid attachment point while not hindering the shoulder from moving. There are sections cut out of the areas that cover the middle back and upper abdomen area to allow the torso to bend and to provide greater flexibility without compromising rigidity. In addition, a torso vest pad 167 is contemplated to line the inside surfaces of the vest 142 for added comfort and is made of foam, cloth, or any comparable material that satisfies this function. It may or may not have a skin or casing enveloping it, such as fabric. The vest 142 and the padding 167 are contemplated to be about. 3/16 inch thick but may be any thickness that doesn't hinder function. The padding 167 is contemplated to be made of foam, cloth, or any comparable material that satisfies this function but any material may be used without departing from the scope of the present invention. It is also contemplated to attach to the vest 142 either by being molded directly to it or by using an adhesive, such as a high-strength spray adhesive, an epoxy, contact cement, glue, or tape, but any suitable adhesive may be used without departing from the scope of the present invention.

As illustrated in FIG. 67, the front scapular rotation rail housing 149 is a rigid rectangular arc that protrudes, parallel to the torso, from the chest area of the vest 142 on the effected side. The axis of its arc coincides with the sternoclavicular joint of the wearer. An arced, rectangular slot 160 lies within the housing 149 and is enclosed by the housing 149 on all sides except for the upper end. The axis of its arc also coincides with the sternoclavicular joint. It is contemplated that an arced obround slot 158 is cut perpendicularly into the front face of the housing 149 until it intersects the void created by the first slot 160. The included angle of the slot 158 is contemplated to be equal to the rotational range of the wearer's scapula about the sternoclavicular joint. Also on the front face of the housing 149, a round hole 157 is cut perpendicularly until it intersects the void created by the first slot 160.

In an identical manner to the front housing 149, the rear scapular rotation rail housing 151, shown in FIG. 68, is a rigid, rectangular arc that protrudes from the upper back area of the vest 142 on the effected side in such a way that if the face of the first housing 149, which is parallel to the torso, were projected towards the rear it would coincide with the corresponding face on the second housing 151. Additionally, it has an identical arced obround slot 159 but no round hole.

On the other side of the upper rear surface of the vest 142, the dummy scapular rotation rail housing 161 is contemplated to be a third rigid, rectangular, protruding arc. It is symmetrical to the second housing 151 from one half of the body to the other but has no slots or holes; it is essentially a dummy protrusion that provides evenness if the wearer decides to lay on their back. It is contemplated that each housing is made of a rigid urethane or any other rigid material that can be molded directly to the vest 142. Additionally, the housings 149, 151, 161 need not be molded to vest 142. They may be separate pieces that attach to the vest 142 using screws or epoxy, for example, without departing from the scope of the present invention.

Similarly to the shoulder brace 21, it is contemplated that the torso vest 142 could either be worn directly on the skin or on top of clothing, depending on what the user finds to be more comfortable or secure. If worn on top of clothing, the clothing is presumed to be thin enough for the straps 166 to be fully engageable and for the orthosis to be held securely.

As with the shoulder brace 21, the primary function of the torso vest 142 is to serve as an attachment point for the components and assemblies that comprise the orthosis and, in this case, orthosis-ROM. Because the torso vest 142 is secured to the torso, most of the weight of the orthosis, and any tugging forces that might be placed on it, is borne by the torso. In other words, the weight of the components and assemblies that attach to the torso vest 142, and any forces that, might be placed on it—especially those that are expected to be encountered during resistance training—is distributed throughout the torso vest 142. These forces are then transferred from the torso vest 142 to the torso. This makes the orthosis feel more like an extension of the body than something attached to it.

The use of the torso vest 142 as the primary means of wearing orthosis-ROM and as an attachment point for the components and assemblies that comprise it is advantageous over the way that common arm orthoses are worn for the same three reasons stated previously for the shoulder brace 21: (1) the weight of the orthosis, and any forces that might be placed on it, is distributed throughout, the torso, whereas, with the more common arm orthosis, its weight and any forces that might be placed on it is distributed primarily to the upper and lower arm; (2) the torso vest in conjunction with the shoulder sleeve does not rely on a clamping force, which could cause discomfort and reduced circulation, to attach to the upper arm; (3) upper arm rotation is permitted, which means that full forearm supination or pronation can occur. The discussion surrounding these advantages is the same as that for the shoulder brace 21.

It is contemplated that the torso vest 142 could also be rigid and configured to serve as a scoliosis brace for wearers who suffer from scoliosis, in addition to its original purpose. It may also be configured to alleviate other conditions of the posture.

In one aspect of orthosis-ROM, the front scapular rotation rail 148, illustrated in FIGS. 59, 61, 63-67 and 132, is a flat, doubly-arced, obround bar. It is slidingly disposed within the arced, rectangular slot 160 on the front of the torso vest 142. It is seen that the two arcs, one of which is longer than the other, are tangent to each other and have opposite curvature. When the rail 148 sits in the slot, the axis of the longer arc coincides with the sternoclavicular joint so that it rotates about the joint as it slides back and forth. An arced obround slot 487, with an axis that also coincides with the sternoclavicular joint, cuts completely through the section of the rail 148 with the longer arc and is contemplated to have an included angle that equals the rotational range of the scapula of the wearer about the joint. However, it is immaterial whether the included angle is less or more than this rotational range. A threaded hole 486 passes through and is coincident with the axis of the semicircular arc on the end of the rail 148 with the longer arc. It is contemplated that the hole 486 be M2 size but any size maybe used without departing from the scope of the present invention. A round hole 488 passes through and is coincident with the axis of the semicircular arc on the end of the rail 148 with the shorter arc. It is contemplated that the hole 488 be sized for an M5 screw but any diameter may be used without departing from the scope of the present invention.

The rear scapular rotation rail 162 is illustrated FIGS. 60, 62, 65, 68 and 132. It is contemplated to be slidingly disposed within the arced, rectangular slot 160 on the back of the torso vest 142 and is identical to the first except that it doesn't have a slot cut through it. The threaded hole 491 is identical to the threaded hole 486 and the round hole 492 is identical to the round hole 488. Both rails are contemplated to be about 0.125 inches thick but can have any thickness without, departing from the scope of the present invention. They are contemplated to be made of metal, urethane, composites, plastic, rubber, silicone, resin, polymers, ceramics, or metals, but any material may be used without departing from the scope of the present invention.

It is contemplated that the scapular rotation rails 148, 162 overcome the sliding friction with or without the help of lubrication from a grease or oil. In another embodiment, the rails 148, 162 may roll, rather than slide, by means of embedded ball or roller bearings.

Figure 64:
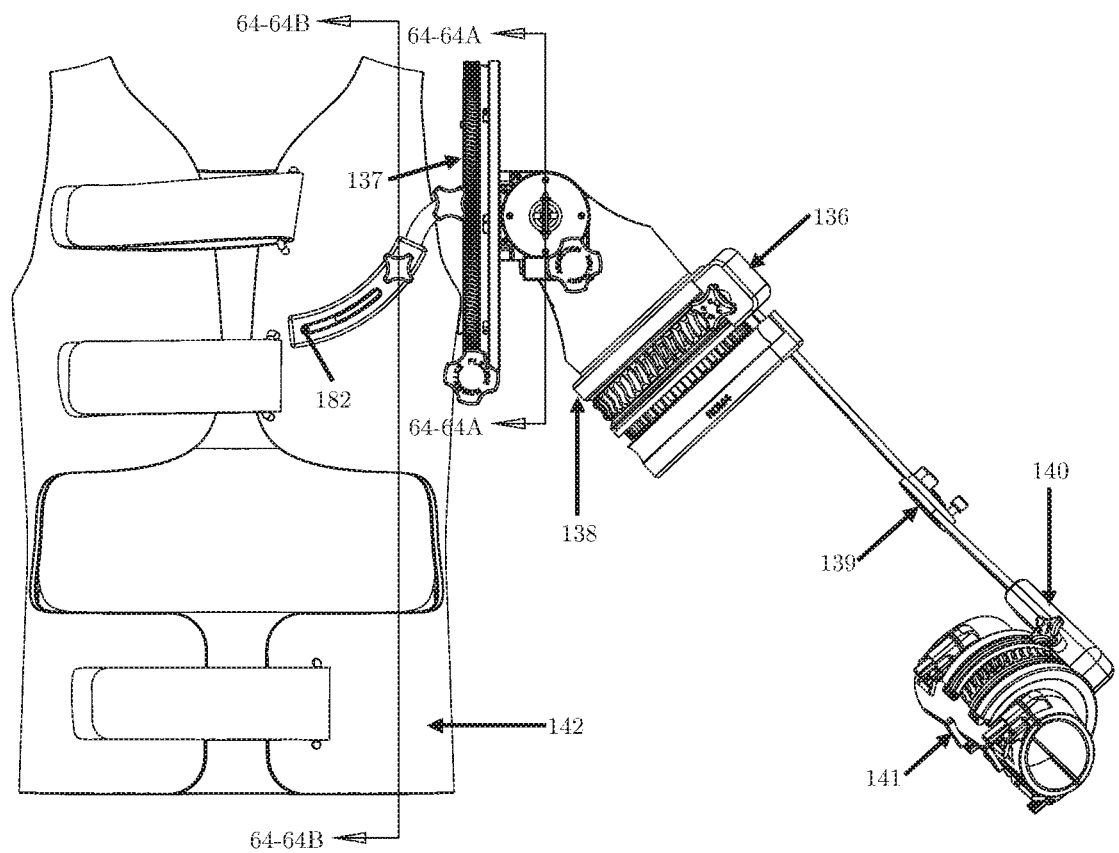
FIG. 64 is a front view of the embodiment of the orthosis depicted in FIG. 59.
Figure 65:
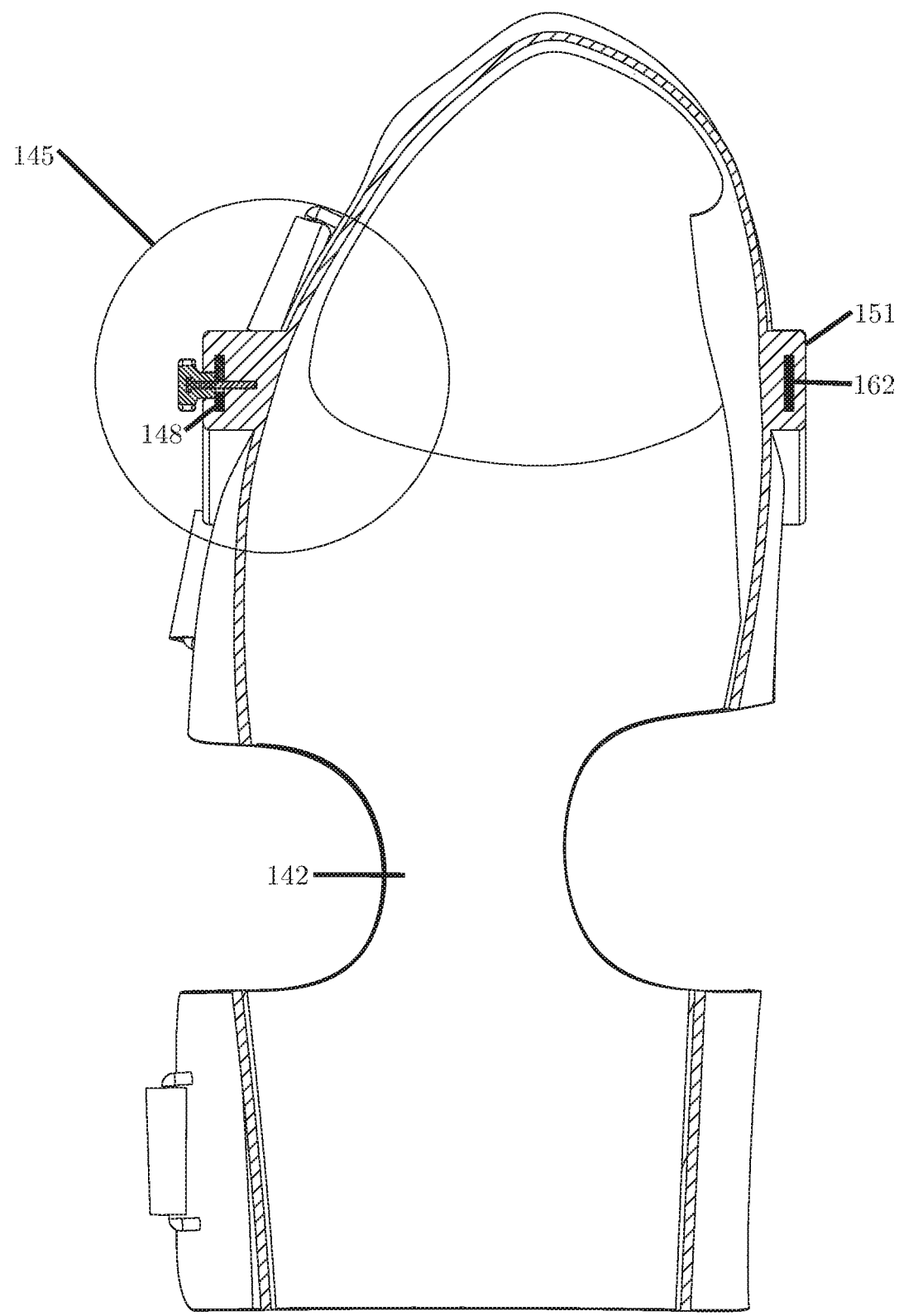
FIG. 65 is a cross-sectional view, taken along plane 64-64B of FIG. 64, of the embodiment of the orthosis depicted in FIG. 59.
Figure 66:
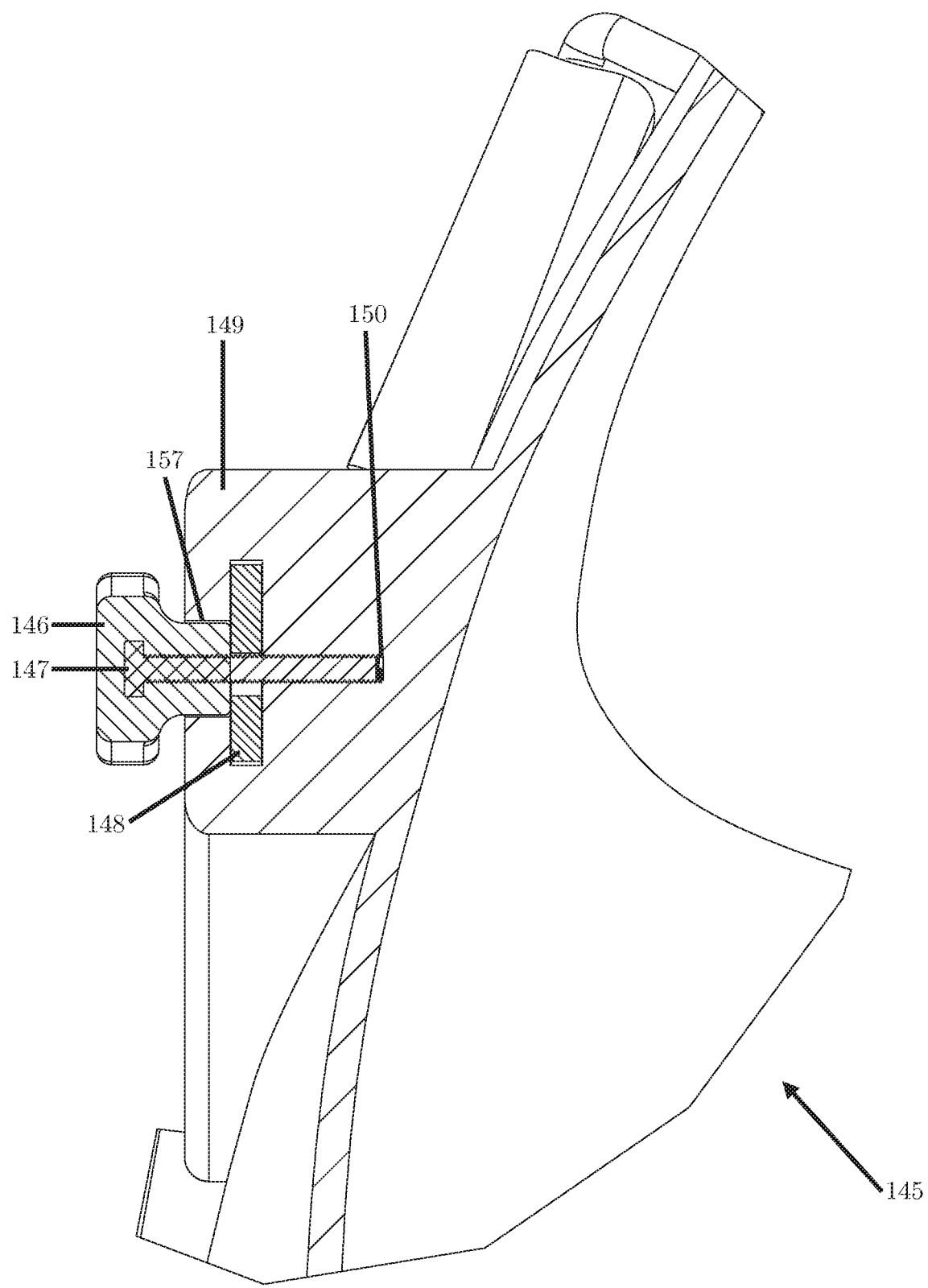
FIG. 66 is a cross-sectional detail view, taken along plane 64-64B of FIG. 64 and encircled by the circle 145 in FIG. 65, that shows the engagement of the scapular lock knob with the torso vest and the front scapular rotation rail of FIG. 132.

As shown in FIGS. 65-67, a scapular rotation lock knob 146 has a hex screw 147 embedded in it whose end passes through the round hole 157 on the face of the front scapular rotation rail housing 149, through the slot 160 of the front scapular rotation rail 148, and threads into a threaded hole 150 that is molded into the back surface of the slot 160. One end of the knob 146 is cylindrical and fits through the hole 157 on the housing 149. When the knob 146 is tightened, the bottom surface of its cylindrical end clamps the rail 148 against the back of the slot 160, stopping the rail 148 from being able to rotate and locking scapular elevation/depression at the selected location within its range of travel. As depicted in FIG. 67 and FIG. 64, a socket head screw 182 is contemplated to be screwed into the threaded hole 486 on the rail 148 such that the bottom of the head and the tip are flush with the rail 148. The head of the screw 182 then rests between the walls of the slot 158 on the housing 149 and travels within the slot 158 as the scapula elevates and depresses. It hits the end of the inner wall of the slot 158 when the rail 148 is moved to the extent of the clavicle's rotation about the sternoclavicular joint, or its highest point of permissible scapular elevation, preventing the rail 148 from being able to slide any further. The same screw 182 is identically installed on the rear scapular rotation rail 162 in the hole 491 and serves the same purpose. As illustrated in FIG. 60, the head of the screw rest between the walls of the slot 159.

While orthosis-ROM permits scapular elevation/depression using scapular rotation rails 148, 162 that rotate about the sternoclavicular joint of the wearer by sliding within slots, scapular elevation/depression may be permitted in other ways without departing from the scope of the present invention. For example, instead of being doubly-arced and slidingly disposed to slots, the rails 148, 162 may instead be straight and mounted directly to hinges that are coincident with the sternoclavicular joint.

In another aspect of orthosis-ROM, the front flexion-extension bracket 155, illustrated in FIGS. 67, 117, 59, 63 and 117, is a flat bar with a right angle bend. A threaded hole 417 passes through one face of the bend and two mounting holes 416 pass through the other, perpendicular face. It is contemplated that the hole 417 is an M5 hole and that the holes 416 are sized for M2 screws, but any sizes may be used without departing from the scope of the present invention. It is also contemplated that the axis of the threaded hole 417 is coincident with the axis of the hole 488 on the front scapular rotation rail 148, that a hex screw 154 is embedded in a scapular hinge lock knob 153, that the end of the bolt 154 passes through both holes, and that the end of the screw 154 is capped with an acorn nut 156. The bottom surface of the knob 153 is round and flat. When it's tightened, it clamps the front flexion-extension bracket 155 to the front scapular rotation rail 148 so that it can't rotate. Otherwise, the bracket 155 is free to rotate about the screw 154.

It is contemplated that a rear flexion-extension bracket 163, illustrated in FIGS. 68, 118, 60 and 70, has identical features to the front flexion-extension bracket 155 and that the axis of its threaded hole 421 is coincident with the hole 492 on the rear scapular rotation rail 163, that the end of the hex screw 154 passes through both holes, and that the end of the bolt 154 is capped with an acorn nut 156 in such a way that the rear flexion-extension bracket 163 is clamped against the rear scapular rotation 162 but is just loose enough for the bracket 163 to be able to rotate around the bolt 154. The rear flexion-extension bracket 163 has two mounting holes 420. The bolt 154 serves as a hinge for the front and rear brackets 155, 163. The brackets 155, 163 are contemplated to be about 0.125 inches thick but may be any thickness without departing from the scope of the present invention.

In another aspect of orthosis-ROM, the flexion-extension assembly 137, shown from several different perspectives in FIGS. 69-80, is attached to the orthosis through the front and rear scapular rotation rails 148, 162. The front and rear flexion-extension brackets 155, 163 are mounted to and form a part of the assembly 137. While the orthosis is being worn, the assembly 137 is contemplated to permit the wearer's arm and shoulder to move through flexion/extension and to allow it to be controlled and locked. Additionally, through a set of components mounted to it, it is contemplated to permit shoulder adduction/abduction and allow it to be controlled and locked. When the assembly 137 is mounted, it is configured so that its central axis is coincident with the shoulder joint and parallel to the front of the torso.

The first set of components involved in controlling flexion and extension are a flexion-extension axle 175, a flexion-extension wheel 174, a flexion-extension worm gear 172, a flexion-extension clutch 190, a flexion-extension clutch handle 173, and a flexion-extension retention disk 183.

The flexion-extension axle 175, illustrated in FIG. 123, is a cylindrical shell with blind, threaded mounting holes 447 on the annulus at one end and a flange 448 at the other. The mounting holes are contemplated to be M2 but may be any size without departing from the scope of the present invention. First the flexion-extension wheel 174 mounts on the axle 175.

The flexion-extension wheel 174, illustrated in FIG. 121, is a cylindrical shell with three diametrical steps and a shoulder 437 that is cut into the inner annulus of the side with the largest diameter step. When the wheel 174 is mounted, the shoulder 437 butts up against the flange 448 and prevents the wheel 174 and adjacent, components from falling off the axle 175 in the direction of the flange 448. It is cut so that the annulus of the flange 448 face and wheel 174 face are coplanar when the wheel 174 is installed. The smallest diametrical step is a ring of rectangular dog clutch teeth 435 while the other two steps 432, 433 are smooth. There are contemplated to be four equally circumferentially-spaced blind, threaded holes 434, each cut into the face of a clutch tooth 435, whose axis is normal to the axis of the flexion-extension wheel 174. Each hole 434 is contemplated to be size 4-48, but any size may be used without departing from the scope of the present invention. As shown in the cross-sectional view of FIG. 76, a ball-nose spring plunger 196 is threaded into each threaded hole 434 and the ball 197 of each plunger 196 extends slightly beyond the face of its accompanying tooth 435. The annulus of the wheel 174 on the flange side contains a number of blind, threaded mounting holes 436.

The flexion-extension worm gear 172, illustrated in FIG. 122, is contemplated to be mounted on the axle 175 after the flexion-extension wheel 174. The worm gear 172 has a shoulder 443 cut into the inner annulus on one side and a slot 442 with dog clutch teeth 441 cut into the annulus on the other side. The teeth 441 have identical geometry to those on the flexion-extension wheel 174.

The flexion-extension retention disk 183, illustrated in FIG. 124, is a flat, annular disk with a number of through holes 452 in locations that correspond to the locations of the threaded mounting holes 447 on the flexion-extension axle 175. It is contemplated to be about 0.125 inches thick but may be any thickness without departing from the scope of the present invention.

Figure 71:
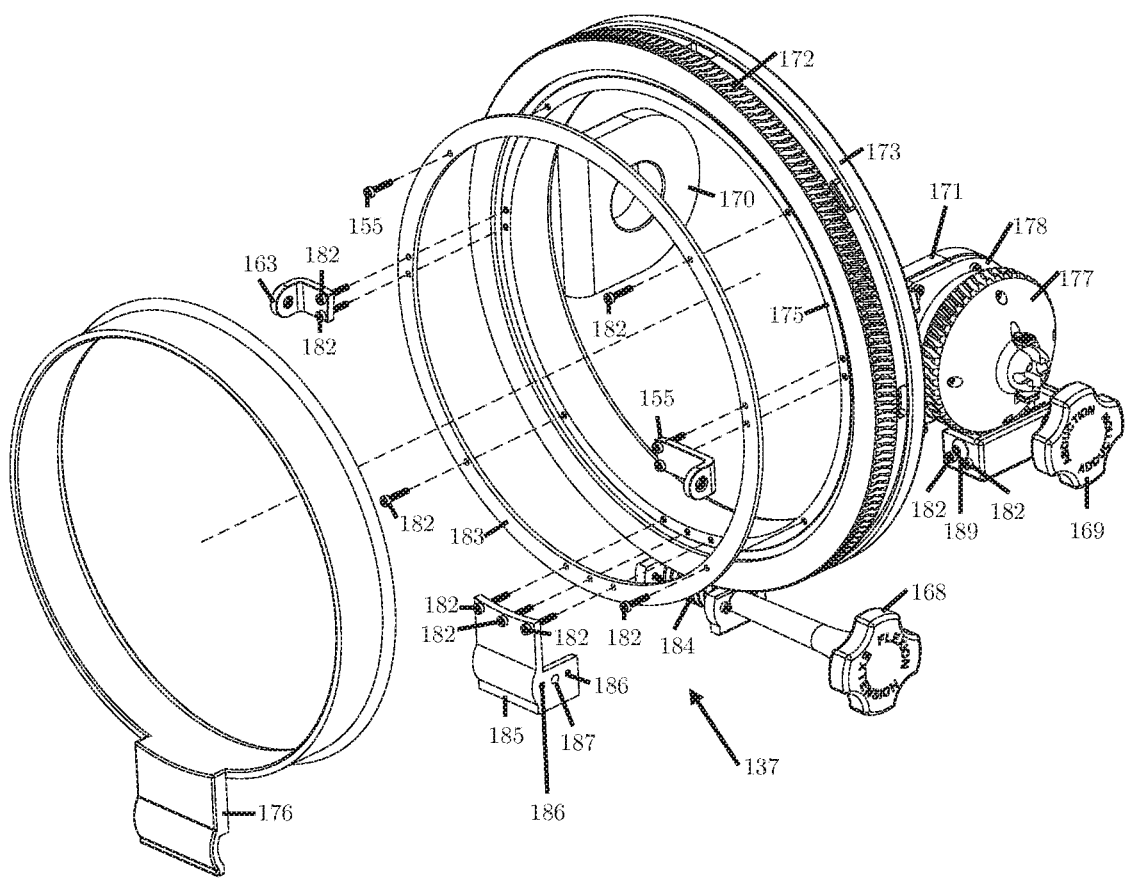
FIG. 71 is an exploded front left perspective view, of the embodiment of the flexion-extension assembly shown in FIG. 69, that emphasizes the components that are screwed to the flexion-extension axle and the flexion-extension pad.
Figure 72:
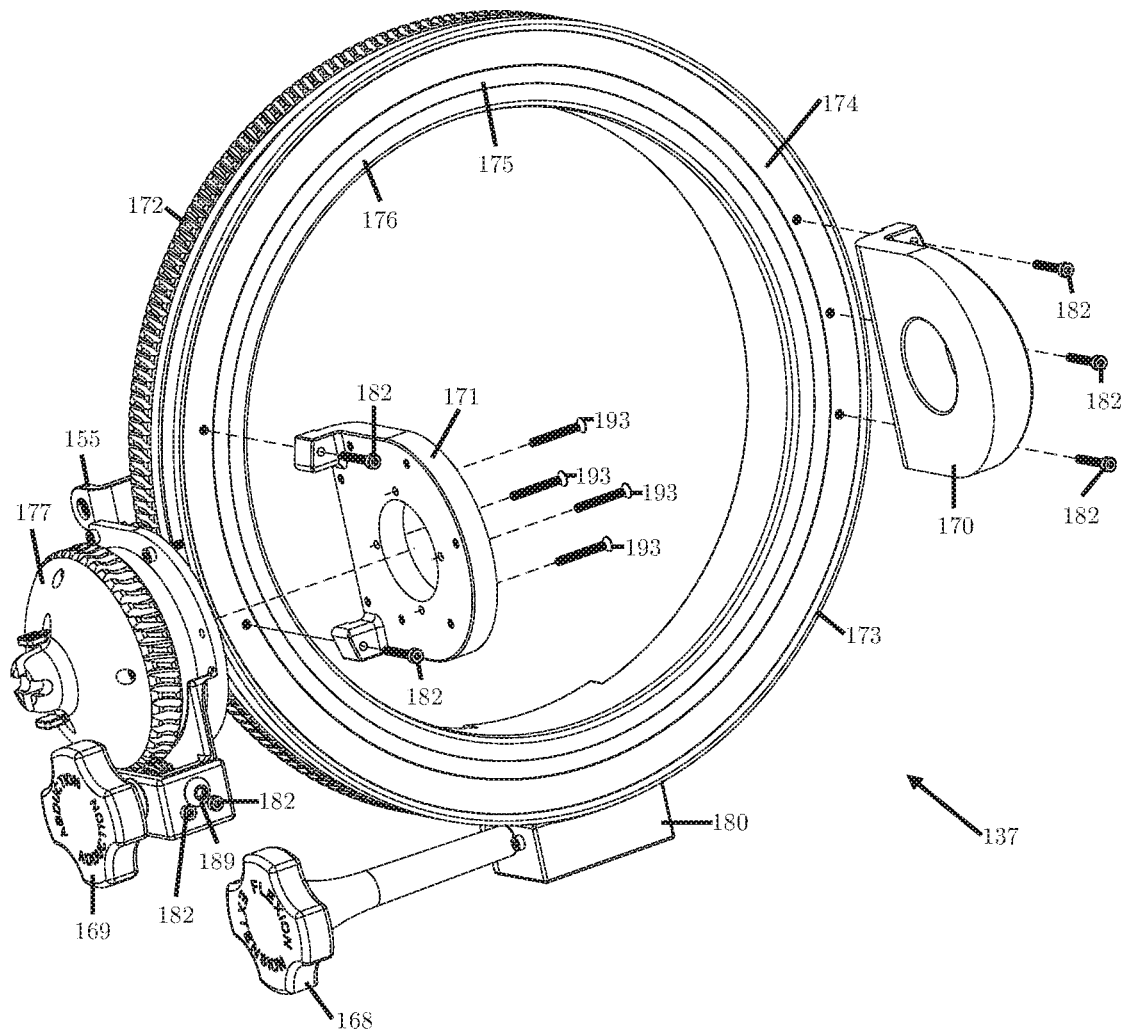
FIG. 72 is an exploded front right perspective view, of the embodiment of the flexion-extension assembly shown in FIG. 69, that emphasizes how the front journal adduction-abduction pillow block bearing, rear journal adduction-abduction pillow block bearing, and adduction-abduction components are mounted to the assembly.

As shown more closely in FIG. 71, the end of a socket head screw 182 passes through each through hole 452, is threaded into each threaded mounting hole 447, and clamps the retention disk 183 tightly against the flexion-extension axle 175. The total width of the flexion-extension wheel 174 and the flexion-extension worm gear 172 between the flange 448 and the retention disk 183 are such that enough of a gap exists for both the wheel 174 and the worm gear 172 to rotate freely with or without lubrication and with minimal side-to-side movement.

While the flexion-extension wheel 174 and the flexion-extension worm gear 172 rotate freely on the axle 175, in the style of a plain bearing, it is contemplated that another embodiment of the wheel 174 and worm gear 172 may use some type of rolling-contact, bearing.

As illustrated in FIG. 126, the flexion-extension clutch 190 is contemplated to be a cylindrical shell with clutch teeth 460 cut along the inside cylindrical surface that have an identical profile to those of the flexion-extension wheel 174 and the flexion-extension worm gear 172, however, the ends of each tooth 460 are tapered. The clutch 190 is installed after the flexion-extension wheel 174 with its teeth 460 slidingly disposed to the teeth 435 of the wheel 174. The axial length of its teeth 460 is slightly less than the axial length of the wheel teeth 435 so that when the clutch 190 is at its maximum engagement (when it butts up against the second diametral step 432 of the wheel 174) it isn't hanging over the edge of the wheel 174. When the teeth 435 on the wheel 174 and the worm gear 172 are lined up, it is contemplated that the clutch 190 can then be shifted axially into the slot 442 so that it is engaged with both sets of teeth simultaneously. When the clutch 190 is pushed into the worm gear's slot 442 as far as possible it is contemplated that the clutch teeth 460 are 50% engaged with the wheel 174 and 50% engaged with the worm gear 172.

In another aspect of the flexion-extension clutch 190, there are four equally-circumferentially spaced spherical sectors 462 cut into the face of the teeth 460 near one end and another four equally-circumferentially spaced spherical sectors 462 cut into the teeth 460 at the other end. The sector 462 locations correspond to the locations of the ball-nose spring plungers 196 installed in the flexion-extension wheel 174 and they are sized to be slightly larger than the balls 197 of the plungers 196. The axial position of the first set of sectors 462 along the face of the clutch teeth 460 is such that when the clutch 190 is fully engaged with the wheel teeth 435 the balls 197 aren't depressed into their corresponding bodies but instead rest in the sector cavities 462. Similarly, the axial position of the second set of sectors 462 along the bottom of the clutch teeth 460 is such that when the clutch 190 is fully engaged with the worm gear's slot teeth 441, the balls 197 aren't depressed into their corresponding bodies but instead rest in the sector cavities 462.

Figure 76:
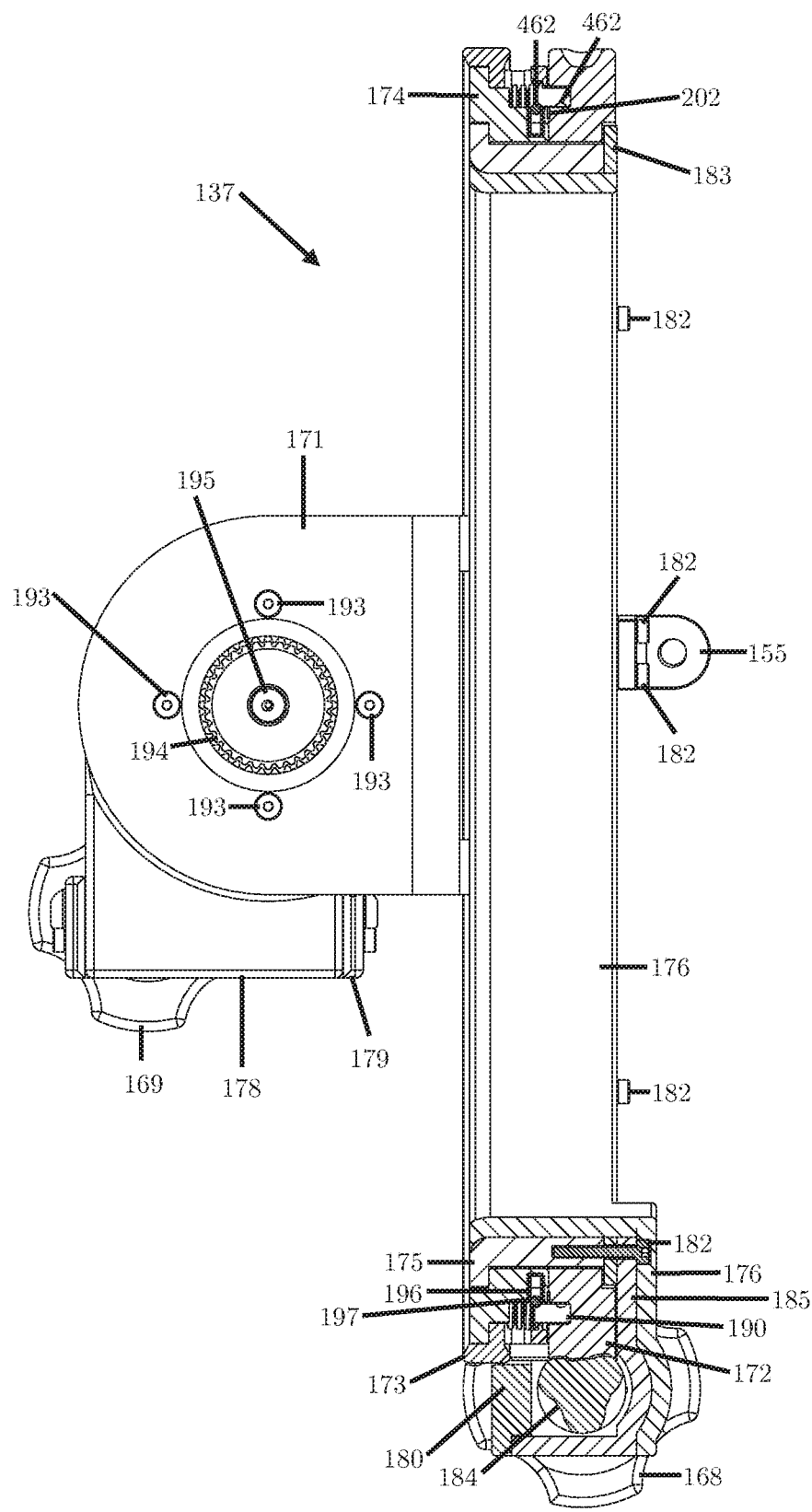
FIG. 76 is a cross-sectional view, taken along plane 75-75 of FIG. 75, that shows the engagement of the components assembled to the flexion-extension axle.
Figure 77:
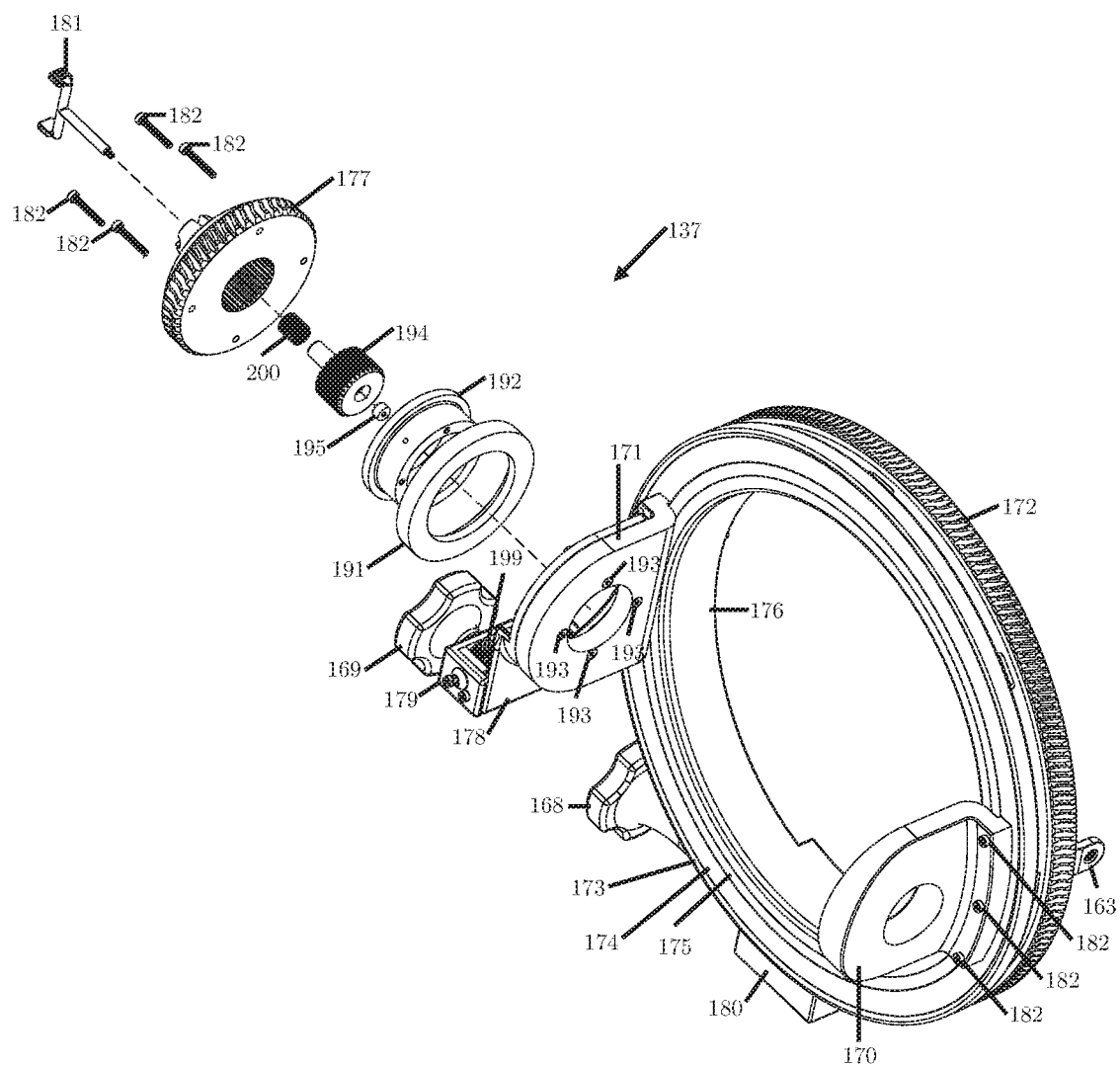
FIG. 77 is an exploded rear right perspective view, of the embodiment of the flexion-extension assembly shown in FIG. 69, that emphasizes the components mounted to the front journal adduction-abduction pillow block bearing and which are responsible for adduction and abduction.

In another aspect of the flexion-extension clutch 190, there is one external thread 461 (e.g., an acme thread) wrapped around its perimeter. The detail view 459 of FIG. 127 shows the thread 461 and its profile more clearly. As shown in FIG. 76, the thread 461 does not interfere with the worm gear slot 442 when the clutch 190 is fully engaged in the slot 442.

As illustrated in FIG. 119, the flexion-extension handle 173 is contemplated to have the basic shape of a cylindrical shell with two diametrical steps and a shoulder 427 that is cut into the inner annulus of the side with the largest diameter step. As shown in FIG. 76, the innermost diameter cylindrical surface is slidingly disposed to the outer cylindrical surface of the second diametrical step 432 of the flexion-extension wheel 174 and the shoulder 427 butts up against the third step 433 of the wheel 174. The annulus on the opposite side butts up against the side of the worm gear 172 and does so with a tolerance that allows the handle 173 to spin with or without lubrication and with minimal axial slip. The section of the handle's 173 inner cylindrical surface that is not slidingly disposed to the outer cylindrical surface of the second diametrical step 432, save for a small overlap, has internal threads 425 (e.g., acme threads) cut along the entire surface that match the profile of the external thread 461 of the flexion-extension clutch 190. The detail view 428 of FIG. 120 shows the threads 425 and their profile more closely. The handle 173 has a grip portion 424 that spans part of the axial length of the handle 173 and has outwardly drafted walls that make it easier for fingers to grasp. The profile of the grip portion is seen more easily in FIG. 76. The external thread 461 of the clutch 190 is engaged with the internal threads 425 of the handle 173 so that the clutch 190 acts as a leadscrew and the handle 173 acts as the nut of a leadscrew mechanism. Since the handle 173 is fixed in its translation, the rotation of the handle 173 actuates the leadscrew back and forth, with the direction of actuation depending on the direction or rotation. A number of see-holes 426 are cut through the threaded section of the handle 173 and are equally-circumferentially spaced. As the handle is being rotated, they allow the wearer to see the clutch translate back and forth and to see what axial position it's in. When the clutch 190 is engaged with the worm gear 172 slot, the rotation of the worm gear 172 and the wheel 174 is coupled, whereas when the clutch 190 is disengaged, the rotation of the worm gear 172 and wheel 174 is separate. Due to the presence of the ball-nose spring plungers 196, rotating the handle 173 from the fully engaged or fully disengaged position depresses each plunger 196 and thus requires extra force to get the rotation started. As the opposite extent is being reached, the balls 197 release themselves into the sector cavities 462 of the clutch 190. The abrupt decrease in the torque required to rotate the handle 173 as the balls 197 are releasing encourages the last few degrees of rotation. The release of the balls 197 is contemplated to cause an audible click that lets the wearer know that the extent has been reached. It is contemplated that the leadscrew mechanism formed by the clutch 190 and the handle 173 is self-locking so that the clutch 190 cannot be translated to backdrive the handle 173 and, thus, that the clutch 190 cannot slip out of place due to vibration or some other external force.

In another aspect of the flexion-extension assembly 137, a second set of components is involved in controlling flexion and extension. As illustrated in, FIGS. 71, 73, 76, 78, 101 and 102, first, a flexion-extension gearbox 185 with mounting through holes 188 is mounted to the flexion-extension axle 175 with socket cap screws 182 that first pass through the mounting holes 188, then through the mounting holes 452 in the flexion-extension retention disk 183, before being threaded into the threaded mounting holes 447 of the axle 175. The mounting holes 188 are contemplated to be sized for M2 screws but may be any diameter without departing from the scope of the present invention.

Figure 78:
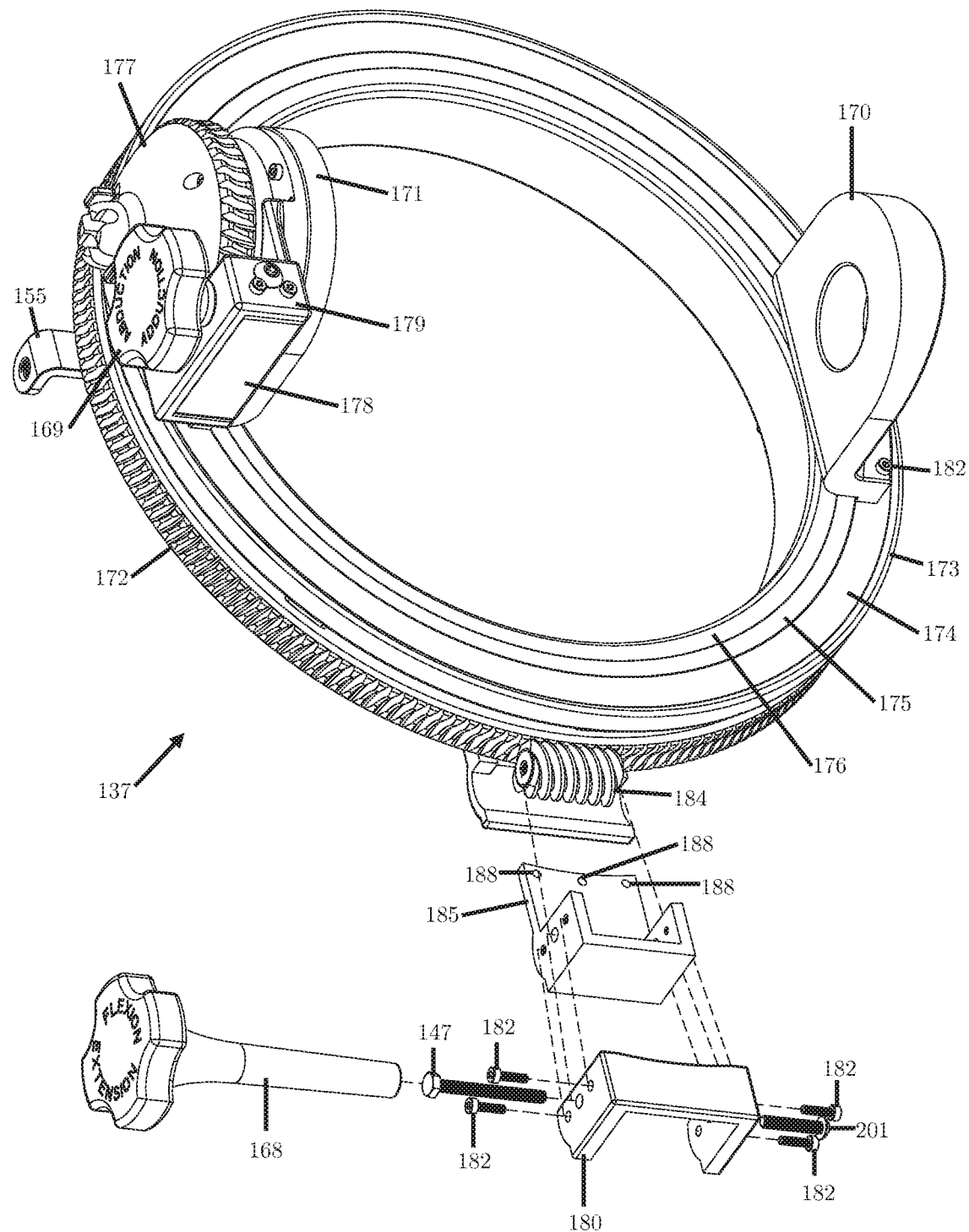
FIG. 78 is an exploded bottom right perspective view of the embodiment of the flexion-extension assembly shown in FIG. 69, that emphasizes the components of the flexion-extension gearbox assembly.
Figure 79:
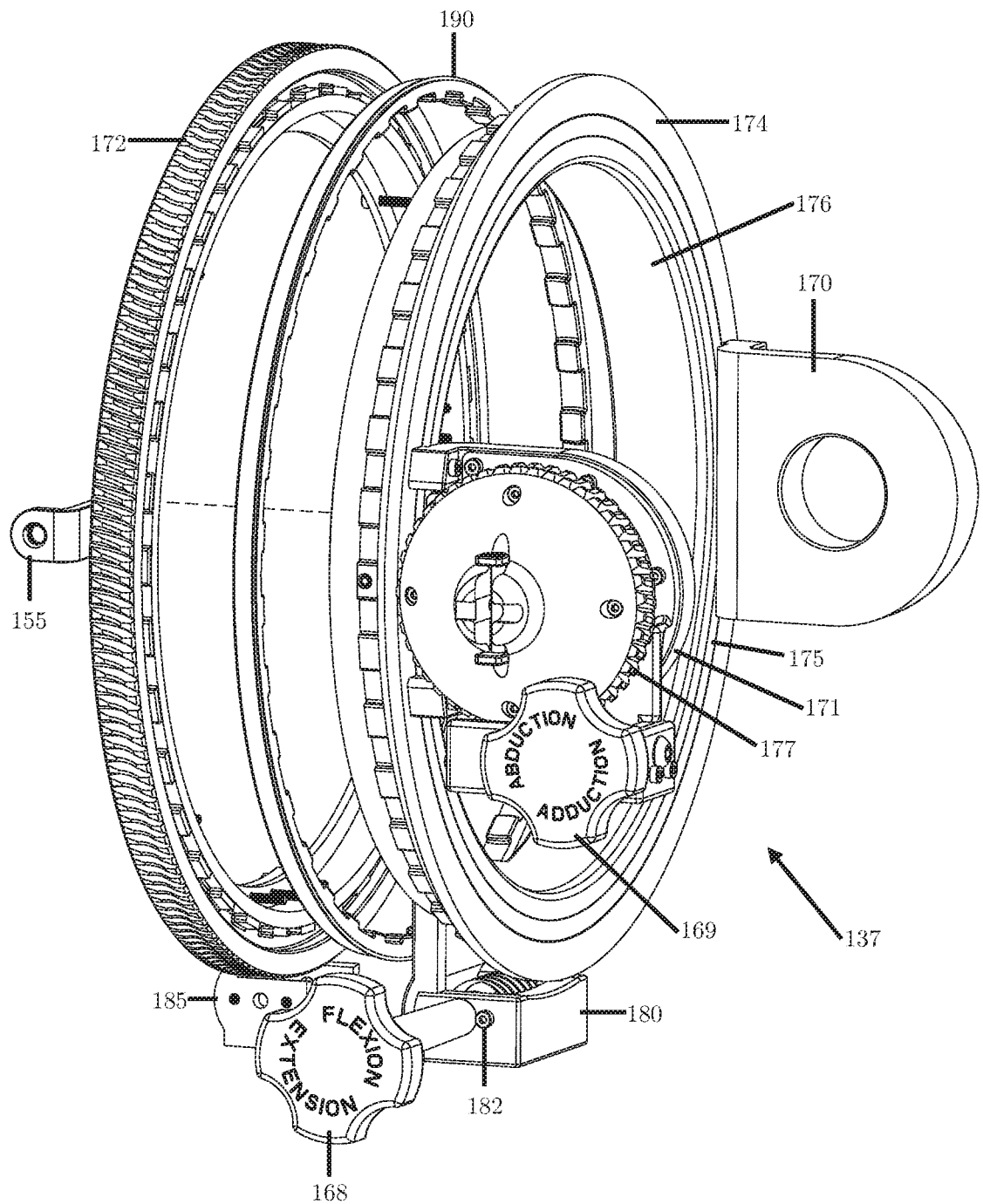
FIG. 79 is an exploded front right perspective view of the embodiment of the flexion-extension assembly shown in FIG. 69, that emphasizes how the flexion-extension clutch engages with the flexion-extension wheel and the flexion-extension worm gear.
Figure 114:
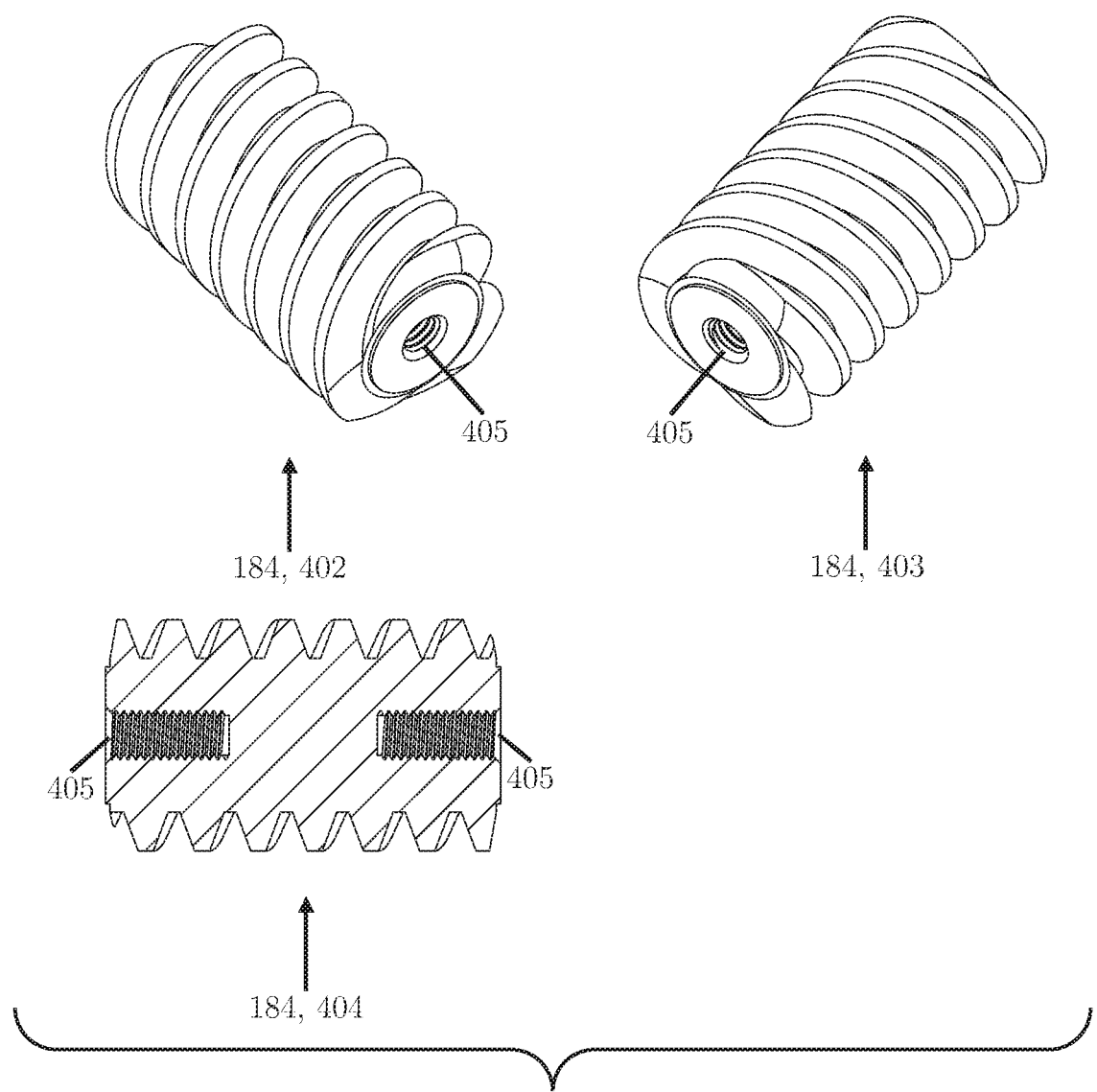
FIG. 114 contains a front right perspective view 402, a rear right perspective view 403, and an axial cross section view 404 of one contemplated embodiment of the flexion-extension worm of the present invention, with the way it's assembled within the flexion-extension assembly being shown in FIG. 78.

It is contemplated that a flexion-extension worm 184 is mounted on screws between the walls of the gearbox 185 and is coupled with the worm gear 172. As shown in FIG. 114, the worm 184 has a threaded mounting hole 405 on each side. The exploded view of FIG. 78 illustrates how the end of rounded head screw 201 is passed through the shaft hole 322 of the flexion-extension gearbox cover 180 and through the shaft hole 187 of the flexion-extension gearbox, on one side, before being threaded into the threaded mounting hole 405 of the worm 184. On the other side, the hex screw 147 is passed through the shaft hole 322 of the flexion-extension gearbox cover 180 and through the shaft hole 187 of the flexion-extension gearbox, on one side, before being threaded into the threaded mounting hole 405 of the worm 184. The shaft holes 187 are contemplated to be sized for M3 screws but may be any diameter without departing from the scope of the present invention. Accordingly, the hex screw 147 and the rounded head screw 201 are contemplated to be M3 but may be any size without departing from the scope of the present invention. The hex screw 147 is embedded in a flexion-extension knob 168 so that turning the knob 168 turns the worm 184 and hence the worm gear 172. One of the faces of the gearbox 185 is open and the cover 180 is screwed to it instead for ease of manufacture. The end of a socket cap screw 182 is passed through each mounting hole 321 of the cover 180 and is threaded into its corresponding threaded mounting hole 186 on the gearbox 185 to secure it in place. The mounting holes 321 are contemplated to be sized for M2 screws, the threaded mounting holes 186 are contemplated to use M2 threads, and the socket cap screws 182 are contemplated to be M2, but any size screws may be used with corresponding hole sizes without departing from the scope of the present invention. When the flexion-extension clutch 190 is engaged with the flexion-extension worm gear 172, turning the flexion-extension knob 168 rotates both the flexion-extension worm gear 172 and the flexion-extension wheel 174. When the clutch 190 is disengaged only the worm gear 172 rotates. It is contemplated that the worm-gear assembly is self-locking so that the worm 184 cannot be backdriven by the worm gear 172 and, therefore, so that the angle rotated to with the knob 168 will automatically be held. The conditions under which self-locking occurs were discussed previously in connection with inequality (1). Being able to switch shoulder flexion/extension between a state of being locked and a state of being free to move allows certain resistance exercises or adaptive movements to be performed. It is noted that other possible techniques for implementing the shaft of the worm 184 may be used without departing from the scope of the present invention. Such techniques include but are not limited to installation of the worm 184 on a milled shaft with a key or setscrew, or manufacturing the worm 184 and shaft together as one piece.

The worm gear 172 to worm 184 ratio is contemplated to be approximately 63 but any ratio may be used without departing from the scope of the present invention. A ratio of 63 means that it would take 31.5 (half of 63) turns of the flexion-extension knob 168 to rotate the arm from a position of full flexion to full extension and vice versa. It is noted that the ideal ratio is one in which it doesn't take an excessive number of revolutions to get from a position of full flexion to one of full extension. Additionally, a double-enveloping, or globoid, worm gear and worm pair may be used without departing from the scope of the present invention.

In another aspect of the flexion-extension assembly 137, a flexion-extension pad 176, illustrated in FIG. 125, is contemplated to line the exposed area of the flexion-extension axle 175 and one side of the flexion-extension gearbox 185 for added comfort while the orthosis is being worn. FIGS. 69-80 show how the pad 176 lines the assembly 137. It is contemplated to be about 3/16 inch thick but may be any thickness without departing from the scope of the present invention. It is contemplated to be made of foam, cloth, or any comparable material that satisfies this function but any material may be used without departing from the scope of the present invention. It is contemplated to attach to the assembly 137 using an adhesive, such as a high-strength spray adhesive, an epoxy, contact cement, glue, or tape, but any suitable adhesive may be used without departing from the scope of the present invention.

The flexion-extension assembly 137 mounts to the front and rear flexion-extension brackets 155, 163. The ends of a set of socket cap screws 182 first pass through the mounting holes 416, 420 in the brackets 155, 163 and then through the mounting holes 452 in the flexion-extension retention disk 183 before being threaded into the threaded mounting holes 447 of the flexion-extension axle 175. The exploded view of FIG. 71 shows this clearly. Because the brackets 155, 163 can pivot, the entire flexion-extension assembly 137 can pivot. The ability to pivot can be stopped by twisting the flexion-extension hinge lock knob 153 so that the front flexion-extension bracket. 155 is clamped to the front scapular rotation rail 148. The ability of the assembly 137 to pivot allows it to eliminate interference with the upper side of the torso as the arm is being raised, allows it to increase the arm's range of motion when it's tucked into the side of the body, and allows the wearer to reach laterally over the head without interference. The ability to lock the assembly's 137 pivot allows the user to stop the rotation when undesired and lock the rotation at a desired angle to facilitate an exercise, activity, or adaptation.

Figure 95:
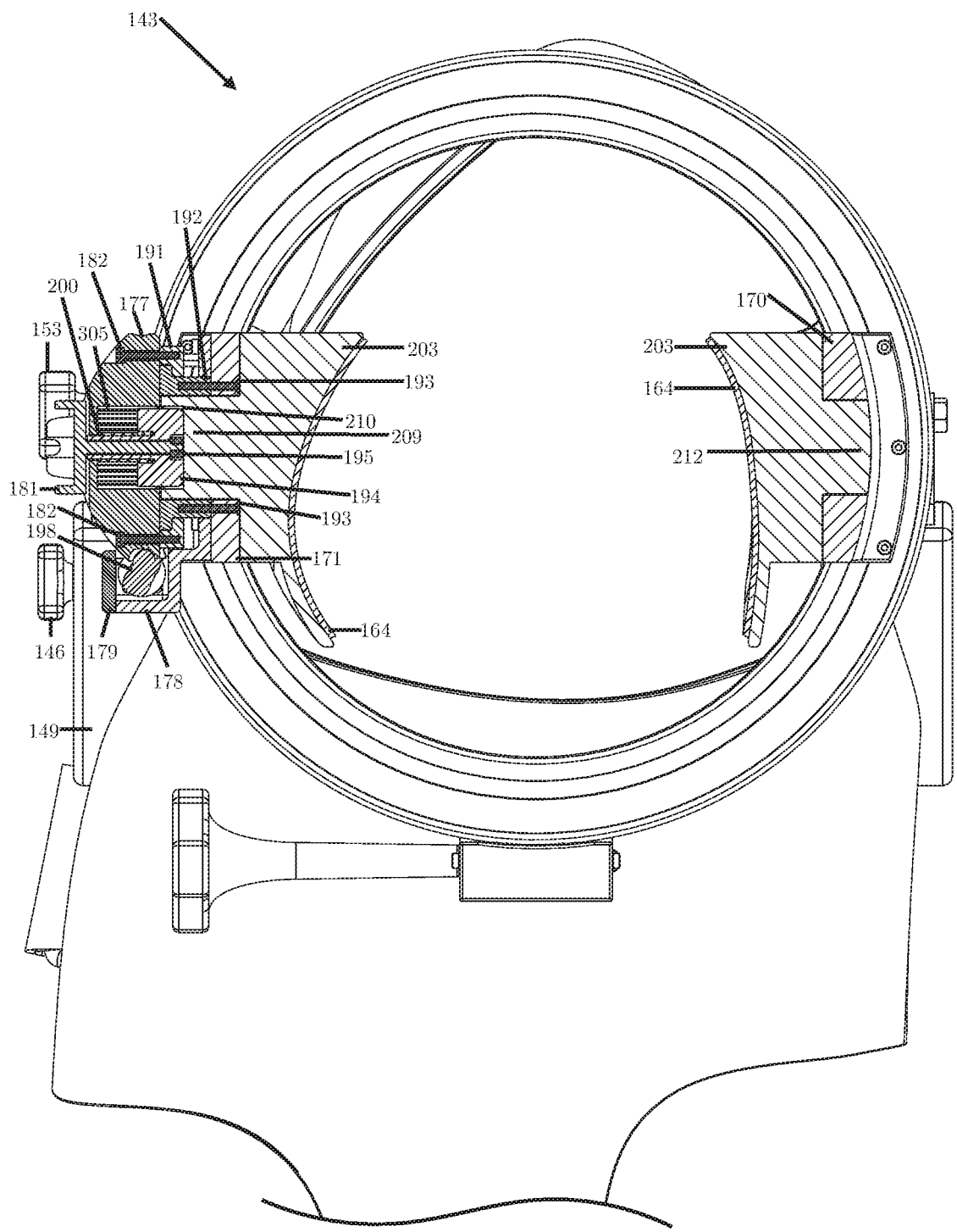
FIG. 95 is a broken cross-sectional view, taken along plane 64-64A of FIG. 64, that shows the engagement of the shoulder sleeve assembly with the flexion-extension assembly.
Figure 96:
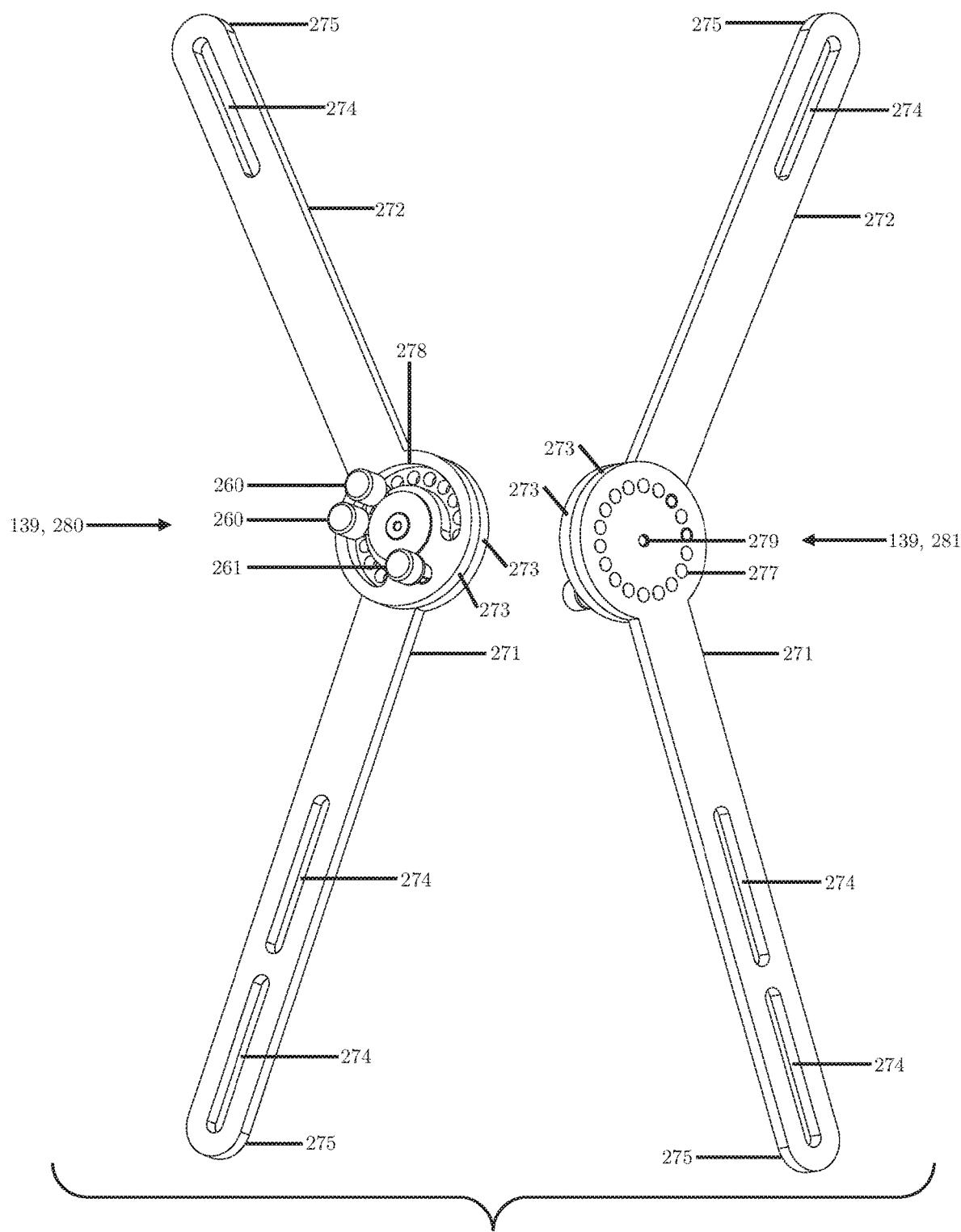
FIG. 96 contains a front left perspective view 280 and a rear right perspective view 281 of a second contemplated embodiment of the splint arm assembly of FIG. 20 and is shown assembled to the orthosis in FIG. 59.
Figure 108:
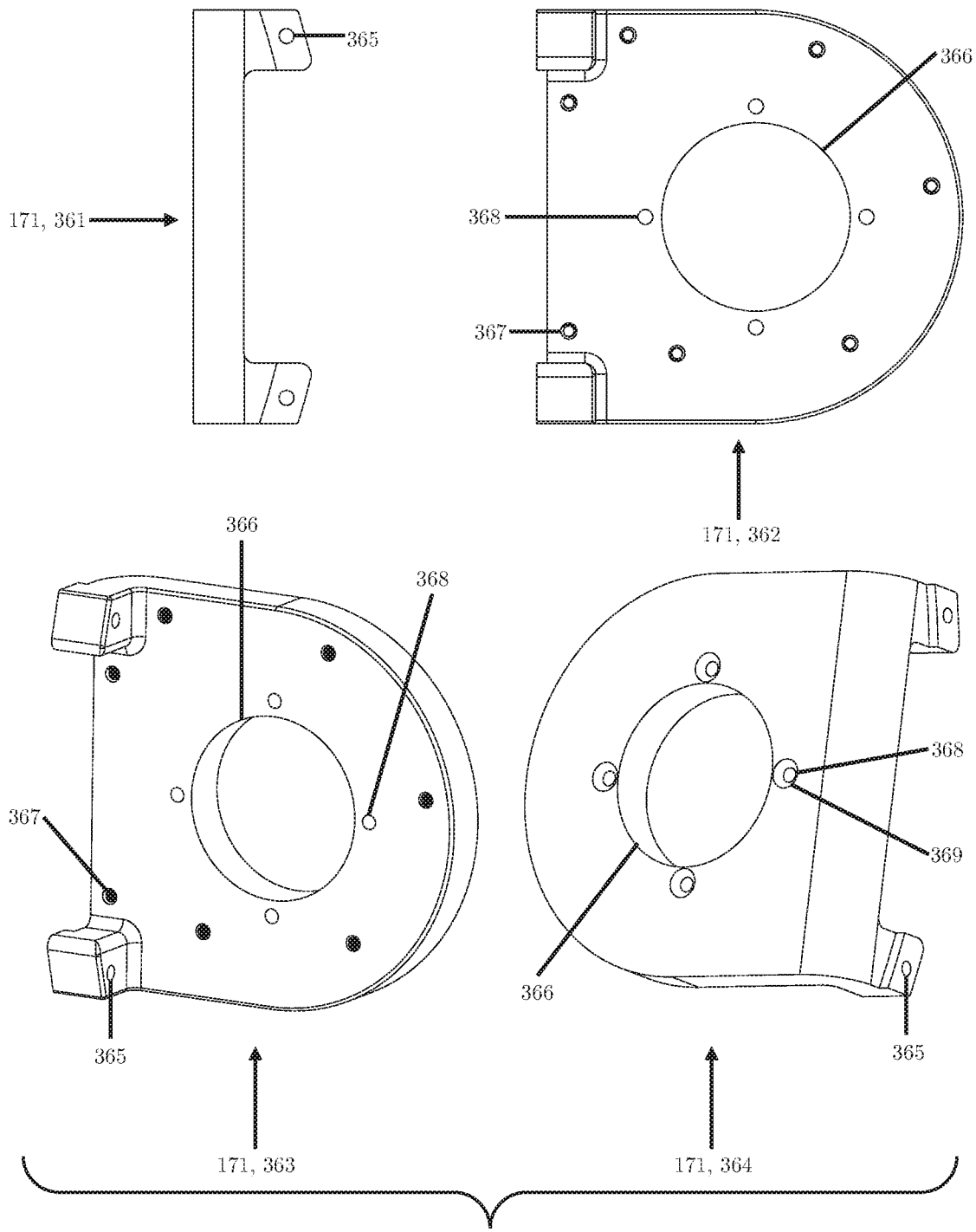
FIG. 108 contains a left side view 361, a front view 362, a front right perspective view 363, and a rear left perspective view 364 of one contemplated embodiment of the front journal adduction-abduction pillow block bearing of the present invention and is shown assembled within the flexion-extension assembly in FIG. 69.
Figure 109:
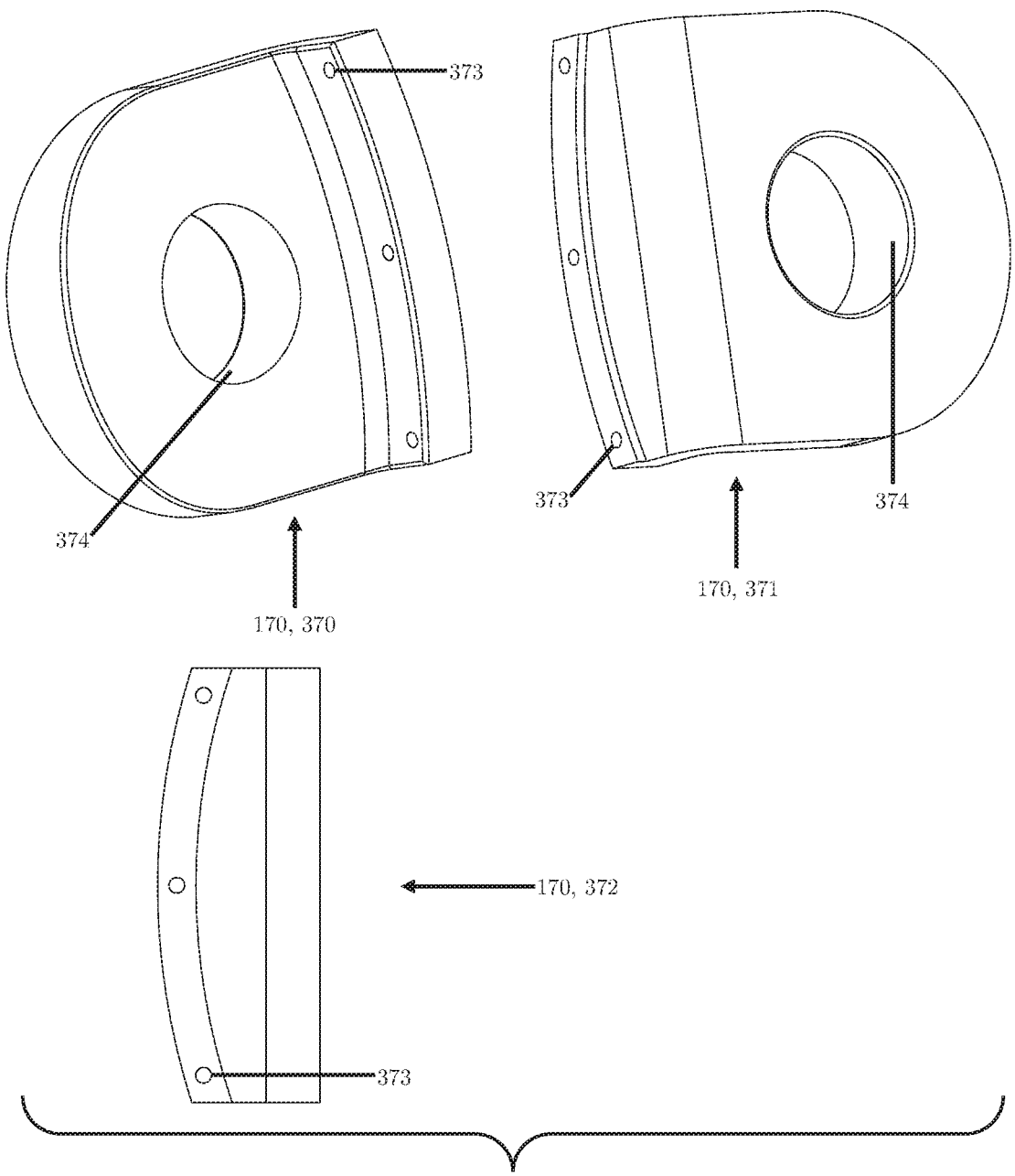
FIG. 109 contains a front left perspective view 370, a rear right perspective view 371, and a right side view 372 of one contemplated embodiment, of the rear journal adduction-abduction pillow block bearing of the present invention and is shown assembled within the flexion-extension assembly in FIG. 70.

In another aspect of the flexion-extension assembly 137, a set of components are mounted to the flexion-extension wheel 174 that are responsible for permitting the shoulder of the wearer to move through adduction or abduction and allowing adduction and abduction to be controlled. Illustrated in FIGS. 69-80, these include front and rear journal adduction-abduction pillow block bearings 171, 170, an adduction-abduction gearbox 178, an adduction-abduction gearbox cover 179, an adduction-abduction bearing flange 192, an adduction-abduction retention disk 191, an adduction-abduction worm gear 177, an adduction-abduction clutch 194, an adduction-abduction spring 200, a clutch pin 181, a clutch pin retention nut 195, and an adduction-abduction worm 198. FIG. 95 shows the interaction of these components most clearly. First, the front and rear journal adduction-abduction pillow block bearings 171, 170 are mounted to the flexion-extension wheel 174. As shown in FIG. 108, the front journal adduction-abduction pillow block bearing 171 has mounting holes 365. As shown in FIG. 109, the rear journal adduction-abduction pillow block bearing 170 has mounting holes 373. As illustrated more closely in FIG. 72, the end of a socket cap screw 182 is first passed through each mounting hole 365 of the front bearing 171 and through each mounting hole 373 of the rear bearing 170 and then threaded into the corresponding threaded mounting hole 436 of the flexion-extension wheel 174. The front and rear bearings 171, 170 have shaft holes 366, 374. The bearings 171, 170 are diametrically opposed and have coaxial shaft holes, the common axis of which is normal to and intersects the axis of the flexion-extension axle 175.

Figure 106:
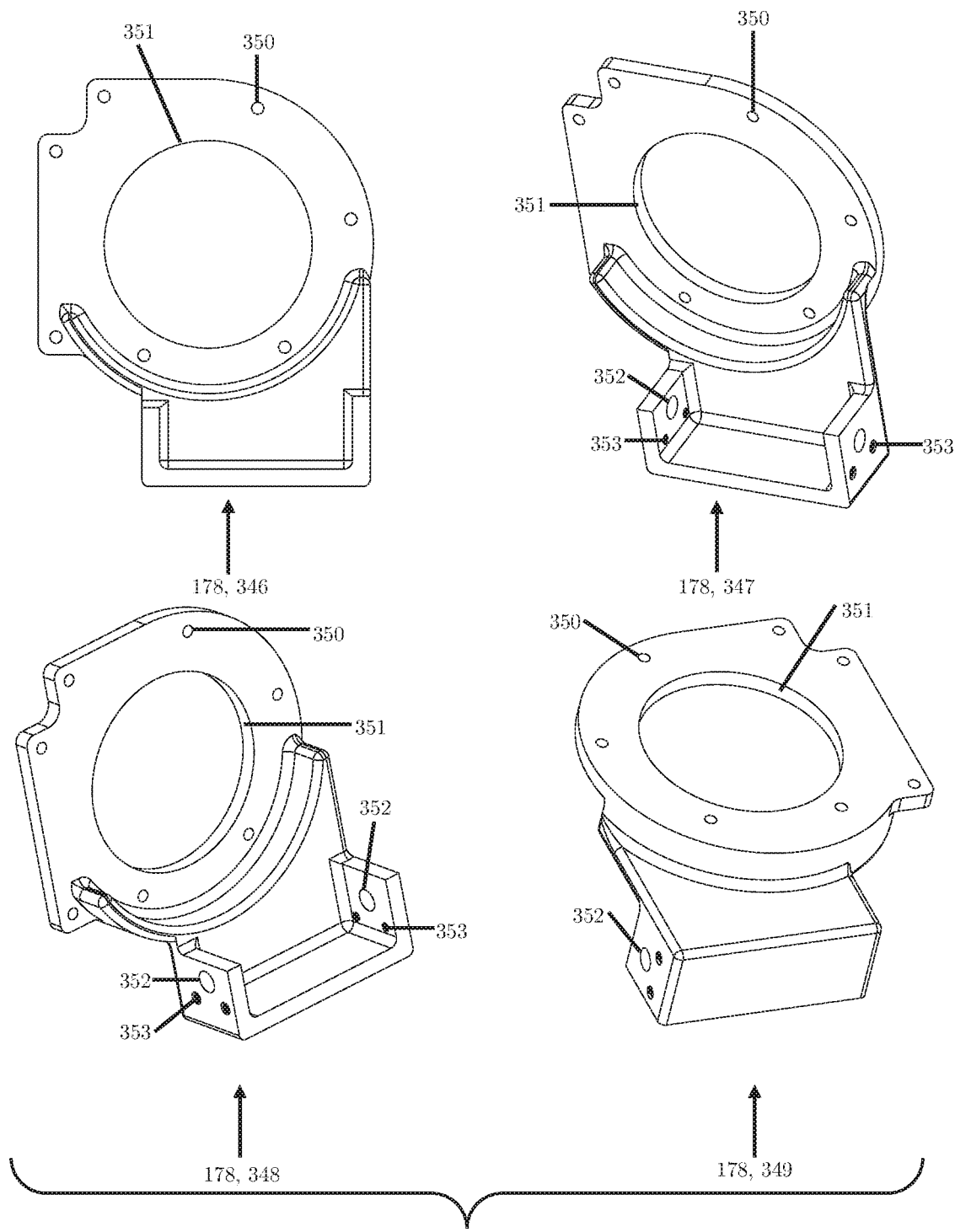
FIG. 106 contains a front view 346, a front right perspective view 347, a front left perspective view 348, and a rear top perspective view 349 of one contemplated embodiment of the adduction-abduction gearbox of the present invention and is shown assembled within the flexion-extension assembly in FIG. 69.
Figure 107:
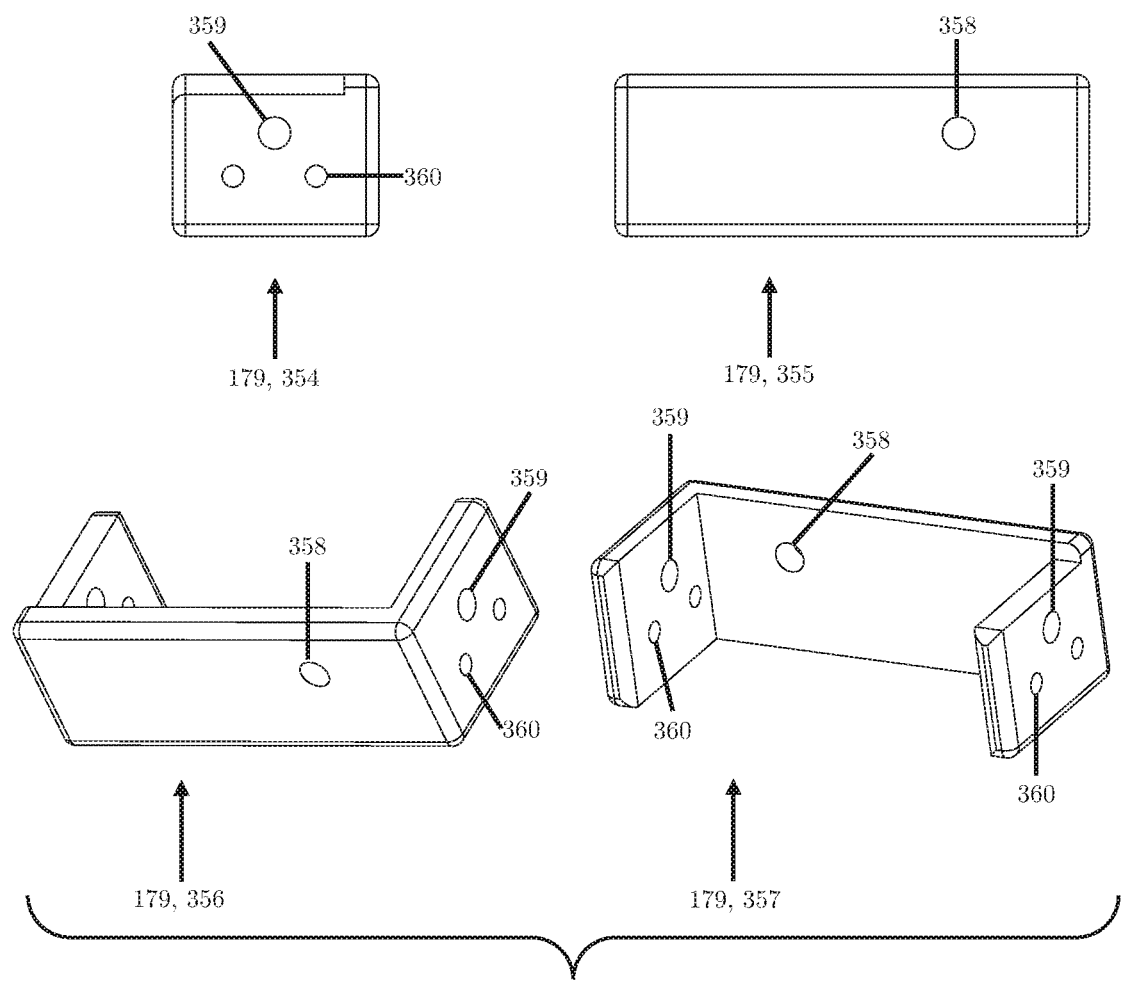
FIG. 107 contains a left side view 354, a front view 355, a front, right perspective view 356, and a rear left perspective view 357 of one contemplated embodiment, of the adduction-abduction gearbox cover of the present invention and is shown assembled within the flexion-extension assembly in FIG. 69.

As shown in FIG. 106, the adduction-abduction gearbox 178 has a set of mounting through holes 350 that lie on the same face. And as shown in FIG. 108, the front bearing 171 has a set of corresponding blind, threaded mounting holes 367 lying on one face. It is contemplated that the gearbox 178 is mounted to the front bearing 171 using socket cap screws 182 that pass through the mounting holes in the gearbox 350 and that are threaded into threaded mounting holes 367 on the face of the front bearing 171. The mounting holes 350 are contemplated to be sized for M2 screws, the threaded mounting holes 367 are contemplated to use M2 threads, and the socket cap screws 182 are contemplated to be M2, but any size screws may be used with corresponding hole sizes without departing from the scope of the present, invention. The gearbox 178 has a shaft hole 351 that is larger in diameter than that of the front bearing 171. Additionally, the "box" end of the gearbox 178 is contemplated to have an open side for ease of manufacture. As shown in FIG. 107, the adduction-abduction gearbox cover has four mounting holes 360. The cover 179 is screwed to the gearbox 178 by passing the end of a socket cap screw 182 through each mounting hole 360 and threading it into a corresponding threaded mounted through hole 353 on the gearbox 178. The cover 179 covers the open side. The mounting holes 360 are contemplated to be sized for M2 screws, the threaded mounting holes 353 are contemplated to use M2 threads, and the socket cap screws 182 are contemplated to be M2, but any size screws may be used with corresponding hole sizes without departing from the scope of the present invention.

Figure 105:
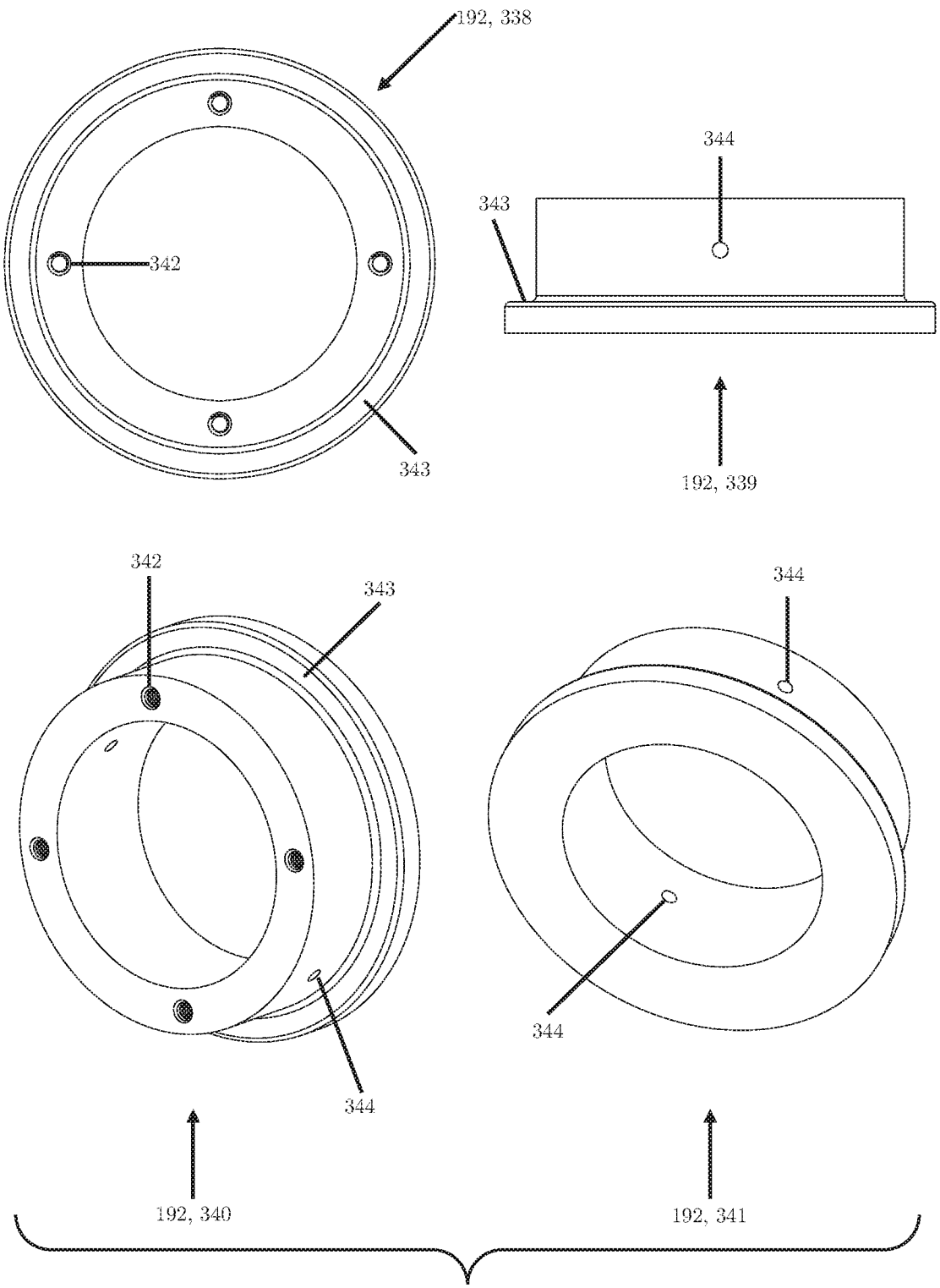
FIG. 105 contains a front view 338, a right side view 339, a front right perspective view 340, and a rear top perspective view 341 of one contemplated embodiment of the adduction-abduction bearing flange of the present invention and is shown assembled within the flexion-extension assembly in FIG. 75.

As shown in FIG. 105, the adduction-abduction bearing flange 192 has a set of blind, threaded mounting holes 342 that lie on the same face. And as shown in FIG. 108, the front bearing 171 has a set of corresponding mounting through holes 368 lying on one face. The bearing flange 192 is mounted to the front bearing 171. The flange 192 is a cylindrical shell with a diametrically stepped outer diameter and the threaded mounting holes 342 lying on the annulus of the smaller step. This same annulus mates to the front bearing 171 surface that faces away from the body. The axis of the bearing flange 192 is coincident with the axis of the front bearing 171 and the outer surface of the smaller cylindrical step is slidingly disposed to the shaft hole 351 of the gearbox 178. The end of a flathead screw 193 is passed through each mounting hole 368 on the front bearing 171 and threaded into the corresponding threaded mounting hole 368 on the bearing flange 342. When installed, the head of each flathead screw 193 rests in a corresponding countersink 369 on the back of the front bearing 171 so that it sits flush with the back surface. The mounting holes 368 are contemplated to be sized for M2 screws, the threaded mounting holes 342 are contemplated to use M2 threads, and the flathead screws 193 are contemplated to be M2, but any size screws may be used with corresponding hole sizes without departing from the scope of the present invention.

Figure 104:
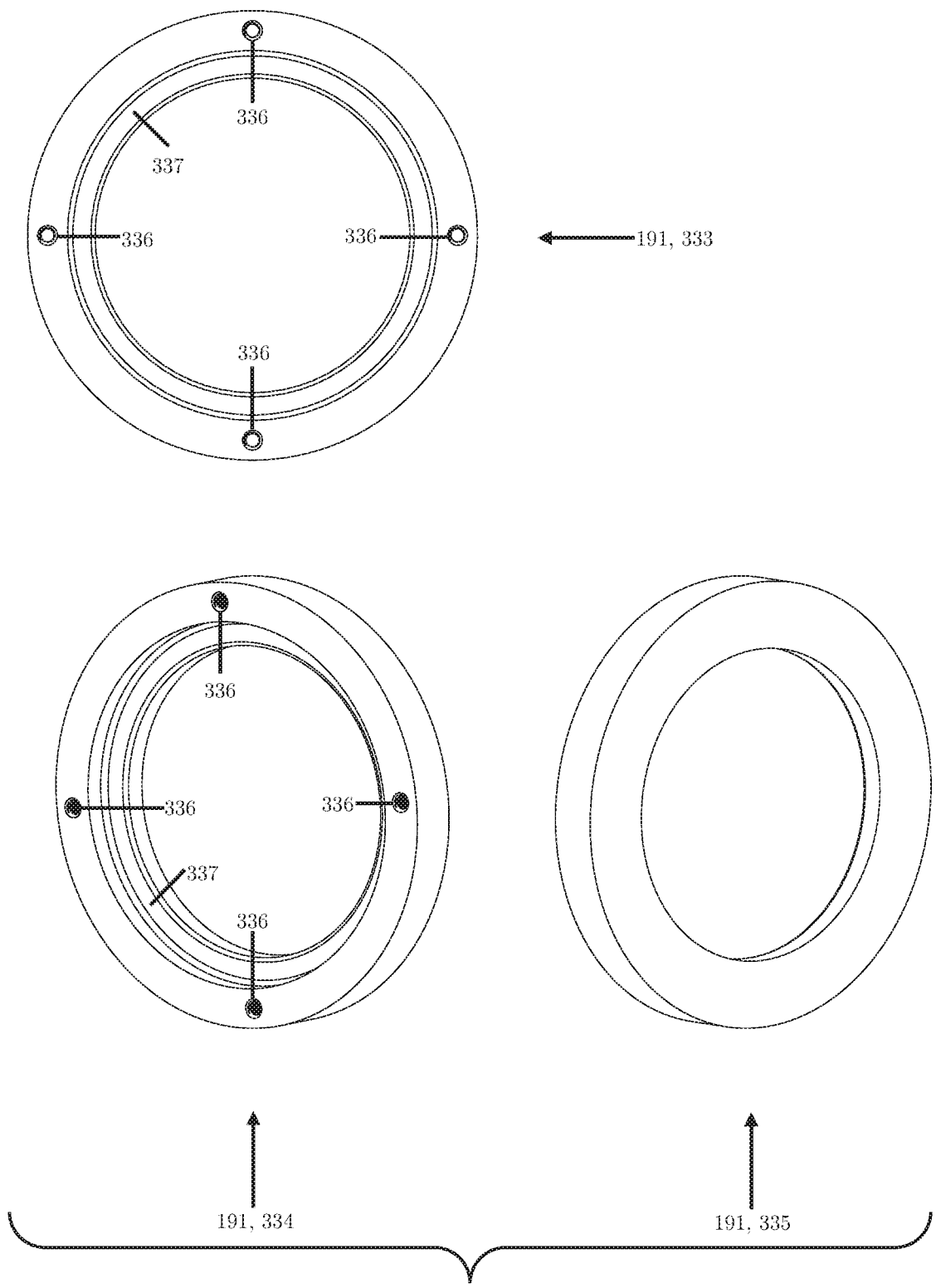
FIG. 104 contains a front view 333, a front right perspective view 334, and a rear right perspective view 335 of one contemplated embodiment of the worm gear retention disk of the present invention and is shown assembled within the flexion-extension assembly in FIG. 75.

The adduction-abduction retention disk 191 is shown in FIG. 104. It is contemplated that the retention disk 191 is a cylindrical shell with two internal diametrical steps. The annulus of the larger step has a set of threaded mounting holes 336. The inner cylindrical surface of the disk's 191 smaller step is slidingly disposed to the outer cylindrical surface of the smaller cylindrical step of the adduction-abduction bearing flange 192 and the inner cylindrical surface of the disk's 191 larger step is slidingly disposed to the outer cylindrical surface of the larger cylindrical step of the bearing flange 192. The flange face 337 of the retention disk 191 butts up against the flange face 343 of the bearing flange 192. The retention disk 191 can rotate freely, with or without lubrication from a grease or oil, on the bearing flange 192.

Figure 103:
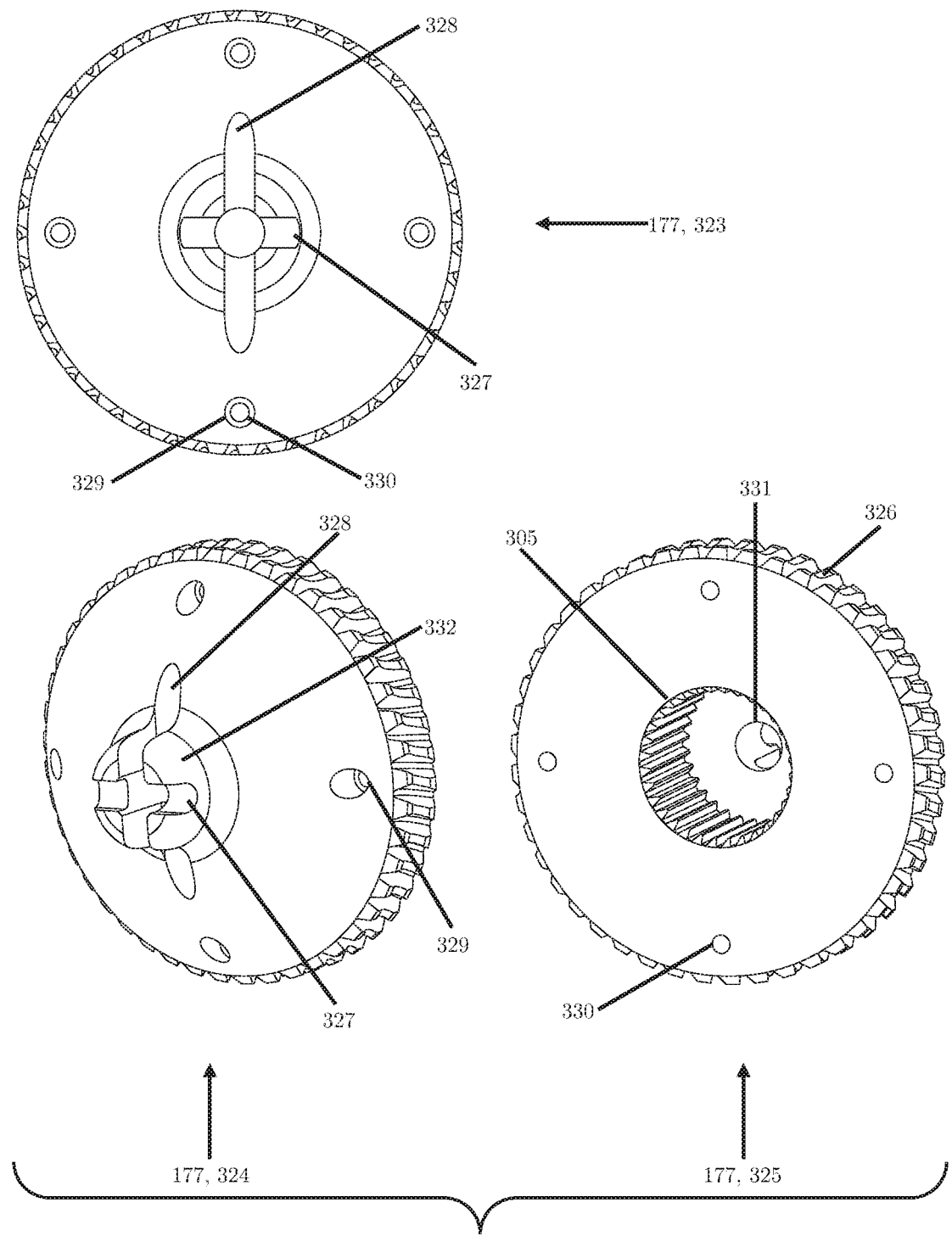
FIG. 103 contains a front view 323, a front right perspective view 324, and a rear left perspective view 325 of one contemplated embodiment of the adduction-abduction worm gear of the present invention and is shown assembled within the flexion-extension assembly in FIG. 69.

The adduction-abduction worm gear 177 is shown in FIG. 103. It is contemplated that the worm gear 177 is mounted to the adduction-abduction retention disk 191, with the axes of each being coincident, using a number of counterbored socket cap screws 182 that pass through mounting through holes 330 on the worm gear 177 and thread into the threaded mounting holes 336 on the retention disk 191. The mounting holes 330 are contemplated to be sized for M2 screws, the threaded mounting holes 336 are contemplated to use M2 threads, and the socket cap screws 182 are contemplated to be M2, but any size screws may be used with corresponding hole sizes without departing from the scope of the present invention. When mounted, the rotation of the worm gear 177 is coupled to the rotation of the retention disk 191 and it can rotate freely with or without lubrication from a grease or oil. The annular face of the disk's 191 larger internal step protrudes slightly past the annular face of the bearing flange's 192 larger step so that the face of the worm gear 177 does not get clamped against the annular face of the bearing flange 192. This prevents the rotation of the worm gear 177 from being inhibited.

Figure 88:
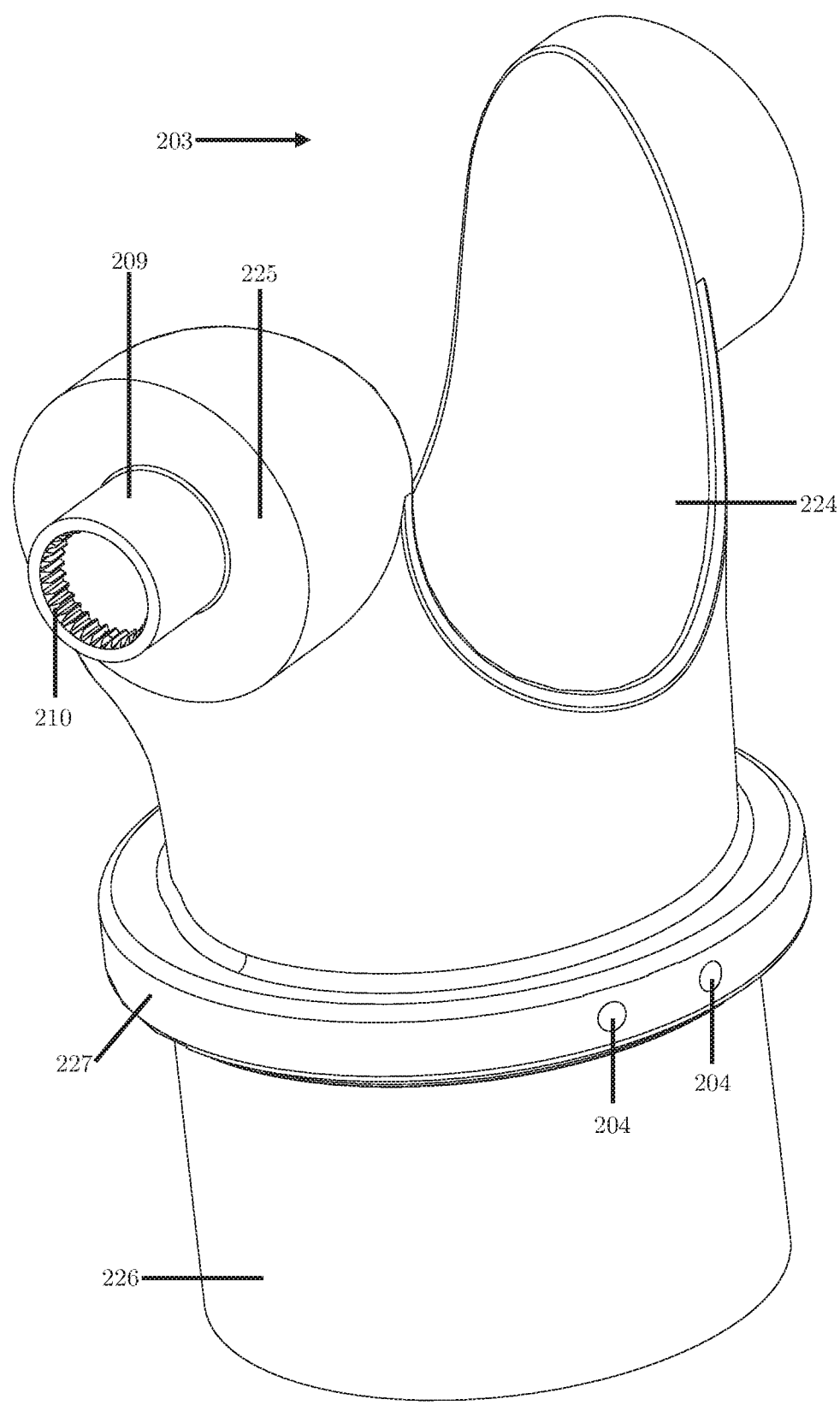
FIG. 88 is a top front perspective view of one contemplated embodiment of the shoulder sleeve of the present invention and is shown assembled within the shoulder sleeve assembly in FIG. 81.
Figure 89:
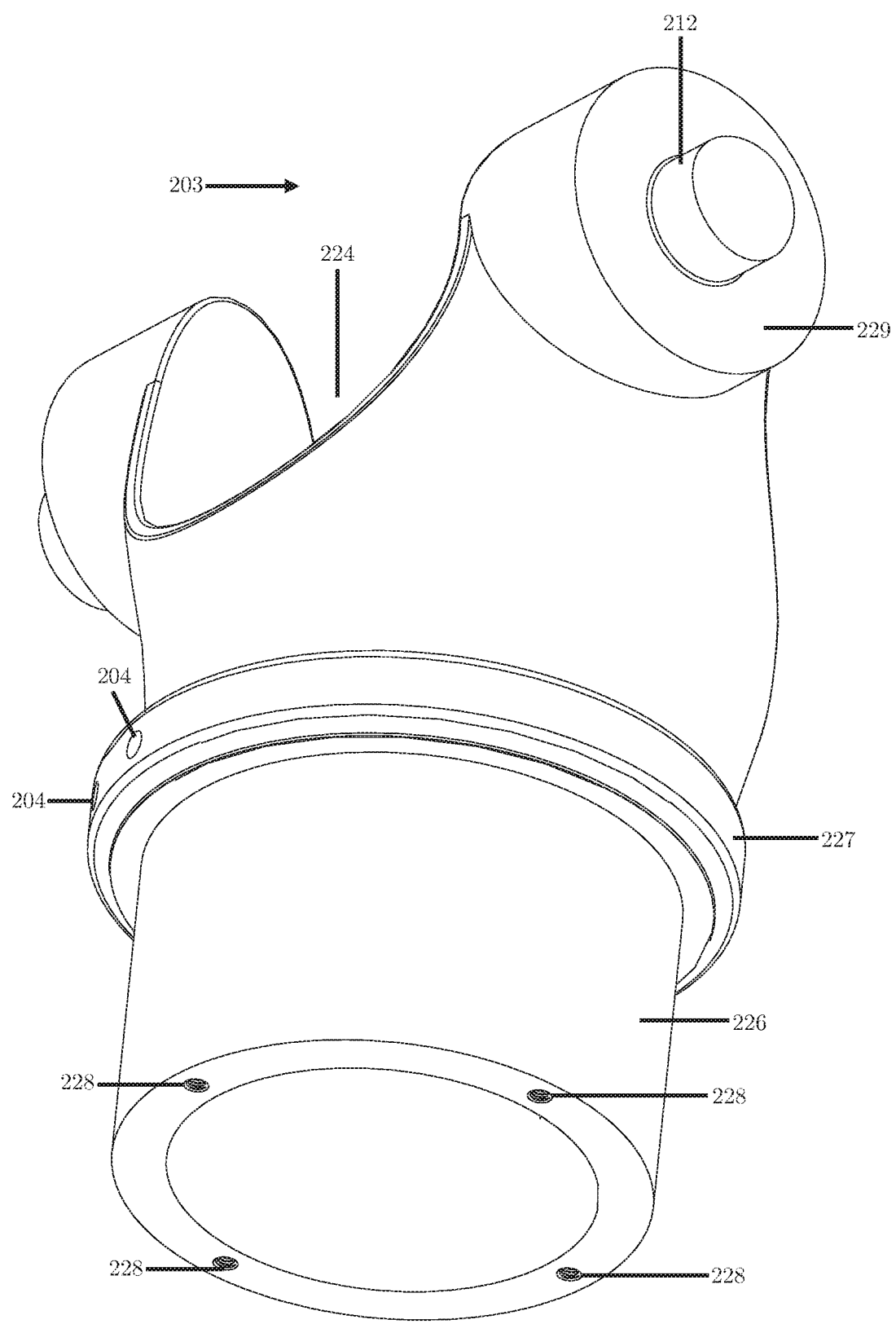
FIG. 89 is a bottom rear perspective view of the embodiment of the shoulder sleeve shown in FIG. 88.
Figure 110:
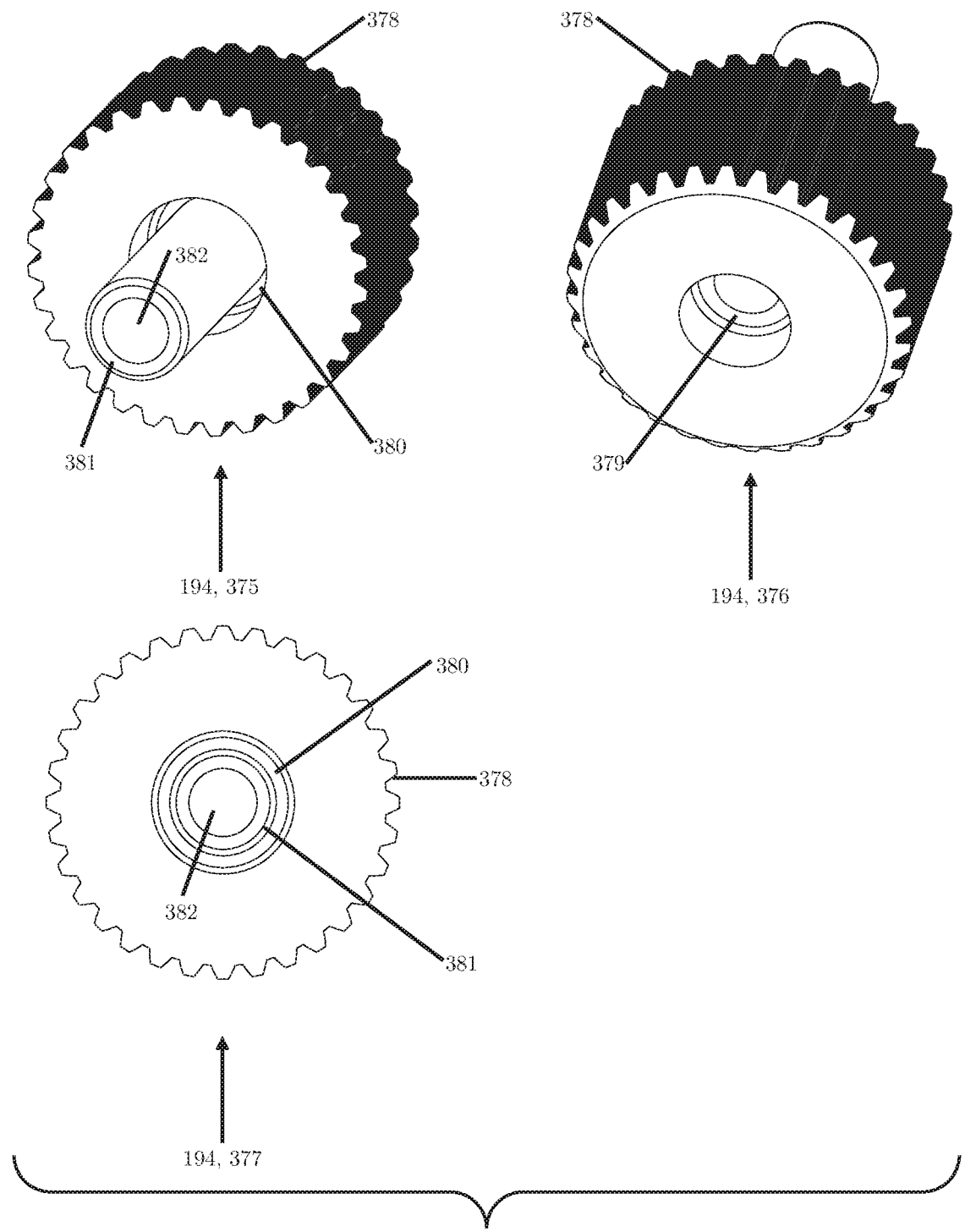
FIG. 110 contains a front right perspective view 375, a rear left perspective view 376, and a front view 377 of one contemplated embodiment of the adduction-abduction clutch of the present invention, with the way it's assembled within the flexion-extension assembly being shown in FIG. 77.

The shoulder sleeve 203 is part of the shoulder sleeve assembly 138 and is shown in FIGS. 88-89. As shown in FIG. 95, the front shaft 209 of the shoulder sleeve 203 is mounted in the front, bearing 171 and extends axially until it reaches the face of the worm gear 177. The front shaft 209 is slidingly disposed to both the shaft hole 366 of the bearing 171 and the shaft hole 345 of the bearing flange 192. The end of the shaft 209 has an internal, coaxial spline 210 cut to a certain axial depth. The opposing face of the worm gear 177 also has an internal, coaxial spline 305 cut to a certain depth, as shown in FIG. 103. The adduction-abduction clutch 194, illustrated in FIG. 110, is a cylinder with an external, coaxial spline 378 whose teeth are slidingly disposed to the teeth of the worm gear's spline 177 or both the worm gear 177 and the shoulder sleeve's 203 spline simultaneously. It is contemplated that the adduction-abduction clutch 194 either rests entirely within the spline 305 of the worm gear 177 at one extent or engages halfway with the worm gear 177 and halfway with the shoulder sleeve 203 at the opposite extent. When the clutch 194 is engaged, the rotation of the worm gear 177, retention disk 191, and shoulder sleeve 203 is coupled, but when it's disengaged, the rotation of the shoulder sleeve 203 is independent. The clutch 194 also has a cylindrical shaft 381 that protrudes from the face opposite the shoulder sleeve 203 into a shaft hole 331 that runs through the worm gear 177 and into the spline 305 cavity. A shaft hole 382 runs through the shaft 381 and the entire length of the clutch 194. Around the base of the shaft 381, a cylindrical shell-shaped slot 380 is cut to a certain depth. The adduction-abduction spring 200 is a compression spring with closed ends that has one end engaged with the slot 380 and the other end pressing against the inner face of the worm gear's spline 305 cavity. The spring 200 tries to keep the clutch 194 in the engaged position, as illustrated in FIG. 95, and is preloaded at this extent so that it is always in a compressed state. As the clutch 194 is being pulled toward the worm gear 177, the spring 200 compresses itself into the slot 380 on the clutch 194 and has not reached its solid length by the time the clutch teeth 378 are fully inside of the worm gear 177. The slot. 380 is what helps ensure that the clutch teeth 378 are able to rest fully inside the worm gear 177 before the solid length has been reached and that the spring 200 is still compressed when the clutch 194 is engaged.

Figure 111:
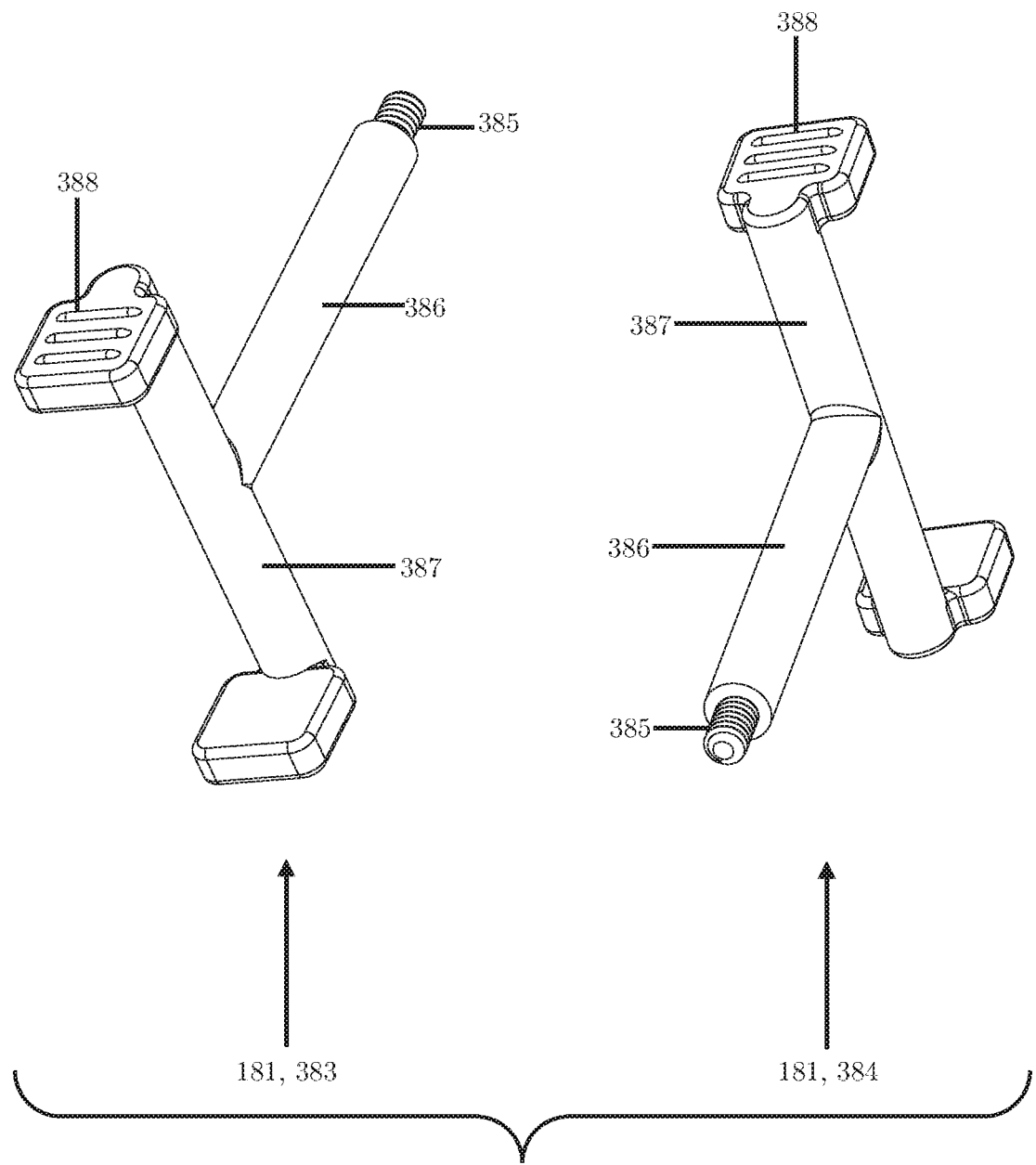
FIG. 111 contains a front right perspective view 383 and a rear right perspective view 384 of one contemplated embodiment of the clutch pin of the present invention, with the way it's assembled within the flexion-extension assembly being shown in FIG. 77.
Figure 112:
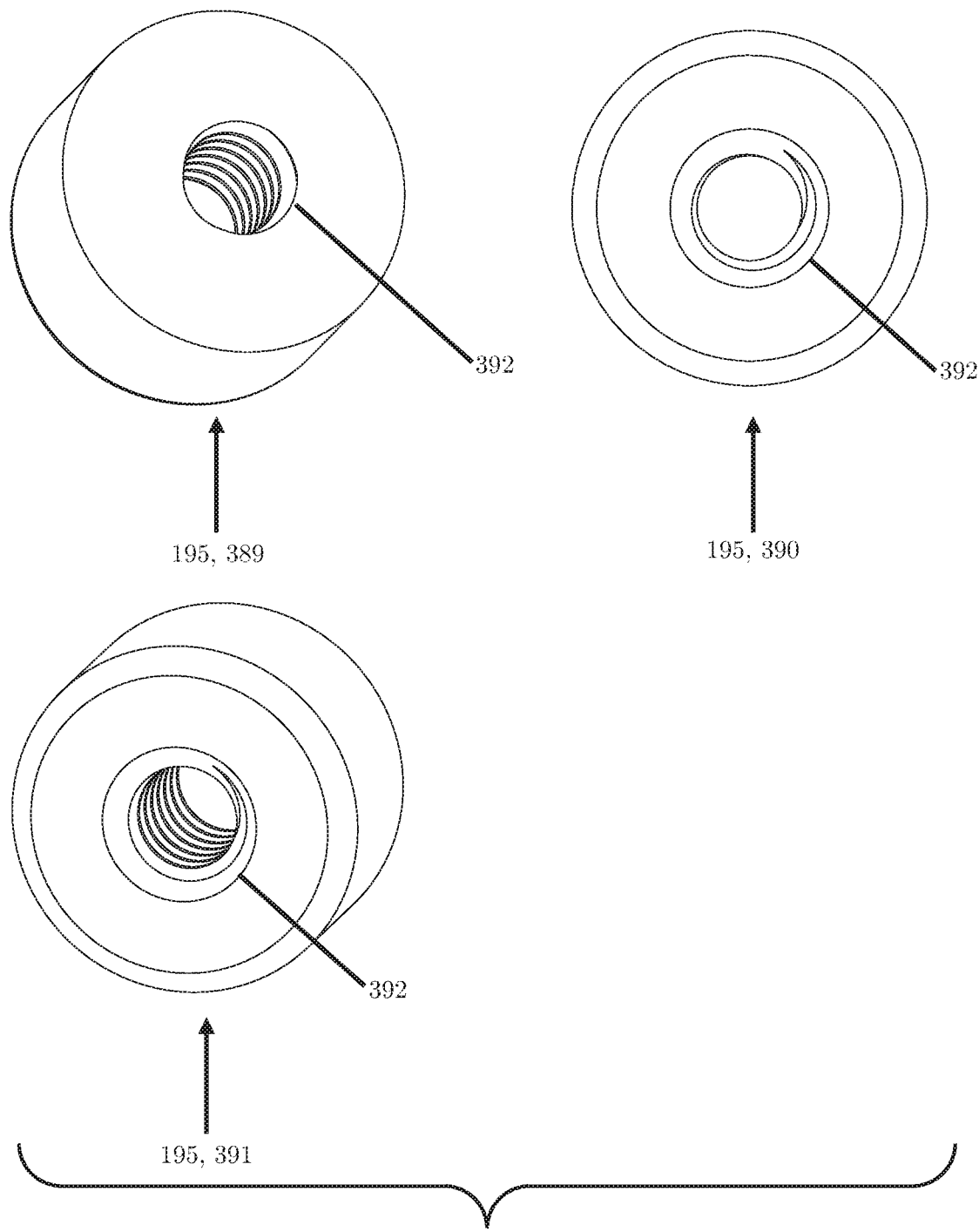
FIG. 112 contains a rear right perspective view 389, a front view 390, and a front right perspective view 391 of one contemplated embodiment of the clutch pin retention nut of the present invention, with the way it's assembled within the flexion-extension assembly being shown in FIG. 77.

The clutch pin 181, illustrated in FIG. 111, has a cylindrical "T" shape and a cylindrical, threaded tip 385 projecting from the end of the shaft 386. The shaft 386 is slidingly disposed to the shaft hole 382 that goes through the clutch 194. The clutch pin retention nut 195, shown in FIG. 112, is a cylinder with a threaded axial hole 392 passing through it. It is threaded onto the threaded tip 385, with the threads locked together with a threadlocker, and rests inside of a counterbore 379 in the clutch 194. In this regard, the pin 181 is able to rotate within the clutch's shaft hole 382 and pulling the pin 181 back slides the clutch 194 axially, regardless of the pin's 181 rotation angle. The clutch pin 181 has a handle 387 portion with finger grip areas 388 that, when squeezed, facilitate translating the pin 181 back and forth. As illustrated in FIG. 69, when the clutch 194 is in the engaged position the handle 387 rests in a groove 328 cut on a protrusion 332 on the worm gear 177. When it is being moved to the disengaged position, the handle 387 can be pulled axially beyond the protrusion, rotated 90°, and lowered into a second groove 327 on the worm gear protrusion 332 that is axially displaced from the first, groove 328 such that, when the handle 387 rests in the slot 327, the clutch 194 is held in place, within the worm gear 177, against the force of the spring 200.

Figure 80:
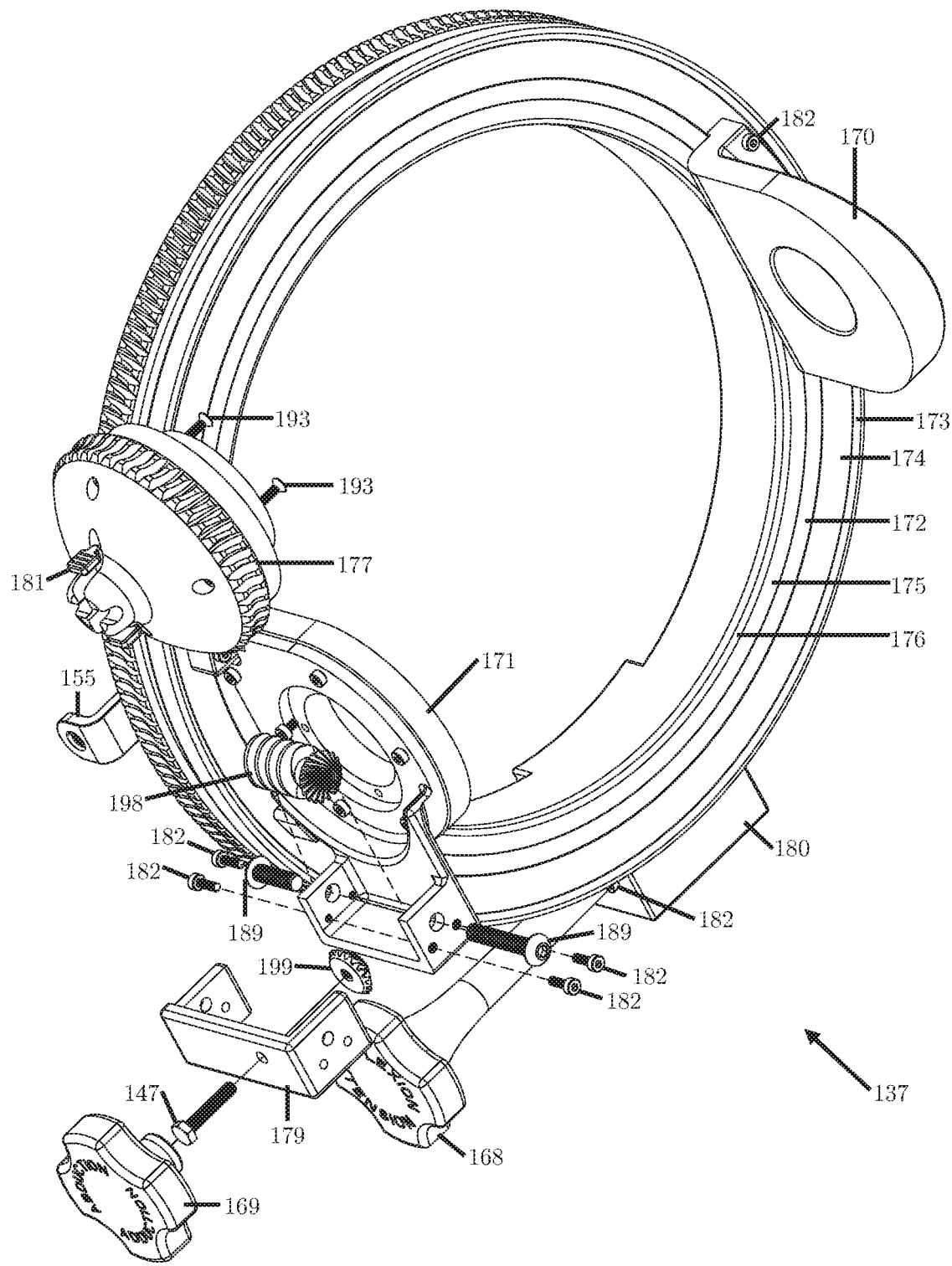
FIG. 80 is an exploded top right perspective view of the embodiment of the flexion-extension assembly shown in FIG. 69, that emphasizes the components responsible for adduction and abduction.
Figure 113:
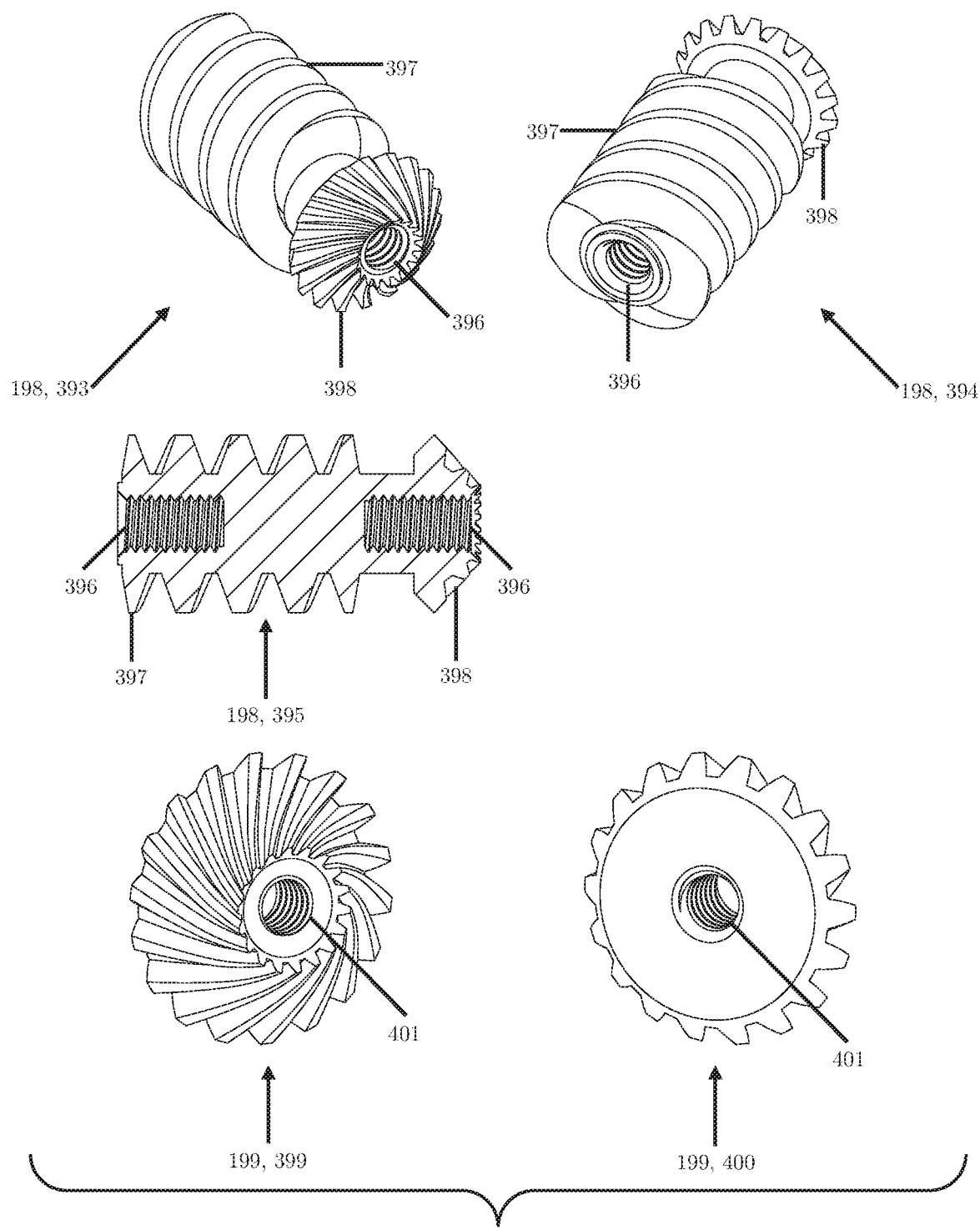
FIG. 113 contains a front right perspective view 393, a rear left perspective view 394, and an axial cross section view 395 of one contemplated embodiment of the adduction-abduction worm of the present invention, and also contains a front right perspective view 399 and a back left perspective view 400 of one contemplated embodiment of the adduction-abduction bevel gear of the present invention, the way both are assembled within the flexion-extension assembly being shown in FIG. 80.

The adduction-abduction worm 198, illustrated in FIG. 113, is coupled to the adduction-abduction worm gear 177 and is mounted on screws that are mounted to the adduction-abduction gearbox 178. The exploded view of FIG. 80 depicts the interactions between the components involved. The worm 198 has a blind, threaded mounting hole 396 on each end. On each side of the gearbox 178, the end of a rounded head screw 189 is passed through the shaft hole 359 on the adduction-abduction gearbox cover 179 and through the shaft hole 352 on the gearbox 178 before being threaded into the threaded mounting hole 396 on the worm 198. The threads are contemplated to be locked together with a threadlocker. The shaft holes 359, 352 are contemplated to be sized for M4 screws and the rounded screws 182 are contemplated to be M4, but any size screws may be used with corresponding hole sizes without departing from the scope of the present invention. The worm is contemplated to have a worm thread portion 397 on one end and a bevel gear portion 398 on the other end that is coupled to another bevel gear 199 whose axis is perpendicular to that of the first. The second bevel gear 199, illustrated in FIG. 113, is mounted to a hex screw 147 that is mounted to the gearbox cover 179 and has its head embedded in the adduction-abduction knob 169. The bevel gear 199 has a threaded, through hole 401 for mounting. The end of the hex screw 147 is passed through the shaft hole 358 on the gearbox cover 179 and threaded into the threaded mounting hole 401 on the bevel gear 199. The threads are contemplated to be locked together with a threadlocker. The shaft hole 358 is contemplated to be sized for an M3 screw and the hex screw 147 is contemplated to be M3, but any size screw may be used with a corresponding hole size without departing from the scope of the present invention. When the knob 169 is rotated in either direction, the second bevel gear 199 rotates the first bevel gear 398, which rotates the worm teeth 397 section of the worm 198, which rotates the worm gear 177. The shoulder sleeve shaft 209 then also rotates if the clutch 194 is engaged. It is contemplated that the worm-gear assembly is self-locking so that the worm 198 cannot be backdriven by the worm gear 177 and, therefore, so that the adduction-abduction angle rotated to with the knob 169 will automatically be held. The conditions under which self-locking occurs were discussed previously in connection with inequality (1). Being able to switch shoulder adduction/abduction between a state of being locked and a state of being free to move allows certain resistance exercises or adaptive movements to be performed. It is noted that other possible techniques for implementing the shaft of the worm 198 and of the bevel gear 199 may be used without departing from the scope of the present invention. Such techniques include but are not limited to installation of the worm 198 and/or bevel gear 199 on a milled shaft with a key or setscrew, or manufacturing the worm 198 and shaft and/or bevel gear 199 and shaft together as one piece.

The worm gear 177 to worm 198 ratio is contemplated to be approximately 22.5, but any ratio may be used without departing from the scope of the present invention. A ratio of 22.5 means that it would take 11.25 (half of 22.5) turns of the adduction-abduction knob 169 to rotate the arm from a position of full abduction to full adduction and vice versa. It is noted that the ideal ratio is one in which it doesn't take an excessive number of revolutions to get from a position of full abduction to one of full adduction. Additionally, a double-enveloping, or globoid, worm gear and worm pair may be used without departing from the scope of the present invention.

Figure 81:
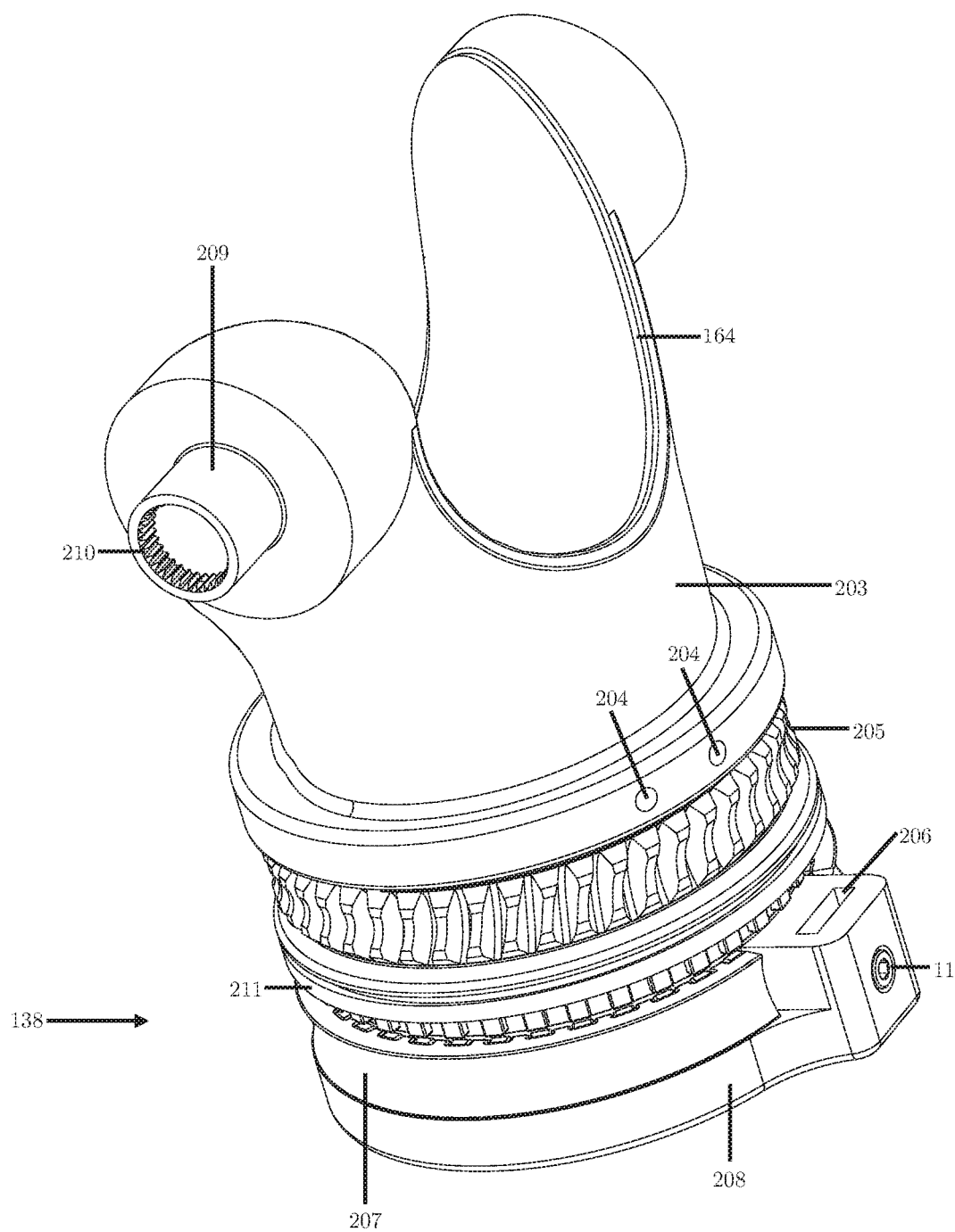
FIG. 81 is a top front perspective view of one contemplated embodiment of the shoulder sleeve assembly of the present invention and is shown assembled to the orthosis in FIG. 59.
Figure 82:
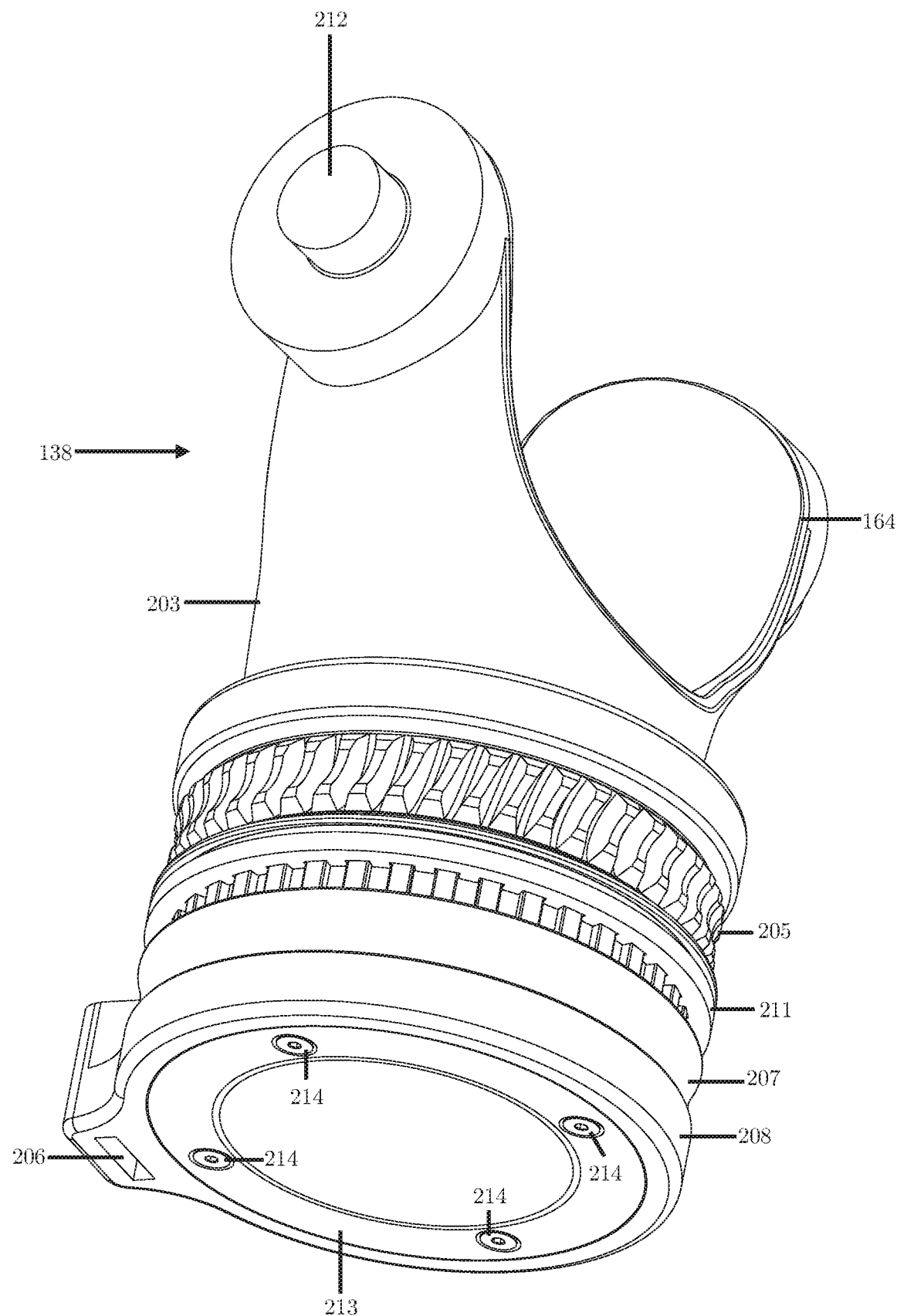
FIG. 82 is a bottom rear perspective view of the embodiment of the shoulder sleeve assembly shown in FIG. 81.
Figure 83:
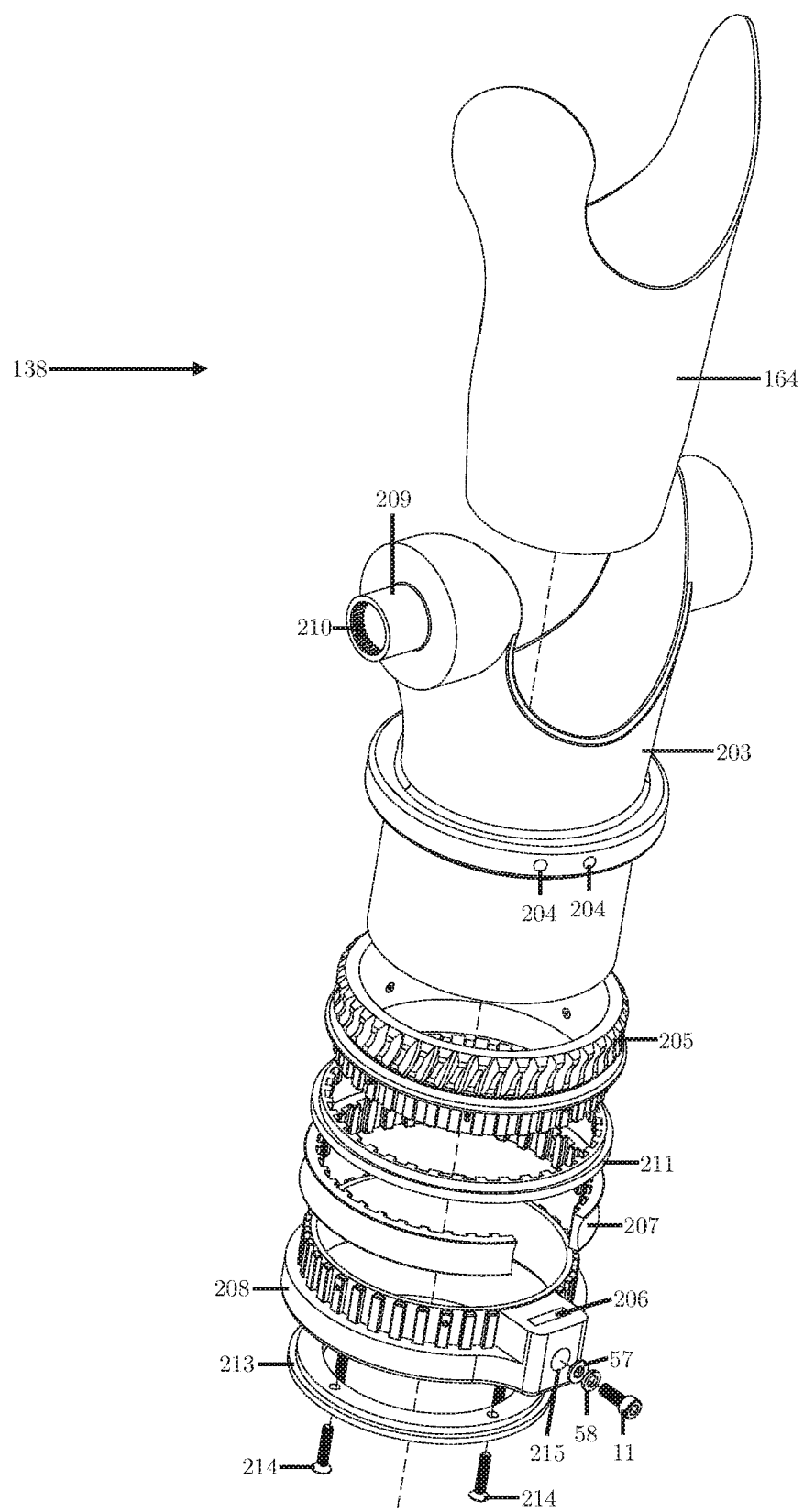
FIG. 83 is an exploded view of the embodiment of the shoulder sleeve assembly shown in FIG. 81.

In another aspect of orthosis-ROM, a shoulder sleeve assembly 138, illustrated in FIGS. 81-83 is mounted to the front and rear journal adduction-abduction pillow block bearings 171, 170. It is shown without the shoulder sleeve 203 in FIG. 84 and with the internal external-rotation gearbox assembly 136 coupled to it in FIGS. 85-87. The shoulder sleeve assembly 138 is contemplated to be the physical medium through which the forces of shoulder flexion-extension and adduction-abduction are applied to the upper arm and the anchor point from which internal-external rotation is achieved. The main components are the shoulder sleeve 203, the internal-external rotation worm gear 205, the worm gear retention ring 211, the rotary motion carriage ring 208, the internal-external rotation clutch 207, the shoulder sleeve retention ring 213, and the shoulder sleeve pad 164. The interaction between the spline 210 of the shoulder sleeve 203, the spline 305 of the adduction-abduction worm gear 177, and the adduction-abduction clutch 194 was discussed previously.

The shoulder sleeve 203, illustrated in FIGS. 88-89, is contemplated to have the basic shape of a cylindrical shell but with several modifications. It is worn around the upper arm and shoulder like a sleeve and has its axis coincident with the internal-external rotation axis of the upper arm. It starts near the top of the shoulder and stops near the middle of the upper arm. The inner cylindrical surface, instead of being cylindrical, is molded to the shape of the shoulder and is lined with a layer of padding 164 for added comfort and a better fit. Starting from the transition point of the shoulder to the upper arm, the inner shape progresses, linearly, from being molded to the shape of the shoulder to being perfectly cylindrical at the opposite end of the sleeve. The sleeve is intended to hold the shoulder and upper arm as firmly and tightly as possible while allowing the arm to rotate internally and externally within it. When the shoulder rotates throughout any of its three rotational degrees of freedom, the external shape of the shoulder remains essentially the same while that of the upper arm changes drastically due to humeral rotation and the resulting shift, of the muscle and flesh attached to the humerus. This is the reason for the progressive change in shape of the inner surface: the shifting of muscle and flesh increases down the upper arm with the distance from the shoulder and the progressive cylindrical shape allows the upper arm to rotate about its axis without hitting the walls of sleeve (instead only scraping against them). Additionally, the extra space created by the progressive cylinder allows the upper arm room to expand when the elbow is being flexed (e.g. during a bicep curl exercise). The opening 224 of the sleeve 203 is large enough for the arm to slide through and for the shoulder to slip into place. The front and rear surfaces of the shoulder area each have a cylindrical shaft with two diametrical steps projecting from it. The front shaft surface has a shaft with first step 225 and second step 209 projecting from it. The rear surface has a shaft with first step 229 and second step 212 projecting from it. The shafts are coaxial and coincident with the adduction-abduction rotation axis of the shoulder. The end of the second step 209 of the front shaft has the internal, coaxial spline 210, previously discussed in relation to the adduction-abduction components, cut into it axially. The end of the second step of the rear shaft 212 does not have a spline cut into it.

The outside surface of the sleeve 203 is contemplated to be a normal projection of the inside surface except for a few differences, the first of which is that there are no front and rear shafts 225, 209, 229, 212. The second is that the end of the sleeve 203 opposite the shoulder is cylindrical up to a certain axial depth. The cylinder serves as an axle 226 for components to rotate on. At the end of that axial depth, the cylinder steps up to a larger diameter cylinder 227 that is relatively short in axial length and acts as an axle shoulder for components mounted to the axle to press against. There are two mounting through holes 204 on the outer cylindrical surface of the axle shoulder 227, with countersinks 223, illustrated in FIG. 87, on the inside surface of the sleeve 203, whose axis is normal to the cylindrical axis of the sleeve 203. The annular face at the end of the sleeve 203 has a number of equally-circumferentially spaced, blind threaded holes 228.

Figure 90:
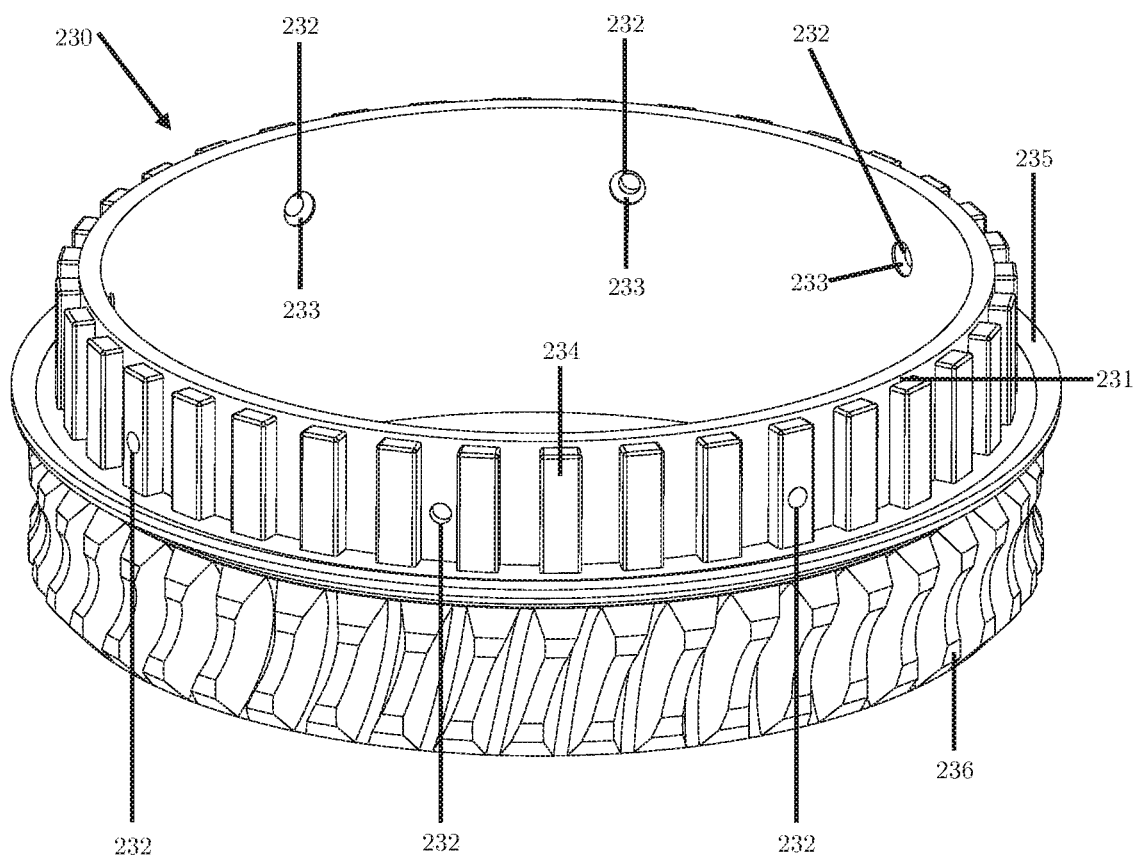
FIG. 90 is a front top perspective view of one contemplated embodiment of the internal-external rotation worm gear of the present invention and is shown assembled within the shoulder sleeve assembly in FIG. 81.

The internal-external rotation worm gear 230, illustrated in FIG. 90, has the basic shape of a cylindrical shell with the outside cylindrical surface being divided into three axial sections. The section at one end is a set of worm gear teeth 236, the section in the middle is a revolved protrusion 235 that forms half of a groove that accepts a dovetail, and the section at the end is a set of dog clutch teeth 234 that run parallel to the axis of the shell. The dovetail protrusion 235 opens towards the clutch teeth section 234. In the clutch teeth section 234, there are a number of equally-circumferentially spaced mounting through holes 232 with a countersink 233, on the inside surface of the shell, whose axes are normal to the axis of the shell. It is contemplated that the worm gear 230 is mounted coaxially on the shoulder sleeve axle 226 with the worm gear 236 end butting up against the sleeve shoulder 227. The worm gear 230 is slidingly disposed to the axle 226 and rotates with or without lubrication from a grease or oil.

Figure 91:
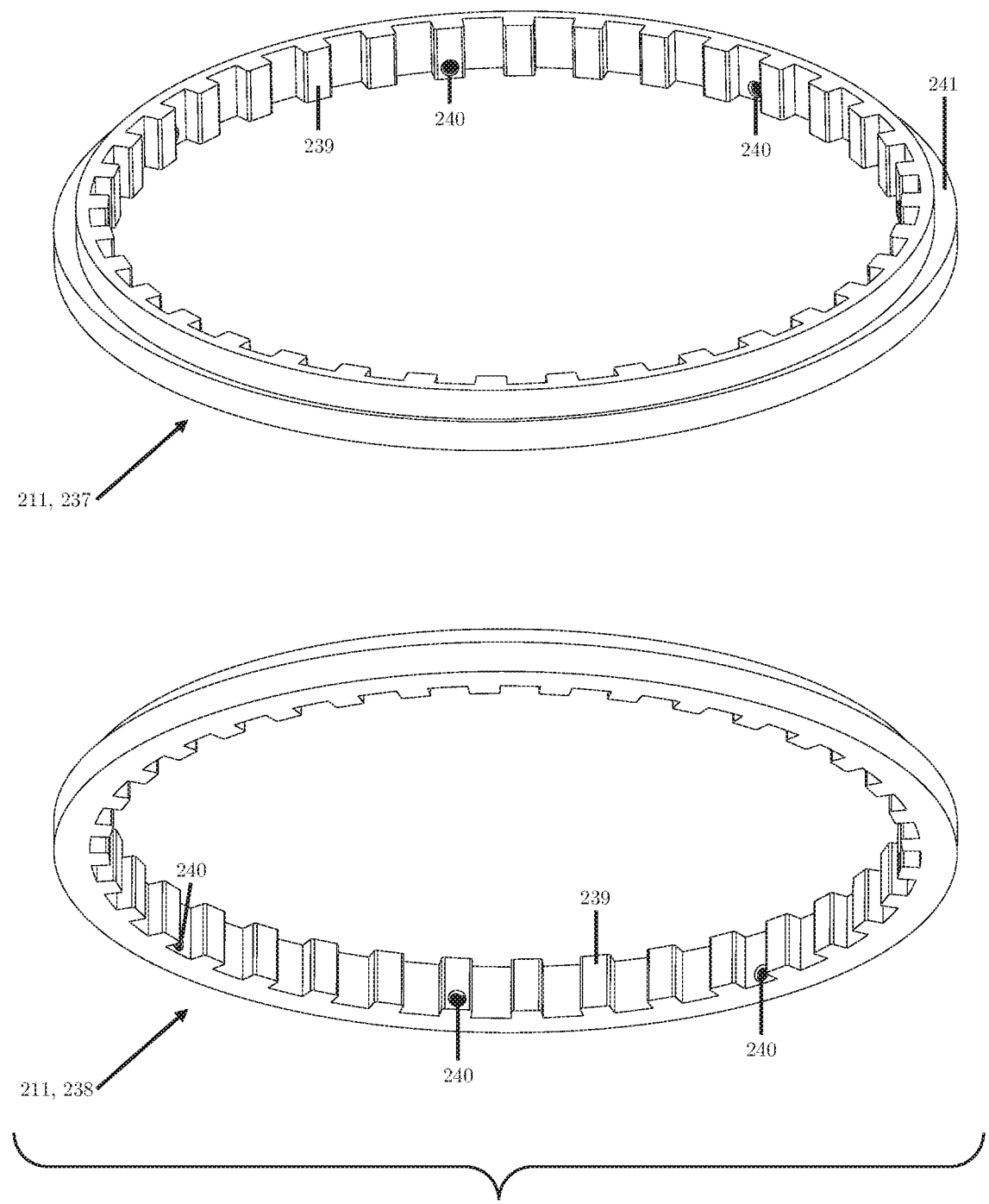
FIG. 91 contains a front top perspective view 237 and a front bottom perspective view 238 of one contemplated embodiment of the worm gear retention ring of the present invention and is shown assembled within the shoulder sleeve assembly in FIG. 81.

The worm gear retention ring 211, illustrated in FIG. 91, has the basic shape of a cylindrical shell. The inside cylindrical surface is a set of dog clutch teeth 239 that run parallel to the axis of the shell and mate with the clutch teeth 234 on the internal-external rotation worm gear 230. Along the teeth 239 there are a number of equally-circumferentially spaced threaded, mounting blind holes 240 whose axes are normal to the axis of the shell. The circumferential locations correspond to those of the mounting through holes 232 of the internal-external rotation worm gear 230. The outside cylindrical surface contains a revolved protrusion 241 that forms half of a groove that accepts a dovetail. It matches and corresponds to that of the internal-external rotation worm gear 230. The axial length of the shell is less than the axial length of the clutch teeth 234 on the internal-external rotation worm gear 230. It is contemplated that the retention ring 211 is mounted coaxially on the worm gear 230 with its clutch teeth 239 mating with those of the worm gear 234. The mounting holes 232 on the worm gear 230 are aligned with the threaded mounting holes 240 on the retention ring 211. The end of a flathead screw 216 is passed through each mounting hole 232 on the worm gear 230, is threaded into the corresponding threaded hole 240 of the retention ring 211, and has its head sitting in the corresponding countersink 233. The mounting holes 232 are contemplated to be sized for M2 screws, the threaded mounting holes 240 are contemplated to use M2 threads, and the flathead screws 216 are contemplated to be M2, but any size screws may be used with corresponding hole sizes without departing from the scope of the present invention. The dovetail groove 241 of the retention ring 211 opens towards the worm gear teeth 234.

Figure 93:
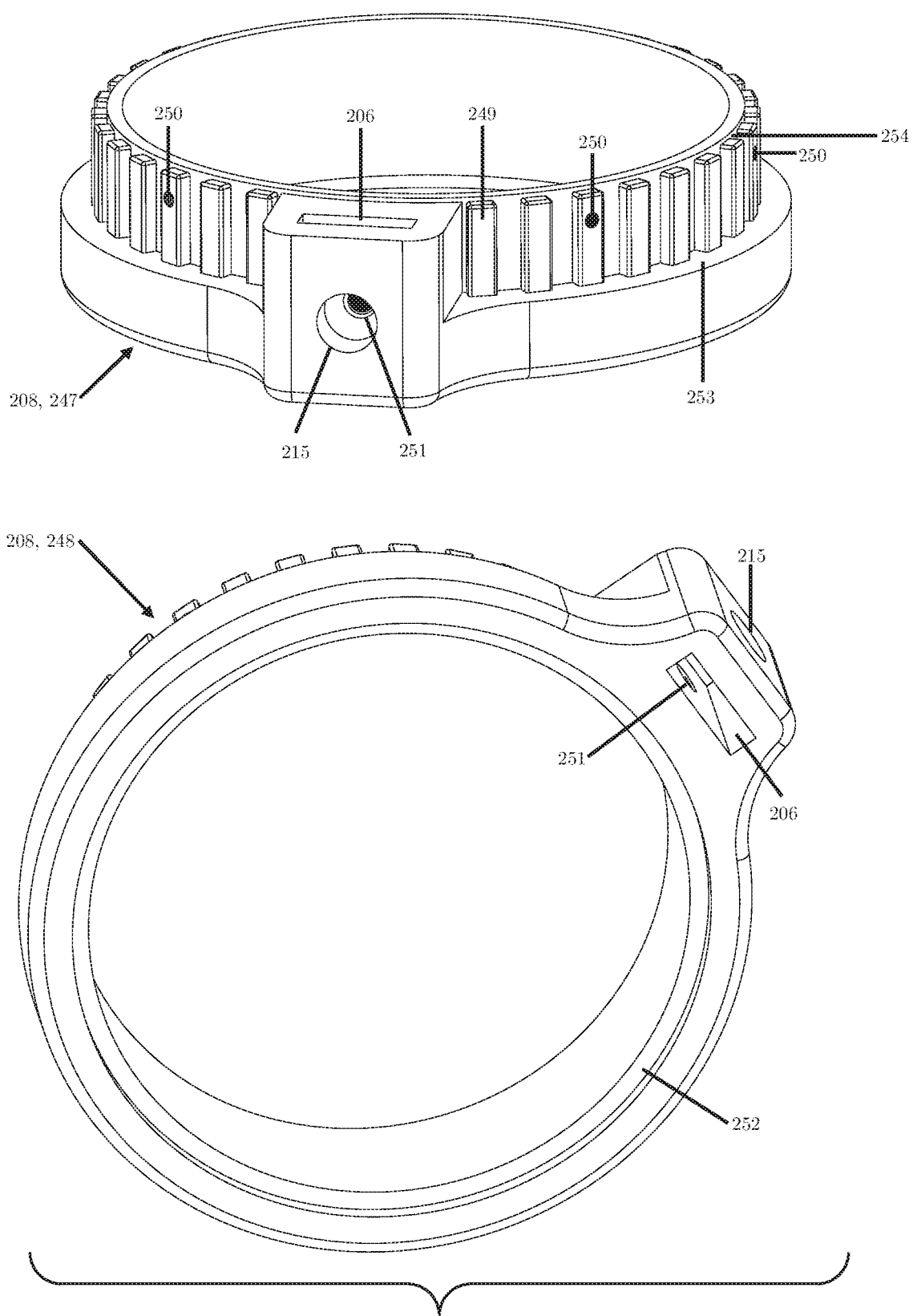
FIG. 93 contains a front top perspective view 247 and a front bottom perspective view 248 of one contemplated embodiment of the rotary motion carriage ring of the present invention and is shown assembled within the shoulder sleeve assembly in FIG. 81.

The rotary motion carriage ring 208, illustrated in FIG. 93, performs almost the same function as the linear motion carriage 54 of the first embodiment of the orthosis of the present invention. It has the basic shape of a cylindrical shell with two diametrical steps and a shoulder 252 that is cut into the inner annulus of the side with the largest diameter step. The outside surface of the smaller step has a set of dog clutch teeth 249 that run parallel to the axis of the shell and match the geometric profile of the clutch teeth 234 on the internal-external rotation worm gear 230. Along the teeth 249 there are a number of equally-circumferentially spaced blind, threaded holes 250 whose axes are normal to the axis of the shell. Each threaded hole 250 has a ball-nose spring plunger 217 threaded into it and the ball of each plunger 217 extends slightly beyond the face of its accompanying tooth. The threaded hole 250 and the ball-nose spring plunger 217 are contemplated to use 4-48 threads but any size may be used without departing from the scope of the present invention. There is a solid block with a rectangular hole 206 running through it projected from the surfaces of both diametrical steps. As a result, the clutch teeth 249 do not wrap around the full circumference of the carriage ring 208. There is a through hole 215 on the front face of the block and a coaxial, threaded mounting hole 251 on the back inner face of the rectangular hole 206. The threaded mounting holes 250 are contemplated to use M5 threads but any size may be used without departing from the scope of the present invention. It is contemplated that the carriage ring 208 is mounted coaxially on the shoulder sleeve axle 226, adjacent to the worm gear 230, with the clutch teeth end butting up against the clutch teeth end of the worm gear 230. In this assembled position, the annular face of the carriage ring shoulder 252 extends a short distance beyond the face of the bottom of the shoulder sleeve 203. The carriage ring 208 is slidingly disposed to the axle 226 and rotates with or without lubrication from a grease or oil. The worm gear 230 has a cylindrical separation lip 231 and the carriage ring 208 has a cylindrical separation lip 254. When the worm gear 230 and carriage ring 208 rotate against each other, the separation lips 231, 254 serve as relief gaps that ensure that the clutch teeth 249, 234 do not have a chance of catching against each other during rotation.

Figure 92:
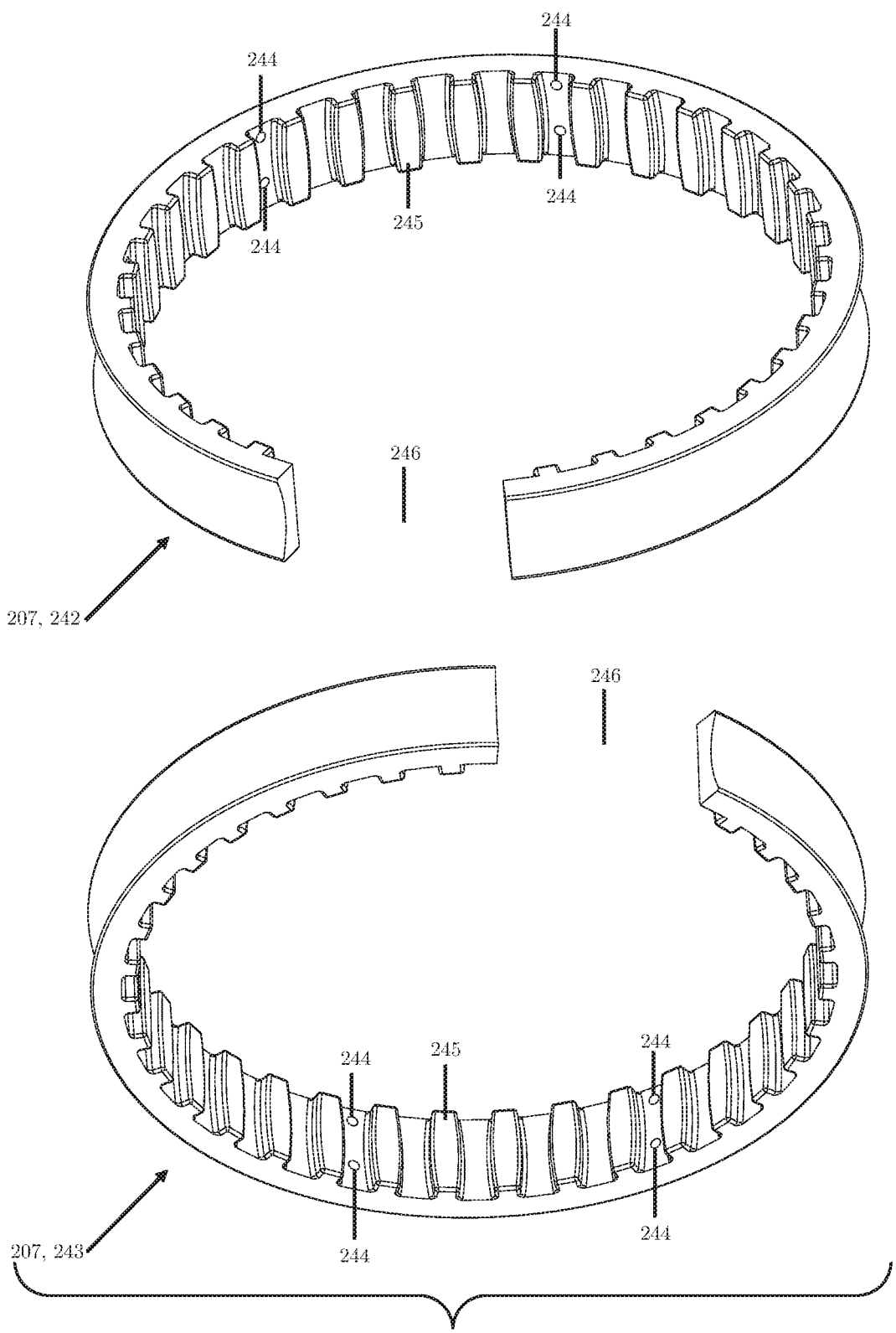
FIG. 92 contains a front top perspective view 242 and a front bottom perspective view 243 of one contemplated embodiment of the internal-external rotation clutch of the present invention and is shown assembled within the shoulder sleeve assembly in FIG. 81.

The internal-external rotation clutch 207, illustrated in FIG. 92, has the basic shape of a cylindrical shell. The inside cylindrical surface is a set of dog clutch teeth 245 that run parallel to the axis of the shell and mate with the clutch teeth 234 on both the internal-external rotation worm gear 230 and the rotary motion carriage ring 208. The outside cylindrical surface is concavely curved to make it easier for the wearer to grip 207. The clutch 207 is installed after the worm gear 230 with its teeth slidingly disposed to the clutch teeth 249 of the carriage ring 208. When the clutch teeth 249 on the carriage ring 208 and the worm gear 230 are lined up, it is contemplated that the clutch 207 can then be shifted axially so that it is engaged with both sets of teeth simultaneously. When the clutch 207 is maximally engaged with the worm gear's clutch teeth 234 it is contemplated that the clutch teeth 245 are 50% engaged with the carriage ring 208 and 50% engaged with the worm gear 230. The end of each clutch tooth 245 is tapered to make it narrower than the openings created by the worm gear's clutch teeth 234. This facilitates the initial engagement of the clutch 207 but makes it so that there is no slip at full engagement with the worm gear 230.

In another aspect of the internal-external rotation clutch 207, there are eight equally-circumferentially spaced spherical sectors 244 cut into the bottom of the teeth 245 near one end and another eight equally-circumferentially spaced spherical sectors 244 cut into the teeth 245 at the other end. The sector 244 locations correspond to the locations of the ball-nose spring plungers 217 installed in the rotary motion carriage ring 208 and they are sized to be slightly larger than the balls of the plungers 217. The axial position of the first set of sectors 244 along the bottom of the clutch teeth 245 is such that when the clutch 207 is fully engaged with the carriage ring teeth 249 the balls aren't depressed into their corresponding bodies but instead rest in the sector cavities 244. Similarly, the axial position of the second set of sectors 244 along the bottom of the clutch teeth 245 is such that when the clutch 207 is fully engaged with the worm gear's clutch teeth 234 the balls aren't depressed into their corresponding bodies but instead rest in the sector cavities 244.

When the clutch 207 is engaged with the worm gear clutch teeth 234, the rotation of the worm gear 230 and the carriage ring 208 is coupled, whereas when the clutch is disengaged, the rotation of the worm gear 230 and carriage ring 208 is separate. Due to the presence of the ball-nose spring plungers 217, shifting the handle from the fully engaged or fully disengaged position depresses each plunger 217 and thus requires extra force to get the translation started. As the opposite extent is being reached, the balls release themselves into the sector cavities 244 of the clutch 207. The abrupt decrease in the force required to translate the clutch 207 as the balls are releasing causes the clutch 207 to be pulled into place. The release of the balls is contemplated to cause an audible click that lets the wearer know that the extent has been reached.

Figure 86:
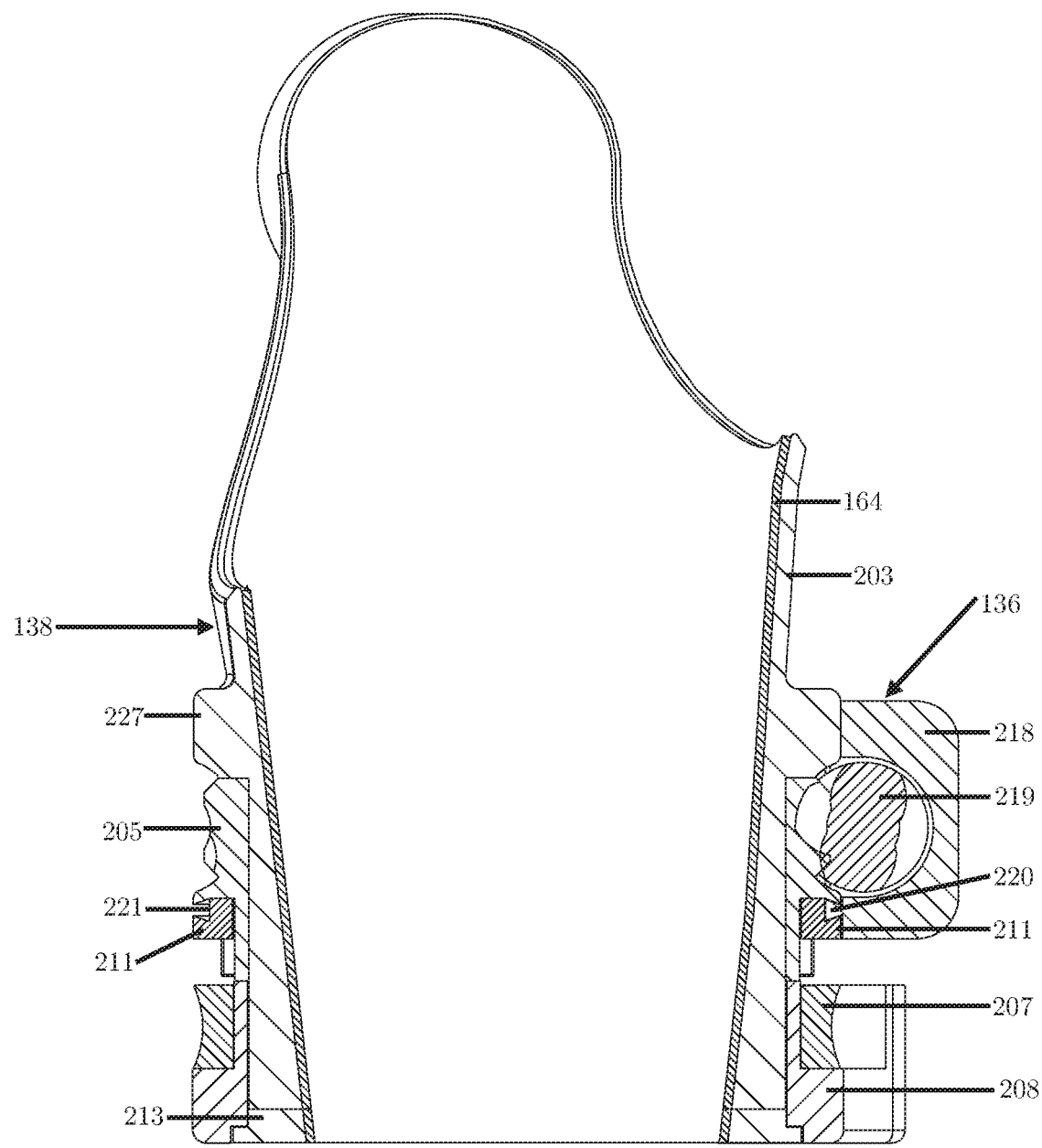
FIG. 86 is a cross-sectional view, taken along plane 85-85 of FIG. 85, that shows the engagement of the shoulder sleeve assembly components with the internal-external rotation gearbox assembly.
Figure 87:
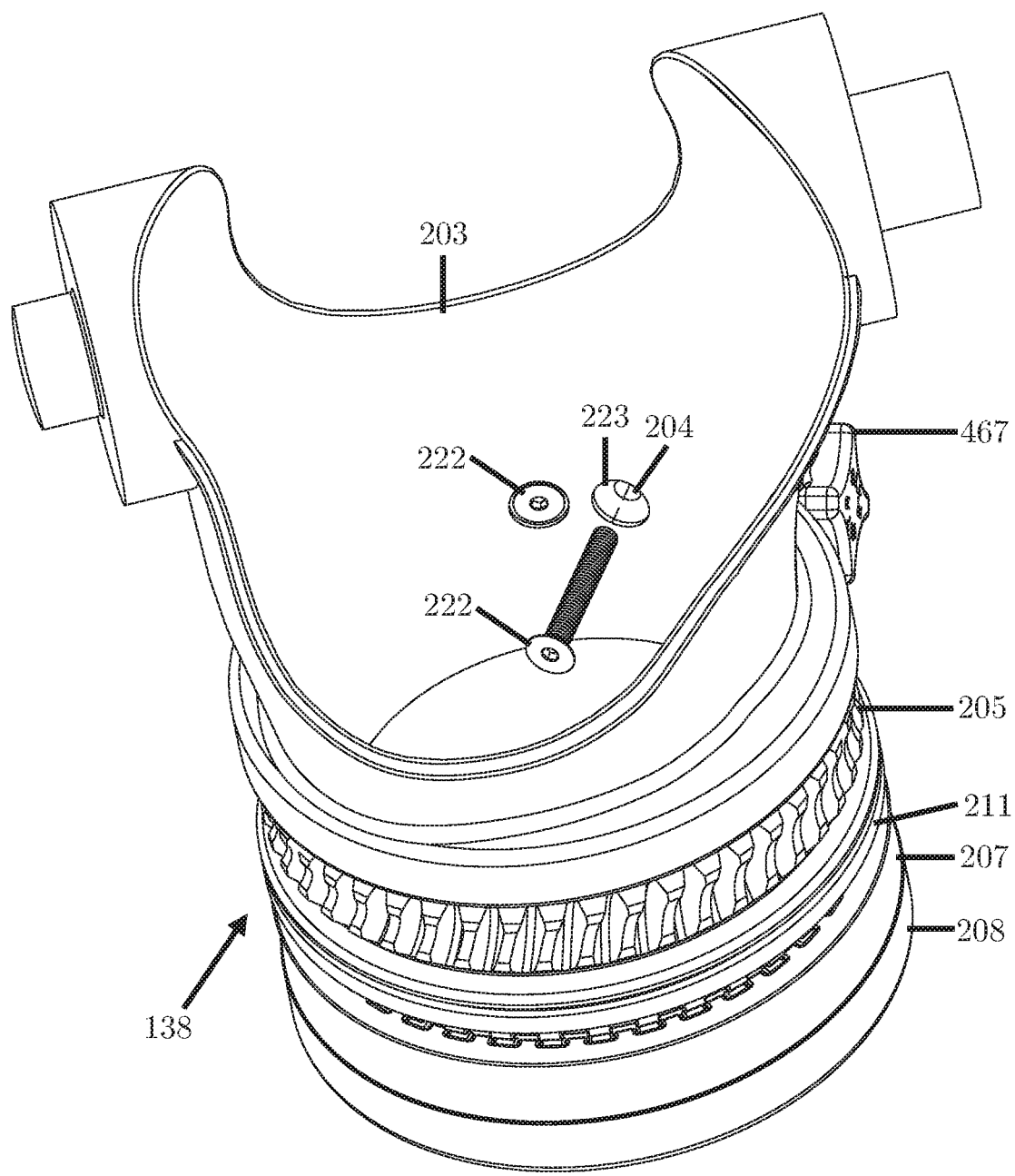
FIG. 87 is an exploded top left perspective view of the shoulder sleeve assembly, without the shoulder sleeve pad, engaged with the internal-external rotation gearbox assembly.
Figure 94:
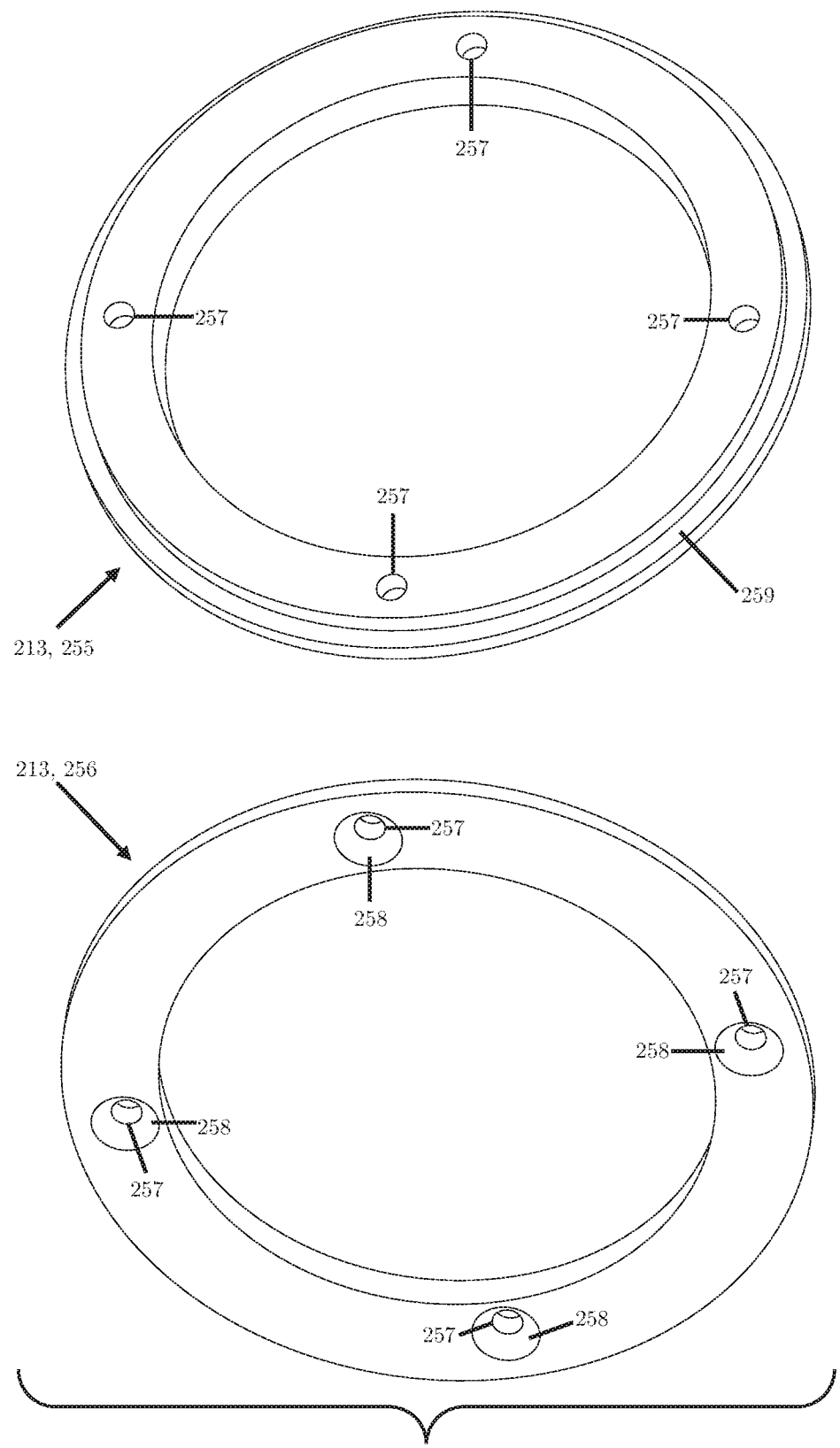
FIG. 94 contains a front top perspective view 255 and a front bottom perspective view 256 of one contemplated embodiment of the shoulder sleeve retention ring of the present invention and is shown assembled within the shoulder sleeve assembly in FIG. 81.

The shoulder sleeve retention ring 213, illustrated in FIG. 94, has the basic shape of a cylindrical shell with two diametrical steps. The annulus of the larger diameter step has four equally-circumferentially spaced mounting through holes 257 with a countersink 258. The inner cylindrical surface is a continuation of the shoulder sleeve 203 inner surface, which was formed by the progression from the shoulder surface shape to a cylindrical shape. FIG. 86 makes the nature of this continuation clear. It is contemplated that the shoulder sleeve retention ring 213 is mounted coaxially with the shoulder sleeve 203 and that the face of the smaller diametrical step mates to the bottom face of the shoulder sleeve 203. The outer cylindrical surface of the smaller diametrical step is slidingly disposed to the inner cylindrical surface of the carriage ring 208 and the outer cylindrical surface of the larger diametrical step 259 is slidingly disposed to the inner cylindrical surface of the carriage ring shoulder 252. The end of a flathead screw 216 is placed through each mounting through hole 257 and threaded into each blind, threaded mounting hole 228 on the bottom face of the shoulder sleeve 203. The mounting holes 257 are contemplated to be sized for M5 screws, the threaded mounting holes 228 are contemplated to use M5 threads, and the flathead screws 216 are contemplated to be M5, but any size screws may be used with corresponding hole sizes without departing from the scope of the present invention. When installed, the bottom surfaces of the retention ring 213 and the carriage ring 252 are flush with one another.

It is contemplated that a shoulder sleeve pad 164 lines the inside surfaces of the shoulder sleeve 203 and the shoulder sleeve retention ring 213. It is created by thickening this surface and cutting across it normal to the sleeve's 203 axis near the bottom. It is contemplated to be about $3/16$ inch thick but may be any thickness without, departing from the scope of the present invention. Additionally, it is contemplated to be made of foam, cloth, or any comparable material that satisfies this function but any material may be used without departing from the scope of the present invention. It is contemplated to attach to the assembly 137 using an adhesive, such as a high-strength spray adhesive, an epoxy, contact cement, glue, or tape, but any suitable adhesive may be used without departing from the scope of the present invention.

Figure 115:
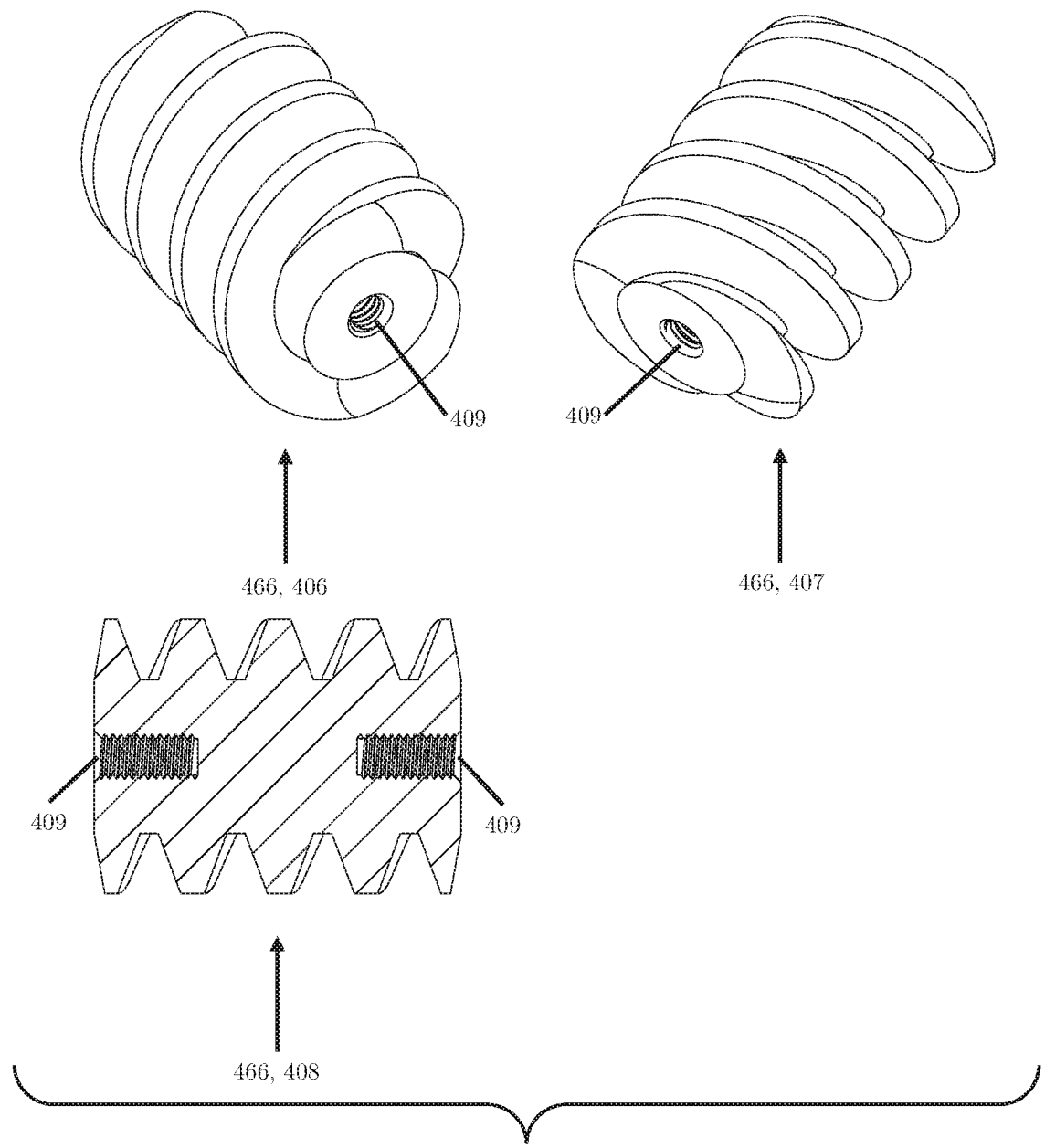
FIG. 115 contains a front right perspective view 406, a rear right perspective view 407, and an axial cross section view 408 of one contemplated embodiment of the internal-external rotation worm of the present invention and is shown assembled to the internal-external rotation gearbox in FIG. 128.

In another aspect of orthosis-ROM, the internal-external rotation gearbox assembly 136 is assembled to the shoulder sleeve assembly 138. The main components of the internal-external rotation gearbox assembly 136, illustrated in FIGS. 128-129, are the internal-external rotation gearbox 465, the internal-external rotation worm 466, and the internal-external rotation knob 467. The internal-external rotation gearbox 465 is contemplated to have the basic shape of a thin-walled box with one open side. The side with the open face is arced with a radius of curvature that matches that of the axle shoulder 227 of the shoulder sleeve 203. There are two blind, threaded mounting holes 469 along the top perimeter of the open face whose axes are normal to the axis of the arc of the open face. The hole 469 locations correspond to those of the mounting through holes 204 on the cylindrical face of the axle shoulder 227. There is an arced dovetail 468 along the bottom perimeter of the box with a profile that corresponds to that of the dovetail groove created by the internal-external rotation worm gear 230 and the worm gear retention ring 211. The internal-external rotation worm 466, illustrated in FIG. 115, is mounted on screws between the side walls of the gearbox 465. Each end of the worm 466 has a blind, threaded mounting hole 409. On one side, the end of a rounded head screw 189 is passed through the shaft hole 471 on the gearbox 465 and threaded into the threaded mounting hole 409 on the worm 466. On the other side, the end of a hex head screw 472 is passed through the shaft hole 471 on the gearbox 465 and threaded into a threaded mounting hole 409 on the worm 466. The threads are contemplated to be locked with threadlocker. It is contemplated that the shaft holes 471 are sized for an M4 screw and that the screws 189, 472 are M4, but any size may be used without departing from the scope of the present invention. The head of the hex screw 472 is embedded in the internal-external rotation knob 467. It is noted that other possible techniques for implementing the shaft of the worm 466 may be used without departing from the scope of the present invention. Such techniques include but are not limited to installation of the worm 466 on a milled shaft with a key or setscrew, or manufacturing the worm 466 and shaft together as one piece.

The gearbox assembly 136 is mounted, with the axis of the arced face of the gearbox 465 coincident with the cylindrical axis of the sleeve 203 and the top perimeter of the arced face mating with the outer cylindrical surface of the axle shoulder 227 of the shoulder sleeve 203, by passing a flathead screw 222 through each axle shoulder mounting hole 204 on the shoulder sleeve 203 and threading it into the corresponding threaded mounting hole 469 on the gearbox 465 and by placing the gearbox's dovetail 468 in the dovetail groove created by the internal-external rotation worm gear 230 and the worm gear retention disk 191. This would, therefore, be done at the time of installation of the worm gear retention ring 211. The threads are contemplated to be locked with a threadlocker. It is contemplated that the mounting holes 204 are sized for M5 screws and that the screw 222 is M5, but any size may be used without departing from the scope of the present invention.

When the gearbox assembly 136 is mounted, the worm 466 teeth are coupled with the internal-external rotation worm gear teeth 234. When the knob 467 is rotated in either direction, the worm 466 and the worm gear 230 rotate as a result. The rotary motion carriage ring 208 then also rotates if the clutch 207 is engaged. It is contemplated that the worm-gear assembly is self-locking so that the worm cannot be backdriven by the worm gear 230 and, therefore, so that the angle rotated to with the knob 467 will automatically be held as it is being rotated. The presence of the dovetail 468 on the gearbox 465 allows the worm gear 230 to rotate while the gearbox assembly 136 remains fixed. The dovetail 468 provides additional support to the mounting screws 216 to prevent the assembly from shifting during rotation. In order to use a second set of mounting screws in lieu of the dovetail 468, the gearbox 465 would have to be made longer to reach a place on the shoulder sleeve 203 that they could be anchored to. The conditions under which self-locking occurs were discussed previously in connection with inequality (1). Being able to switch shoulder internal/external rotation between a state of being locked and a state of being free to move allows certain resistance exercises or adaptive movements to be performed.

The worm gear 230 to worm 466 ratio is contemplated to be approximately 22.5, but any ratio may be used without departing from the scope of the present invention. A ratio of 22.5 means that it would take 11.25 (half of 22.5) turns of the internal-external rotation knob 467 to rotate the arm from a position of full internal rotation to full external rotation and vice versa. It is noted that the ideal ratio is one in which it doesn't take an excessive number of revolutions to get from a position of full internal rotation to one of full external rotation. Additionally, a double-enveloping, or globoid, worm gear and worm pair may be used without departing from the scope of the present invention.

Figure 84:
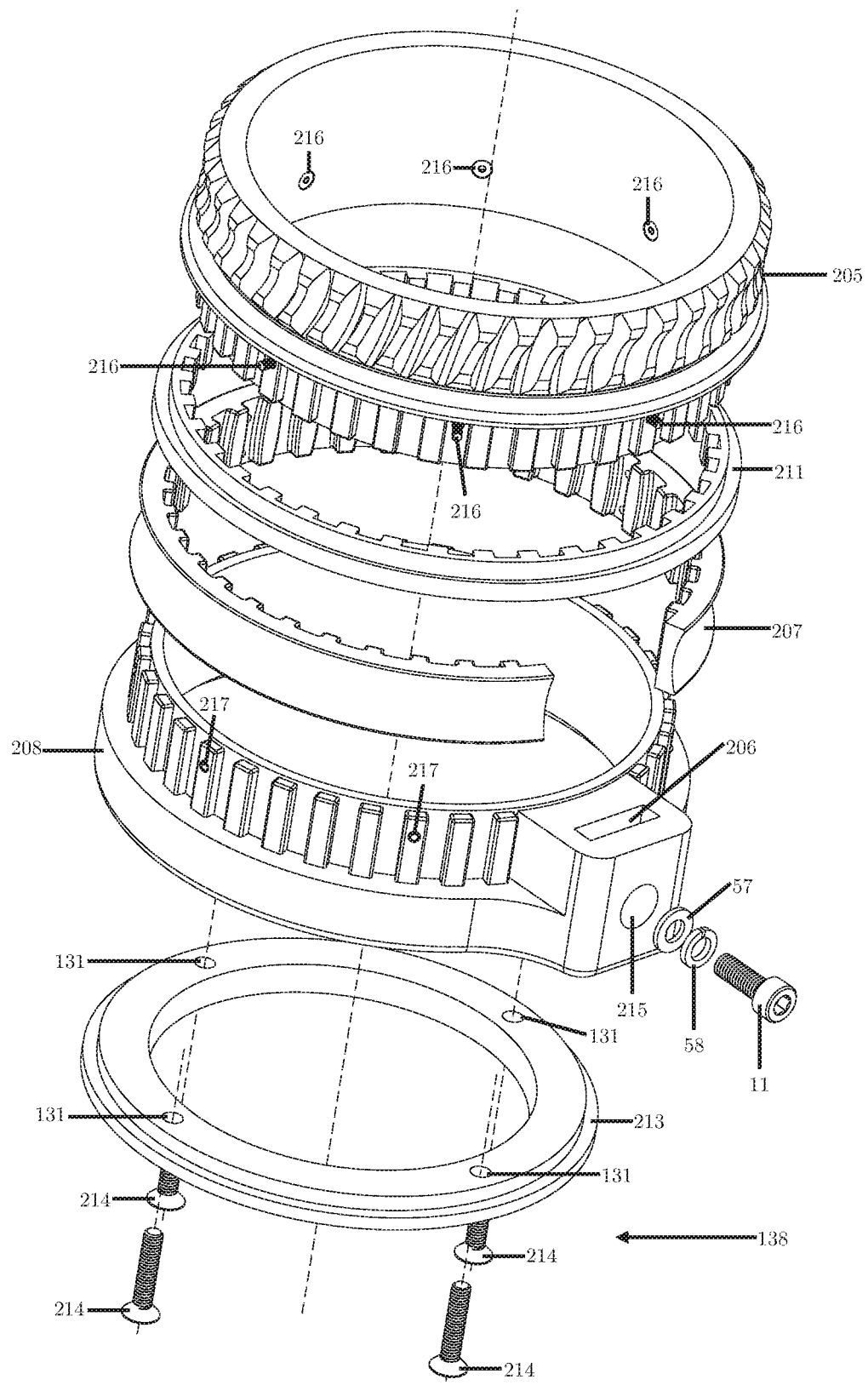
FIG. 84 is the exploded view of the shoulder sleeve assembly shown in FIG. 81 without the shoulder sleeve pad and the shoulder sleeve, which are the two topmost components.
Figure 85:
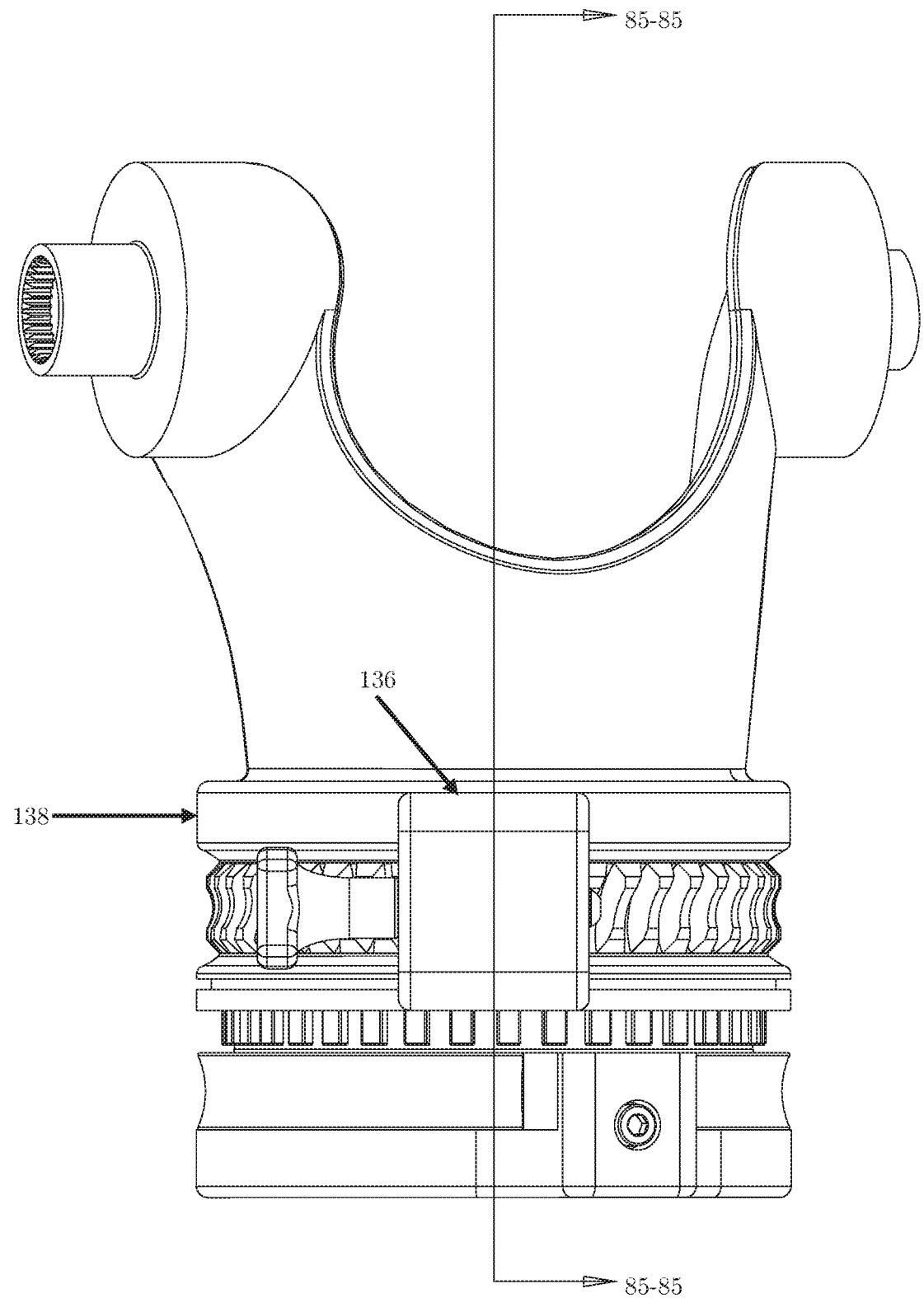
FIG. 85 is a side view of the shoulder sleeve assembly assembled to the internal-external rotation gearbox assembly and is normal to a face of the internal-external rotation gearbox.
Figure 99:
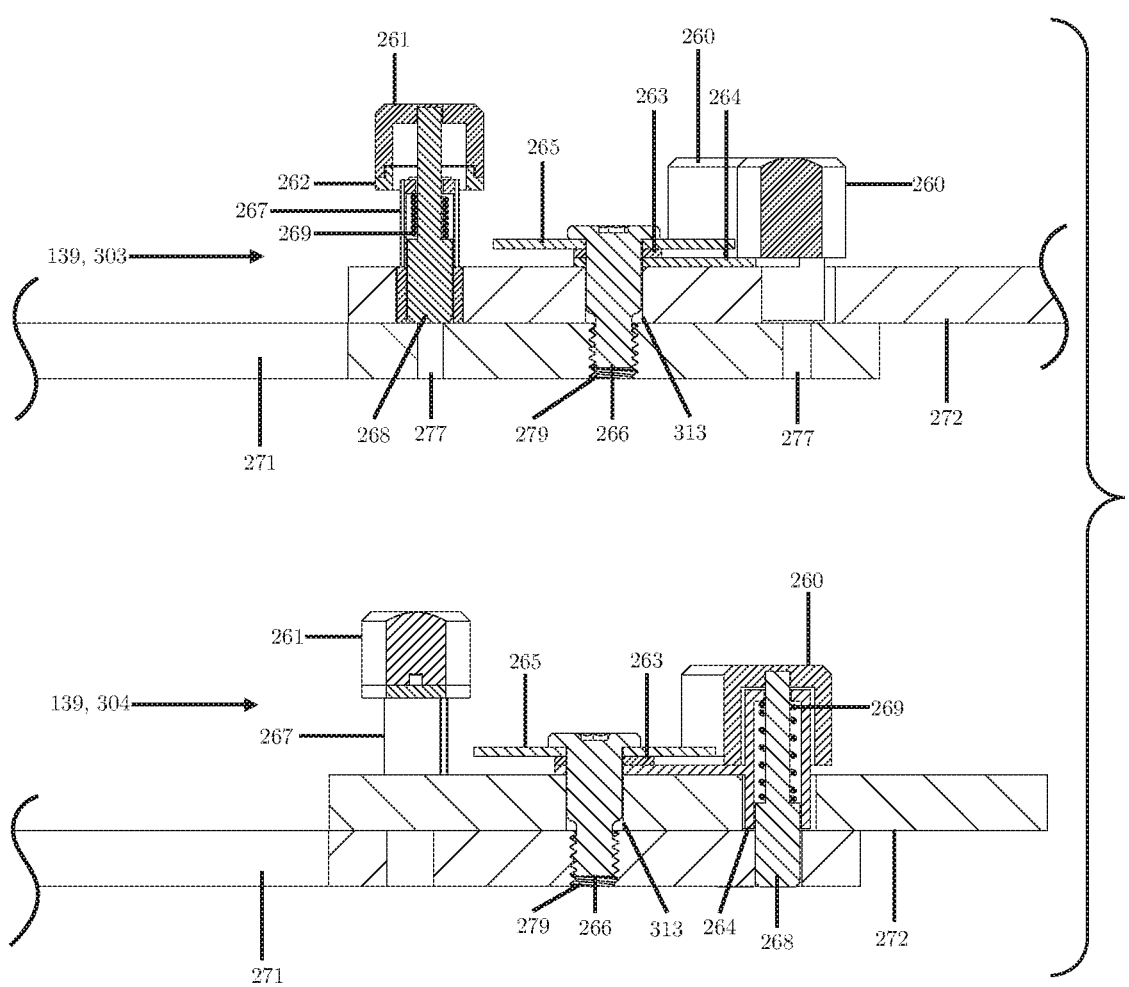
FIG. 99 contains a broken cross-sectional view 303, taken along plane 98-98A of FIG. 98, that shows the engagement of the hinge lock plunger and accompanying components with the upper and lower splint arms, and also contains a broken cross-sectional view 304, taken along plane 98-98B of FIG. 98, that shows the engagement of the extension plunger and accompanying components with the upper and lower splint arms.
Figure 100:
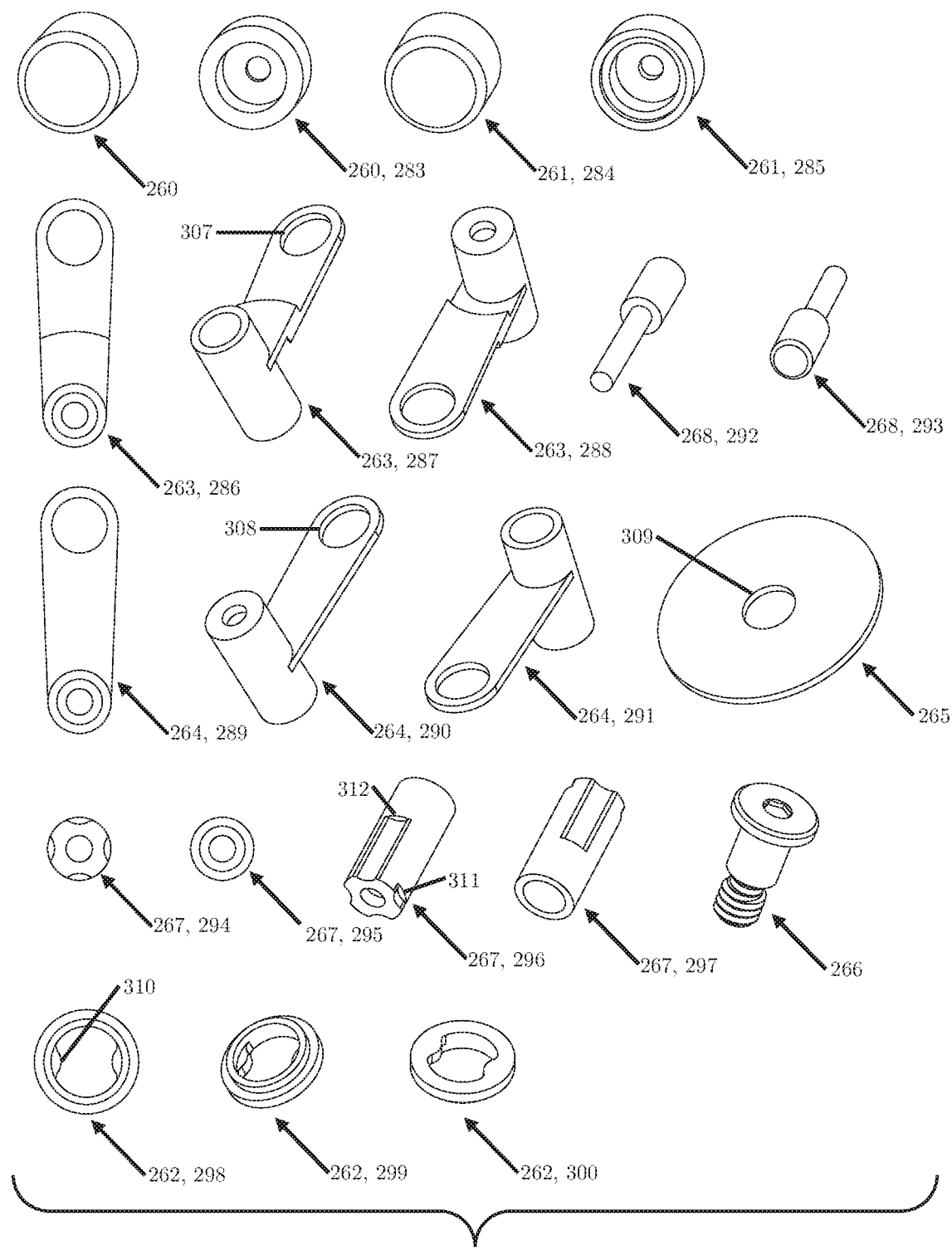
FIG. 100 contains front perspective views of all the hardware, except for the springs, used in the embodiment of the splint arm assembly shown in FIG. 97, at the same scale (but not to scale)
Figure 101:
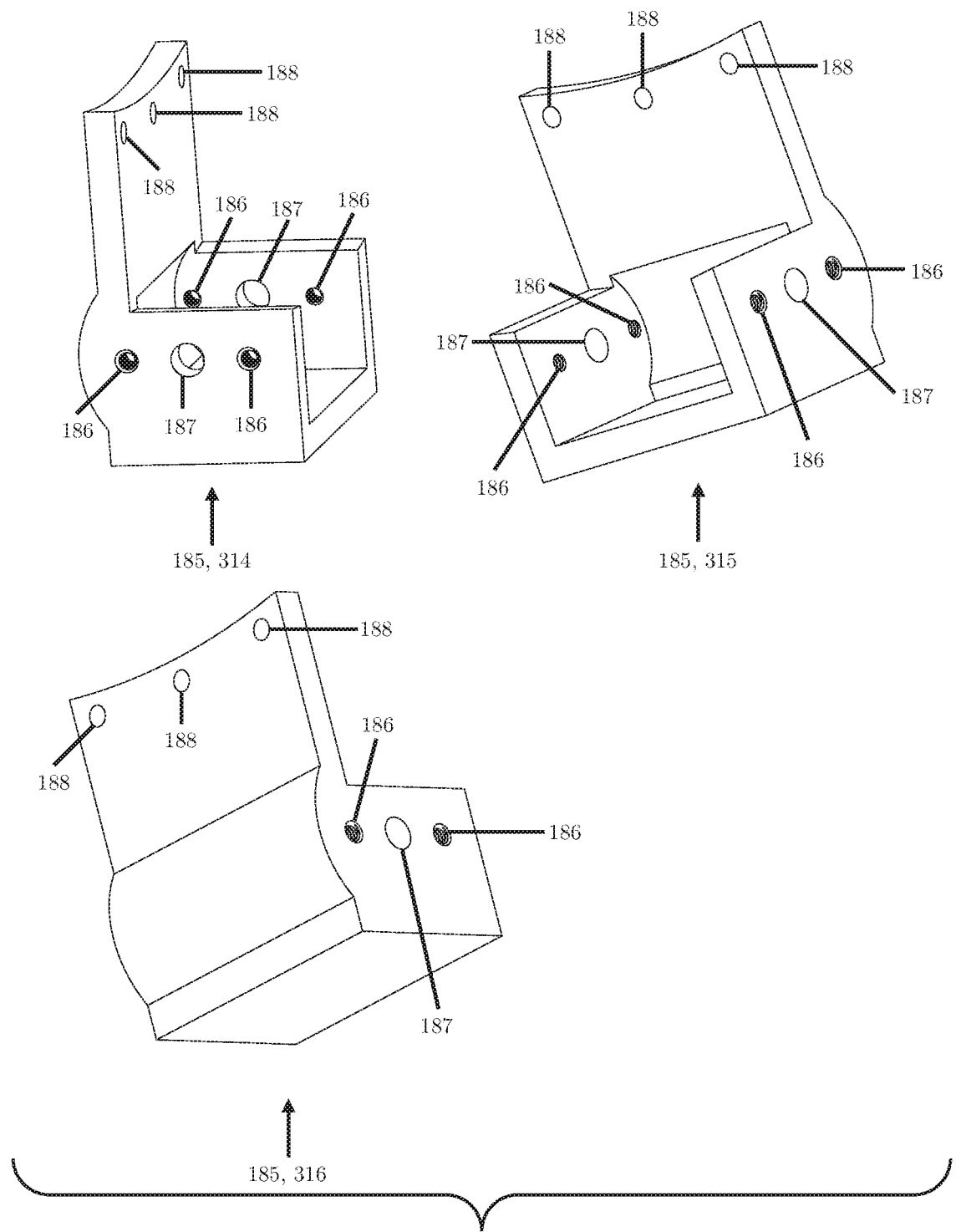
FIG. 101 contains a front right perspective view 314, a rear right perspective view 315, and a front left perspective view 316 of one contemplated embodiment of the flexion-extension gearbox of the present invention and is shown assembled within the flexion-extension assembly in FIG. 70.
Figure 102:
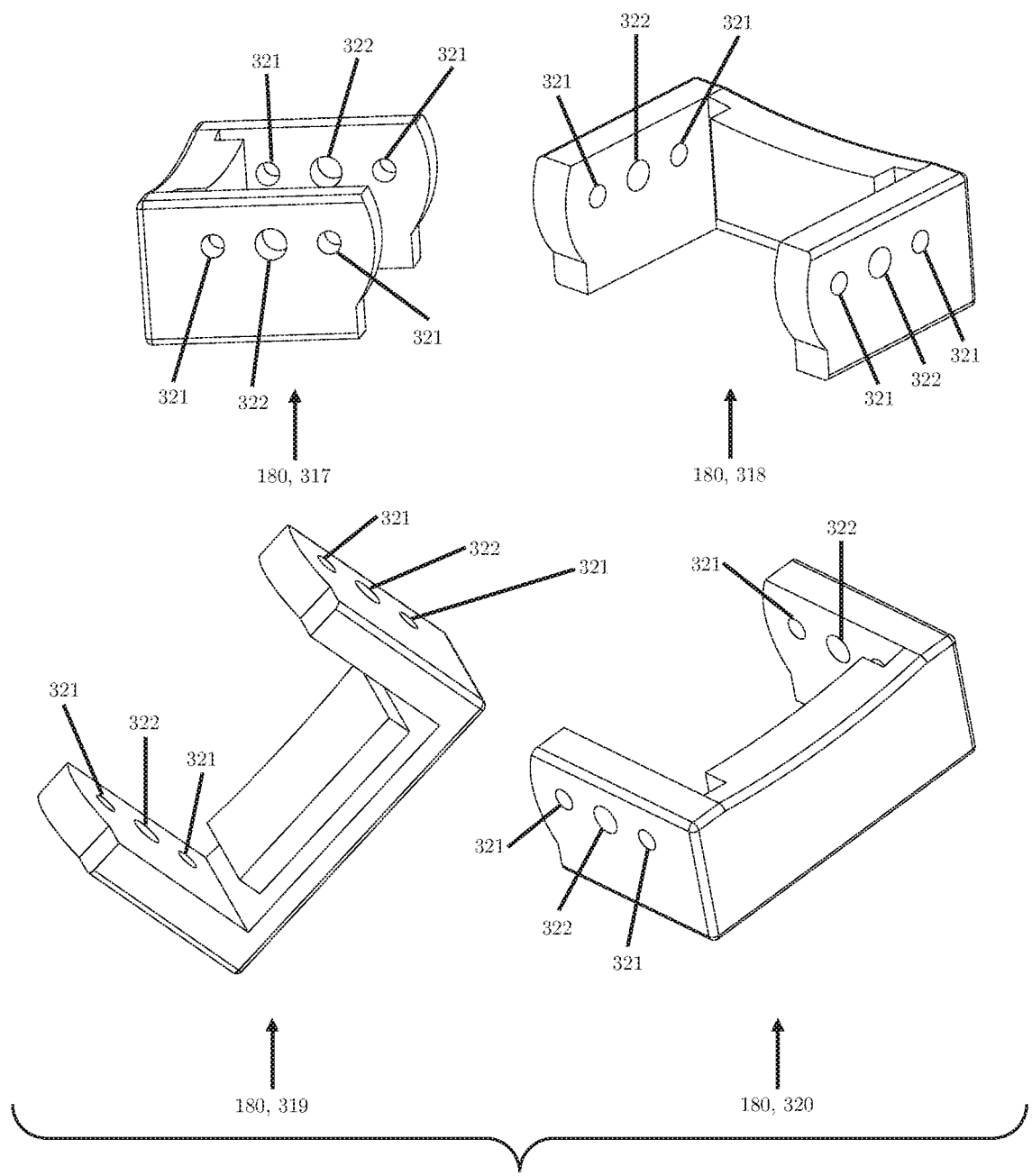
FIG. 102 contains a front right perspective view 317, a rear right perspective view 318, a bottom right perspective view 319, and a rear left perspective view 320 of one contemplated embodiment of the flexion-extension gearbox cover of the present invention and is shown assembled within the flexion-extension assembly in FIG. 69.

In another aspect of orthosis-ROM, a second embodiment of the splint arm assembly 139 is illustrated in FIGS. 96-99. FIG. 100 shows the main hardware used in the assembly 139. The assembly 139 permits the elbow flexion/extension of the wearer and allows the angle of flexion/extension to be locked or the range to be limited. It contains an upper splint arm 272 and a lower splint arm 271. The upper splint arm 272 is slidingly disposed to the rectangular through hole 206 of the rotary motion carriage ring 208. Similarly to the first embodiment of the upper splint arm 15, the basic shape of the second embodiment of the upper splint arm 272 is contemplated to be a rectangular bar. There is contemplated to be one obround slot 274 near the top end of the bar. Near the bottom end there is a circular disk 273 with an arced obround slot 278, a plunger tube through hole 306 situated at a defined radial distance, and a mounting through hole 313 through the center axis. The bar is slid up and down within the rectangular hole 206 for height adjustment and clamped against the inner back wall of the hole 206 using a screw 11 that passes through the obround slot 278 of the splint arm 272 and threads into the threaded mounting hole 251 on the inner back wall. The threads are contemplated to be locked with a threadlocker. As shown in FIG. 84, the screw 11 is preceded by a flat washer 57 and a split lock washer 58 and, when all three are installed, they rest in the mounting hole 215, as shown in FIG. 81. The flat washer 57 helps distribute the pressure from the screw 11 over a larger area on the upper splint arm 272 and the split lock washer 58 puts a preload on the screw 11 that makes it more difficult for it to loosen inadvertently. The mounting hole 215 is contemplated to be sized for a standard M5 flat washer and the flat washer 57, split lock washer 58, and screw 11 are contemplated to be M5, but any size may be used without departing from the scope of the present invention. The height of the upper splint arm within 272 the rectangular hole 206 is selected so that the axis of the elbow is coincident with the axis of the circular disk 273. This ensures that the arm can be flexed at the elbow without hindrance.

Figure 97:
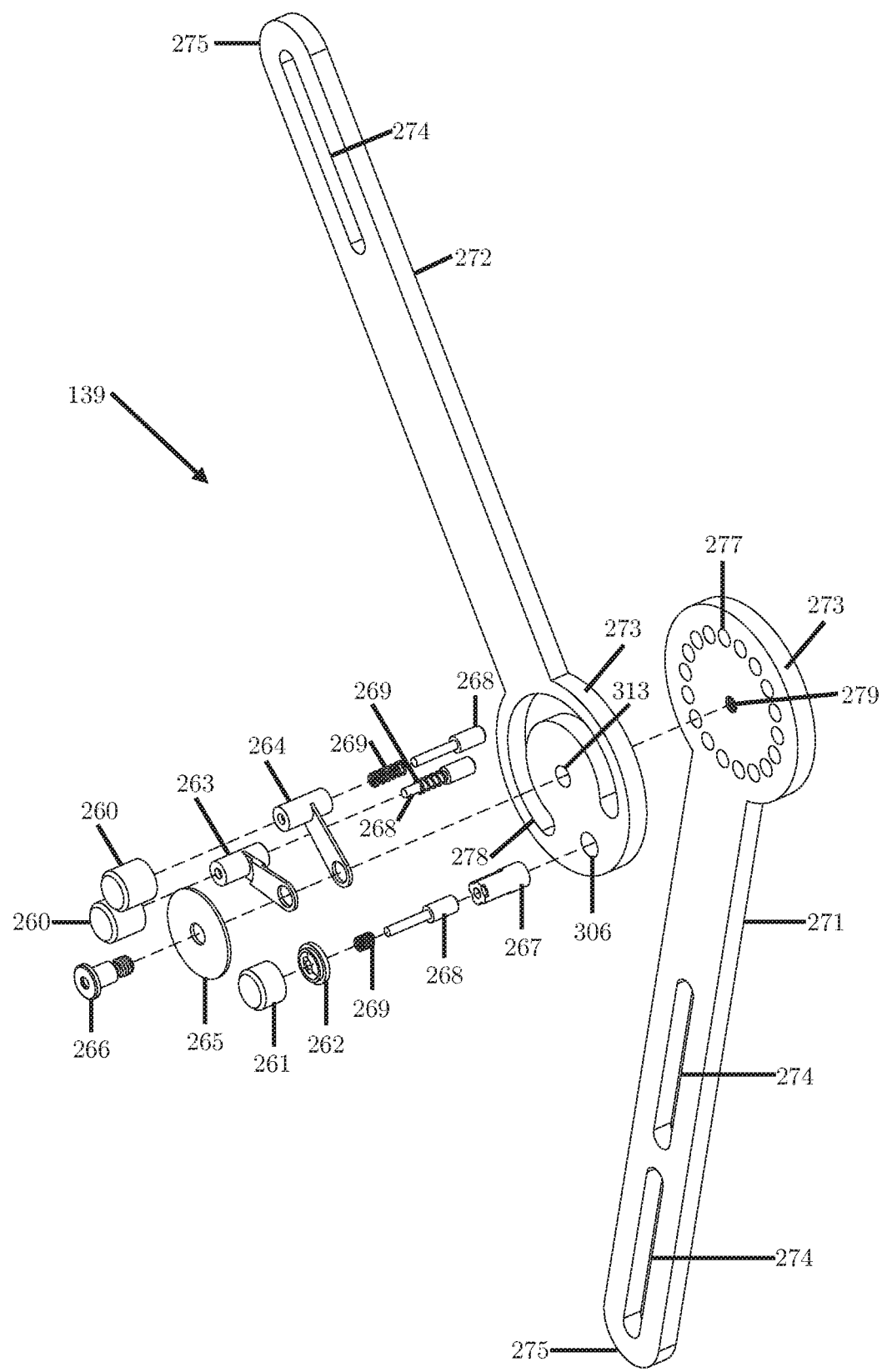
FIG. 97 is an exploded front left perspective view of the embodiment of the splint arm assembly shown in FIG. 96.
Figure 98:
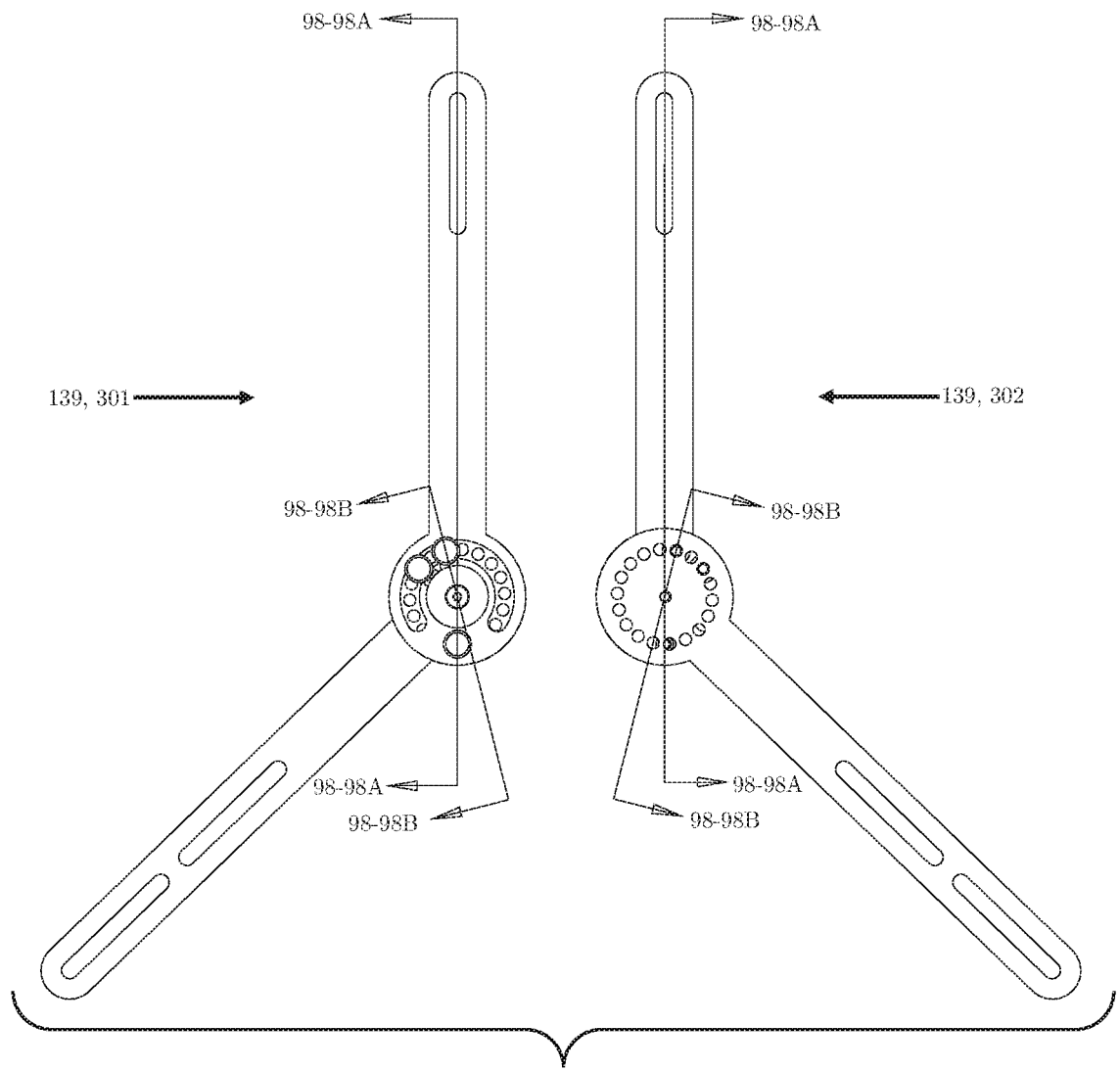
FIG. 98 contains a front view 301 and a back view 302 of the embodiment of the splint arm assembly shown in FIG. 96.

It is contemplated that screwed to the second embodiment of the upper splint arm 15 at the center of the circular disk 273 is a second embodiment of the lower splint arm 271 of the present invention. Similarly to the first embodiment of the lower splint arm 13, the basic shape of the second embodiment of the lower splint arm 271 is contemplated to be a rectangular bar. There are contemplated to be two obround slots 274 near the top end of the bar. Near the bottom end there are a number of equally-circumferentially-spaced through holes 277 at a defined radial distance and a threaded mounting through hole 279 through the center axis. There are two cylindrical retractable spring plungers whose axes are coincident with an axis of one the through holes: there is a flexion selector plunger and an extension selector plunger that allow the angle of elbow flexion or extension, respectively, to be limited. As shown in FIG. 97, the components that comprise the flexion selector plunger are the flexion selector tube housing 263, the tube housing cap 260, the plunger compression spring 269, and the plunger shaft 268. The components that comprise the extension selector plunger are the extension selector tube housing 264, the tube housing cap 260, the plunger compression spring 269, and the plunger shaft 268. The flexion selector plunger and extension selector plunger are identical except for a slight difference in shape between the flexion selector tube housing 263 and extension selector tube housing 264. As shown in FIG. 99, the plunger shaft 268 is slidingly disposed to the inside tube of the extension selector tube housing 264 at one end and a hole in the end of the extension selector tube housing 264 at the other end. At the same end, the plunger shaft 268 is engaged with a hole in the tube housing cap 260 and is contemplated to either be press fit into this hole or affixed with epoxy, glue, solder, a weld, or another appropriate attachment method. The plunger compression spring 269 lies inside the extension selector housing tube 264, is wrapped around the plunger shaft 268, is disposed between a wall on the plunger shaft 268 and a wall on the extension selector tube housing 264, and is always in a compressed condition. Although not shown, the configuration is exactly the same for the flexion selector tube housing 263. In the figure, the nose of the plunger shaft 268 is in an extended position and is protruded into the coincident through hole 277 as far as possible without sticking out of the other side. When the cap 260 is pulled, the nose of each plunger shaft 268 is in the retracted position and sits entirely inside its tube. The plunger shaft 268 cannot be locked in the retracted position for neither the flexion selector plunger nor the extension selector plunger. As shown in FIG. 100, the flexion selector tube housing 263 has a flat portion with a mounting hole 307 and the extension selector tube housing 264 has a flat portion with a mounting hole 308 that are both coincident with the central axis of the circular disks 273. This allows the tube portion of the housings 263, 264 to pivot about the axis to select different through holes 277 and therefore different angles. The upper splint arm 272, lower splint arm 271, housings 263, 264, and a circular indicator disk 265 that has a mounting through hole 309 are clamped together by passing the end of the shoulder screw 266 through all of the mounting holes and threading it into the threaded mounting hole 279 of the lower splint arm 271. The threads are contemplated to be locked together with a threadlocker. The circular indicator disk 309 is contemplated to serve as a surface where a label may be engraved, etched, painted, adhered, or the like. The screwed joint is contemplated to be tight enough for the surfaces of each splint arm circular disk 273 to be flush against one another yet loose or lubricated enough for the joint to serve as an axis about which the upper and lower splint arms 272, 271 can be rotated with respect to each other.

The flexion and extension plungers serve the same purpose as the screws 84 used in the first embodiment of the present invention for controlling the flexion-extension range of motion. It is contemplated that, with the plunger tube housings 263, 264 installed and resting within the arced obround slot 274 of the upper splint arm 272, that by extending the nose of each plunger 268 into one of the through holes 277 of the lower splint arm 271 that the flexion-extension range of motion can either be limited or locked. The plunger tube housing(s) 263, 264 hitting against the end(s) of the arced obround slot 278 prevent the splint arms 272, 271 from rotating with respect to each other. More specifically, the flexion selector tube housing 263 limits how much the elbow can flex and the extension selector tube housing 264 limits how much the elbow can extend.

In addition to the flexion and extension retractable spring plungers, a third cylindrical retractable spring plunger—the hinge lock plunger—is affixed to the splint arm assembly 139. As shown in FIG. 97, the components that comprise the hinge lock plunger are the hinge lock plunger tube housing 267, the plunger shaft 268, the plunger compression spring 269, the hinge lock cap retention disk 262, and the hinge lock cap 261. As shown in FIG. 99, the end of the hinge lock plunger tube housing is installed in the plunger tube through hole 306 of the upper splint arm 272. It is contemplated to either be press fit in or slid in and affixed with epoxy, glue, solder, a weld, or another appropriate attachment method. It allows the splint arms 271, 272 to quickly be locked at any angle by extending the nose of the plunger shaft 268 into one of the through holes 277 of the lower splint arm 271. As shown in FIG. 99, the plunger shaft 268 is slidingly disposed to the inside tube of the hinge lock plunger tube housing 267 at one end and a hole in the end of the housing 267 at the other end. At the same end, the plunger shaft 268 is engaged with a hole in the cap 261 and is contemplated to either be press fit into this hole or affixed with epoxy, glue, solder, a weld, or another appropriate attachment method. The plunger spring 269 lies inside the hinge lock plunger tube housing 267, is wrapped around the plunger shaft 268, and is disposed between a wall on the plunger shaft 268 and a wall on the housing 267. The hinge lock cap retention disk 262 is engaged with the hole on the bottom of the hinge lock cap 261 and is contemplated to either be press fit into this hole or affixed with epoxy, glue, solder, a weld, or another appropriate attachment method. In the figure, the nose of the plunger shaft 268 sits entirely inside its tube and is locked in a retracted position through the engagement of the tabs 310 on the hinge lock retention disk 262 with the retraction groove 312 on the plunger tube housing 267. When the cap 261 is pulled so that the retention disk 262 is displaced axially beyond the top of the plunger tube housing 267 and is rotated 90°, it can be released such that the tabs 310 engage the extension groove 312 on the plunger tube housing 267 and the nose of the plunger shaft 268, if coincident with a through hole 277 on the lower splint arm circular disk 273, engages that through hole 277. Doing this locks the elbow at the angle of flexion/extension that corresponds to the through hole 277 and does so within the range of motion limited by the flexion retractable spring plunger and the extension retractable spring plunger. Doing the reverse locks the plunger shaft 268 back in a retracted position and lets the elbow flex and extend within its limited range. The capacity to limit or lock the range of motion potentially serves to allow the wearer to complete certain resistance exercises, to achieve certain stretches, or to achieve certain positions of comfort, among other uses.

While the shoulder screw 11 is used to join the upper splint arm 272 and lower splint arm 271 and to act as a bearing, other fastening methods that permit the two arms to rotate with respect to one another may be used without departing from the scope of the present invention. Such methods include but are not limited to a rivet, a nut and bolt, or a press-fitted shaft. Additionally, a bearing, such as a roller bearing, may be used on each of the circular disks 273 without departing from the scope of the present invention.

While a retractable spring plunger system is used on the splint arm assembly 139 to allow elbow flexion/extension to be limited or locked, a worm gear, worm, and clutch system, similar to the ones used for shoulder flexion/extension, shoulder adduction/abduction, and shoulder internal/external, rotation may be used to allow the splint arms to be locked at the angle rotated to and switched back and forth between a state of being locked and a state of being free to move, without departing from the scope of the present invention. Such a system would be implemented by having a worm gear affixed to one of the arms. The worm gear would be coupled with a worm that is attached to a knob. Rotating the knob would rotate the splint arms toward or away from each other. There would then be a user operated clutch that would engage or disengage the rotation of the worm gear from the rotation of the splint arms with respect to each other. Such a system would allow for progressive flexion or extension and wouldn't be limited to discrete angles.

In another aspect of orthosis-ROM, it is contemplated that a second embodiment of the supination-pronation gearbox assembly of the present invention 140, illustrated in FIGS. 130-131, is slidingly disposed to the end of the second embodiment of lower splint arm 271. The main components are the supination-pronation gearbox 475, the supination-pronation worm 476, and the supination-pronation knob 477. The end of the lower splint arm 271 with the obround slot 274 slides into a rectangular hole 480 on the supination-pronation gearbox 475 in a similar manner to that of the upper splint arm 272 with the rotary motion carriage ring 208. The capacity to slide the gearbox assembly 140 back and forth allows the position of the wrist cuff along the wrist and forearm to be adjusted. When the desired position is reached, the gearbox assembly 140 is clamped in place with a screw 11 that passes through the obround slot 274 of the lower splint arm 271 and threads into the threaded, mounting through hole 481. As shown in FIG. 131, the screw 11 is preceded by a flat washer 57 and a split lock washer 58 and, when all three are installed, they rest in the mounting hole 483 of the gearbox 475. The flat washer 57 helps distribute the pressure from the screw 11 over a larger area on the lower splint arm 271 and the split lock washer 58 puts a preload on the screw 11 that makes it more difficult for it to loosen inadvertently. The mounting hole 483 is contemplated to be sized for a standard M5 flat washer, the threaded mounting hole 481 is contemplated to use M5 threads, and the flat washer 57, split lock washer 58, and screw 11 are contemplated to be M5, but any sizes may be used without departing from the scope of the present invention.

In another aspect of the supination-pronation gearbox assembly 140, the supination-pronation gearbox 475 has an open face that's arced. When the gearbox assembly 140 is assembled to the lower splint arm 271, the axis of the arc is coincident with the axis of the forearm.

Figure 116:
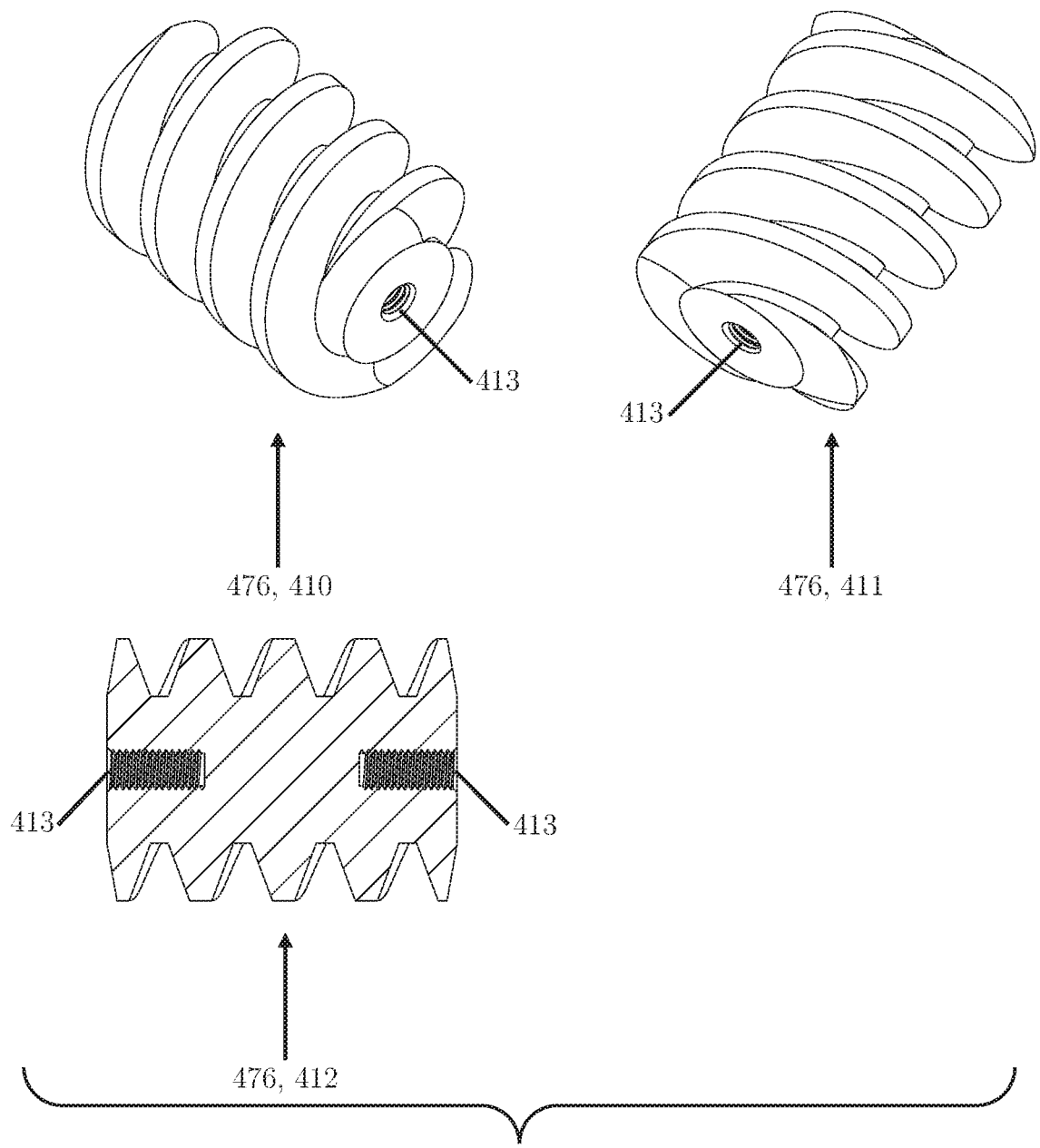
FIG. 116 contains a front right perspective view 410, a rear right perspective view 411, and an axial cross section view 412 of one contemplated embodiment of the supination-pronation worm of the present invention and is shown assembled to the supination-pronation gearbox in FIG. 130.
Figure 117:
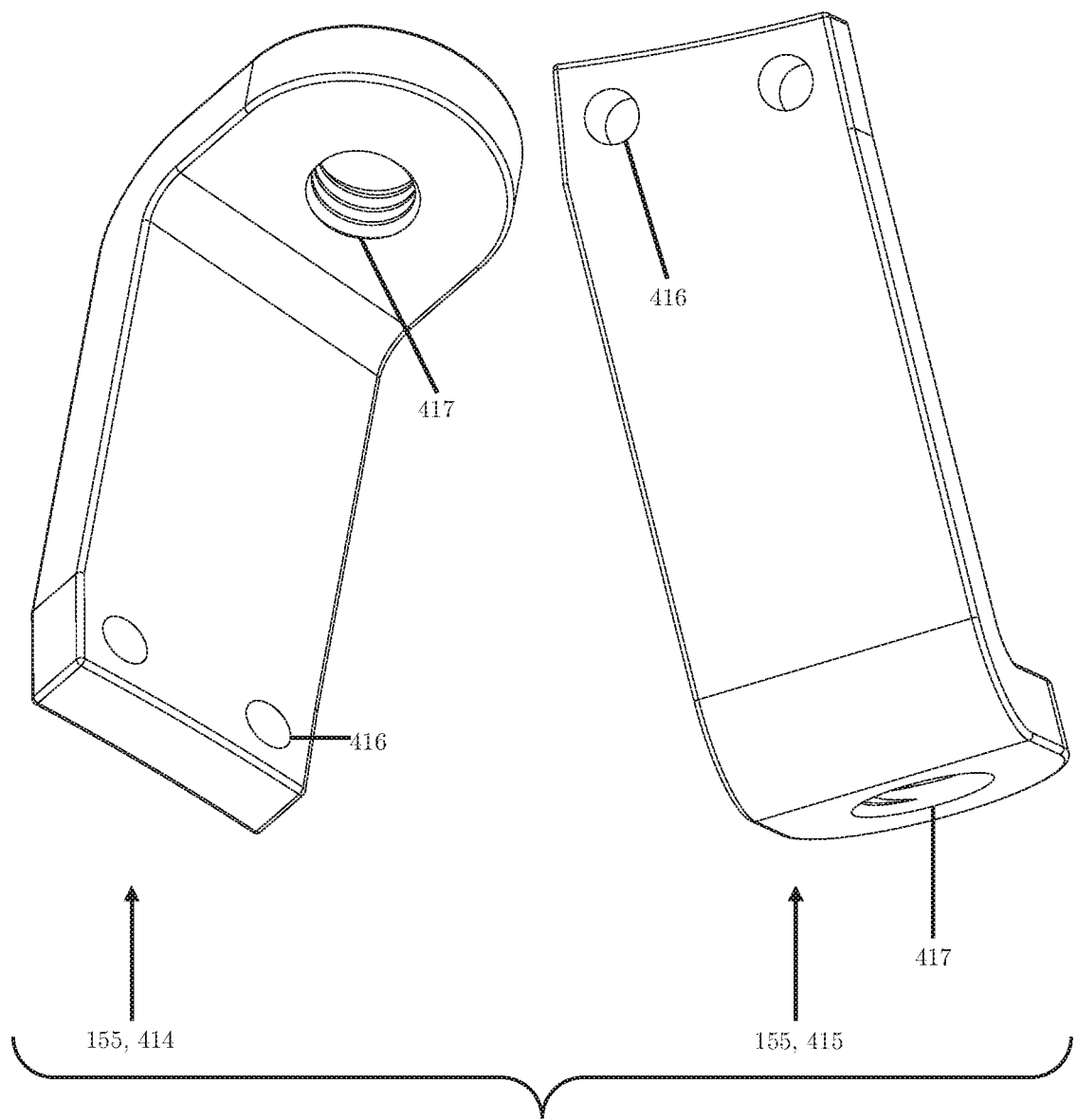
FIG. 117 contains a rear left perspective view 414 and a front left perspective view 415 of one contemplated embodiment of the front flexion-extension bracket of the present invention and is shown assembled within the flexion-extension assembly in FIG. 69.
Figure 118:
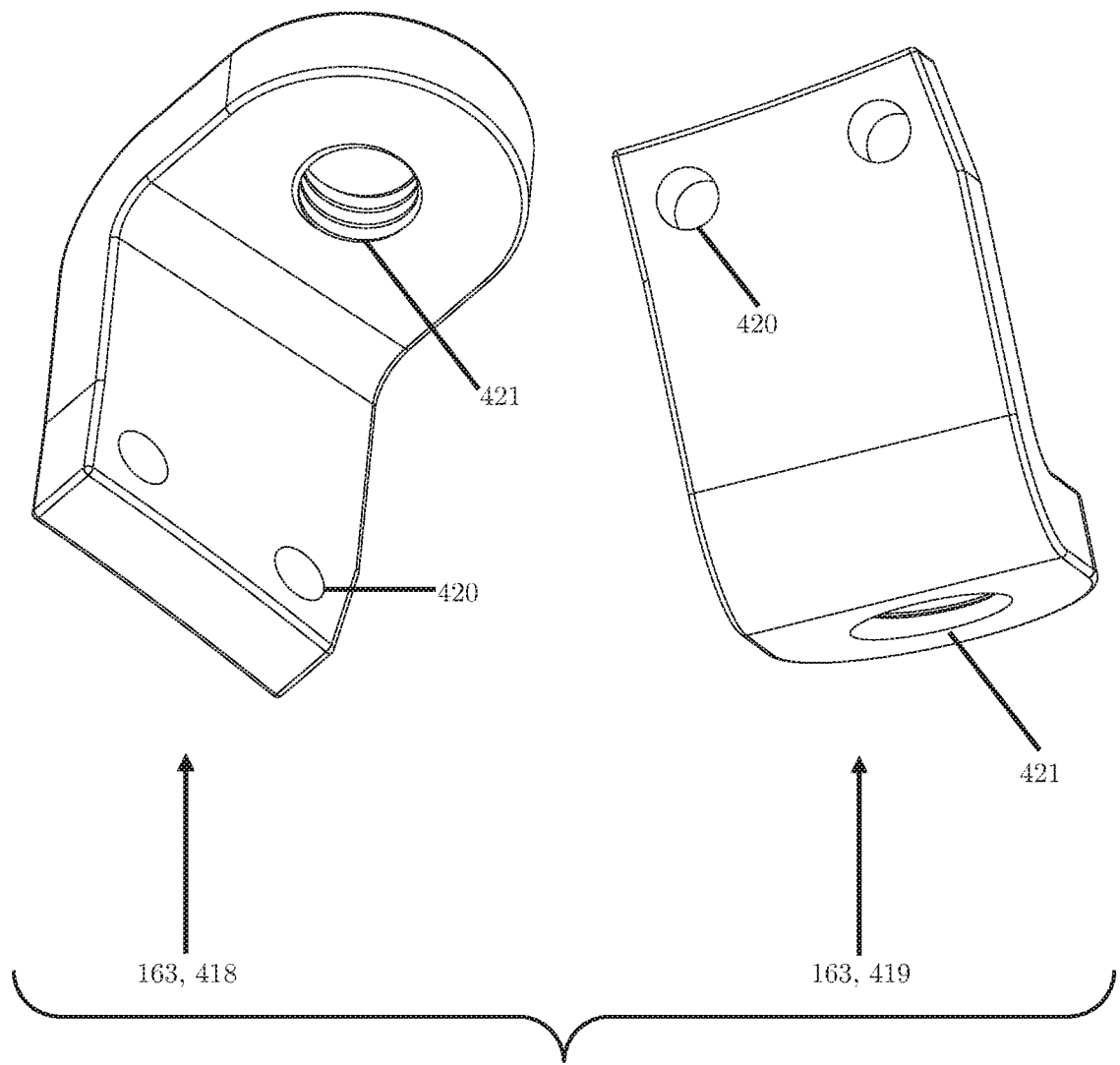
FIG. 118 contains a rear left perspective view 418 and a front left, perspective view 419 of one contemplated embodiment of the rear flexion-extension bracket of the present invention and is shown assembled within the flexion-extension assembly in FIG. 70.

The supination-pronation worm 476, illustrated in FIG. 116, is mounted on screws between the side walls of the gearbox 475. Each end of the worm 476 has a blind, threaded mounting hole 413. On one side, the end of a rounded head screw 201 is passed through the shaft hole 482 on the gearbox 475 and threaded into the threaded mounting hole 413 on the worm 476. On the other side, the end of a hex head screw 147 is passed through the shaft hole 482 on the gearbox 475 and threaded into a threaded mounting hole 413 on the worm 476. The threads are contemplated to be locked with threadlocker. It is contemplated that the shaft, holes 482 are sized for an M3 screw and that the screws 201, 147 are M3, but any size nay be used without departing from the scope of the present invention. The head of the hex screw 147 is embedded in the supination-pronation rotation knob 477. It is noted that other possible techniques for implementing the shaft of the worm 476 may be used without departing from the scope of the present invention. Such techniques include but are not limited to installation of the worm 476 on a milled shaft with a key or setscrew, or manufacturing the worm 476 and shaft together as one piece.

The worm 476 is coupled with a worm gear that is assembled to the wrist cuff assembly. It is contemplated that the worm-gear assembly is self-locking so that the worm 476 cannot be backdriven by the gear and, therefore, so that the angle selected with the knob 477 will automatically be held as the knob 477 is being rotated. The conditions under which self-locking occurs were discussed previously in connection with inequality (1). Being able to switch forearm supination/pronation between a state of being locked and a state of being free to move allows certain resistance exercises or adaptive movements to be performed.

In another aspect of orthosis-ROM, it is contemplated that a third embodiment of the wrist cuff assembly—the ratchet lock wrist cuff assembly 141—is clamped to the wrist and lower forearm. Illustrated in FIGS. 133-143, the main components of the assembly are the upper wrist cuff 496, lower wrist cuff 494, upper wrist cuff pad 497, lower wrist cuff pad 495, front spring ring 493, rear spring ring 501, worm gear ring 506, pawl 529, ratchet lever 500, thumbscrew clutch 503, and wrist cuff rails 525.

The upper and lower wrist cuffs 496, 494 are padded and clamp together using a ratchet lock system in lieu of the straps 29 used in the first embodiment of the wrist cuff assembly 28 and the thumbscrews 1 used in the second embodiment of the wrist cuff assembly 141. It is contemplated that the upper and lower cuffs 496, 494 are custom molded to conform to the shape of the wrist and forearm of a particular user or that the upper and lower cuffs 496, 494 are molded to fit the general shape of a forearm and that the padding is then sufficiently thick to make up for any discrepancy in shape when the cuffs are clamped together. The upper wrist cuff pad 497 and lower wrist cuff pad 495 are contemplated to be molded to shape of the forearm on the side that contacts the forearm and to the inside surface of the upper wrist cuff 496 and lower wrist cuff 494, respectively.

The upper and lower pads 497, 495 are contemplated to be about $3/16$ inch thick but may be any thickness without departing from the scope of the present invention. Additionally, they are contemplated to be made of foam, cloth, or any comparable material that satisfies this function but any material may be used without departing from the scope of the present invention. They are contemplated to attach to their respective cuffs using an adhesive, such as a high-strength spray adhesive, an epoxy, contact cement, glue, or tape, but any suitable adhesive may be used without departing from the scope of the present invention.

The lower wrist cuff 494 is illustrated in FIGS. 147-149. A ratchet tower 499 protrudes, from each corner of the lower wrist cuff 494, in the direction of clamping and has the form of a rigid length of cable tie. The upper wrist cuff 496 is illustrated in FIGS. 144-146. There is a slot 537 at each corner of the upper wrist cuff 496 that corresponds to and engages with each ratchet tower 499 such that the ratchet tower 499 is slidingly engaged with the slot 537. This is shown most clearly in FIG. 138. Additionally, there is a pawl 529 mounted on a rounded head screw 502 that acts as a hinge. At each corner, the end of the screw 502 is passed through the mounting hole on upper screw post 540, through the mounting hole 572 on the pawl 529, and threaded into the threaded, mounting through hole on the other post 539. When the pawl 529 is rotated to a certain angle, its tooth 574 engages a tooth on the corresponding ratchet tower 499, and when it is rotated in the opposite direction there is no engagement. FIG. 143 shows the front two pawls 529 in the disengaged position. A ball-nose spring plunger 509 is installed in a plunger hole 534 on the upper wrist cuff 496 and is contemplated to either be press fit into this hole or affixed with epoxy, glue, solder, a weld, or another appropriate attachment method. The ball 528 of the ball-nose spring plunger 509 pushes on the back of the pawl 529 to keep it engaged with ratchet tower teeth 499. A lever 500, illustrated in FIG. 153, mounted on screws 502 that act a hinge, pushes backwards on the front of the pawl 529, against the force of the ball-nose spring plunger 509, to disengage it from the ratchet tower 499 teeth. On each side of the lever 499, the end of a rounded head screw 502 is passed through the mounting hole on the lower screw post 532 and threaded into the threaded, mounting through hole on the other low screw post 541. The lever 500 pushes on the pawl 529 through the engagement of a pair of posts 579 affixed to the lever 500 with a corresponding pair of tabs 573 affixed to the pawl 529. When the lever 500 is shifted towards the ratchet tower 499—into a position of engagement—the ratchet tower 499 and pawl 529 act as a normal ratchet-pawl mechanism. The lever 500 is locked in the engaged or disengaged position using ball-nose spring plungers 507 and spherical index sector cavities 580 on the lever FIG. 153 that make it so that a force is required to shift the lever 500, which depresses the balls of the plunger 507, from one position to the next and thus to switch the balls of the plungers 507 from engaging one pair of index sectors 580 to engaging the next pair of index sectors 580. Thus when all four levers 500 are in the disengaged position, the upper wrist cuff 496 can slide up and down freely along the ratchet towers 499 for removal or adjustment, and when the levers 500 are engaged, the upper wrist cuff 496 is able to slide down the ratchet towers 499 towards the lower cuff 494 but is not able to slide in the opposite direction, which is what provides the clamping force. A pair of handles 498 on the upper wrist cuff 496 provide a location to grab that facilitates its installation and removal. The amount of pressure exerted by the assembly 141 on the wrist and forearm at the four corners is adjusted by squeezing the upper and lower wrist cuff 496, 494 together enough to cause a set of lower ratchet teeth to be selected. They are squeezed together until the desired level of comfort is reached. When the assembly 141 is sufficiently clamped, rotating the assembly 141 exerts a torque on the forearm that causes it to rotate and vice versa.

The mounting hole and thread sizes for the upper screw posts 540, 539 and lower screw posts 532, 541 are contemplated to be size 0-80 and the rounded head screw 502 is contemplated to be size 0-80, but any size may be used without departing from the scope of the present invention. The ball-nose spring plungers 507 for the lever 500 and corresponding mounting holes 538 are contemplated to have a 0.13 inch diameter and the ball-nose spring plungers 509 for the pawl 529 and corresponding mounting holes 534 are contemplated to have a 0.16 inch diameter, but any diameter may be used without departing from the scope of the present invention.

It is contemplated that between the front and rear ratchet towers 499 of the lower wrist cuff 494, illustrated in FIGS. 147-149, there is a "circumscribed" cylinder, that shares the same axis as the forearm, whose interior stops when it meets the sidewalls of the lower wrist cuff 494 and leaves free the space that the forearm needs to be lowered into to rest in the cuff. At four axial positions along the outer surface of the cylinder a slot is formed by stepping the cylinder diameter down for a certain axial distance that is equal for the four positions. The outer cylindrical surface of each slot has a dovetail 548 wrapped around it. The front and rearmost slots have an insert—a wrist cuff rail—that completes the "circumscribed" cylinder of the lower wrist cuff 494 and has a dovetail groove on the inner surface that corresponds to and engages the dovetail 548 of the slot. The outer cylindrical surface of front and rear wrist cuff rails has a round rail wrapped around it. Additionally, the front and rear wrist cuff rails are each divided into three equal angular segments.

The middle two slots of the lower wrist cuff 494 also have wrist cuff rails that complete the "circumscribed" cylinder. They are formed identically to the front and rear wrist cuff rails except that a dovetail is wrapped around the outer cylindrical surface instead of a round rail. They are also divided into three equal angular segments.

FIG. 154 shows an exploded front top perspective view 581 and an exploded front bottom perspective view 582 of the wrist cuff rails 525. As the figure illustrates, the front wrist cuff rails 522, 523, 524 and rear wrist cuff rails 513, 514, 515 have the round rail 586 wrapped around them and blind, threaded mounting holes 583, whose axes intersect the axis of the are of the dovetail slot. 585 along the inner surface of the slot 585. The middle wrist cuff rails 519, 520, 521, 516, 517, 518 have the dovetail 584 wrapped around them and, similarly to the front and rear wrist cuff rails 522, 523, 524, 513, 514, 515, have blind, threaded mounting holes 583 along the dovetail slot 585.

FIGS. 140, 142 show the rails assembled to the lower wrist cuff 494. They are assembled after the front spring ring 493, rear spring ring 501, and worm gear ring 506 are in place. The lower wrist cuff 494 has a set of mounting through holes 549 that cut through the "circumscribed" cylinder and whose axes intersect the axis of the cylinder. Each hole 549 cuts through the dovetail 548 on the bottom of the lower wrist, cuff 494 and the dovetail 548 starts and restarts at the extents of each hole 549. There is a countersink 552 for each hole 549 along the inner surface of the lower wrist cuff 494. The angular positions of the holes 549 correspond to the positions that the wrist cuff rails 525 are installed in. After each wrist cuff rail 525 is slid into place, with its threaded mounting holes 583 aligned with the corresponding mounting holes 532 on the lower wrist cuff 494, it is installed by passing the end of a flathead screw 87 through the mounting hole 532 and threading it into the corresponding threaded mounting hole 583. Once installed, the head of each flathead screw 87 rests in its corresponding countersink 552. Each mounting hole 532 is contemplated to be sized for an M2 screw and each flathead screw 87 is contemplated to be M2, but any size may be used without departing from the scope of the present invention.

The front and rear spring rings 493, 501, illustrated in FIG. 150, have the basic shape of a cylindrical shell sector whose included angle is slightly less than the smallest included angle of the lower wrist cuff's 494 "circumscribed" cylinder along its axial length. As shown in FIG. 138, this ensures that the ends do not go pass those of the "circumscribed" cylinder. The inner cylindrical surface of each ring 493, 501 has a round rail slot 563 wrapped around its perimeter that corresponds to the round rails 586 of the front and rear wrist cuff rails 522, 523, 524, 513, 514, 515. The outer cylindrical surface of each rail 493, 501 has a dovetail slot 560 wrapped around its perimeter that corresponds to the dovetails 478 of the second embodiment of the supination-pronation gearbox assembly 140.

The worm gear ring 506, illustrated in FIG. 151, has the basic shape of a cylindrical shell sector whose included angle is equal to that of the spring rings 493, 501. The inner cylindrical surface of the worm gear ring has dovetail slots 569 wrapped around its perimeter that correspond to the dovetails 584 of the middle two wrist cuff rails 519, 520, 521, 516, 517, 518. The outer cylindrical surface of the worm gear ring 506 has worm gear teeth 566 cut into it that mesh with the worm 476 teeth of the second embodiment of the supination-pronation gearbox assembly 140. The inner cylindrical surfaces of the springs rings 493, 501, are slidingly disposed to the outer cylindrical surface of the "circumscribed" cylinder, and their round rail slots 563 are engaged with and slidingly disposed to the corresponding round rails 586 of the front and rear wrist cuff rails 522, 523, 524, 513, 514, 515. The inner cylindrical surface of the worm gear ring 506 is slidingly disposed to the outer cylindrical surface of the "circumscribed" cylinder and its dovetail slots 569 are engaged with and slidingly disposed to the corresponding dovetails 584 of the middle two wrist cuff rails 519, 520, 521, 516, 517, 518. The spring rings 493, 501 and worm gear ring 506 rotate about the "circumscribed" cylinder with or without lubrication from a grease or oil.

The included angle of the sector cut from the spring rings 493, 501 and the worm gear ring 506 is about 60° but any included angle may be used without departing from the scope of the present invention. Because this angle and the included angle cut from the "circumscribed" cylinder (cylindrical sector), for the embodiment being presented, is less than 180°, the spring rings 493, 501 and worm gear ring 506 cannot be mounted by rotating them onto the wrist cuff rails 525. Instead the spring rings 493, 501 and worm gear ring 506 must first be slid in place axially onto the "circumscribed" cylinder. Then, each of the wrist cuff rails 525 is slid in place and screwed down. If each set of three rails 525, for the four axial positions, was not split into three equal angular pieces then it would be impossible to slide them in place due the include angle of their are being greater than included angle of the sector missing from the spring rings 493, 501 and worm gear ring 506. Because the included angle of the worm gear ring 506 is greater than 180°, which is the approximate forearm supination/pronation range of the average human being (before there is a risk of discomfort or injury), it is possible to stretch the rotation of the forearm somewhat past the positions of full pronation and full supination. This is particularly important when the arm is hanging and the range for pronation is somewhat greater than when the elbow is propped up on a flat surface.

For added stability, a square rail 526 is wrapped around each annular, sectorial face of the worm gear ring 506 and each spring ring 493, 501 has a corresponding rectangular slot 527 cut into each annular, sectorial face. When the spring rings 493, 501 and worm gear ring 506 are installed, the square rail 526 and square slot 527 are slidingly disposed to each other. With the spring rings 493, 501 assembled, a spring 510 is inserted into the round ring slots 563 at each of the four openings 559 and is cupped by the arced groove 587 of the adjacent wrist cuff rail. Each opening 559 is threaded and a cone-point set screw 508 is threaded in. The opening 559 is contemplated to use M6 threads and the cone-point set screw 508 is contemplated to be M6, but any size may be used without departing from the scope of the present invention. The set screw 508 keeps a preload on the spring 510, and a length of spring 510 is used, such that the springs 510 are always compressed.

On one side of the ratchet lock wrist cuff assembly 141 axis, there is a threaded post on each side of each surface where the spring rings 493, 501 and worm gear ring 506 slide against each other. A screw post 561 is affixed to the front spring ring 493 and is adjacent to a screw post 567 affixed to one end of the worm gear ring 506. A screw post 561 is affixed to the rear spring ring 501 and is adjacent to a screw post 567 affixed to the opposite end of the worm gear ring 506. Each pair of adjacent posts 561 has a hole running through it that is tapped so that the thread continues from one post to the next. The thumbscrew clutch 503 is a thumbscrew that threads into each pair of adjacent posts simultaneously. To engage them, the end of the thumbscrew 503 is threaded into the threaded hole 562 on the front spring ring 493 screw post 561 and then into the adjacent threaded hole 568 on the worm gear ring 506 screw post 567. Then, the end of another thumbscrew 503 is threaded into the threaded hole 562 on the rear spring ring 501 screw post 561 and threaded into the adjacent threaded hole 568 on the worm gear ring 506 screw post 567. The dovetails 478 on the gearbox 475 engage with the dovetail slots 560 on the spring rings 493, 501 and the worm 476 of the gearbox 475 meshes with the worm gear teeth of the worm gear ring 506.

When both thumbscrews 503 are threaded through the adjacent pairs of posts 561, 567 the clutches are engaged and the rotation of the spring rings 493, 501 and the worm gear ring 506 is coupled. Subsequently, the rotation of the worm 476, in either direction, rotates the wrist cuff assembly 141 and therefore the forearm. Because the worm-gear assembly is self-locking, as the spring rings 493, 501 rotate about the "circumscribed" cylinder, the springs 510 on one side of the forearm's axis become more compressed and the springs 510 on the opposite side become less compressed. The springs 510 that are less compressed remain compressed even when the rotation of the spring rings 493, 501 about the "circumscribed cylinder" has reached its maximum. The presence of the springs 510 allows the wearer some flexibility while movements are being performed, which makes the wrist cuff assembly 141 feel more like a real wrist joint, which is not entirely rigid, when it's being worn. It absorbs shock and takes away some of the stiffness that might cause discomfort while certain exercises or activities are being performed. When the thumbscrews 503 are unthreaded from the posts 561, 567 on the worm gear ring 506, the clutches are disengaged and the rotation of the spring rings 493, 501 and the worm gear ring is separate 506. Since the worm-gear assembly is self-locking, the wearer is able to rotate the forearm, and hence wrist cuff assembly. The worm gear ring 506 stays fixed and the spring rings 493, 501, along with the remainder of the wrist, cuff assembly 141, rotate about the worm gear ring 506 via the dovetails 584 and square rails 526.

The worm gear 506 to worm 476 ratio is contemplated to be approximately 22.5, but any ratio may be used without departing from the scope of the present invention. A ratio of 22.5 means that it would take 11.25 (half of 22.5) turns of the supination-pronation knob 476 to rotate the forearm from a position of full supination to full pronation and vice versa. It is noted that the ideal ratio is one in which it doesn't take an excessive number of revolutions to get from a position of full supination to one of full pronation. Additionally, a double-enveloping, or globoid, worm gear and worm pair may be used without departing from the scope of the present invention.

It is contemplated that any and all components of the orthosis of the present invention that are disposed to rotate slidingly against another surface may be configured to use some type of bearing, such as a rolling-contact bearing, instead. It is also contemplated that rails that are used to implement rotation, or any kind of motion, such as dovetails or round rails, may have any cross-sectional profile without, departing from the scope of the present invention.

While dog clutch style clutches were used throughout orthosis-ROM, any style of clutches that provide the same functionality may be used without departing from the scope of the present invention. This may be, for example, a positive clutch or a friction clutch that allows engagement at any point of rotation, without having to line up a set of teeth. The clutches may implement different techniques for shifting them and may also incorporate techniques for locking them, without departing from the scope of the present invention.

It is contemplated that in another embodiment of the wrist cuff assembly 141, an axial length along the upper and lower wrist cuffs 496, 494 instead of being rigid, is made of a semi-flexible material, such as a medium durometer urethane, to allow the wrist a small amount of flexion or extension. The geometry of the axial length may contribute to its flexibility. It may have accordion like ridges in it, for example, that allow it to flex like a bellows boot. The purpose of this would be to make the wrist cuffs 496, 494 less stiff and absorb some of the shock placed on the wrist when loads are being handled with the hands.

Although some material suggestions were given for the components that comprise the orthosis of the present invention, there are several materials that could satisfactorily allow the orthosis to fulfill its intended purpose. Any and all materials may therefore be used for any of the components of the orthosis without departing from the scope of the invention. Some possibilities include but are not limited to metals, composites, plastics, polymers, ceramics, rubbers, urethanes, epoxies, and silicones.

Orthosis-ROM provides a means for whole-arm control and is essentially an exoskeleton. It is therefore contemplated that it could be used as a skeleton to which different robotic elements, such as motors, linear actuators, hydraulics, and pneumatics, could be applied to make it a powered exoskeleton. This would have particular use in creating a myoelectric version to help users with complete arm paralysis. It may also have use in military applications or video came control systems.

From the discussions in the previous paragraphs, it is understood that the orthosis of the present invention has a modular design. This means that different combinations of the functionalities described may be implemented in the orthosis without departing from the scope of the invention. For example, with nothing else being changed, the flexion-extension assembly 137 of orthosis-ROM need not have a clutch and a worm-gear system to control flexion or extension. It may simply have an axle 175 that permits flexion or extension by allowing the wheel 174, connected to the shoulder sleeve assembly 138, to rotate on it. As another example, the shoulder sleeve assembly 138 might not have an internal-external rotation clutch 207 and may simply be configured such that internal/external rotation is always locked at an angle with the worm-gear system. In other words, it would not be possible to switch internal/external rotation to a state in which it is free to move. Any substitutions similar to the ones in the examples given could be made, in any combination, for the degrees of freedom that are controllable by orthosis-ROM without departing from the scope of the present invention.

In addition to the orthosis of the present invention being modular, it is understood that the angular positions of each degree of freedom may be permanently fixed and nonadjustable. For example, with orthosis-ROM, the rotary motion carriage ring 208 and shoulder sleeve 203 may form one body, meaning that the angle of internal or external rotation is fixed. The same might be accomplished, for example, by the upper splint arm 272 being affixed directly to the shoulder sleeve 203 and forming one body. The remaining degrees of freedom, if included in a particular build of the orthosis, may be any combination of fixed, free, adjustable, and lockable as previously described. Additionally, with orthosis-ROM, the rotary motion carriage ring 208 and upper splint arm 272 may be combined into one body, meaning that the position of the axis of the circular disk 273 is nonadjustable. The lower splint arm 271 and the supination-pronation gearbox 475 may similarly be combined to form one body without departing from the scope of the present invention.

When the axes supported by the orthosis of the present invention are in a state of being free to move, the corresponding bodies may be adapted to resist their respective rotations without departing from the scope of the present invention. Such adaptations include, but are not limited to, the use of oil, hydraulic fluid, weights, friction, friction clamps, setscrews, and springs to provide that resistance. For example, the rotary motion carriage ring 208 of orthosis-ROM may be adapted to use one or more toroidal springs disposed between the rotary motion carriage ring 208 and the shoulder sleeve 203 such that internally or externally rotating the arm becomes progressively more difficult. In this case, the springs could be used as resistance to train the muscles or to force the linear motion carriage ring 208, and hence the arm, to rest at an equilibrium angle of internal or external rotation.

While the embodiment of orthosis-ROM previously described was configured for a user with one effected arm, the orthosis could be configured for a user with two effected arms by mirroring the assemblies connected to the torso vest 142, as well as their means of attachment, to the other side of the body. This means that there would be no dummy scapular rotation rail housing 161 on the rear of the vest 142 and that the front and rear scapular rotation rail housings 149, 151 on one side of the body would be mirrored to the other side of the body.

As made apparent from the foregoing, the orthosis of the present invention is not intended to be limited to the particular embodiment(s) delineated herein and illustrated in the accompanying figures of the drawings. As will be appreciated by those skilled in the art, various embodiments of the orthosis may be constructed that incorporate selected ones of the advantages and structures described herein.

The figures of the drawings are intended to illustrate the general characteristics of structures described in connection with the embodiment(s) and to supplement the written description associated with the orthosis. In connection therewith, the figures are not drawn to scale and, therefore, are not intended to reflect the precise structural or performance characteristics of any given embodiment. Moreover, the drawings should not, be interpreted as defining or limiting the range of values or properties encompassed by any enumerated embodiment. Each of the embodiments, however, is contemplated to incorporate structures permitting the orthosis to provide an adjustable amount of forced forearm pronation or supination and an adjustable amount of forced shoulder internal or external rotation to the user. Additionally, each of the embodiments is contemplated to incorporate structures permitting the orthosis to provide an adjustable amount of forced shoulder adduction, abduction, flexion, and extension, a means of locking the elbow at different angles, and a means of limiting the elbow's range of flexion or extension.

As will be appreciated by those skilled in the art, there are many variations that may be employed that are contemplated to accomplish the same results as the embodiment(s) of the orthosis described herein. For example, the materials selected for the construction of the orthosis may include any number of readily available plastics, metals, resins, epoxies, polymers, composites, and/or ceramics, as noted above. Further, a wide range of assembly structures, such as recesses and corresponding projections, set screws, welds, or pins may easily be used for locating the various structural elements of the orthosis without departing from the basic functionality of the devices detailed herein. For example, in one embodiment of the orthosis the linear motion carriage 18 and the upper splint arm 15 might be cast or molded to be one solid piece.

As should be appreciated from the foregoing, the orthosis, consistent with the present invention, is configured for at least the following:

1) provide an adjustable amount of forced forearm pronation or supination by allowing the forearm rotation to be limited or locked and to be switched between a state of being limited or locked and a state of being free to move
2) provide an adjustable amount of shoulder internal or external rotation by allowing it to be limited or locked and to be switched between a state of being limited or locked and a state of being free to move
3) provide an adjustable amount of shoulder flexion or extension by allowing it to be limited or locked and to be switched between a state of being limited or locked and a state of being free to move
4) provide an adjustable amount of shoulder adduction or abduction by allowing it to be limited or locked and to be switched between a state of being limited or locked and a state of being free to move
5) allow the flexion of the elbow to be limited or locked and to be switched between a state of being limited or locked and a state of being free to move
6) by means of the above three functions, allow the arm to assume the anatomical positions necessary for the muscles of an injured arm or shoulder to receive stimulation through resistance training, to assume desired positions for prolonged stretches, and to adapt to certain movements Any and all variations to the designs disclosed herein that accomplish these six functions, among others, are considered to be within the scope of this disclosure. None of the variations, however, are contemplated to detract from the basic functionality of the disclosed embodiments of the orthosis of the present invention.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above descriptions and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed:

1. An orthosis providing to a wearer at least one of forearm supination, forearm pronation, shoulder internal rotation, shoulder external rotation, shoulder adduction, shoulder abduction, shoulder flexion, shoulder extension, elbow flexion, elbow extension, shoulder elevation, and shoulder depression, comprising:
    a torso assembly adapted to be secured to the wearer's torso,
    wherein the torso assembly defines a torso axis;
    an upper arm assembly connected to the torso assembly and adapted to be secured around the wearer's upper arm,
    wherein the upper arm assembly defines an upper arm assembly axis;
    a wrist assembly adapted to be secured around the wearer's wrist,
    wherein the wrist assembly defines a wrist assembly axis; and
    a splint arm assembly comprising an upper splint arm, a lower splint arm, and a pivot pivotally connecting the upper splint arm to the lower splint arm,
    wherein the upper splint arm adjustably connects to the upper arm assembly,
    wherein the lower splint arm adjustably connects to the wrist assembly, and wherein the pivot permits alteration of a first angle between the upper arm assembly axis and the wrist assembly axis;
    a scapular assembly comprising a front scapular rotation rail, a rear scapular rotation rail, a front pivot pivotally connecting the front scapular rotation rail to a chest side of the torso assembly, and a rear pivot pivotally connecting the rear scapular rotation rail to a back side of the torso assembly,
    wherein the scapular assembly defines a scapular assembly axis,
    wherein the front pivot permits adjustment of a first location of the front scapular rotation rail around the scapular assembly axis, and
    wherein the rear pivot permits adjustment of a first location of the rear scapular rotation rail around the scapular assembly axis.

2. The orthosis of claim 1, further comprising:
    an upper arm adjustment assembly connecting the upper splint arm to the upper arm assembly,
    wherein the upper arm adjustment assembly permits adjustment of a first distance between the upper arm assembly and the pivot.

3. The orthosis of claim 2, wherein the upper arm adjustment assembly also permits adjustment of a second location of the upper splint arm around the upper arm assembly axis.

4. The orthosis of claim 2, further comprising:
    an internal-external rotation assembly connecting the upper arm adjustment assembly to the upper arm assembly,
    wherein the internal-external rotation assembly defines an internal-external rotation assembly axis, and wherein the internal-external rotation assembly is rotatable around the internal-external rotation assembly axis.

5. The orthosis of claim 1, further comprising:
an internal-external rotation assembly connecting the upper splint arm to the upper arm assembly,
wherein the internal-external rotation assembly permits adjustment of a second location of the upper splint arm around the upper arm assembly axis.

6. The orthosis of claim 1, further comprising:
a lower arm adjustment assembly connecting the lower splint arm to the wrist assembly,
wherein the lower arm adjustment assembly permits adjustment of a second distance between the pivot and the wrist assembly.

7. The orthosis of claim 6, wherein the lower arm adjustment assembly also permits adjustment of a third location of the lower splint arm around the wrist assembly axis.

8. The orthosis of claim 1, further comprising:
a lower arm adjustment assembly connecting the lower splint arm to the wrist assembly,
wherein the lower arm adjustment assembly permits adjustment of a third location of the lower splint arm around the wrist assembly axis.

9. The orthosis of claim 1, wherein the torso assembly comprises a vest securable around the wearer's torso.

10. The orthosis of claim 1, further comprising:
a flexion-extension assembly connecting the torso assembly to the upper arm assembly,
wherein the flexion-extension assembly defines a flexion-extension assembly axis, and
wherein the flexion-extension assembly facilitates rotation of the flexion-extension assembly around the flexion-extension assembly axis.

11. The orthosis of claim 10, further comprising:
an adduction-abduction assembly connected to the flexion-extension assembly,
wherein the adduction-abduction assembly permits alteration of a second angle between the upper arm assembly axis and the torso axis.

12. The orthosis of claim 10, wherein the scapular assembly connects to the flexion-extension assembly.

* * * * *